United States Patent
Purcell et al.

(10) Patent No.: US 11,910,787 B2
(45) Date of Patent: *Feb. 27, 2024

(54) RODENTS HAVING A HUMANIZED TMPRSS GENE

(71) Applicant: Regeneron Pharmaceuticals, Inc., Tarrytown, NY (US)

(72) Inventors: Lisa Purcell, Garnerville, NY (US); Alexander O. Mujica, Elmsford, NY (US); Yajun Tang, White Plains, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 610 days.

This patent is subject to a terminal disclaimer.

(21) Appl. No.: 17/099,942

(22) Filed: Nov. 17, 2020

(65) Prior Publication Data

US 2021/0068377 A1 Mar. 11, 2021

Related U.S. Application Data

(60) Division of application No. 16/052,700, filed on Aug. 2, 2018, now Pat. No. 10,863,729, which is a (Continued)

(51) Int. Cl.
*C07K 14/47* (2006.01)
*C12N 15/09* (2006.01)
(Continued)

(52) U.S. Cl.
CPC ...... *A01K 67/0275* (2013.01); *A01K 67/0278* (2013.01); *C07K 14/47* (2013.01); (Continued)

(58) Field of Classification Search
CPC ............ A01K 67/0275; A01K 67/0278; A01K 2207/15; A01K 2217/072; A01K 2227/10; (Continued)

(56) References Cited

U.S. PATENT DOCUMENTS 6,586,251 B2 7/2003 Economides et al.
7,294,754 B2 11/2007 Poueymirou et al.
(Continued)

FOREIGN PATENT DOCUMENTS

CN 101443348 A 5/2009
CN 102482347 A 5/2012
(Continued)

OTHER PUBLICATIONS

De Aberasturi et al., British J. Cancer 112: 4-8, doi.10.1038/bjc.2014.403, 2015; available online Sep. 9, 2014.*
(Continued)

*Primary Examiner* — Kevin K Hill
(74) *Attorney, Agent, or Firm* — Scully, Scott, Murphy & Presser, P.C.; Trisha Agrawal

(57) ABSTRACT

Genetically modified rodents such as mice and rats, and methods and compositions for making and using the same, are provided. The rodents comprise a humanization of at least one endogenous rodent Tmprss gene, such as an endogenous rodent Tmprss2, Tmprss4, or Tmprss11d gene.

21 Claims, 16 Drawing Sheets

Specification includes a Sequence Listing.

Related U.S. Application Data continuation of application No. 15/442,857, filed on Feb. 27, 2017, now Pat. No. 10,070,632.

(60) Provisional application No. 62/301,023, filed on Feb. 29, 2016.

(51) Int. Cl.

| | |
|---|---|
| *C12N 15/63* | (2006.01) |
| *C12N 9/64* | (2006.01) |
| *C12N 5/0735* | (2010.01) |
| *C12N 15/86* | (2006.01) |
| *A61K 48/00* | (2006.01) |

(52) U.S. Cl.
CPC ......... *C12N 5/0606* (2013.01); *C12N 9/6424* (2013.01); *C12N 15/63* (2013.01); *C12N 15/86* (2013.01); *A01K 2207/15* (2013.01); *A01K 2217/072* (2013.01); *A01K 2227/10* (2013.01); *A01K 2227/105* (2013.01); *A01K 2267/0337* (2013.01); *A61K 48/00* (2013.01); *C07K 2319/00* (2013.01); *C12N 15/09* (2013.01); *C12N 2710/10332* (2013.01)

(58) Field of Classification Search
CPC ...... A01K 2227/105; A01K 2267/0337; C07K 14/47; C07K 2319/00; C12N 5/0606; C12N 9/6424; C12N 15/09; C12N 15/63; C12N 15/8509; C12N 2510/00
See application file for complete search history.

(56) References Cited

U.S. PATENT DOCUMENTS

| | | | |
|---|---|---|---|
| 7,576,259 | B2 | 8/2009 | Poueymirou et al. |
| 7,659,442 | B2 | 2/2010 | Poueymirou et al. |
| 10,070,631 | B2 * | 9/2018 | Purcell ................. C12N 9/6424 |
| 10,070,632 | B2 * | 9/2018 | Purcell ................. C12N 5/0606 |
| 2004/0132156 | A1 | 7/2004 | Parry et al. |
| 2005/0003416 | A1 | 1/2005 | Wu |
| 2005/0022256 | A1 | 1/2005 | Laferia |
| 2005/0026255 | A1 | 2/2005 | Morser et al. |
| 2006/0101531 | A1 | 5/2006 | Vasioukhin et al. |
| 2008/0078000 | A1 | 3/2008 | Poueymirou et al. |
| 2013/0111616 | A1 | 5/2013 | Macdonald et al. |
| 2013/0111617 | A1 | 5/2013 | Macdonald et al. |
| 2013/0117873 | A1 | 5/2013 | Wang et al. |
| 2013/0273070 | A1 | 10/2013 | Purcell Ngambo |
| 2014/0134662 | A1 | 5/2014 | Flavell et al. |
| 2014/0235933 | A1 | 8/2014 | Lee et al. |
| 2014/0245466 | A1 | 8/2014 | Macdonald et al. |
| 2014/0245467 | A1 | 8/2014 | Macdonald et al. |
| 2014/0310828 | A1 | 10/2014 | Lee et al. |
| 2015/0089678 | A1 | 3/2015 | Murphy et al. |
| 2015/0106961 | A1 | 4/2015 | Rojas et al. |
| 2015/0143558 | A1 | 5/2015 | McWhirter et al. |
| 2015/0143559 | A1 | 5/2015 | McWhirter et al. |
| 2015/0282463 | A1 | 10/2015 | Murphy et al. |
| 2015/0320021 | A1 | 11/2015 | Wang et al. |
| 2015/0327524 | A1 | 11/2015 | Murphy et al. |
| 2015/0342163 | A1 | 12/2015 | Voronina et al. |
| 2015/0366174 | A1 | 12/2015 | Burova et al. |
| 2016/0157469 | A1 | 6/2016 | Burova et al. |
| 2016/0345549 | A1 | 12/2016 | Gurer et al. |
| 2017/0142943 | A1 | 5/2017 | Mujica et al. |
| 2017/0164588 | A1 | 6/2017 | Olson et al. |
| 2017/0245482 | A1 | 8/2017 | Purcell et al. |
| 2018/0139940 | A1 | 5/2018 | Macdonald et al. |

FOREIGN PATENT DOCUMENTS

| | | |
|---|---|---|
| CN | 103547148 A | 1/2014 |
| CN | 104661677 A | 5/2015 |
| JP | 2015-516975 A | 6/2015 |
| RU | 2 425 880 C2 | 2/2011 |
| WO | 2011/044050 A2 | 4/2011 |
| WO | 2012/112544 A2 | 8/2012 |
| WO | 2013/063556 A1 | 5/2013 |
| WO | 2013/158516 A1 | 10/2013 |
| WO | 2013/192030 A1 | 12/2013 |
| WO | 2014/039782 A2 | 3/2014 |
| WO | 2014/197612 A1 | 12/2014 |
| WO | 2015/042557 A1 | 3/2015 |
| WO | 2015/077071 A1 | 5/2015 |
| WO | 2015/196051 A1 | 12/2015 |
| WO | 2016/085889 A1 | 6/2016 |
| WO | 2016/089692 A1 | 6/2016 |
| WO | 2016/094481 A1 | 6/2016 |
| WO | 2016/164492 A2 | 10/2016 |
| WO | 2015/171861 A1 | 11/2016 |

OTHER PUBLICATIONS

NCBI NP_004253.1, Mar. 15, 2015.*
English-language translation of Chinese Office Action and Search Report dated Dec. 2, 2020 received in Chinese Application No. 201780010404.0.
Anderson P., "Post-Transcriptional Control of Cytokine Production", Nature Immunology 9(4):353-359 (Apr. 2008).
Bahgat M.M. et al., "Inhibition of Lung Serine Proteases in Mice: A Potentially New Approach to Control Influenza Infection", Virology Journal 8:27 (15 pagers) (2011).
Bertram S. et al., "TMPRSS2 and TMPRSS4 Facilitate Trypsin-Independent Spread of Influenza Virus in Caco-2 Cells", Journal of Virology 84(19):10016-10025 (Oct. 2010).
Bertram S. et al., "Novel Insights into Proteolytic Cleavage of Influenza Virus Hemagglutinin", Rev. Med. Virol. 20:298-310 (2010).
Bodewes R. et al., "Animal Models for the Preclinical Evaluation of Candidate Influenza Vaccines", Expert Reviews Vaccines 9(1):59-72 (2010).
Böttcher-Friebertshäuser E. et al., "Inhibition of Influenza Virus Infection in Human Airway Cell Cultures by an Antisense Peptide-Conjugated Morpholino Oligomer Targeting the Hemagglutinin-Activating Protease TMPRSS2", Journal of Virology 85(4):1554-1562 (Feb. 2011).
Böttcher-Friebertshäuser E. et al., "Cleavage of Influenza Virus Hemagglutinin by Airway Proteases TMPRSS2 and HAT Differs in Subcellular Localization and Susceptibility to Protease Inhibitors", Journal of Virology 84 (11):5605-5614 (Jun. 2010).
Böttcher E. et al., "MDCK Cells that Express Proteases TMPRSS2 and HAT Provide a Cell System to Propagate Influenza Viruses in the Absence of Trypsin and to Study Cleavage of HA and its Inhibition", Vaccine 27:6324-6329 (2009).
Böttcher E. et al., "Proteolytic Activation of Influenza Viruses by Serine Proteases TMPRSS2 and HAT from Human Airway Epithelium", Journal of Virology 80(19):9896-9898 (Oct. 2006).
Brevini T.A.L. et al., "No Shortcuts to Pig Embryonic Stem Cells", Theriogenology 74:544-550 (2010).
Bugge T.H. et al., "Type II Transmembrane Serine Proteases", The Journal of Biological Chemistry 284 (35):23177-23181 and Supplementary Tables (Aug. 28, 2009).
Cao S. et al., "Isolation and Culture of Primary Bovine Embryonic Stem Cell Colonies by a Novel Method", Journal of Experimental Zoology 311A:368-376 (2009).
Dennis, Jr. M.B., "Welfare Issues of Genetically Modified Animals", ILAR Journal 43(2):100-109 (2002).
Devoy A. et al., "Genomically Humanized Mice: Technologies and Promises", Nature Reviews Genetics 13:14-20 (Jan. 2012).
Guipponi M. et al., "The Transmembrane Serine Protease (TMPRSS3) Mutated in Deafness DFNB8/10 Activates the Epithelial Sodium Channel (ENaC) In Vitro", Human Molecular Genetics 11(23):2829-2836 (2002).
Harari D. et al., "Bridging the Species Divide: Transgenic Mice Humanized for Type-I Interferon Response", PLoS One 9(1):e84259, XP055553720, DOI:10.1371/journal.pone.0084259 (Jan. 9, 2014).
Hofker M.H. et al., "Transgenic Mouse Methods and Protocols", Methods in Molecular Biology 209:51-67 (2002-2003).

(56) References Cited

OTHER PUBLICATIONS

Hooper J.D. et al., "Type II Transmembrance Serine Proteases", The Journal of Biological Chemistry 276 (2):857-860 (Jan. 12, 2001).
Houdebine L-M, "Methods to Generate Transgenic Animals", Genetic Engineering in Livestock, New Applications and Interdisciplinary Perspectives, Engelhard M. et al., XVI, 1 46, p. 8, illu. pp. 31-47 (2009).
Kühn N. et al., "The Proteolytic Activation of (H3N2) Influenza A Virus Hemagglutinin is Facilitated by Different Type II Transmembrane Serine Proteases", Journal of Virology 90(9):4298-4307 (May 2016).
Kühn N. et al., "Studies on the Host Response to Influenza A Virus Infections in Mouse Knock-Out Mutants", Thesis-University of Veterinary Medicine Hannover pp. 1-74 (2015).
Macchiarini F. et al., "Humanized Mice: Are We There Yet?", JEM 202(10):1307-1311 (Nov. 21, 2005).
MacDonald L.E. et al., "Precise and In Situ Genetic Humanization of 6 Mb of Mouse Immunoglobulin Genes", PNAS 111(14):5147-5152 (Apr. 8, 2014).
Murphy A.J. et al., "Mice With Megabase Humanization of Their Immunoglobulin Genes Generate Antibodies as Efficiently as Normal Mice", PNAS 111(4):5153-5158 (Apr. 8, 2014).
Paris D.B.B.P. et al., "Equine Embryos and Embryonic Stem Cells: Defining Reliable Markers of Pluripotency", Theriogenology 74:516-524 (2010).
Radigan K.A. et al., "Modeling Human Influenza Infection in the Laboratory", Infection and Drug Resistance 8:311-320 (2015).
Rajagowthamee R. et al., "Animal Models for Influenza Virus Pathogenesis, Transmission, and Immunology", Journal of Immunological Methods 410:60-79 (2014).
Rongvaux A. et al., "Human Thrombopoietin Knockin Mice Efficiently Support Human Hematopoiesis In Vivo", PNAS 108(6):2378-2383 (Feb. 8, 2011).
Rybchin V.N., "Fundamentals of Genetic Engineering", Textbook for High Schools, Saint-Petersburg, Publishing House SPbSTU 522:411-413 (2002), cited in Russian Office Action dated Jul. 13, 2020 received in Russian Patent Application No. 2018131152.
Sun Y., "Characterization of the TMPRSS2 Protease as a Modulator of Prostate Cancer Metastasis", Defense Technical Information Center, pp. 1-12 (Mar. 2009).
Szabo R. et al., "Type II Transmembrane Serine Proteases in Development and Disease", The International Journal of Biochemistry & Cell Biology 40:1297-1316 (2008).
Tong C. et al., "Generating Gene Knockout Rats by Homologous Recombination in Embryonic Stem Cells", Nature Protocols 6(6):827-844 (Jun. 2011).
Tong C. et al., "Production of p53 Gene Knockout Rats by Homologous Recombination in Embryonic Stem Cells", Nature 467:211-215 (Sep. 2010).
Valenzuela D.M. et al., "High-Throughput Engineering of the Mouse Genome Coupled With High-Resolution Expression Analysis", Nature Biotechnology 21(6):652-659 (Jun. 2003).
Vuagniaux G. et al., "Synergistic Activation of ENAC by Three Membrane-Bound Channel-Activating Serine Proteases (mCAP1, mCAP2, and mCAP3) and Serum- and Glucocorticoid-Regulated Kinase (Sgk1) in Xenopus Docytes", J. Gen. Physiol. 120:191-201 (Aug. 2002).
Willinger T. et al., "Human IL-3/GM-CSF Knock-in Mice Support Human Alveolar Macrophage Development and Human Immune Responses in the Lung", PNAS 108(6):2390-2395 (Feb. 8, 2011).
Willinger T. et al., Improving Human Hemato-Lymphoid-System Mice by Cytokine Knock-in Gene Replacement, Trends in Immunology 32(7):321-327 (Jul. 2011).
Zhou H. et al., "Developing ITA Transgenic Rats for Inducible and Reversible Gene Expression", International Journal of Biological Sciences 5(2):171-181 (2009).
GenBank NCBI Reference Sequence No. NG_047085.1 (13 pages) (Sep. 13, 2017).
GenBank NCBI Reference Sequence No. NM_005656.3 (5 pages) (Apr. 30, 2017).
GenBank NCBI Reference Sequence No. NM_015775.2 (5 pages) (Apr. 25, 2017).
GenBank NCBI Reference Sequence No. NM_001173551.1 (5 pages) (Apr. 17, 2017).
GenBank NCBI Reference Sequence No. NM_004262.2 (4 pages) (Sep. 9, 2016).
GenBank NCBI Reference Sequence No. NM_145403.2 (4 pages) (Sep. 4, 2016).
GenBank NCBI Reference Sequence No. CH471057.1 (4 pages) (Mar. 23, 2015).
GenBank NCBI Reference Sequence No. NP_004253.1 (3 pages) (Mar. 15, 2015).
GenBank NCBI Reference Sequence No. NM_145561.2 (3 pages) (Feb. 15, 2015).
GenBank NCBI Reference Sequence No. NG_011858.2 (13 pages) (May 4, 2014).
NCBI CCDS Report for TMPRSS11D, https://www.ncbi.nlm.nih.gov/CCDS/CcdsBrowse.cgi?REQUEST=CCDS&DATA=CCDS3518; downloaded Dec. 7, 2017 (2 pages).
ENSG00000153802, https://www.ensembl.org/Homo_sapiens/Gene/Summary?g=ENSG00000153802; downloaded Dec. 7, 2017 (2 pages).
"Studies on the Host Response to Influenza A Virus Infections in Mouse Knock-Out Mutants", Abstract, [online], University of Veterinary Medicine Hannover Helmholtz Centre for Infection Research Braunschweig Department: Infection Genetics (2015).
International Search Report and Written Opinion dated Jun. 19, 2017 received in International Application No. PCT/US2017/019574.
Russian Office Action dated Jul. 13, 2020 received in Russian Patent Application No. 2018131152, together with an English-language translation.

\* cited by examiner

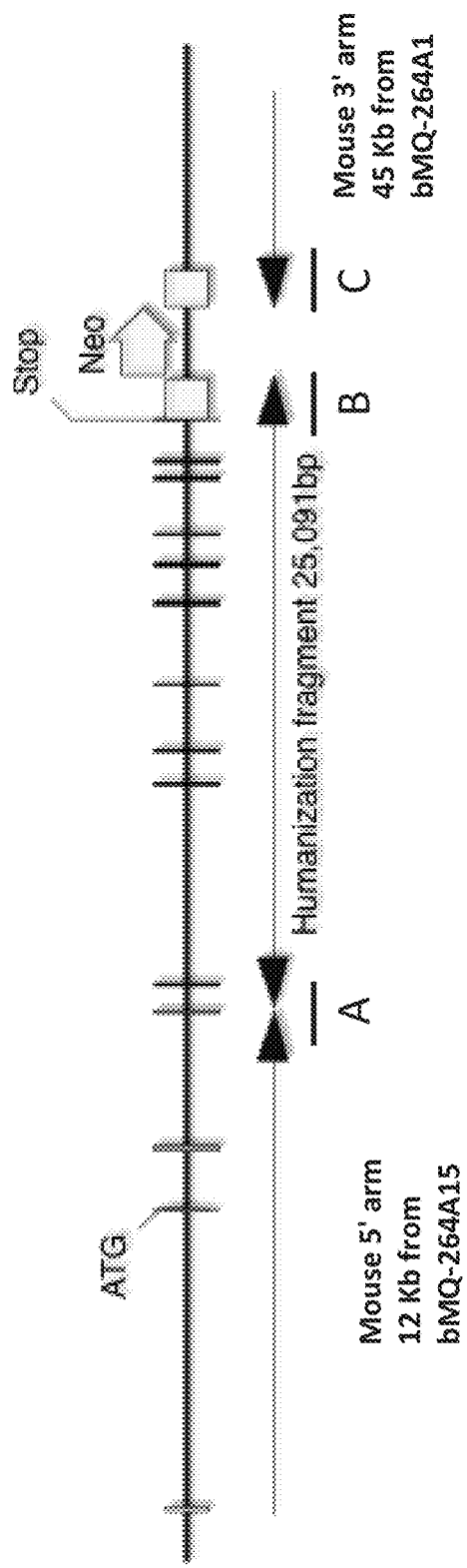

| | |
|---|---|
| A. 5' mouse // 5' human (SEQ ID NO:22) | AGCACCCCTC TCTTCCGCAG AGTCTAAGAA ATCGCTGTGT TTAGCCCTCG CCCTGGGCAC TGTCCTCACG GGAGCTGCTG TGGCTGCTGT CTTGCTTTGG // AAGTTCAGTA AGTGCAGGGA GCCTCGATCC CACCATGTGC TCCTGCAGTC CCCAGTGCTC TGAGCCAGAC CCTGCTCTCT GGGCTATTGA GACCTCTGGA GGCCCTCCGT GAGGTTCCTC TCTTACATAA CGAGGCTGTC TCTCTTCCCT TCTCTTG |
| B. human//XhoI//(*loxP*) Cassette (SEQ ID NO:23) | GGTCAGAGGA CCAAAGGTGA GGCAAGGCCA GACTTGGTGC TCCTGTGGTT// CTCGAG//*ATAACTTCG TATAATGTAT GCTATACGAA GTTAT* ATGCATGGCC TCCGGCGCGG GTTTTGGCGG CGCCCGCCGG CGCCCCCCTC CTCACGGCGA GGGCTGCCAC GTCAGAACGAA GGGGCAGCG AGCGTCCTGA |
| C. Cassette (*loxP*)/ICEU1/NheI// mouse (SEQ ID NO:24) | ATTGTTTGC CAAGTTCTAA TTCCATCAGA CCTCGACCTG CAGCCCCTAG *ATAACTTCGT ATAATGTATG CTATACGAAG TTAT*/GCTAGTAACTATAACGGTCCTAAGGTAGCGA // GCTAGC // TCCACGTGGC TTTGTCCCAG ACTTCCTTTG TCTTCAACAA CCTTCTGCAA |

Figure 1B

Tmprss2 protein alignment

```
                        10         20         30         40         50         60
hTMPRSS2        MALNSGSPPAIGPYYENHGYQPENPYPAQPTVVPTVYEVHPAQYYPSPVPQYAPRVLTQA
mTmprss2        MALNSGSPPGIGPCYENHGYQSEHICPPRPPVAPNGYNLYPAQYYPSPVPQYAPRITTQA
7010 mutant pro MALNSGSPPGIGPCYENHGYQSEHICPPRPPVAPNGYNLYPAQYYPSPVPQYAPRITTQA
                ********.****.******.*..*.***.****.****************.****.***

70         80         90        100        110        120
hTMPRSS2        SNPVVCTQPKSPSGTVCTSKTKKALCITTLGTFLVGAALAAGLLWKFMGKCSNSGIEQ
mTmprss2        STSVIHTHPKS-SGALCTSKKSKKSLCLALALGTVLTGAAVAAVLLWKFMG.NCSTSEMEQ
7010 mutant pro STSVIHTHPKS-SGALCTSKKSKKSLCLALALGTVLTGAAVAAVLLWKFMGKCSNSGIEQ
                *..*..*.***.****.******.**.****.*.****.****.*****.        *

130        140        150        160        170        180
hTMPRSS2        DSSGTCINPSNWCDGVSHCPGGEDENRCVRLYGPNFILQVYSSQRKSWHPVCQDDWNENY
mTmprss2        GSSGTCISSSLWCDGVAHCPNGEDENRCVRLYGQSFILQVYSSQRKAWYPVCQDDWSESY
7010 mutant pro DSSGTCINPSNWCDGVSHCPGGEDENRCVRLYGPNFILQVYSSQRKSWHPVCQDDWNENY
                .******...*.****.***.************..**********.*.*******.*.*

190        200        210        220        230        240
hTMPRSS2        GRAACRDMGYKNNFYSSQGIVDDSGSTSFMKLNTSAGNVDIYKKLYHSDACSSKAVVSLR
mTmprss2        GRAACKDKDMGYKNNFYSSQGIPDQSGATSFMKLNVSSGNVDLYKKLYHSDCSSRMVVSLR
7010 mutant pro GRAACRDMGYKNNFYSSQGIVDDSGSTSFMKLNTSAGNVDIYKKLYHSDACSSKAVVSLR
                *****.*.*************.*.**.*******.*.****.*******.**..*****

250        260        270        280        290        300
hTMPRSS2        CIACGVNLNSSRQSRIVGGESALPGAWPWQVSLHVQNVHVCGGSIITPEWIVTAAHCVEK
mTmprss2        CIECGVRS-VKRQSRIVGGLNASPGDWPWQVSLHVQGVHVCGGSIITPEWIVTAAHCVEE
7010 mutant pro CIACGVNLNSSRQSRIVGGESALPGAWPWQVSLHVQNVHVCGGSIITPEWIVTAAHCVEK
                **.***.   .********  *.**.*********.***********************
```

Figure 1D

Tmprss4 protein alignment

```
                        10        20        30        40        50        60
hTMPRSS4         MLQDPDSDQPLNSLDVKPLRKPRIPMETFRKVGIPITAALLSLASIIVVLIKVILDKY
mTmprss4         MESDSGQPLNNRDIVPFRKPRRPQETFKKVGIPITAVLLSLIAVLLIVALLIKVILDKY
7224 mutant pro  MESDSGQPLNNRDIVPFRKPRRPQETFKKVGIPITAVLLSLIALVIVALLIKVILDKY
                    ** ******  ***** ****  **** ********** *** ** ** ********

70        80        90       100       110       120
hTMPRSS4         YFLCGQPLHFIPRKQLCDGEELDCPLGEDEEHCVKSFPEGPAVAVRLSKDRSTLQVLDSA
mTmprss4         YFICGSPLTFIQRGQLCDGHLDCASGEDEEHCVKDFPEKPGVAVRLSKDRSTLQVLDAA
7224 mutant pro  YFLCGQPLHFIPRKQLCDGEELDCPLGEDEEHCVKSFPEGPAVAVRLSKDRSTLQVLDSA
                 ** ** ** ** * *****  ***  ******* *** ************ *****

130       140       150       160       170       180
hTMPRSS4         GNWFSACEDNFTEALAETACRQMGYSSKPTFRAVEIGPDQLDVVEITENSQELRMRNSS
mTmprss4         GTWASVCFDNFTEALAKTACRQMGYDSQPAFRAVEIRPDQNLPVAQVTGNSQELQVQNGS
7224 mutant pro  GNWFSACEDNFTEALAETACRQMGYSSKPTFRAVEIGPDQLDVVEITENSQELRMRNSS
                 * * * * ******** ******** * * ****** ***  *   *  **** ****

190       200       210       220       230       240
hTMPRSS4         GPCLSGSLVSLHCLACGKSLKTPHVGGEEASVDSWPWQVSIQYDKQHVCGGSILDPHWV
mTmprss4         RSCLSGSLVSLRCLDCGKSLKTPHVGGVEAPVDSWPWQVSIQYNKQHVCGGSILDPHWI
7224 mutant pro  GPCLSGSLVSLHCLACGKSLKTPHVGGVEEASVDSWPWQVSIQYDKQHVCGGSILDPHWV
                   ********* ** ********* *** * ***********  ********** * *

250       260       270       280       290       300
hTMPRSS4         LTAAHCFRKHTDVFNWKVRAGSDKLGSFPSLAVAKIIIIEFNPMYPKDNDIALMKLQFPL
mTmprss4         LTAAHCFRKYLDVSSWKVRAGSNILGNSPLPVAKIFIAEPNPLYPKEKDIALVKLQMPL
7224 mutant pro  LTAAHCFRKHTDVFNWKVRAGSDKLGSFPSLAVAKIIIIEFNPMYPKDNDIALMKLQFPL
                 ********* **  ******  **  * * *** *   **** ** ****  ***  *
```

Figure 2D

Tmprss4 protein alignment

```
                    310        320        330        340        350        360
hTMPRSS4         TFSGTVRPICLPFFDEELTPATPLWIIGWGFTKQNGGKMSDILLQASVQVIDSTRCNADD
mTmprss4         TFSGSVRPICLPFSDEVLVPATPVWVIGWGFTEENGGKMSDMLLQASVQVIDSTRCNAED
7224 mutant pro  TFFSGTVRPICLPFFDEELTPATPLWIIGWGFTKQNGGKMSDILLQASVQVIDSTRCNADD
                 ** **:***** ** ** :***::*:*****.:****.****:************

370        380        390        400        410        420
hTMPRSS4         AYQGEVTEKMMCAGIPEGGVDTCQGDSGGPLMYQSDQWHVVGIVSWGYGCGGPSTPGVYT
mTmprss4         AYEGEVTAEMLCAGTPQGGKDTCQGDSGGPLMYHSDKWQVVGIVSWGHGCGGPSTPGVYT
7224 mutant pro  AYQGEVTEKMMCAGIPEGGVDTCQGDSGGPLMYQSDQWHVVGIVSWGYGCGGPSTPGVYT
                 **:****.::*** *:**.***********:**:*:*************

430
hTMPRSS4         KVSAYLNWIYNVWKAEL
mTmprss4         KVTAYLNWIYNVRKSEM
7224 mutant pro  KVSAYLNWIYNVWKAEL
                 **:********.*:*:
``` solid line: TM
solid box: LDLRa
doted box: SRCR domain
doted line: peptidase S1

Figure 2D (Continued)

Tmprss11d protein alignment

```
                      310        320        330        340        350        360
hTMPRSS11D         PPGSTAYVTGWGAQEYAGHTVPELRQGQVRIISNDVCNAPHSYNGAILSGMLCAGVPQGG
mTmprss11d         IPGSVAYVTGWGSLIYGGNAVTNLRQGEVRIISSEECNTPAGYSGSVLPGMLCAGMRSGA
7226 mutant pro

RODENTS HAVING A HUMANIZED TMPRSS GENE

CROSS REFERENCE TO RELATED APPLICATIONS

This application is a divisional of U.S. patent application Ser. No. 16/052,700, filed Aug. 2, 2018, which is a continuation of U.S. patent application Ser. No. 15/442,857, filed Feb. 27, 2017, now U.S. Pat. No. 10,070,632, which claims the benefit of priority from U.S. Provisional Application No. 62/301,023, filed Feb. 29, 2016, the entire contents of which are incorporated herein by reference.

INCORPORATION BY REFERENCE OF SEQUENCE LISTING

The Sequence Listing in the ASCII text file, named as 33093YA_10234US04_SequenceListing.txt of 275 KB, created on Nov. 2, 2020, and submitted to the United States Patent and Trademark Office via EFS-Web, is incorporated herein by reference.

BACKGROUND

Type II transmembrane serine proteases are a family of proteases characterized by an N-terminal transmembrane domain (Bugge et al., *J. Biol. Chem.* 284 (35): 23177-23181, 2009; Hooper et al., *J. Biol. Chem.* 272(2): 857-860, 2001). All members of this family are expressed as single-chain zymogens and are proteolytically activated by cleavage within a highly conserved R/(IV)VGG motif. One member of the family, transmembrane protease, serine type 4 (TMPRSS4), has been shown to activate the epithelial sodium channel (ENaC) regulating the sodium and water flux across epithelia (Guipponi et al. 2002 *Hum. Mol. Genet.* 11:2829, Vuagniaux et al. 2002 *J. Gen. Physiol.* 120:191). The proteolytical activators of TMPRSS4 are unknown; however, data available to date suggests that the protein is autoactivated. When activated, the catalytic domain of TMPRSS4 remains bound to the N-terminus of the protein via a disulphide linkage. TMPRSS4, TMPRSS2 and TMPRSS11D (or Human Airway Trypsin-like protease; "HAT") have been shown in vitro to cleave influenza A hemagglutinin (HA), which is the first essential step in the viral life cycle. This cleavage is essential for activity of HA, as the protein is synthesized as a precursor protein (HA0) and requires cleavage into HA1 and HA2 for activity. RNAi knock-down of TMPRSS4 in Caco-2 cells resulted in reduced spread of the virus. In addition, TMPRSS4 was shown to be strongly upregulated in the lungs of mice infected with influenza (Böttcher el al. 2006 *J. Virol.* 80:9896; Böttcher et al. 2009 *Vaccine* 27: 6324; Böttcher-Friebershäusser et al. 2010 *J. Virol.* 84: 5604; Bertam et al. 2010 *J. Virol.* 84:10016; Bertam et al. 2010 *J. Virol.* 84:10016; Böttcher-Friebershäusser et al. 2011 *J. Virol.* 85: 1554; Bahgat et al. 2011 *Virol. J.* 8:27).

Development of an in vivo system, e.g., a rodent model of infection, is needed in order to identify and test compounds including antibodies that specifically target human type II transmembrane serine proteases for the treatment and prevention of viral infection and other diseases.

SUMMARY

The present invention encompasses the recognition that it is desirable to engineer rodent animals to provide in vivo systems for identifying and developing new therapeutics. For example, the present invention encompasses the recognition that rodents having a humanized Tmprss gene are desirable for use in identifying and developing therapeutics for the treatment and prevention of viral infections.

In one aspect, the invention provides a rodent whose genome contains a humanized Tmprss gene that includes a nucleotide sequence of an endogenous rodent Tmprss gene and a nucleotide sequence of a cognate human TMPRSS gene, wherein the humanized Tmprss gene is under control of a 5' regulatory sequence(s), such as the promoter and/or enhancer(s), of the endogenous rodent Tmprss gene.

In some embodiments, the humanized Tmprss gene in rodents disclosed herein encodes a humanized Tmprss protein that contains an ectodomain substantially identical (e.g., at least 85%, 90%, 95%, 98%, 99% or 100% identical in sequence) to the ectodomain of a human TMPRSS protein. In some embodiments, the humanized Tmprss protein contains a cytoplasmic and transmembrane portion that is substantially identical (e.g., at least 85%, 90%, 95%, 98%, 99% or 100% identical in sequence) to the cytoplasmic and transmembrane portion of an endogenous rodent Tmprss protein.

In some embodiments, a rodent disclosed herein contains a humanized Tmprss gene that includes a nucleotide sequence of an endogenous rodent Tmprss gene and a nucleotide sequence of a cognate human TMPRSS gene, wherein the nucleotide sequence of the cognate human TMPRSS gene encodes a polypeptide substantially identical (e.g., at least 85%, 90%, 95%, 98%, 99% or 100% identical in sequence) to the ectodomain of the human TMPRSS protein encoded by the cognate human TMPRSS gene. In some embodiments, a rodent disclosed herein contains a humanized Tmprss gene that includes a nucleotide sequence of an endogenous rodent Tmprss gene and a nucleotide sequence of a cognate human TMPRSS gene, wherein the nucleotide sequence of the endogenous rodent Tmprss gene encodes a polypeptide substantially identical (e.g., at least 85%, 90%, 95%, 98%, 99% or 100% identical in sequence) to the cytoplasmic and transmembrane portion of the endogenous rodent Tmprss protein encoded by the endogenous rodent Tmprss gene.

In some embodiments, a rodent disclosed herein contains a humanized Tmprss gene located at an endogenous rodent Tmprss locus that results from a replacement of a contiguous genomic sequence of an endogenous rodent Tmprss gene with a contiguous genomic sequence of a cognate human TMPRSS gene. In specific embodiments, the contiguous genomic sequence of a cognate human TMPRSS gene being inserted includes exon sequences encoding an ectodomain substantially identical with the ectodomain of the human TMPRSS protein encoded by human TMPRSS gene. In some embodiments, the contiguous genomic sequence of a cognate human TMPRSS gene also includes the 3' UTR of the cognate human TMPRSS gene.

In some embodiments, a rodent disclosed herein is heterozygous for a humanized Tmprss gene at an endogenous rodent Tmprss locus. In other embodiments, a rodent is homozygous for a humanized Tmprss gene at an endogenous rodent Tmprss locus.

In further embodiments, a rodent contains two or more humanized Tmprss genes at different endogenous rodent Tmprss loci with each endogenous rodent Tmprss locus being humanized with a respective cognate human TMPRSS gene; for example, two or more of humanized Tmprss2, humanized Tmprss4, and humanized Tmprss11d genes.

In some embodiments, a rodent disclosed herein contains a humanized Tmprss2 gene that includes a nucleotide sequence of an endogenous rodent Tmprss2 gene and a nucleotide sequence of a human TMPRSS2 gene, wherein the humanized Tmprss2 gene is under control of the promoter of the endogenous rodent Tmprss2 gene.

In some embodiments, the humanized Tmprss2 gene encodes a humanized Tmprss2 protein that contains an ectodomain substantially identical (e.g., at least 85%, 90%, 95%, 98%, 99% or 100% identical in sequence) with the ectodomain of the human TMPRSS2 protein encoded by the human TMPRSS2 gene used in humanization. The human TMPRSS2 protein contains, in some embodiments, an amino acid sequence at least 85% identical (e.g., at least 90%, 95%, 98%, 99% or 100% identical) with the amino acid sequence as set forth in SEQ ID NO: 4. In some embodiments, a humanized Tmprss2 protein contains an ectodomain substantially identical (e.g., at least 85%, 90%, 95%, 98%, 99% or 100% identical) with the amino acid sequence composed of residues W106 to G492 or the C-terminal 387 amino acids of a human TMPRSS2 protein as set forth in, e.g., SEQ ID NO: 4. In some embodiments, the humanized Tmprss2 gene encodes a humanized Tmprss2 protein that further contains a cytoplasmic and transmembrane portion that is substantially identical (e.g., at least 85%, 90%, 95%, 98%, 99% or 100% identical) with the cytoplasmic and transmembrane portion of the rodent Tmprss2 protein encoded by the endogenous rodent Tmprss2 gene being humanized. An exemplary endogenous rodent Tmprss2 protein is set forth in SEQ ID NO: 2.

In some embodiments, a rodent contains a humanized Tmprss2 gene that includes a nucleotide sequence of an endogenous rodent Tmprss2 gene and a nucleotide sequence of a human TMPRSS2 gene, wherein the nucleotide sequence of the human TMPRSS2 gene encodes an ectodomain substantially identical (e.g., at least 85%, 90%, 95%, 98%, 99% or 100% identical in sequence) with the ectodomain of the human TMPRSS2 protein encoded by the human TMPRSS2 gene. In specific embodiments, the nucleotide sequence of a human TMPRSS2 gene is a contiguous genomic sequence of a human TMPRSS2 gene containing coding exon 4 through the stop codon in coding exon 13 of the human TMPRSS2 gene. In particular embodiments, the contiguous genomic sequence of a human TMPRSS2 gene further contains the 3' UTR of the human TMPRSS2 gene. In some embodiments, the nucleotide sequence of an endogenous rodent Tmprss2 gene included in a humanized Tmprss2 gene encodes a cytoplasmic and transmembrane portion that is substantially identical (e.g., at least 85%, 90%, 95%, 98%, 99% or 100% identical) with the cytoplasmic and transmembrane portion of the endogenous rodent Tmprss2 protein encoded by the endogenous rodent Tmprss2 gene.

In particular embodiments, a humanized Tmprss2 gene contains coding exons 1-2 of an endogenous rodent Tmprss2 gene, and coding exon 4 through coding exon 13 of a human TMPRSS2 gene, wherein the humanized Tmprss2 gene encodes a humanized Tmprss2 protein that contains a cytoplasmic and transmembrane portion that is substantially identical with the cytoplasmic and transmembrane portion of the rodent Tmprss2 protein encoded by the endogenous rodent Tmprss2 gene, and an ectodomain that is substantially identical with the ectodomain of the human TMPRSS2 protein encoded by the human TMPRSS2 gene. The humanized Tmprss2 gene contains an exon 3 that in some embodiments is coding exon 3 of a human TMPRSS2 gene, and in other embodiments is coding exon 3 of an endogenous rodent Tmprss2 gene. In some embodiments, the humanized Tmprss2 gene contains an exon 3 that includes a 5' portion of coding exon 3 of an endogenous rodent Tmprss2 gene and a 3' portion of coding exon 3 of a human TMPRSS2 gene.

In some embodiments, a rodent disclosed herein contains a humanized Tmprss4 gene that includes a nucleotide sequence of an endogenous rodent Tmprss4 gene and a nucleotide sequence of a human TMPRSS4 gene, wherein the humanized Tmprss4 gene is under control of the promoter of the endogenous rodent Tmprss4 gene.

In some embodiments, the humanized Tmprss4 gene encodes a humanized Tmprss4 protein that contains an ectodomain substantially identical (e.g., at least 85%, 90%, 95%, 98%, 990 or 100% identical in sequence) with the ectodomain of the human TMPRSS4 protein encoded by the human TMPRSS4 gene used in humanization. The human TMPRSS4 protein contains, in some embodiments, an amino acid sequence at least 85% identical (e.g., at least 90%, 95%, 98%, 99% or 100% identical) with the amino acid sequence as set forth in SEQ ID NO: 11. In some embodiments, a humanized Tmprss4 protein contains an ectodomain substantially identical (e.g., at least 85%, 90%, 95%, 98%, 99% or 100% identical) with the amino acid sequence composed of residues K54 to L437 or the C-terminal 384 amino acids of a human TMPRSS4 protein as set forth in, e.g., SEQ ID NO: 11. In some embodiments, the humanized Tmprss4 gene encodes a humanized Tmprss4 protein that further contains a cytoplasmic and transmembrane portion that is substantially identical (e.g., at least 85%, 90%, 95%, 98%, 99% or 100% identical) with the cytoplasmic and transmembrane portion of the rodent Tmprss4 protein encoded by the endogenous rodent Tmprss4 gene being humanized. An exemplary endogenous rodent Tmprss4 protein is set forth in SEQ ID NO: 9.

In some embodiments, a rodent contains a humanized Tmprss4 gene that includes a nucleotide sequence of an endogenous rodent Tmprss4 gene and a nucleotide sequence of a human TMPRSS4 gene, wherein the nucleotide sequence of a human TMPRSS4 gene encodes an ectodomain substantially identical with the ectodomain of the human TMPRSS4 protein encoded by the human TMPRSS4 gene. In specific embodiments, the nucleotide sequence of a human TMPRSS4 gene is a contiguous genomic sequence containing coding exon 4 through the stop codon in coding exon 13 of a human TMPRSS4 gene. In some embodiments, the nucleotide sequence of an endogenous rodent Tmprss4 gene included in a humanized Tmprss4 gene encodes a cytoplasmic and transmembrane portion that is substantially identical with the cytoplasmic and transmembrane portion of the rodent Tmprss4 protein encoded by the endogenous rodent Tmprss4 gene.

In particular embodiments, a humanized Tmprss4 gene contains coding exon 1 through coding exon 3 of an endogenous rodent Tmprss4 gene, and coding exon 4 through the stop codon in coding exon 13 of a human TMPRSS4 gene.

In some embodiments, a rodent disclosed herein contains a humanized Tmprss11d gene that includes a nucleotide sequence of an endogenous rodent Tmprss/Id gene and a nucleotide sequence of a human TMPRSS11D gene, wherein the humanized Tmprss11d gene is under control of the promoter of the endogenous rodent Tmprss11d gene.

In some embodiments, the humanized Tmprss11d gene encodes a humanized Tmprss11d protein that contains an ectodomain substantially identical (e.g., at least 85%, 90%, 95%, 98%, 99% or 100% identical in sequence) with the ectodomain of the human TMPRSS11D protein encoded by the human TMPRSS11D gene used in humanization. The human TMPRSS11D protein contains, in some embodiments, an amino acid sequence at least 85% identical (e.g., at least 90%, 95%, 98%, 99% or 100% identical) with the amino acid sequence as set forth in SEQ ID NO: 18. In some embodiments, a humanized Tmprss11d protein contains an ectodomain substantially identical (e.g., at least 85%, 90%, 95%, 98%, 99% or 100% identical) with the amino acid sequence composed of residues A42-I418 or the C-terminal 377 amino acids of a human TMPRSS11D protein as set forth in, e.g., SEQ ID NO: 18. In some embodiments, the humanized Tmprss/Id gene encodes a humanized Tmprss11d protein that further contains a cytoplasmic and transmembrane portion that is substantially identical (e.g., at least 85%, 90%, 95%, 98%, 99% or 100% identical) with the cytoplasmic and transmembrane portion of the endogenous rodent Tmprss11d protein encoded by the endogenous rodent Tmprss1/d gene being humanized. An exemplary endogenous rodent Tmprss11d protein is set forth in SEQ ID NO: 16.

In some embodiments, a rodent contains a humanized Tmprss11d gene that includes a nucleotide sequence of an endogenous rodent Tmprss11d gene and a nucleotide sequence of a human TMPRSS11D gene, wherein the nucleotide sequence of the human TMPRSS11D gene encodes an ectodomain substantially identical with the ectodomain of the human TMPRSS11D protein encoded by the human TMPRSS11D gene. In specific embodiments, the nucleotide sequence of a human TMPRSS11d gene is a contiguous genomic sequence containing coding exon 3 through the stop codon in coding exon 10 of a human TMPRSS11D gene. In particular embodiments, the contiguous genomic sequence of a human TMPRSS11D gene further contains the 3' UTR of the human TMPRSS11D gene. In some embodiments, the nucleotide sequence of an endogenous rodent Tmprss11d gene included in a humanized Tmprss11d gene encodes a cytoplasmic and transmembrane portion that is substantially identical with the cytoplasmic and transmembrane portion of the rodent Tmprss11d protein encoded by the endogenous rodent Tmprss11d gene.

In particular embodiments, a humanized Tmprss11d gene contains coding exons 1-2 of an endogenous rodent Tmprss11d gene, and coding exon 3 through coding exon 13 of a human TMPRSS11D gene.

In another aspect, the invention provides an isolated rodent cell or tissue whose genome contains a humanized Tmprss gene as described herein. In specific embodiments, the humanized Tmprss gene is selected from the group consisting of a humanized Tmprss2 gene, a humanized Tmprss4 gene, and a humanized Tmprss11d gene.

In still another aspect, the invention provides a rodent embryonic stem cell whose genome contains a humanized Tmprss gene as described herein. In specific embodiments, the humanized Tmprss gene is selected from the group consisting of a humanized Tmprss2 gene, a humanized Tmprss4 gene, and a humanized Tmprss11d gene.

In another aspect, a rodent embryo generated from the rodent embryonic stem cell disclosed herein is also provided.

In one aspect, the invention provides a nucleic acid vector suitable for use in humanizing an endogenous Tmprss gene in a rodent. In some embodiments, the nucleic acid vector includes a human Tmprss nucleic acid sequence (e.g., a human genomic DNA encoding the ectodomain of a human TMPRSS protein), flanked by a 5' homology arm and a 3' homology arm. The 5' and 3' homology arms are nucleic acid sequences that are placed at 5' and 3', respectively, to the human Tmprss nucleic acid sequence and are homologous to genomic DNA sequences at an endogenous Tmprss locus in a rodent that flank a rodent genomic DNA encoding the ectodomain of a cognate rodent Tmprss protein. Thus, the 5' and 3' homology arms are capable of mediating homologous recombination and replacement of the rodent genomic DNA encoding the ectodomain of the cognate rodent Tmprss protein with the human Tmprss nucleic acid sequence to form a humanized Tmprss gene as described herein.

In a further aspect, the invention is directed to a method of providing a rodent whose genome contains a humanized Tmprss gene. The method includes modifying the genome of a rodent to replace a genomic sequence of an endogenous rodent Tmprss gene with a genomic sequence of a cognate human TMPRSS gene to form a humanized Tmprss gene.

In some embodiments, the invention provides a method of making a rodent (such as a mouse or a rat) having a humanized Tmprss gene, the method including the steps of (a) inserting a genomic fragment into an endogenous rodent Tmprss locus in a rodent embryonic stem cell, wherein the genomic fragment contains a nucleotide sequence of a cognate human TMPRSS gene, thereby forming a humanized Tmprss gene (such as those described herein); (b) obtaining a rodent embryonic stem cell comprising the humanized Tmprss gene of (a); and (c) creating a rodent using the rodent embryonic stem cell of (b).

In some embodiments, the humanized Tmprss gene is selected from the group consisting of a humanized Tmprss2 gene, a humanized Tmprss4 gene, and a humanized Tmprss11d gene. In various embodiments, the humanized Tmprss gene encodes a humanized Tmprss protein that contains an ectodomain substantially identical (e.g., at least 90%, 95%, 98%, 99% or 100% identical in sequence) to the ectodomain of the human TMPRSS protein encoded by the human TMPRSS gene used for humanization. In specific embodiments, the humanized Tmprss protein contains the ectodomain of a human TMPRSS protein selected from the group consisting of a human TMPRSS2 protein, a human TMPRSS4 protein, and a human TMPRSS11D protein. In specific embodiments, the humanized Tmprss protein further contains a cytoplasmic and transmembrane portion that is substantially identical with the cytoplasmic and transmembrane portion of the rodent Tmprss protein encoded by the endogenous rodent Tmprss gene being humanized.

In another aspect, the invention provides a method of using a rodent disclosed herein to assess the therapeutic efficacy of a compound (e.g., candidate inhibitors that specifically target a human TMPRSS protein) in treating influenza virus infection. The method can include the steps of providing a rodent described herein, administering an influenza virus and a candidate compound to the rodent: and monitoring the presence and severity of influenza virus infection in the rodent to determine the therapeutic efficacy of the drug candidate.

In some embodiments, the influenza virus is administered to the rodent before the compound. In other embodiments, the influenza virus is administered to the rodent after the compound.

In some embodiments, the candidate compound is an antibody or antigen-binding fragment thereof specific for a human TMPRSS protein. In specific embodiments, the candidate compound is an antibody or antigen-binding fragment thereof specific for a human TMPRSS protein selected from the group consisting of a human TMPRSS2 protein, a human TMPRSS4 protein, and a human TMPRSS11D protein.

Other features, objects, and advantages of the present invention are apparent in the detailed description that follows. It should be understood, however, that the detailed description, while indicating embodiments of the present invention, is given by way of illustration only, not limitation. Various changes and modifications within the scope of the invention will become apparent to those skilled in the art from the detailed description.

BRIEF DESCRIPTION OF THE DRAWINGS

The Drawings included herein, which are composed of the following Figures, are for illustration purposes only and not for limitation.

FIGS. 1A-1D. Exemplary strategy for humanization of mouse Tmprss2.

FIG. 1A shows a diagram, not to scale, of the genomic organization of mouse Tmprss2 and human TMPRSS2 genes. Exons are represented by thin bars placed across the genomic sequences, with the first coding exon for both genes indicated by the start codon "ATG" above the exon, and the last coding exon indicated by the "Stop" codon above the exon. A mouse genomic fragment of about 25,291 bp to be deleted and a human genomic fragment of about 25,091 bp to be inserted are indicated. Locations of probes used in an assay described in Example 1 are indicated. TM: transmembrane domain; SRCR: scavenger receptor cysteine-rich like domain; LDLRa: low density lipoprotein receptor class A.

FIG. 1B illustrates, not to scale, an exemplary modified BAC vector for humanization of an endogenous mouse Tmprss2 gene, along with the junction sequences (SEQ ID NOS. 22, 23 and 24).

FIG. 1C illustrates, not to scale, a humanized Tmprss2 allele after the neomycin cassette has been deleted, along with the junction sequences (SEQ ID NOS: 22 and 25).

FIG. 1D sets forth a sequence alignment of a human TMPRSS2 protein (SEQ ID NO: 4), a mouse Tmprss2 protein (SEQ ID NO: 2), and a humanized Tmprss2 protein ("7010 mutant pro") (SEQ ID NO: 7).

FIGS. 2A-2D. Exemplary strategy for humanization of mouse Tmprss4.

FIG. 2A shows a diagram, not to scale, of the genomic organization of mouse Tmprss4 and human TMPRSS4 genes. Exons are represented by thin bars placed across the genomic sequences, with the first exon (also the first coding exon) for both genes indicated by the start codon "ATG" above the exon, and the last coding exon indicated by the "Stop" codon above the exon. The mouse genomic fragment of about 11,074 bp to be deleted and the human genomic fragment of about 14,963 bp to be inserted are indicated. Locations of probes used in an assay described in Example 2 are indicated. TM: transmembrane domain; SRCR: scavenger receptor cysteine-rich like domain; LDLRa: low density lipoprotein receptor class A.

FIG. 2B illustrates, not to scale, an exemplary modified BAC vector for humanization of an endogenous mouse Tmprss4 gene, along with the junction sequences (SEQ ID NOS: 38, 39 and 40).

FIG. 2C illustrates, not to scale, a humanized Tmprss4 allele after the neomycin cassette has been deleted, along with the junction sequences (SEQ ID NOS: 41 and 40).

FIG. 2D sets forth a sequence alignment of a human TMPRSS4 protein (SEQ ID NO: 11), a mouse Tmprss4 protein (SEQ ID NO: 9), and a humanized Tmprss4 protein ("7224 mutant pro") (SEQ ID NO: 14).

FIG. 3A shows a diagram, not to scale, of the genomic organization of mouse Tmprss11d and human TMPRSS11D genes. Exons are represented by thin bars placed across the genomic sequences, with the first exon (also the first codon exon) for both genes indicated by the start codon "ATG" above the exon, and the last coding exon indicated by the "Stop" codon above the exon. A mouse genomic fragment of about 35,667 bp to be deleted and a human genomic fragment of about 33,927 bp to be inserted are indicated. Locations of probes used in an assay described in Example 3 are indicated. TM: transmembrane domain; SEA: domain found in sea urchin sperm protein, enterokinase and agrin.

FIG. 3B illustrates, not to scale, an exemplary modified BAC vector for humanization of an endogenous mouse Tmprss11d gene, along with the junction sequences (SEQ ID NOS: 57, 58 and 59).

FIG. 3C illustrates, not to scale, a humanized Tmprss11 allele after the neomycin cassette has been deleted, along with the junction sequences (SEQ ID NOS: 57 and 60).

FIG. 3D sets forth a sequence alignment of a human TMPRSS11D protein (SEQ ID NO: 18), a mouse Tmprss11d protein (SEQ ID NO. 16), and a humanized Tmprss11d protein ("7226 mutant pro") (SEQ ID NO: 21).

DETAILED DESCRIPTION OF CERTAIN EMBODIMENTS

Figure 1A:
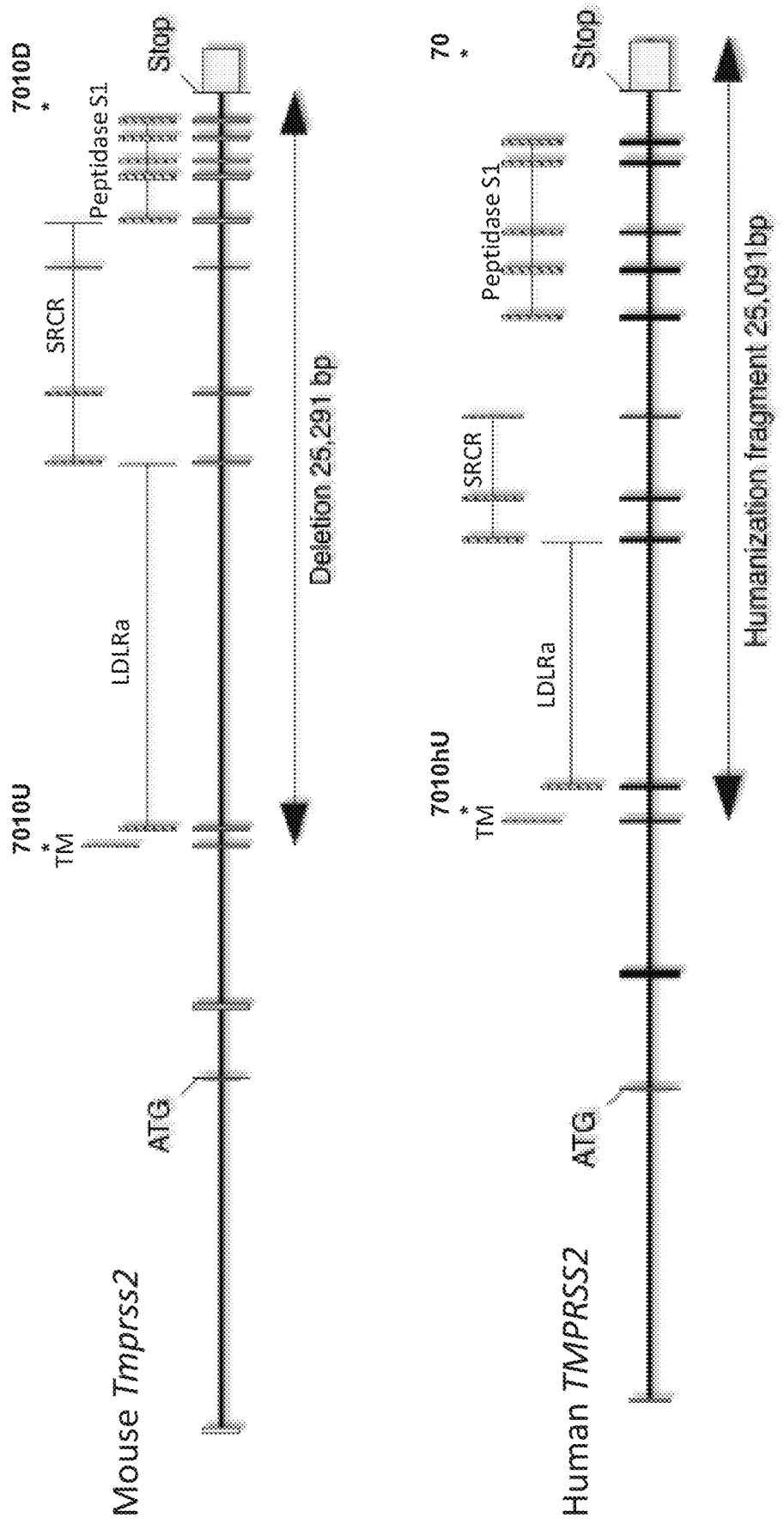

The present invention relates to genetically modified rodents (e.g., mice and rats) having a humanized gene encoding a type II transmembrane serine protease (or "Tmprss", for transmembrane protease/serine). The genetically modified rodents are suitable for use in screening for candidate compounds that specifically target a human TMPRSS molecule for the treatment and prevention of diseases such as influenza virus infection. Accordingly, the present invention provides genetically modified rodents having a humanized Tmprss gene, cells and tissues isolated from the genetically modified rodents, methods and compositions for making the genetically modified rodents, and use of the genetically modified rodents for screening and testing therapeutic compounds. The various embodiments of the present invention are further described below.

Type II Transmembrane Serine Proteases ("Tmprss")

Type II transmembrane serine proteases, also referred to herein as "Tmprss" for non-human molecules or "TMPRSS" for human molecules ("transmembrane protease/serine"), are a family of proteins characterized by an N-terminal transmembrane domain and a C-terminal extracellular serine protease domain. At least 18 members have been identified in the family, which are grouped into four subfamilies (Bugge el al. (2009), supra). All members share several common structural features that define the family, including (i) a short N-terminal cytoplasmic domain, (ii) a transmembrane domain, and (iii) an ectodomain that contains a protease domain and a stem region that links the transmembrane domain with the protease domain. The stem region contains a combination of modular structural domains of six different types: a SEA (sea urchin sperm protein/enteropeptidase/agrin) domain, a group A scavenger receptor domain, a LDLA (low-density lipoprotein receptor class A) domain, a CUB (Cls/Clr urchin embryonic growth factor, bone morphogenetic protein-1) domain, a MAM (meprin/A5 antigen/receptor protein phosphatase mu) domain, and a frizzled domain. See review by Bugge et al. (2009), supra. For example, TMPRSS2 and TMPRSS4, both of which belong to the hepsin/TMPRSS subfamily, have a group A scavenger receptor domain, preceded by a single LDLA domain in the stem region. TMPRSS11D, also known as "HAT" for human airway trypsin-like protease that belongs to the HAT/DESC subfamily, has a single SEA domain. See FIG. 1 of Bugge et al. (2009), supra.

Type II transmembrane serine proteases are produced initially as inactive proenzymes that require activation by cleavage following a basic amino acid residue in a consensus activation motif preceding the protease domain. Some of the activated proteases remain membrane bound as a result of a disulfide bond between the prodomain and the protease domain. The extracellular domains are considered to be critical for cellular localization, activation, inhibition, and/or substrate specificity of these proteases (Bugge el al. (2009), supra; Szabo et al., *Int. J. Biochem. Cell Biol.* 40: 1297-1316 (2008)).

Various biochemical and pathophysiological information has been documented for members of the type II transmembrane serine proteases. TMPRSS2, TMPRSS4 and TMPRSS11D have been shown in vitro to cleave influenza A hemagglutinin (HA), which is the first essential step in the viral lifecycle. Genetically modified rodent animals having humanized Tmprss gene disclosed herein provide useful in vivo systems that allow for a thorough understanding of the biological functions of the TMPRSS molecules, as well as for screening therapeutic compounds that specifically target human TMPRSS molecules.

Exemplary Tmprss sequences, including mouse, human and humanized Tmprss nucleic acid and protein sequences, are provided in this application and are summarized in the following table. Primer and probe sequences used in the assays described in the examples section, and insertion junction sequences of exemplary humanized Tmprss alleles, are also included in the table.

SUMMARY DESCRIPTION OF SEQUENCES

| SEQ ID NO | Description | Features |
| --- | --- | --- |
| 1 | *Mus musculus* Tmprss2, mRNA, NM_015775.2 | Length: 3175 bp<br>CDS: 231-1703<br>Exons: 1-177; 178-245 (second exon, and first coding exon); 246-465; 466-552; 553-672; 673-799; 800-910; 911-954; 955-1123; 1124-1299; 1300-1395; 1396-1538; 1539-1691; 1692-3161. |
| 2 | *Mus musculus* Tmprss2, protein | Length: 490 aa |
| 3 | *Homo sapiens* TMPRSS2, transcript variant 2, mRNA, NM_005656.3 | Length: 3212 bp<br>CDS: 135-1613<br>Exons: 1-78; 79-149 (second exon, and first coding exon); 150-372; 373-459; 460-579; 580-706; 707-817; 818-861; 862-1033; 1034-1209; 1210-1305; 1306-1448; 1449-1601; 1602-3204. |
| 4 | *Homo sapiens* TMPRSS2, transcript variant 2, protein | Length: 492 aa<br>Ectodomain: begins at W106. |
| 5 | Humanization Tmprss2 genomic fragment | Length: 27,947 bp<br>1-84: mouse sequence<br>85-25175: human sequence (total 25091 bp)<br>25176-27866: XhoI-LoxP-Cassette-loxP-ICeUI-NheI (total 2691 bp)<br>27867-27947: mouse sequence |
| 6 | Humanization Tmprss2 genomic fragment with cassette deleted | Length: 25,333 bp<br>1-84: mouse sequence<br>85-25175: human sequence (total 25091 bp)<br>25176-25252: XhoI-loxP-ICeuI-NheI (77 bp)<br>25253-25333: mouse sequence |
| 7 | Humanized Tmprss2 protein | Length: 491 aa |
| 8 | *Mus musculus* Tmprss4, mRNA, NM_145403.2 | Length: 2267 bp<br>CDS: 289-1596<br>Exons: 1-291 (first exon and first coding exon); 292-325; 326-439; 440-592; 593-722; 723-824; 825-865; 866-1025; 1026-1192; 11.93-1291; 1292-1434; 1435-1584; 1585-2267. |
| 9 | *Mus musculus* Tmprss4, protein | Length: 435 aa |
| 10 | *Homo sapiens* TMPRSS4, transcript variant 4, mRNA, NM_001173551.1 | Length: 3543 bp<br>CDS: 292-1599<br>Exons: 1-294 (first exon and first coding exon); 295-328; 329-442; 443-595; 596-725; 726-827; 828-868; 869-1028; 1029-1195; 1196-1294; 1295-1437; 1438-1587; 1588-3529. |
| 11 | *Homo sapiens* TMPRSS4, transcript variant 4, protein | Length: 437 aa<br>Ectodomain: begins at K54. |
| 12 | Humanization Tmprss4 genomic fragment containing cassette | Length: 20,078 bp<br>1-18: mouse sequence<br>19-5014: SalI/XhoI-LoxP-hUbi-EM7-Neo-Pm-Cre-loxP-ICeuI-NheI (total 4996 bp)<br>5015-19977: HUMAN sequence (total 14963 bp) 19978-20078: mouse sequence |
| 13 | Humanization Tmprss4 genomic fragment with cassette deleted | Length: 15159 bp<br>1-18: mouse sequence<br>19-95: SalI/XhoI-LoxP-ICeuI-NheI (total 77 bp) 96-15058:<br>HUMAN sequence (total 14963 bp)<br>15059-15159: mouse sequence |
| 14 | Humanized Tmprss4 Protein | Length: 435 aa |
| 15 | *Mus musculus* Tmprss11d, mRNA, NM_145561.2 | Length: 2046 bp<br>CDS: 36-1289<br>Exons: 1-43 (first exon and first coding exon), 44-165, 166-284; 285-352; 353-507; 508-546; 547-724; 725-984; 985-1127; 1128-2046. |
| 16 | *Mus musculus* Tmprss11d, protein | Length: 417 aa |
| 17 | *Homo sapiens* TMPRSS11D, mRNA, NM_004262.2 | Length: 2800 bp<br>CDS: 66-1322<br>Exons: 1-73 (first exon and first coding exon); 74-195; 196-314; 315-382; 383-540; 541-579; 580-757; 758-1017; 1018-1160; 1161-2783. |
| 18 | *Homo sapiens* TMPRSS11D, protein | Length: 418 aa<br>Ectodomain begins at A42. |

| SEQ ID NO | Description | Features |
|---|---|---|
| 19 | Humanization Tmprss11d genomic fragment containing cassette | Length: 38,992 1-19: mouse sequence 20-33,946: HUMAN sequence (total 33,927 bp) 33,947-38,942: XhoI-LoxP-hUbi-EM7-Neo-Pm-Cre-loxP-ICeuI-NheI (total 4,996 bp) 38,943-38,992: mouse sequence |
| 20 | Humanization Tmprss11d genomic fragment with cassette deleted | Length: 34,073 bp 1-19: mouse sequence 20-33,946: HUMAN sequence (total 33,927 bp) 33,947-34,023: XhoI-LoxP-ICeuI-NheI (77 bp) 34,024-34,073: mouse sequence |
| 21 | Humanized Tmprss11d Protein | 418 aa |
| 22 | 5' mouse/5' human junction sequence for Tmprss2 humanization | 5' mouse//5' human |
| 23 | 3' human/cassette junction sequence for Tmprss2 humanization | Human//XhoI//loxP Cassette |
| 24 | Cassette/3' mouse junction sequence for Tmprss2 humanization | Cassette (loxP)/ICEUI//NheI//mouse |
| 25 | 3' human/loxP/ 3' mouse junction for Tmprss2 humanization | 3' human//XhoI//(loxP)/ICEUI//NheI//3' mouse |
| 26-37 | Primers and probes for loss of allele and gain of allele assays for Tmprss2 humanization | Table 1 |
| 38 | 5' mouse/Cassette junction sequence for Tmprss4 humanization | 5' mouse//SalI-XhoI//(loxP) Cassette |
| 39 | Cassette/5' human junction sequence for Tmprss4 humanization | Cassette (loxP)/ICEUI//NheI//5' human |
| 40 | 3' human/3' mouse junction sequence for Tmprss4 humanization | 3' human/3' mouse |
| 41 | 5' mouse/loxP/ 5' human junction for Tmprss4 humanization | 5' mouse//SalI/XhoI//(loxP)/ICEUI//NheI//5' human |
| 42-56 | Primers and probes for loss of allele and gain of allele assays for Tmprss4 humanization | Table 2 |
| 57 | 5' mouse/5' human junction sequence for Tmprss11d humanization | 5' mouse//5' human |
| 58 | 3' human/cassette junction sequence for Tmprss11d humanization | 3' human//XhoI//(loxP) Cassette |
| 59 | Cassette/3' mouse junction sequence for Tmprss11d humanization | Cassette (loxP)/ICUEI//NheI//3' mouse |
| 60 | 3' human/ loxP/3' mouse junction for Tmprss11d humanization | 3' human//XhoI//(loxP)/ICEUI//NheI//3' mouse |
| 61-72 | Primers and probes for loss of allele and gain of allele assays for Tmprss11d humanization | Table 3 |

Humanized Tmprss Rodent Animals

In one aspect, the present invention provides rodent animals that contain in the germline a humanized Tmprss gene encoding a humanized Tmprss protein.

The term "humanized", when used in the context of nucleic acids or proteins, refers to nucleic acids or proteins whose structures (i.e., nucleotide or amino acid sequences) include portions that correspond substantially or identically with structures of a particular gene or protein found in nature in a rodent animal, and also include portions that differ from that found in the relevant rodent gene or protein and instead correspond more closely or identically with structures found in a corresponding human gene or protein. A rodent containing a humanized gene or expressing a humanized protein is a "humanized" rodent.

In some embodiments, a rodent of the present invention is selected from a mouse, a rat, and a hamster. In some embodiments, a rodent of the present invention is selected from the superfamily Muroidea. In some embodiments, a genetically modified rodent of the present invention is from a family selected from Calomyscidae (e.g., mouse-like hamsters), Cricetidae (e.g., hamster, New World rats and mice, voles), Muridae (true mice and rats, gerbils, spiny mice, crested rats), Nesomyidae (climbing mice, rock mice, with-tailed rats, Malagasy rats and mice), Platacanthomyidae (e.g., spiny dormice), and Spalacidae (e.g., mole rates, bamboo rats, and zokors). In some certain embodiments, a genetically modified rodent of the present invention is selected from a true mouse or rat (family Muridae), a gerbil, a spiny mouse, and a crested rat. In some certain embodiments, a genetically modified mouse of the present invention is from a member of the family Muridae.

In some embodiments, the rodent disclosed herein contains a humanized Tmprss gene in the genome that includes a nucleotide sequence of an endogenous rodent Tmprss gene and a nucleotide sequence of a human TMPRSS gene, wherein the nucleotide sequence of the endogenous rodent Tmprss gene and the nucleotide sequence of the human TMPRSS gene are operably linked to each other such that the humanized Tmprss gene encodes a Tmprss protein and is under control of a 5' regulatory element(s), such as the promoter and/or enhancer(s), of the endogenous rodent Tmprss gene.

The present invention is particularly directed to like-for-like humanization; in other words, a nucleotide sequence of an endogenous rodent Tmprss gene is operably linked to a nucleotide sequence of a cognate human TMPRSS gene to form a humanized gene. For example, in some embodiments, a nucleotide sequence of an endogenous rodent Tmprss2 gene is operably linked to a nucleotide sequence of a human TMPRSS2 gene to form a humanized Tmprss2 gene. In other embodiments, a nucleotide sequence of an endogenous rodent Tmprss4 gene is operably linked to a nucleotide sequence of a human TMPRSS4 gene to form a humanized Tmprss4 gene. In still other embodiments, a nucleotide sequence of an endogenous rodent Tmprss11d gene is operably linked to a nucleotide sequence of a human TMPRSS11D gene to forma humanized Tmprss11d gene.

In some embodiments, a genetically modified rodent of this invention contains a humanized Tmprss gene in its genome, wherein the humanized Tmprss gene encodes a humanized Tmprss protein that contains an ectodomain that is substantially identical with the ectodomain of a human TMPRSS protein. The term "ectodomain" refers to the portion of a transmembrane protein that extends outside of the cell membrane, i.e., the extracellular portion of a transmembrane protein. The ectodomain of a TMPRSS molecule includes a protease domain and a stem region that links the transmembrane domain with the protease domain. By an ectodomain or polypeptide that is "substantially identical with the ectodomain of a human TMPRSS protein", it is meant in some embodiments, a polypeptide that is at least 85%, 90%, 95%, 95%, 99% or 100% identical in sequence with the ectodomain of a human TMPRSS protein; in some embodiments, a polypeptide that differs from the ectodomain of a human TMPRSS protein by not more than 10, 9, 8, 7, 6, 5, 4, 3, 2 or 1 amino acid(s); in some embodiments, a polypeptide that differs from the ectodomain of a human TMPRSS protein only at the N- or C-terminus of the ectodomain, e.g., by lacking amino acids or having additional amino acids at the at the N- or C-terminus of the ectodomain; and in some embodiments, a polypeptide that is substantially the ectodomain of a human TMPRSS protein. By "substantially the ectodomain" of a human TMPRSS protein, it is meant a polypeptide that is identical with the ectodomain, or differs from the ectodomain by lacking 1-5 (i.e., 1, 2, 3, 4 or 5) amino acids or having additional 1-5 amino acids at the N- or C-terminus.

In some embodiments, the humanized Tmprss gene encodes a humanized Tmprss protein that further contains a cytoplasmic and transmembrane portion that is substantially identical with the cytoplasmic and transmembrane portion of an endogenous rodent Tmprss protein. By a cytoplasmic and transmembrane portion or polypeptide that is "substantially identical with the cytoplasmic and transmembrane portion of an endogenous rodent Tmprss protein", it is meant in some embodiments, a polypeptide that is at least 85%, 90%, 95%, 95%, 99% or 100% identical in sequence with the cytoplasmic and transmembrane portion of an endogenous rodent Tmprss protein; in some embodiments, a polypeptide that differs from the cytoplasmic and transmembrane portion of an endogenous rodent Tmprss protein by not more than 10, 9, 8, 7, 6, 5, 4, 3, 2 or 1 amino acid(s); in some embodiments, a polypeptide that differs from the cytoplasmic and transmembrane portion of an endogenous rodent Tmprss protein only at the C-terminus, e.g., by lacking amino acids or having additional amino acids at the at the C-terminus of the transmembrane domain; and in some embodiments, a polypeptide composed of the cytoplasmic domain and substantially the transmembrane domain of an endogenous rodent Tmprss protein. By "substantially the transmembrane domain" of an endogenous rodent Tmprss protein, it is meant a polypeptide that is identical with the transmembrane domain, or differs from the transmembrane domain by lacking 1-5 amino acids or having additional 1-5 amino acids at the C-terminus.

In some embodiments, the humanized Tmprss gene in the genome of a genetically modified rodent includes a nucleotide sequence of an endogenous rodent Tmprss gene and a nucleotide sequence of a cognate human TMPRSS gene, wherein the nucleotide sequence of the cognate human TMPRSS gene encodes a polypeptide substantially identical to the ectodomain of the human TMPRSS protein encoded by the human TMPRSS gene. In certain embodiments, the nucleotide sequence of a cognate human TMPRSS gene in a humanized Tmprss gene encodes the ectodomain of the human TMPRSS protein encoded by the human TMPRSS gene.

In some embodiments, the humanized Tmprss gene in the genome of a genetically modified rodent includes a nucleotide sequence of an endogenous rodent Tmprss gene and a nucleotide sequence of a cognate human TMPRSS gene, wherein the nucleotide sequence of an endogenous rodent Tmprss gene encodes a polypeptide substantially identical to the cytoplasmic and transmembrane portion of the endogenous rodent Tmprss protein encoded by the rodent Tmprss gene. In specific embodiments, the nucleotide sequence of an endogenous rodent Tmprss gene present in a humanized Tmprss gene encodes the cytoplasmic and transmembrane domains of the endogenous rodent Tmprss protein encoded by the endogenous rodent Tmprss gene.

In some embodiments, a humanized Tmprss gene results from a replacement of a nucleotide sequence of an endogenous rodent Tmprss gene at an endogenous rodent Tmprss locus with a nucleotide sequence of a cognate human TMPRSS gene.

In some embodiments, a contiguous genomic sequence of a rodent Tmprss gene at an endogenous rodent Tmprss locus has been replaced with a contiguous genomic sequence of a cognate human TMPRSS gene to form a humanized Tmprss gene.

In specific embodiments, a contiguous genomic sequence of a human TMPRSS gene inserted into an endogenous rodent Tmprss gene includes exons, in full or in part, of a human TMPRSS gene, that encode an ectodomain that is substantially identical with the ectodomain of the human TMPRSS protein encoded by the human TMPRSS gene.

In certain embodiments, the genomic sequence of an endogenous rodent Tmprss gene that remains at an endogenous rodent Tmprss locus after the humanization replacement and is operably linked to the inserted contiguous human TMPRSS genomic sequence encodes a cytoplasmic and transmembrane portion that is substantially identical with the cytoplasmic and transmembrane portion of the endogenous rodent Tmprss protein encoded by the endogenous rodent Tmprss gene.

In circumstances where an endogenous Tmprss protein and a human TMPRSS protein share common amino acids near the junction between the transmembrane domain and the ectodomain, it may not be necessary to insert a human TMPRSS genomic sequence that encodes precisely the ectodomain of the human TMPRSS protein. It is possible to insert a slightly longer or shorter genomic sequence of a human TMPRSS gene, which encodes substantially the ectodomain of the human TMPRSS protein, in operable linkage to a genomic sequence of an endogenous rodent Tmprss gene that encodes the cytoplasmic domain and substantially the transmembrane domain of the endogenous rodent Tmprss protein, such that the humanized Tmprss protein encoded by the resulting humanized Tmprss gene includes an ectodomain that is identical with the ectodomain of the human TMPRSS protein and a transmembrane domain that is identical with the transmembrane domain of the endogenous rodent Tmprss protein.

In some embodiments, the nucleotide sequence of a human TMPRSS gene included in a humanized Tmprss gene also includes the 3' untranslated region ("UTR") of the human TMPRSS gene. In certain embodiments, in addition to the 3' UTR of a human TMPRSS gene, a humanized Tmprss gene also includes an additional human genomic sequence from the human TMPRSS gene locus, following the human TMPRSS 3' UTR. The additional human genomic sequence can consist of at least 10-200 bp, e.g., 50 bp, 75 bp, 100 bp, 125 bp, 150 bp, 175 bp, 200 bp, or more, found in the human TMPRSS gene locus immediately downstream of the 3' UTR of the human TMPRSS gene. In other embodiments, the nucleotide sequence of a human TMPRSS gene present in a humanized Tmprss gene does not include a human 3' UTR; instead, the 3' UTR of an endogenous rodent Tmprss gene is included and follows immediately the stop codon of the humanized Tmprss gene. For example, a humanized Tmprss gene can include a nucleotide sequence of an endogenous rodent Tmprss gene containing exon sequences encoding the cytoplasmic and transmembrane domains of the endogenous rodent Tmprss protein, followed by a nucleotide sequence of a human TMPRSS gene containing exon sequences encoding the ectodomain through the stop codon of the human TMPRSS protein, with the 3' UTR of the endogenous rodent Tmprss gene following immediately after the stop codon.

In some embodiments, a humanized Tmprss gene results in an expression of the encoded humanized Tmprss protein in a rodent. In some embodiments, a humanized Tmprss protein is expressed in a pattern comparable with, or substantially the same as, a counterpart rodent Tmprss protein in a control rodent (e.g., a rodent without the humanized Tmprss gene). In some embodiments, a humanized Tmprss protein is expressed at a level comparable with, or substantially the same as, a counterpart rodent Tmprss protein in a control rodent (e.g., a rodent without the humanized Tmprss gene). In certain embodiments, a humanized Tmprss protein is expressed and detected at the cell surface. In certain embodiments, a humanized Tmprss protein or a soluble form (e.g., a shed ectodomain form) is expressed and detected in serum of a rodent, e.g., at a level comparable with, or substantially the same as, a counterpart rodent Tmprss protein or a soluble form thereof in a control rodent. In the context of comparing a humanized gene or protein in a humanized rodent with an endogenous rodent gene or protein in a control rodent, the term "comparable" means that the molecules or levels being compared may not be identical to one another but are sufficiently similar to permit comparison there between so that conclusions may reasonably be drawn based on differences or similarities observed; and the term "substantially the same" in referring to expression levels means that the levels being compared are not different from one another by more than 20%, 19%, 18%, 17%, 16%, 15%, 14%, 13%, 12%, 11%, 10%, 9%, 8%, 7%, 6%, 5%, 4%, 3%, 2%, or 1%.

In some embodiments, the present invention further provides an isolated cell or tissue from a rodent animal as described herein. In some embodiments, a cell is selected from a dendritic cell, lymphocyte (e.g., a B or T cell), macrophage and a monocyte. In some embodiments, a tissue is selected from adipose, bladder, brain, breast, bone marrow, eye, heart, intestine, kidney, liver, lung, lymph node, muscle, pancreas, plasma, serum, skin, spleen, stomach, thymus, testis, ovum, and a combination thereof.

In some embodiments, the present invention provides a rodent embryonic stem cell whose genome contains a humanized Tmprss gene as described herein. In some embodiments, a rodent embryonic stem cell is a mouse embryonic stem cell. In other embodiments, a rodent embryonic stem cell is a rat embryonic stem cell. A rodent embryonic stem cell containing a humanized Tmprss gene in its genome can be used to make a humanized rodent animal, as further described herein below.

In some embodiments, a rodent provided herein is heterozygous for a humanized Tmprss gene in its genome. In other embodiments, a rodent provided herein is homozygous for a humanized Tmprss gene in its genome.

In certain embodiments, a rodent includes multiple, i.e., two or more, humanized Tmprss genes in its genome. In other words, two or more different endogenous Tmprss loci in a rodent have been humanized using nucleotide sequences of cognate human TMPRSS genes. For example, a rodent has been humanized at two or more of the gene loci selected from: Tmprss2, Tmprss4, and Tmprss11d.

Exemplary humanized Tmprss2 rodents (such as mice), humanized Tmprss4 rodents (such as mice), and humanized Tmprss11d rodents (such as mice) are further described below.

Humanized Tmprss2 Rodents

In some embodiments, this invention provides a rodent whose genome contains a humanized Tmprss2 gene that includes a nucleotide sequence of an endogenous rodent Tmprss2 gene and a nucleotide sequence of a human TMPRSS2 gene, and that is under control of a 5' regulatory element(s), such as the promoter and/or enhancer(s), of the endogenous rodent Tmprss2 gene. Examples of rodents include mice and rats.

In some embodiments, a humanized Tmprss2 gene encodes a humanized Tmprss2 protein that contains an ectodomain that is substantially identical with the ectodomain of a human TMPRSS2 protein.

In specific embodiments, the human TMPRSS2 protein has an amino acid sequence having at least 85%, 90%, 95%, 98%, 99% or 100% identity with the amino acid sequence as set forth in SEQ ID NO: 4.

In some embodiments, a humanized Tmprss2 protein contains the C-terminal 387 amino acids of a human TMPRSS2 protein, for example, amino acids 106 to 492 of a human TMPRSS2 protein. In some embodiments, a humanized Tmprss2 protein contains an ectodomain that is substantially identical with the amino acid sequence composed of W106 to G492 of SEQ ID NO: 4. In specific embodiments, a humanized Tmprss2 protein contains an ectodomain having at least 85%, 90%, 95%, 98%, 99% or 100% identity with the amino acid sequence composed of W106 to G492 of SEQ ID NO: 4; an ectodomain that differs from the amino acid sequence composed of W106 to G492 of SEQ ID NO: 4 by not more than 10, 9, 8, 7, 6, 5, 4, 3, 2 or 1 amino acid(s); or an ectodomain that differs from the amino acid sequence composed of W106 to G492 of SEQ ID NO: 4 only at the N- or C-terminus of the ectodomain, e.g., lacking 1-5 amino acids or having additional 1-5 amino acids at the at the N- or C-terminus.

In some embodiments, a humanized Tmprss2 protein further contains a cytoplasmic and transmembrane portion that is substantially identical with the cytoplasmic and transmembrane portion of an endogenous rodent Tmprss2 protein. In some embodiments, a humanized Tmprss2 protein further includes the transmembrane domain and the cytoplasmic domain of an endogenous rodent Tmprss2 protein.

In specific embodiments, a humanized Tmprss2 protein contains the transmembrane domain and the cytoplasmic domain of an endogenous rodent Tmprss2 protein, and the ectodomain of a human TMPRSS2 protein. In particular embodiments, a humanized Tmprss2 gene encodes a humanized Tmprss2 protein having the amino acid sequence as set forth in SEQ ID NO: 7.

In some embodiments, a humanized Tmprss2 gene results from a replacement of a nucleotide sequence of an endogenous rodent Tmprss2 gene at an endogenous rodent Tmprss2 locus with a nucleotide sequence of a human TMPRSS2 gene.

In some embodiments, a contiguous genomic sequence of an endogenous rodent Tmprss2 gene at an endogenous rodent Tmprss2 locus has been replaced with a contiguous genomic sequence of a human TMPRSS2 gene to form a humanized Tmprss2 gene.

In specific embodiments, the contiguous genomic sequence of a human TMPRSS2 gene inserted into an endogenous rodent Tmprss2 gene includes exon sequences, i.e., exons in full or in part, of a human TMPRSS2 gene, that encode an ectodomain that is substantially identical to the ectodomain of the human TMPRSS2 protein encoded by the human TMPRSS2 gene. In circumstances where an endogenous Tmprss2 protein and a human TMPRSS2 protein share common amino acids near the junction of the transmembrane domain and the ectodomain, it may not be necessary to insert a human TMPRSS2 genomic sequence that encodes precisely the ectodomain of the human TMPRSS2 protein, and it is possible to use a slightly longer or shorter human TMPRSS2 genomic sequence that encodes substantially the ectodomain of a human TMPRSS2 protein in order to make a humanized Tmprss2 protein having an ectodomain that is identical with the ectodomain of the human TMPRSS2 protein.

In specific embodiments, a contiguous genomic sequence of a human TMPRSS2 gene being inserted into an endogenous rodent Tmprss2 gene contains at least coding exon 4 through the stop codon in coding exon 13 of the human TMPRSS2 gene.

In certain embodiments, a contiguous genomic sequence of a human TMPRSS2 gene being inserted into an endogenous rodent Tmprss2 gene contains intron 3 and coding exon 4 through the stop codon in coding exon 13 of the human TMPRSS2 gene. In particular embodiments, a contiguous genomic sequence of a human TMPRSS2 gene being inserted into an endogenous rodent Tmprss2 gene contains a 3' portion of coding exon 3, intron 3, and coding exon 4 through the stop codon in coding exon 13 of the human TMPRSS2 gene. In specific embodiments, the 3' portion of coding exon 3 of a human TMPRSS2 gene included in the humanization is about 5-10 base pair in length, i.e., about 5, 6, 7, 8, 9 or 10 base pair of the 3' end of coding exon 3.

In some embodiments, a contiguous genomic sequence of a human TMPRSS2 gene being inserted into an endogenous rodent Tmprss2 gene also contains the 3' UTR of the human TMPRSS2 gene. In specific embodiments, the entire coding exon 13 of a human TMPRSS2 gene is included in the contiguous human TMPRSS2 genomic sequence for humanization, which includes the 3' UTR of the human TMPRSS2 gene. In particular embodiments, a contiguous genomic sequence of a human TMPRSS2 gene includes an additional human genomic sequence downstream of the 3' UTR of the human TMPRSS2 gene. The additional human genomic sequence can be a sequence of at least 10-200 bp, or at least 10, 20, 30, 40, 50, 75, 100, 125, 150, 175, or 200 bp, that is found immediately downstream of the 3' UTR of the human TMPRSS2 gene at a human TMPRSS2 locus.

In some embodiments, the nucleotide sequence of an endogenous rodent Tmprss2 gene remaining at a humanized Tmprss2 locus encodes a polypeptide that is substantially identical with the cytoplasmic and transmembrane portion of the endogenous rodent Tmprss2 protein. In circumstances where an endogenous Tmprss2 protein and a human TMPRSS2 protein share common amino acids near the junction of the transmembrane domain and the ectodomain, it may not be necessary to maintain the endogenous rodent Tmprss2 genomic sequence that encodes precisely the transmembrane domain of the endogenous rodent Tmprss2 protein, and it is possible to maintain a slightly longer or shorter rodent Tmprss2 genomic sequence that encodes substantially the transmembrane domain of the endogenous rodent Tmprss2 protein in the humanization replacement in order to encode a humanized Tmprss2 protein having a transmembrane domain that is identical with the transmembrane of the endogenous rodent Tmprss2 protein. In some embodiments, the nucleotide sequence of an endogenous rodent Tmprss2 gene remaining at a humanized Tmprss2 locus includes exons 1-2 and a 5' portion of coding exon 3 of an endogenous rodent Tmprss2 gene, wherein the 5' portion of coding exon 3 is a substantial portion of codon exon 3, e.g., the entire coding exon 3 except 5-10 base pairs at the 3' end of coding exon 3.

In specific embodiments, a humanized Tmprss2 gene contains coding exons 1-2 and a 5' portion of coding exon 3 of an endogenous rodent Tmprss2 gene, and a 3' portion of coding exon 3 and coding exon 4 through coding exon 13 of a human TMPRSS2 gene, wherein the humanized Tmprss2 gene encodes a humanized Tmprss2 protein that contains a cytoplasmic and transmembrane portion that is substantially identical with the cytoplasmic and transmembrane portion of the rodent Tmprss2 protein, and an ectodomain that is substantially identical with the ectodomain of the human TMPRSS2 protein. In certain embodiments, the humanized Tmprss2 gene encodes a humanized Tmprss2 protein that contains the cytoplasmic domain and the transmembrane domain of the rodent Tmprss2 protein encoded by an endogenous rodent Tmprss2 gene, and the ectodomain of the human TMPRSS2 protein encoded by a human TMPRSS2 gene. In particular embodiments, a humanized Tmprss2 gene encodes a humanized Tmprss2 protein having the amino acid sequence as set forth in SEQ ID NO: 7.

In some embodiments, the exons and introns of a human TMPRSS2 gene and a rodent Tmprss2 gene used in the humanization are those found in SEQ ID NOS: 1, 3 and 5-6.

In some embodiments, a humanized Tmprss2 gene results in an expression of the encoded humanized Tmprss2 protein in a rodent. In some embodiments, a humanized Tmprss2 protein is expressed in a pattern comparable with, or substantially the same as, a counterpart rodent Tmprss2 protein in a control rodent (e.g., a rodent without the humanized Tmprss2 gene). In some embodiments, a humanized Tmprss2 protein is expressed at a level comparable with, or substantially the same as, a counterpart rodent Tmprss2 protein in a control rodent (e.g., a rodent without the humanized Tmprss2 gene). In certain embodiments, a humanized Tmprss2 protein is expressed and detected at the cell surface. In certain embodiments, a humanized Tmprss2 protein or a soluble form (e.g., a shed ectodomain form) is expressed and detected in serum of a rodent, e.g., at a level comparable with, or substantially the same as, a counterpart rodent Tmprss2 protein or a soluble form thereof in a control rodent.

Humanized Tmprss4 Rodents

In some embodiments, this invention provides a rodent whose genome contains a humanized Tmprss4 gene that includes a nucleotide sequence of an endogenous rodent Tmprss4 gene and a nucleotide sequence of a human TMPRSS4 gene, and that is under control of a 5' regulatory element(s), such as the promoter and/or an enhancer(s), of the endogenous rodent Tmprss4 gene. Examples of rodents include mice and rats.

In some embodiments, a humanized Tmprss4 gene encodes a humanized Tmprss4 protein that contains an ectodomain that is substantially identical with the ectodomain of a human TMPRSS4 protein. In specific embodiments, the human TMPRSS4 protein has an amino acid sequence having at least 85%, 90%, 95%, 98%, 99% or 100% identity with the amino acid sequence as set forth in SEQ ID NO: 11.

In some embodiments, a humanized Tmprss4 protein contains the C-terminal 384 amino acids of a human TMPRSS4 protein, for example, amino acids 54 to 437 of a human TMPRSS4 protein. In some embodiments, a humanized Tmprss4 protein contains an ectodomain that is substantially identical with the amino acid sequence composed of K54 to L437 of SEQ ID NO: 11. In specific embodiments, a humanized Tmprss4 protein contains an ectodomain having at least 85%, 90%, 95%, 98%, 99% or 100% identity with the amino acid sequence composed of K54 to L437 of SEQ ID NO: 11; an ectodomain that differs from the amino acid sequence composed of K54 to L437 of SEQ ID NO: 11 by not more than 10, 9, 8, 7, 6, 5, 4, 3, 2 or 1 amino acid(s); or an ectodomain that differs from the amino acid sequence composed of K54 to L437 of SEQ ID NO: 11 only at the N- or C-terminus of the ectodomain, e.g., lacking 1-5 amino acids or having additional 1-5 amino acids at the N- or C-terminus.

In some embodiments, a humanized Tmprss4 protein further contains a cytoplasmic and transmembrane portion that is substantially identical with the cytoplasmic and transmembrane portion of an endogenous rodent Tmprss4 protein. In some embodiments, a humanized Tmprss4 protein further includes the transmembrane domain and the cytoplasmic domain of an endogenous rodent Tmprss4 protein.

In specific embodiments, a humanized Tmprss4 protein contains the transmembrane domain and the cytoplasmic domain of an endogenous rodent Tmprss4 protein, and the ectodomain of a human TMPRSS4 protein. In particular embodiments, a humanized Tmprss4 gene encodes a humanized Tmprss4 protein having the amino acid sequence as set forth in SEQ ID NO: 14.

In some embodiments, a humanized Tmprss4 gene results from a replacement of a nucleotide sequence of an endogenous rodent Tmprss4 gene at an endogenous rodent Tmprss4 locus with a nucleotide sequence of a human TMPRSS4 gene.

In some embodiments, a contiguous genomic sequence of an endogenous rodent Tmprss4 gene at an endogenous rodent Tmprss4 locus has been replaced with a contiguous genomic sequence of a human TMPRSS4 gene to form a humanized Tmprss4 gene.

In specific embodiments, the contiguous genomic sequence of a human TMPRSS4 gene inserted into an endogenous rodent Tmprss4 gene includes exon sequences, i.e., exons in full or in part, of a human TMPRSS4 gene that encode an ectodomain that is substantially identical with the ectodomain of the human TMPRSS4 protein encoded by the human TMPRSS4 gene. In circumstances where an endogenous Tmprss4 protein and a human TMPRSS4 protein share common amino acids near the junction of the transmembrane domain and the ectodomain, it may not be necessary to insert a human TMPRSS4 genomic sequence that encodes precisely the ectodomain of the human TMPRSS4 protein, and it is possible to use a slightly longer or shorter human TMPRSS4 genomic sequence that encodes substantially the ectodomain of a human TMPRSS4 protein in order to make a humanized Tmprss4 protein having an ectodomain that is identical with the ectodomain of the human TMPRSS4 protein.

In specific embodiments, a contiguous genomic sequence of a human TMPRSS4 gene being inserted into an endogenous rodent Tmprss4 gene contains at least coding exon 4 through the stop codon in coding exon 13 of the human TMPRSS4 gene.

In certain embodiments, a contiguous genomic sequence of a human TMPRSS4 gene being inserted into an endogenous rodent Tmprss4 gene includes a 3' portion of intron 3, and coding exon 4 through the stop codon in coding exon 13 of a human TMPRSS4 gene. In specific embodiments, the 3' portion of intron 3 of a human TMPRSS4 gene included in the humanization is about 140-160 base pair in length, i.e., about 140, 145, 150, 155, 160 base pair of the 3' end of intron 3.

In some embodiments, a contiguous genomic sequence of a human TMPRSS4 gene being inserted into an endogenous rodent Tmprss4 gene contains the 3' UTR of the human TMPRSS4 gene. In specific embodiments, a contiguous genomic sequence of a human TMPRSS4 gene being inserted into an endogenous rodent Tmprss4 gene does not contain the 3' UTR of the human TMPRSS4 gene, and the 3' UTR of the endogenous rodent Tmprss4 gene follows immediately after the stop codon in the humanized Tmprss4 gene.

In some embodiments, the nucleotide sequence of an endogenous rodent Tmprss4 gene remaining at a humanized Tmprss4 locus encodes a polypeptide that is substantially identical with the cytoplasmic and transmembrane portion of the endogenous rodent Tmprss4 protein. In circumstances where an endogenous Tmprss4 protein and a human TMPRSS4 protein share common amino acids near the junction of the transmembrane domain and the ectodomain, it may not be necessary to maintain the endogenous rodent Tmprss4 genomic sequence that encodes precisely the transmembrane domain of the endogenous rodent Tmprss4 protein, and it is possible to maintain a slightly longer or shorter rodent Tmprss4 genomic sequence that encodes substantially the transmembrane domain of the endogenous rodent Tmprss4 protein in the humanization replacement in order to encode a humanized Tmprss4 protein having a transmembrane domain that is identical with the transmembrane of the endogenous rodent Tmprss4 protein.

In specific embodiments, a humanized Tmprss4 gene contains coding exons 1-3 of an endogenous rodent Tmprss4 gene, and coding exon 4 through the stop codon of coding exon 13 of a human TMPRSS4 gene. In particular embodiments, a humanized Tmprss4 gene contains coding exons 1-3 and a 5' portion of intron 3 of an endogenous rodent Tmprss4 gene, and a 3' portion of intron 3 and coding exon 4 through the stop codon of coding exon 13 of a human TMPRSS4 gene. In certain embodiments, the humanized Tmprss4 gene encodes a humanized Tmprss4 protein that contains the cytoplasmic domain and the transmembrane domain of the rodent Tmprss4 protein encoded by an endogenous rodent Tmprss4 gene, and the ectodomain of the human TMPRSS4 protein encoded by a human TMPRSS4 gene. In particular embodiments, a humanized Tmprss4 gene encodes a humanized Tmprss4 protein having the amino acid sequence as set forth in SEQ ID NO: 14.

In some embodiments, the exons and introns of a human TMPRSS4 gene and a rodent Tmprss4 gene used in the humanization are those found in SEQ ID NOS: 8, 10 and 12-13.

In some embodiments, a humanized Tmprss4 gene results in an expression of the encoded humanized Tmprss4 protein in a rodent. In some embodiments, a humanized Tmprss4 protein is expressed in a pattern comparable with, or substantially the same as, a counterpart rodent Tmprss4 protein in a control rodent (e.g., a rodent without the humanized Tmprss4 gene encoding the humanized Tmprss4 protein). In some embodiments, a humanized Tmprss4 protein is expressed at a level comparable with, or substantially the same as, a counterpart rodent Tmprss4 protein in a control rodent (e.g., a rodent without the humanized Tmprss4 gene encoding the humanized Tmprss4 protein). In certain embodiments, a humanized Tmprss4 protein is expressed and detected at the cell surface. In certain embodiments, a humanized Tmprss4 protein or a soluble form (e.g., a shed ectodomain form) is expressed and detected in serum of a rodent, e.g., at a level comparable with, or substantially the same as, a counterpart rodent Tmprss4 protein or a soluble form thereof in a control rodent.

Humanized Tmprss11d Rodents

In some embodiments, this invention provides a rodent whose genome contains a humanized Tmprss11d gene that includes a nucleotide sequence of an endogenous rodent Tmprss11d gene and a nucleotide sequence of a human TMPRSS11D gene, and that is under control of a 5' regulatory element(s), such as the promoter and/or enhancer(s) of the endogenous rodent Tmprss11d gene. Examples of rodents include mice and rats.

In some embodiments, a humanized Tmprss11d gene encodes a humanized Tmprss11d protein that contains an ectodomain that is substantially identical with the ectodomain of a human TMPRSS11D protein.

In specific embodiments, the human TMPRSS11D protein has an amino acid sequence having at least 85%, 90/o, 95%, 98%, 99% or 100% identity with the amino acid sequence as set forth in SEQ ID NO: 18.

In some embodiments, a humanized Tmprss11d protein contains the C-terminal 377 amino acids of a human TMPRSS11D protein, for example, amino acids 42 to 418 of a human TMPRSS11D protein. In some embodiments, a humanized Tmprss11d protein contains an ectodomain that is substantially identical with the amino acid sequence composed of A42 to 1418 of SEQ ID NO: 18. In specific embodiments, a humanized Tmprss11d protein contains an ectodomain having at least 85%, 90%, 95%, 98%, 99% or 100% identity with the amino acid sequence composed of A42 to 1418 of SEQ ID NO: 18; an ectodomain that differs from the amino acid sequence composed of A42 to 1418 of SEQ ID NO: 18 by not more than 10, 9, 8, 7, 6, 5, 4, 3, 2 or 1 amino acid(s); or an ectodomain that differs from the amino acid sequence composed of A42 to 1418 of SEQ ID NO: 18 only at the N- or C-terminus, e.g., by lacking 1-5 amino acids or having additional 1-5 amino acids at the N- or C-terminus.

In some embodiments, a humanized Tmprss11d protein further contains a cytoplasmic and transmembrane portion that is substantially identical with the cytoplasmic and transmembrane portion of an endogenous rodent Tmprss11d protein. In some embodiments, a humanized Tmprss11d protein includes the transmembrane domain and the cytoplasmic domain of an endogenous rodent Tmprss11d protein.

In specific embodiments, a humanized Tmprss11d protein contains the transmembrane domain and the cytoplasmic domain of an endogenous rodent Tmprss1 d protein, and the ectodomain of a human TMPRSS1 D protein. In particular embodiments, a humanized Tmprss11d gene encodes a humanized Tmprss11d protein having the amino acid sequence as set forth in SEQ ID NO: 21.

In some embodiments, a humanized Tmprss11d gene results from a replacement of a nucleotide sequence of an endogenous rodent Tmprss11d gene at an endogenous rodent Tmprss11d locus with a nucleotide sequence of a human TMPRSS11D gene.

In some embodiments, a contiguous genomic sequence of an endogenous rodent Tmprss11d gene at an endogenous rodent Tmprss11d locus has been replaced with a contiguous genomic sequence of a human TMPRSS11D gene to form a humanized Tmprss11d gene. In specific embodiments, the contiguous genomic sequence of a human TMPRSS11D gene inserted into an endogenous rodent Tmprss11d gene includes exon sequences, i.e., exons in full or in part, of a human TMPRSS11D gene that encode an ectodomain that is substantially identical with the ectodomain of the human TMPRSS11D protein encoded by the human TMPRSS11D gene. In circumstances where an endogenous Tmprss11d protein and a human TMPRSS11D protein share common amino acids near the junction of the transmembrane domain and the ectodomain, it may not be necessary to insert a human TMPRSS11D genomic sequence that encodes precisely the ectodomain of the human TMPRSS11D protein, and it is possible to use a slightly longer or shorter human TMPRSS11D genomic sequence that encodes substantially the ectodomain of a human TMPRSS 11D protein in order to make a humanized Tmprss11d protein having an ectodomain that is identical with the ectodomain of the human TMPRSS11D protein.

In specific embodiments, a contiguous genomic sequence of a human TMPRSS11D gene being inserted into an endogenous rodent Tmprss11d gene contains at least coding exon 3 through the stop codon in coding exon 10 of a human TMPRSS11D gene.

In certain embodiments, a contiguous genomic sequence of a human TMPRSS11D gene being inserted into an endogenous rodent Tmprss11d gene contains at least a 3' portion of intron 2 and coding exon 3 through the stop codon in coding exon 10 of the human TMPRSS11D gene. In specific embodiments, the 3' portion of intron 2 of a human TMPRSS2 gene included in the humanization is about 444 base pairs in length.

In some embodiments, a contiguous genomic sequence of a human TMPRSS11D gene being inserted into an endogenous rodent Tmprss11d gene contains the 3' UTR of the human TMPRSS11D gene. In specific embodiments, the entire coding exon 10 of a human TMPRSS11D gene is included in the contiguous human TMPRSS11D genomic sequence for humanization, which includes the 3' UTR of a human TMPRSS11D gene. In particular embodiments, a contiguous genomic sequence of a human TMPRSS11D gene includes an additional human genomic sequence downstream of the 3' UTR of the human TMPRSS11D gene. The additional human genomic sequence can be a sequence of 10-200 bp, 50-200 bp, or about 150, 160, 170, 180 bp, that is found immediately downstream of the 3' UTR of the human TMPRSS11D gene at a human TMPRSS11D locus.

In some embodiments, the nucleotide sequence of an endogenous rodent Tmprss11d gene remaining at a humanized Tmprss11d locus encodes a polypeptide that is substantially identical with the cytoplasmic and transmembrane portion of the endogenous rodent Tmprss11d protein encoded by the endogenous rodent Tmprss11d gene. In circumstances where an endogenous Tmprss11d protein and a human TMPRSS11D protein share common amino acids near the junction of the transmembrane domain and the ectodomain, it may not be necessary to maintain the endogenous rodent Tmprss11d genomic sequence that encodes precisely the transmembrane domain of the endogenous rodent Tmprss11d protein, and it is possible to maintain a slightly longer or shorter rodent Tmprss11d genomic sequence that encodes substantially the transmembrane domain of the endogenous rodent Tmprss11d protein in the humanization replacement in order to encode a humanized Tmprss11d protein having a transmembrane domain that is identical with the transmembrane of the endogenous rodent Tmprss11d protein.

In specific embodiments, a humanized Tmprss11d gene contains coding exons 1-2 of an endogenous rodent Tmprss11d gene, and coding exon 3 through coding exon 10 of a human TMPRSS11D gene. In certain embodiments, the humanized Tmprss11d gene encodes a humanized Tmprss11d protein that contains the cytoplasmic domain and the transmembrane domain of the rodent Tmprss11d protein encoded by an endogenous rodent Tmprss11d gene, and the ectodomain of the human TMPRSS11D protein encoded by a human TMPRSS11D gene. In particular embodiments, a humanized Tmprss11d gene encodes a humanized Tmprss11d protein having the amino acid sequence as set forth in SEQ ID NO: 21.

In some embodiments, the exons and introns of a human TMPRSS11D gene and a rodent Tmprss11d gene used in the humanization are those found in SEQ ID NOS: 15, 17 and 19-20.

In some embodiments, a humanized Tmprss11D gene results in an expression of the encoded humanized Tmprss11d protein in a rodent. In some embodiments, a humanized Tmprss11d protein is expressed in a pattern comparable with, or substantially the same as, a counterpart rodent Tmprss11d protein in a control rodent (e.g., a rodent without the humanized Tmprss11d gene encoding the humanized Tmprss11d protein). In some embodiments, a humanized Tmprss11d protein is expressed at a level comparable with, or substantially the same as, a counterpart rodent Tmprss11d protein in a control rodent (e.g., a rodent without the humanized Tmprss11d gene encoding the humanized Tmprss11d protein). In certain embodiments, a humanized Tmprss11d protein is expressed and detected at the cell surface. In certain embodiments, a humanized Tmprss11d protein or a soluble form (e.g., a shed ectodomain form) is expressed and detected in serum of a rodent, e.g., at a level comparable with, or substantially the same as, a counterpart rodent Tmprss 11d protein or a soluble form thereof in a control rodent.

Methods of Making Humanized Tmprss Rodent Animals

Further aspects of this disclosure are directed to methods for making a humanized Tmprss rodent described above, as well as nucleic acid vectors and non-human embryonic stem cells suitable for use in making a humanized Tmprss rodent.

The rodents provided herein can be made using methods known in the art. In exemplary embodiments, a bacterial artificial chromosome (BAC) clone carrying a rodent Tmprss gene can be modified using bacterial homologous recombination and VELOCIGENE® technology (see, e.g., U.S. Pat. No. 6,586,251 and Valenzuela et al. (2003), High-throughput engineering of the mouse genome coupled with high-resolution expression analysis, *Nature Biotech.* 21(6): 652-659). As a result, a rodent Tmprss nucleotide sequence has been deleted from the original BAC clone, and a human Tmprss nucleotide sequence has been inserted, resulting in a modified BAC clone carrying a humanized Tmprss gene, flanked with 5' and 3' rodent homology arms. The modified BAC clone, once linearized, can be introduced into rodent embryonic stem (ES) by, e.g., electroporation. Both mouse ES cells and rat ES cells have been described in the art. See, e.g., U.S. Pat. Nos. 7,576,259, 7,659,442, 7,294,754, and US 2008-0078000 A1 (all of which are incorporated herein by reference) describe mouse ES cells and the VELOCI-MOUSE® method for making a genetically modified mouse; US 2014/0235933 A1, US 2014/0310828 A1, Tong et al. (2010) *Nature* 467:211-215, and Tong et al. (2011) *Nat Protoc.* 6(6): doi:10.1038/nprot.2011.338 (all of which are incorporated herein by reference) describe rat ES cells and methods for making a genetically modified rat.

ES cells having a humanized Tmprss gene integrated in the genome can be selected. In some embodiments, ES cells having a humanized Tmprss integrated into an endogenous rodent Tmprss locus can be selected based on loss of rodent allele and/or gain of human allele assays. Selected ES cells are then used as donor ES cells for injection into a pre-morula stage embryo (e.g., 8-cell stage embryo) by using the VELOCIMOUSE® method (see, e.g., U.S. Pat. Nos. 7,576, 259, 7,659,442, 7,294,754, and US 2008-0078000 A1), or methods described in US 2014/0235933 A1 and US 2014/0310828 A1. The embryo comprising the donor ES cells is incubated until blastocyst stage and then implanted into a surrogate mother to produce an F0 rodent fully derived from the donor ES cells. Rodent pups bearing the humanized Tmprss gene can be identified by genotyping of DNA isolated from tail snips using loss of rodent allele and/or gain of human allele assays.

Rodents heterozygous for a humanized Tmprss gene can be crossed to generated homozygous rodents. Rodents containing one humanized Tmprss gene can be crossed with rodents containing another humanized Tmprss gene to make rodents containing multiple humanized Tmprss genes. For example, rodents containing a humanized Tmprss2 gene can be crossed with rodents containing a humanized Tmprss4 gene to make rodents containing a humanized Tmprss2 gene and a humanized Tmprss4 gene.

Methods Employing Rodents Having Humanized Tmprss Genes

Rodents disclosed herein provide a useful in vivo system and source of biological materials (e.g., cells) expressing humanized Tmprss proteins for identifying and testing compounds that specifically target human TMPRSS proteins.

In one aspect, a rodent disclosed herein is used to determine the ability of a candidate compound, such as an inhibitor of a human TMPRSS protein, to treat and/or prevent influenza virus infection.

In some embodiments, a rodent containing a humanized Tmprss gene and expressing a humanized Tmprss protein disclosed herein is administered with a candidate compound prior to experimental influenza virus infection. The prophylactic efficacy of the compound can be evaluated by determining whether the rodent exhibits fewer and/or less severe symptoms of influenza virus infection, and/or improved viability, as compared to control rodent(s).

In other embodiments, a rodent containing a humanized Tmprss gene and expressing a humanized Tmprss protein comprising the ectodomain of a human TMPRSS protein is administered with a candidate inhibitor of that human TMPRSS protein after experimental influenza virus infection. The treatment efficacy of the candidate inhibitor can be evaluated by determining whether the rodent exhibits fewer and/or less severe symptoms of influenza virus infection, and/or improved viability, as compared to control rodent(s).

Suitable control rodents include, e.g., rodents containing a humanized Tmprss gene without being subjected to the experimental infection; and rodents containing a humanized Tmprss gene subjected to the experimental infection without any compound; and rodents containing a humanized Tmprss gene subjected to the experimental infection and a compound known to be therapeutically effective.

Compounds that can be evaluated in the methods of this invention include candidate TMPRSS inhibitors, for example, a small molecule protease inhibitor, a nucleic acid-based inhibitor (e.g., siRNA, ribozyme, antisense construct, etc.), antigen-binding protein (e.g., antibody or antigen-binding fragment thereof), or a blocking peptide/peptide inhibitor. A TMPRSS inhibitor may function by inhibiting or reducing the ability of a TMPRSS protein to proteolytically cleave hemagglutinin precursor protein (HA0) into the HA1 and HA2 subunits.

In some embodiments, a candidate inhibitor is an antibody or antigen-binding fragment thereof. Both monoclonal and polyclonal antibodies are suitable for purposes of this invention. In specific embodiments, the antibody specifically binds to a TMPRSS protein and inhibits the protease activity of that TMPRSS protein and does not substantially inhibit the protease activity of another TMPRSS protein. For example, an anti-TMPRSS2 antibody inhibitor specifically binds to a TMPRSS2 protein and inhibits the protease activity of the TMPRSS2 protein, and has no effect on the proteolytic activity of TMPRSS4 or TMPRSS11D, or reduces the proteolytic activity of TMPRSS4 or TMPRSS11D by no more than 25% (e.g., by 20%, 15%, 10%, 5%, or less) relative to a non-inhibitory control molecule tested under identical or substantially identical experimental conditions.

In some embodiments, the inhibitor is an anti-TMPRSS2 antibody or antigen-binding fragment thereof. In some embodiments, the inhibitor is an anti-TMPRSS4 antibody or antigen-binding fragment thereof. In other embodiments, the inhibitor is an anti-TMPRSS11D antibody or antigen-binding fragment thereof.

Experimental influenza virus infection can be induced and monitored following known protocols. See, e.g., US 2013/0273070 A1. For example, rodent animals can be administered intranasally with influenza virus. The infected animals can be evaluated to determine the symptoms and severity of the infection. For example, the animals can be analyzed for (1) weight change and survival, (2) cellular changes via flow cytometry, (3) immunochemistry, PAS and H&E staining of whole lungs, and (4) cytokine levels in serum. Control animals known to be susceptible to the virus exhibit a significant increase in the frequency of dendritic cells, the levels influenza-positive alveolar macrophages, neutrophils or epithelial cells in the lungs, and the levels of IFNγ, as compared to uninfected animals.

EXAMPLES

The following examples are provided so as to describe to those of ordinary skill in the art how to make and use methods and compositions of the invention, and are not intended to limit the scope of what the inventors regard as their invention. Unless indicated otherwise, temperature is indicated in Celsius, and pressure is at or near atmospheric.

Example 1. Humanization of an Endogenous Tmprss2 Gene

This example illustrates exemplary methods of humanizing an endogenous gene encoding Tmprss2 in a rodent (e.g., a mouse). The methods described in this example can be employed to humanize an endogenous Tmprss2 gene of a rodent using any human sequence, or combination of human sequences (or sequence fragments) as desired.

A targeting vector for humanization of an endogenous Tmprss2 gene was constructed using bacterial artificial chromosome (BAC) clones and VELOCIGENE® technology (see, e.g., U.S. Pat. No. 6,586,251 and Valenzuela et al. (2003) High-throughput engineering of the mouse genome coupled with high-resolution expression analysis, *Nature Biotech.* 21(6):652-659; incorporated herein by reference).

Briefly, mouse bacterial artificial chromosome (BAC) clone bMQ-264A15 containing a mouse Tmprss2 gene was used and modified as follows. A DNA fragment was generated to include a 5' mouse homology nucleotide sequence, a human TMPRSS2 genomic DNA of about 25,091 bp (containing the last 7 bp of coding exon 3, intron 3, and coding exon 4 through coding exon 13 (including the 3' UTR which is part of coding exon 13), of a human TMPRSS2 gene), a self-deleting neomycin cassette of about 2,691 bp, and a 3' mouse homology sequence. This DNA fragment was used to modify BAC clone bMQ-264A15 through homologous recombination in bacterial cells. As a result, an ectodomain-encoding mouse Tmprss2 genomic fragment (of about 25,291 bp) in the BAC clone was replaced with the human TMPRSS2 genomic fragment of about 25,091 bp, followed by a self-deleting neomycin cassette of about 2691 bp. Specifically, the mouse Tmprss2 genomic fragment that was replaced included the last 7 bp of coding exon 3, intron 3, and coding exon 4 through the stop codon in coding exon 13 of the mouse Tmprss2 gene (FIGS. 1A-1B). The human TMPRSS2 genomic fragment that was inserted included the last 7 bp of coding exon 3, intron 3, and coding exon 4 through coding exon 13 of a human TMPRSS2 gene (including the 3' UTR of human TMPRSS2), and a human 3' genomic sequence of 131 bp downstream of the 3' UTR of human TMPRSS2 (FIGS. 1A-1B). The resulting modified BAC clone included, from 5' to 3', (i) a 5' mouse homology arm containing about 12 kb of mouse genomic DNA including a mouse Tmprss2 5' UTR, mouse Tmprss2 exon 1 (non-coding), coding exons 1-3 (except the last 7 bp of coding exon 3); (ii) a human TMPRSS2 genomic fragment of about 25,091 bp including the last 7 bp of human coding exon 3, intron 3, human coding exons 4 through 13 (including the 3' UTR of human TMPRSS2), and a human 3' genomic sequence; (iii) a self-deleting neomycin cassette of about 2691 bp, followed by (iv) a 3' mouse homology arm of 45 kb containing the mouse Tmprss2 3'UTR and the remaining mouse genomic DNA in the original BAC clone. See FIGS. 1A-1B. The junction sequences are also set forth at the bottom of FIG. 1B. The part of the modified BAC clone containing the human TMPRSS2 genomic fragment and the neomycin cassette, as well as the upstream and downstream insertion junctions, is set forth in SEQ ID NO: 5. The amino acid sequence of the protein encoded by the humanized Tmprss2 gene is set forth in SEQ ID NO: 7. An alignment of this humanized Tmprss2 protein ("7010 mutant protein"), a mouse Tmprss2 protein (SEQ ID NO: 2), and a human TMPRSS2 protein (SEQ ID NO: 4), is provided in FIG. 1D.

Figure 1C:
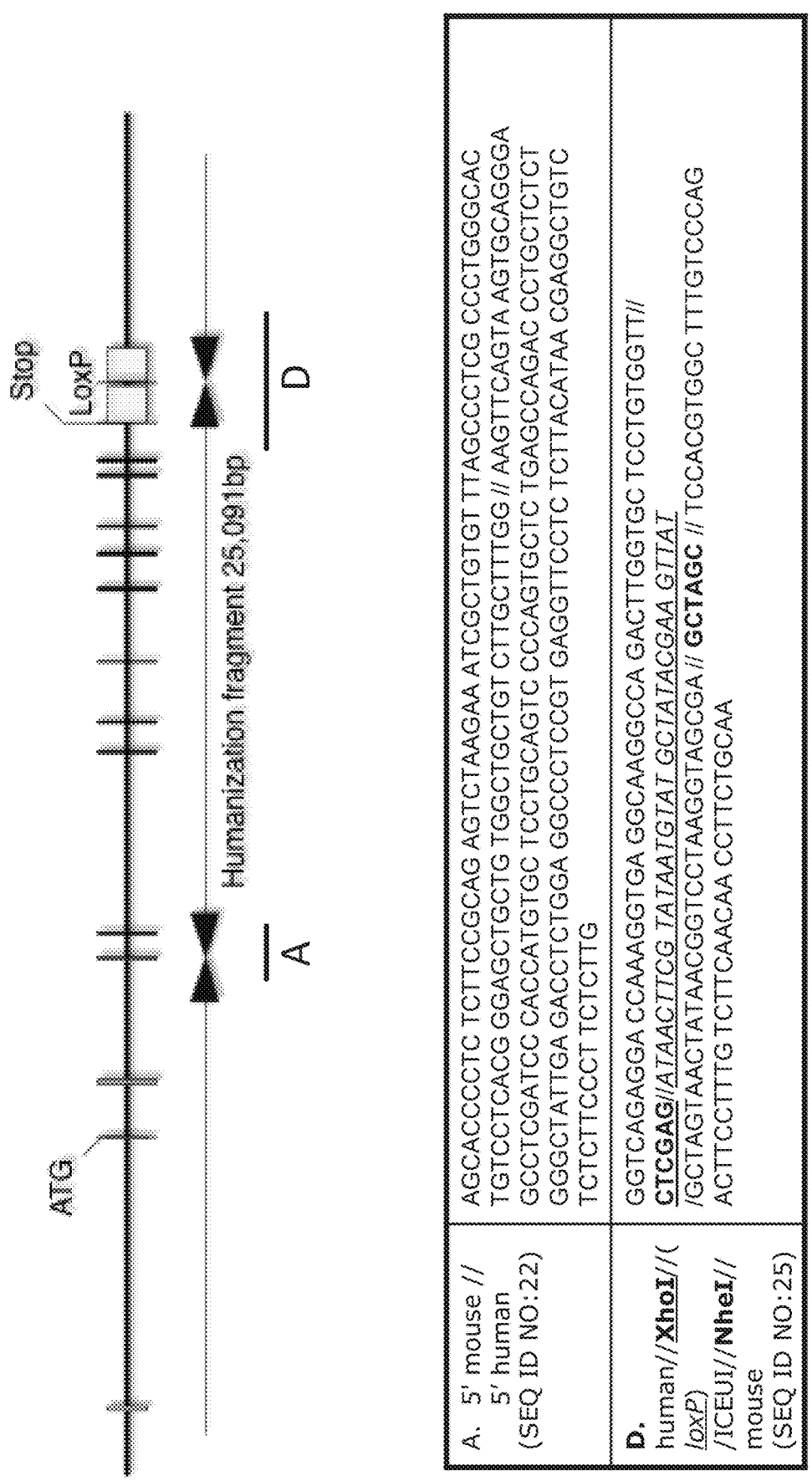
Figure 1D:
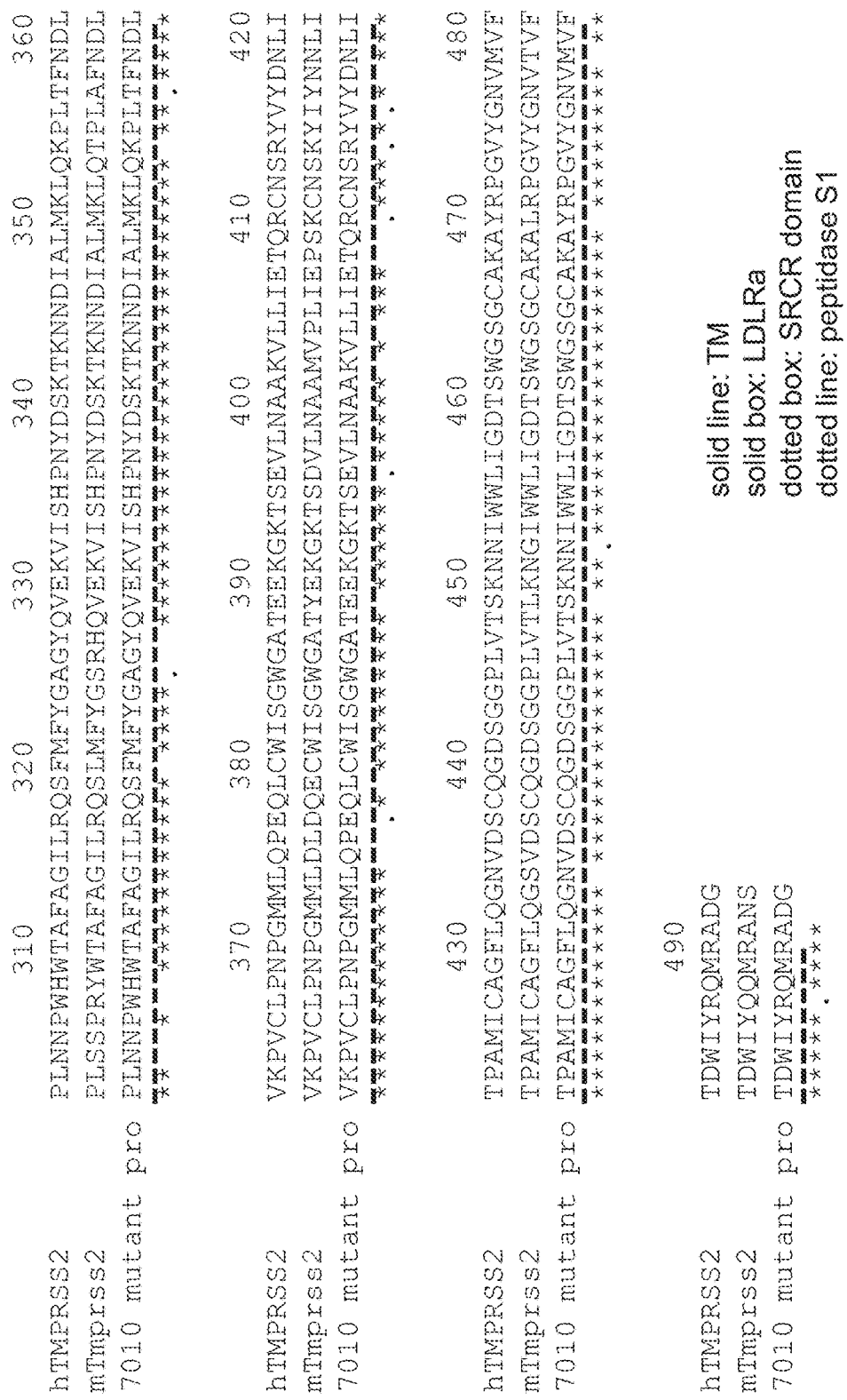

The modified BAC clone containing the humanized Tmprss2 gene, as described above, was used to electroporate mouse embryonic stem (ES) cells to create modified ES cells comprising a humanized Tmprss2 gene. Positively targeted ES cells containing a humanized Tmprss2 gene were identified by an assay (Valenzuela et al., supra) that detected the presence of the human TMPRSS2 sequences (e.g., coding exons 4-13 of human TMPRSS2) and confirmed the loss and/or retention of mouse Tmprss2 sequences (e.g., loss of coding exons 4-13 of mouse Tmprss2). Table 1 sets forth the primers and probes that were used to confirm humanization of an endogenous Tmprss2 gene as described above (FIGS. 1A-1B). Once a correctly targeted ES cell clone has been selected, the neomycin selection cassette can be excised by introducing a Cre recombinase, e.g., via electroporation. Alternatively, the neomycin selection cassette can be removed by crossing the progeny generated from the ES clone with a deletor rodent strain that expresses a Cre recombinase. The humanized Tmprss2 locus after the deletion of the cassette is depicted in FIG. 1C, with the junction sequences shown at the bottom of FIG. 1C.

Selected ES cell clones (with or without the cassette) were used to implant female mice using the VELOCIMOUSE® method (see, e.g., U.S. Pat. No. 7,294,754 and Poueymirou et al., F0 generation mice that are essentially fully derived from the donor gene-targeted ES cells allowing immediate phenotypic analyses, 2007, *Nature Biotech.* 25(1):91-99) to generate a litter of pups containing a humanized Tmprss2 allele in the genome. Mice bearing a humanized Tmprss2 allele can be again confirmed and identified by genotyping of DNA isolated from tail snips using a modification of allele assay (Valenzuela et al., supra) that detects the presence of the human TMPRSS2 gene sequences. Pups are genotyped and cohorts of animals heterozygous for the humanized Tmprss2 locus are selected for characterization. Animals homozygous for the humanized Tmprss2 locus are made by crossing heterozygous animals.

Example 2. Humanization of an Endogenous Tmprss4 Gene

This example illustrates exemplary methods of humanizing an endogenous gene encoding Tmprss4 in a rodent (e.g., a mouse). The methods described in this example can be employed to humanize an endogenous Tmprss4 gene of a rodent using any human sequence, or combination of human sequences (or sequence fragments) as desired.

A targeting vector for humanization of an endogenous Tmprss4 gene was constructed using bacterial artificial chromosome (BAC) clones and VELOCIGENE® technology (see, e.g., U.S. Pat. No. 6,586,251 and Valenzuela el al. (2003), supra).

Figure 2A:
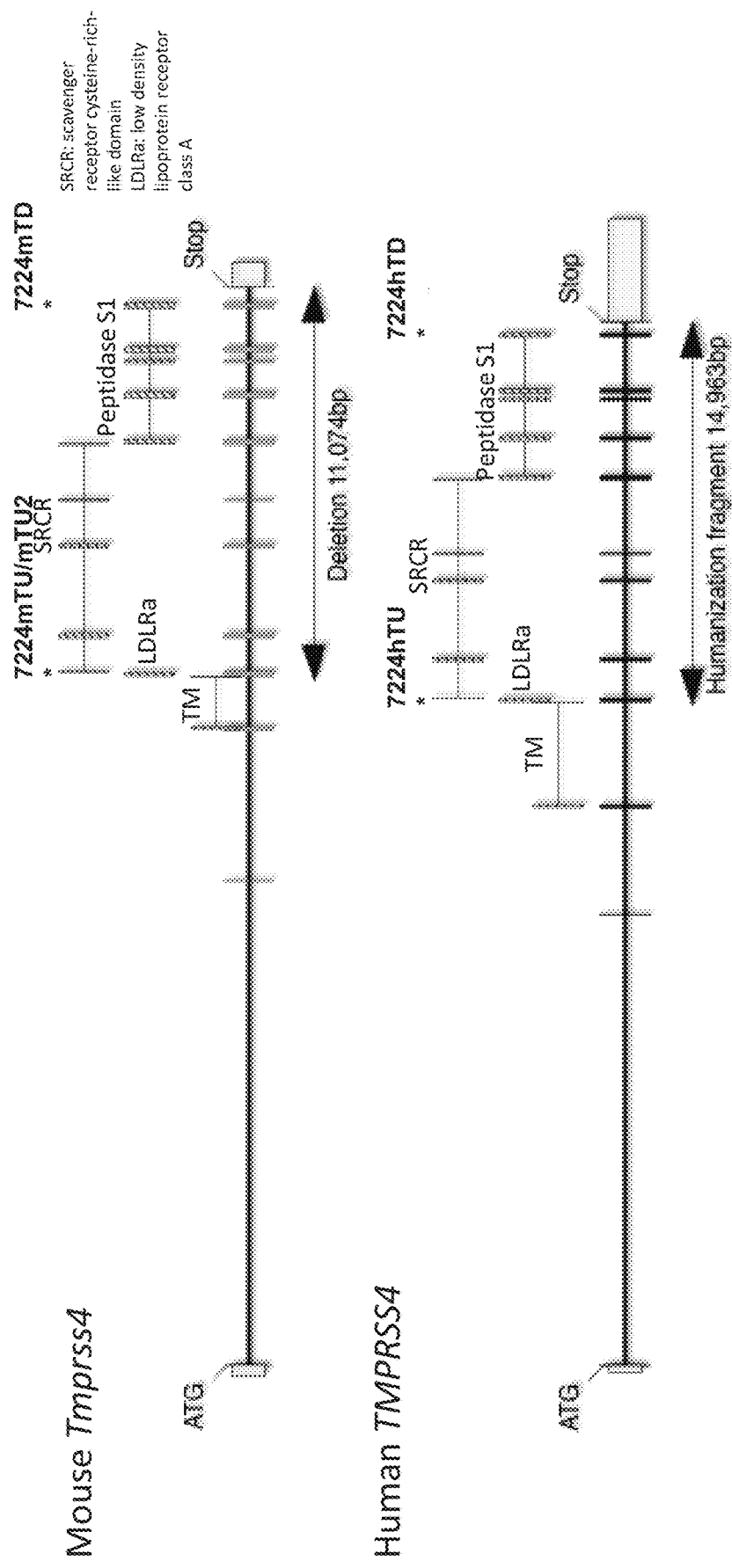
Figure 2B:
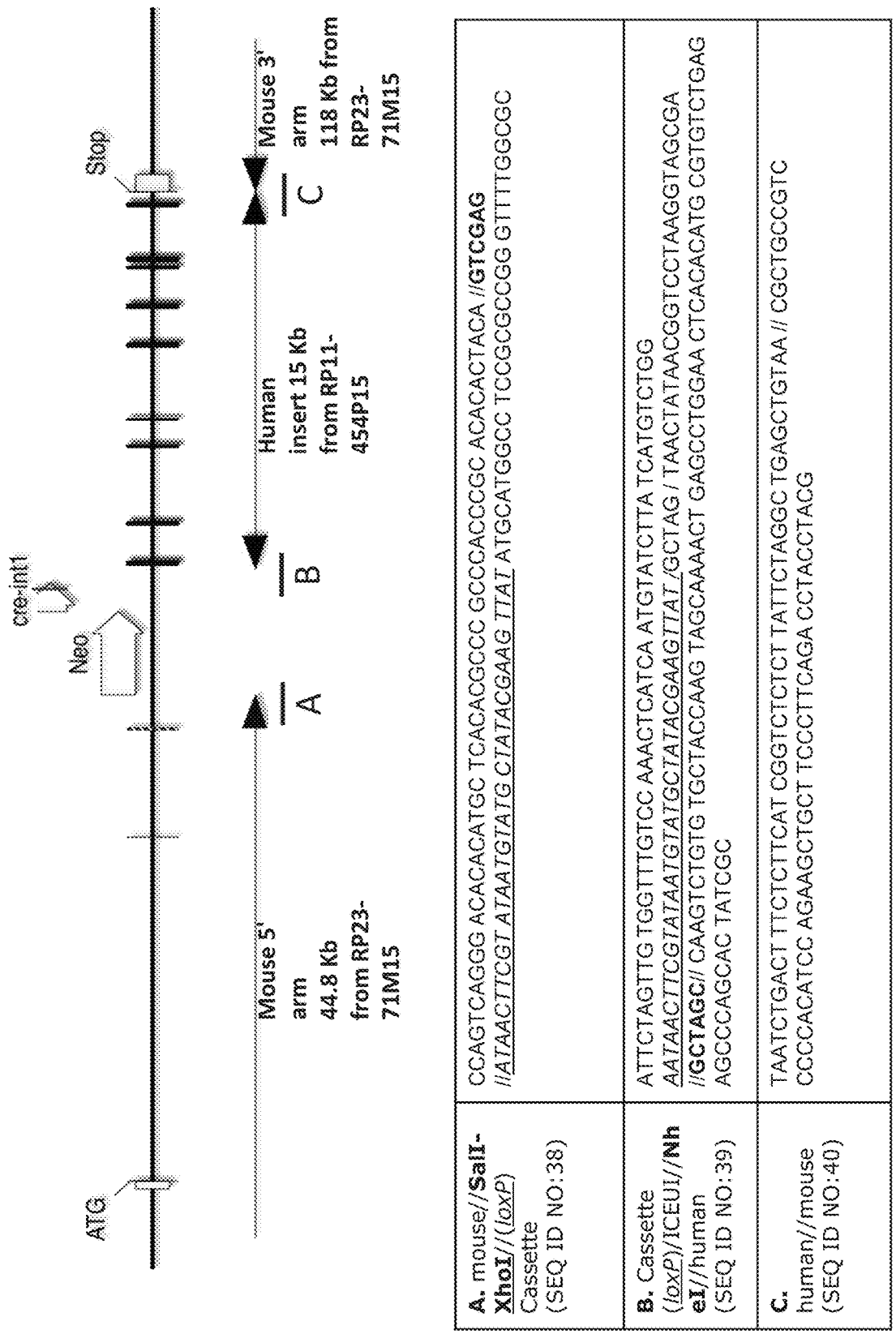

Briefly, mouse bacterial artificial chromosome (BAC) clone RP23-71M15 containing a mouse Tmprss4 gene was used and modified as follows. A DNA fragment was generated to include a 5' mouse homology nucleotide sequence, a self-deleting neomycin cassette of about 4,996 bp, a human genomic DNA of about 14,963 bp (containing coding exon 4 through the stop codon in coding exon 13 of a human TMPRSS4 gene), and a 3' mouse homology sequence. This DNA fragment was used to modify BAC clone RP23-71M15 through homologous recombination in bacterial cells. As a result, an ectodomain-encoding mouse genomic fragment (of about 11,074 bp) in the BAC clone was replaced with a self-deleting neomycin cassette of about 4,996 bp, followed by the human genomic DNA of about 14,963 bp. Specifically, the mouse genomic fragment that was deleted and replaced included the 3' 130 bp of mouse intron 3, coding exon 4 through the stop codon in coding exon 13 of the mouse Tmprss4 gene (FIGS. 2A-2B). The human genomic fragment that was inserted included a 3' portion of human TMPRSS4 intron 3 of about 150 bp, and human TMPRSS4 coding exon 4 through the stop codon in coding exon 13 (FIGS. 2A-2B). The resulting modified BAC clone included, from 5' to 3', a 5' mouse homology arm containing about 44.8 kb of mouse genomic DNA (including a mouse Tmprss4 5' UTR, mouse Tmprss4 coding exons 1 through 3, mouse Tmprss4 intron 3 in part (without the 3' 130 bp), a self-deleting neomycin cassette of about 4996 bp, a 3' portion of human TMPRSS4 intron 3 of about 150 bp,

TABLE 1

| Name | Primer | Sequence (5'-3') | SEQ ID NO |
|---|---|---|---|
| 7010U | Forward | GCCGTGACTGTGACCTTCTC | (SEQ ID NO: 26) |
| | Probe (BHQ) | TGGAGGAGCCACCTGATGCCTC | (SEQ ID NO: 27) |
| | Reverse | GCCTTGCCCTCAATGGAAAC | (SEQ ID NO: 28) |
| 7010D | Forward | GGTTGCACAGCAAGGAAGAAG | (SEQ ID NO: 29) |
| | Probe (BHQ) | CCAGGAGTTCCTGTGAGCCTACCC | (SEQ ID NO: 30) |
| | Reverse | TGGAATGGAAGGAGCTGGAG | (SEQ ID NO: 31) |
| 7010hU | Forward | GTCCCACCTCCTGCAACTG | (SEQ ID NO: 32) |
| | Probe (BHQ) | TGAGCCTTCCCATCAGCCTGGG | (SEQ ID NO: 33) |
| | Reverse | CCACAATGGCACATGGGTCTG | (SEQ ID NO: 34) |
| 7010hTD | Forward | GGTGCTTGCTCCCCAAGA | (SEQ ID NO: 35) |
| | Probe (BHQ) | CCTAAAAGGTGTTGTAATGG | (SEQ ID NO: 36) |
| | Reverse | GGCAATAAAGAAGGAAGACGTTTT | (SEQ ID NO: 37) | human TMPRSS4 coding exons 4 through the stop codon in coding exon 13, followed directly by the mouse Tmprss4 3' UTR and the remaining mouse genomic DNA in the original BAC clone (a 3' mouse homology arm of about 118 kb in total). See FIGS. 2A-2B. The junction sequences are also set forth at the bottom of FIG. 2B. The part of the modified BAC clone containing the neomycin cassette and the human TMPRSS4 genomic fragment, as well as the upstream and downstream insertion junctions, is set forth in SEQ ID NO: 12. The amino acid sequence of the protein encoded by the humanized Tmprss4 gene is set forth in SEQ ID NO: 14. An alignment of this humanized Tmprss4 protein ("7224 mutant pro"), a mouse Tmprss4 protein (SEQ ID NO: 9), and a human TMPRSS4 protein (SEQ ID NO: 11), is provided in FIG. 2D.

Selected ES cell clones (with or without the cassette) were used to implant female mice using the VELOCIMOUSE® method (see, e.g., U.S. Pat. No. 7,294,754 and Poueymirou et al. (2007), supra) to generate a litter of pups containing a humanized Tmprss4 allele in the genome. Mice bearing a humanized Tmprss4 allele were again confirmed and identified by genotyping of DNA isolated from tail snips using a modification of allele assay (Valenzuela et al., supra) that detected the presence of the human TMPRSS4 gene sequences. Pups were genotyped and cohorts of animals heterozygous for the humanized Tmprss4 locus were selected for characterization. Animals homozygous for the humanized Tmprss4 locus were made by crossing heterozygous animals.

TABLE 2

| Name | Primer | Sequence (5'-3') | SEQ ID NO |
|---|---|---|---|
| 7224mTU | Forward | GAGCAGGGCCATGACACAT | (SEQ ID NO: 42) |
| | Probe (BHQ) | ACCATTAGATCCCAGCACTGGACA | (SEQ ID NO: 43) |
| | Reverse | AAACCCTTCCCGAGAGAGAA | (SEQ ID NO: 44) |
| 7224mTU2 | Forward | GAGGAACACTGTGTCAAGGACTT | (SEQ ID NO: 45) |
| | Probe (BHQ) | CCTGAAAAGCCCGGAGTGGCAG | (SEQ ID NO: 46) |
| | Reverse | GGGCAGAGACCACATCTGA | (SEQ ID NO: 47) |
| 7224mTD | Forward | GGAAGCCCTCTCTCGATACTTG | (SEQ ID NO: 48) |
| | Probe (BHQ) | TTCTACCCTGAGGGCATGCAGC | (SEQ ID NO: 49) |
| | Reverse | TGGGATGTAGAAGGTTGTCAGA | (SEQ ID NO: 50) |
| 7224hTU | Forward | CTGAGCCTGGAACTCACACATG | (SEQ ID NO: 51) |
| | Probe (BHQ) | TCTGAGAGCCCAGCACTATCGCC | (SEQ ID NO: 52) |
| | Reverse | GCTGAGGGTCAGGCTTGAG | (SEQ ID NO: 53) |
| 7224hTD | Forward | TCTGCAGGGTAGGGAGAGAAG | (SEQ ID NO: 54) |
| | Probe (BHQ) | TGTTTCAGAAAAGGAAGACTCACGTTACA | (SEQ ID NO: 55) |
| | Reverse | GAGACCGATGAAGAGAAAGTCAGA | (SEQ ID NO: 56) |

Figure 2C:
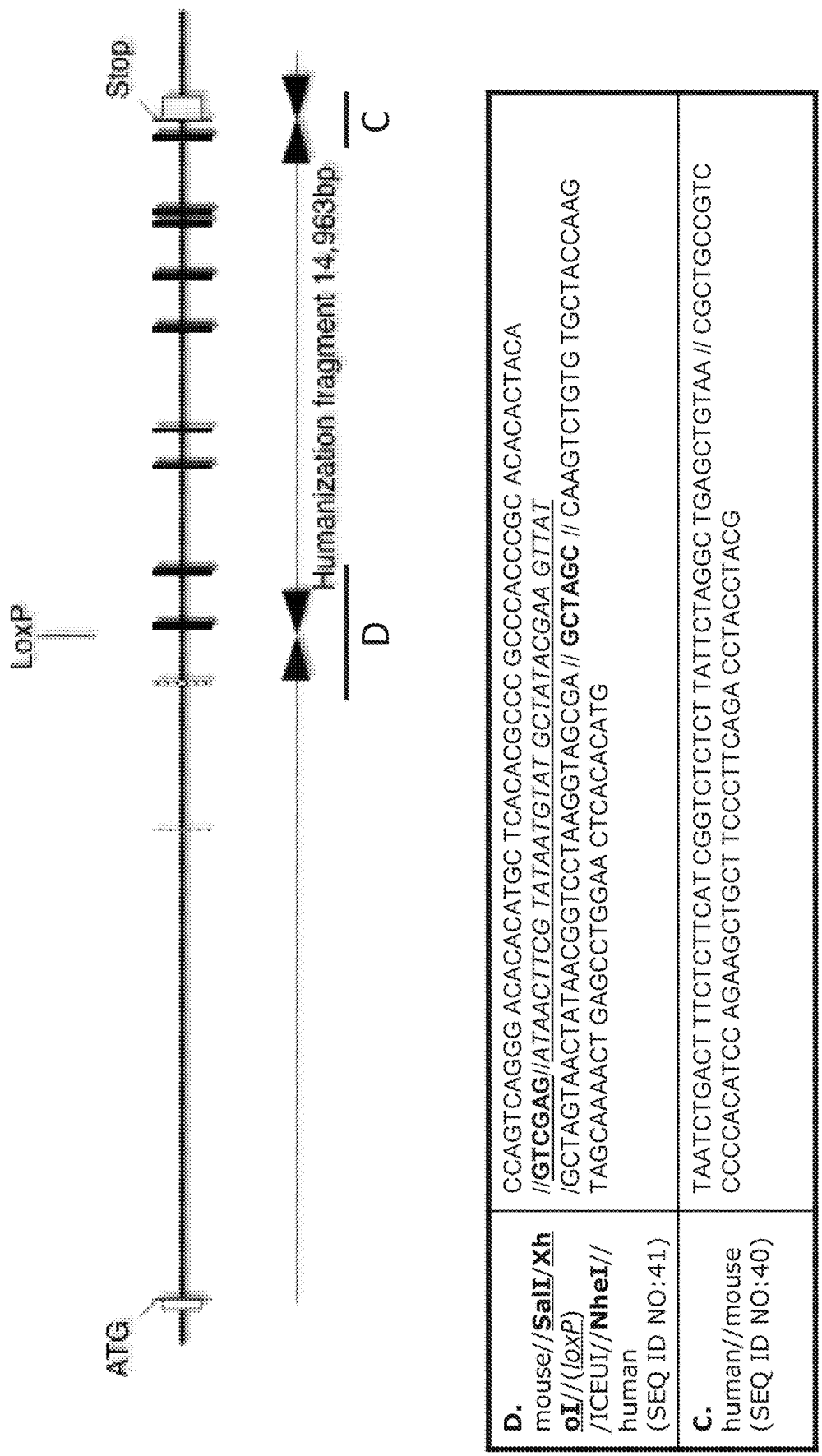

The modified BAC clone containing the humanized Tmprss4 gene, as described above, was used to electroporate mouse embryonic stem (ES) cells to create modified ES cells comprising a humanized Tmprss4 gene. Positively targeted ES cells containing a humanized Tmprss4 gene were identified by an assay (Valenzuela et al., supra) that detected the presence of the human TMPRSS4 sequences (e.g., coding exons 4-13 of human TMPRSS4) and confirmed the loss and/or retention of mouse Tmprss4 sequences (e.g., loss of coding exons 4-13 of mouse Tmprss4). Table 2 sets forth the primers and probes that were used to confirm humanization of an endogenous Tmprss4 gene as described above (FIGS. 2A-2B). Once a correctly targeted ES cell clone has been selected, the neomycin selection cassette can be excised by introducing a Cre recombinase, e.g., via electroporation. Alternatively, the neomycin selection cassette can be removed by crossing the progeny generated from the ES clone with a deletor rodent strain that expresses a Cre recombinase. The humanized Tmprss4 locus after the deletion of the cassette is depicted in FIG. 2C, with the junction sequences shown at the bottom of FIG. 2C.

Example 3. Humanization of an Endogenous Tmprss11d Gene

This example illustrates exemplary methods of humanizing an endogenous gene encoding Tmprss11d in a rodent (e.g., a mouse). The methods described in this example can be employed to humanize an endogenous Tmprss11d gene of a rodent using any human sequence, or combination of human sequences (or sequence fragments) as desired.

A targeting vector for humanization of an endogenous Tmprss11d gene was constructed using bacterial artificial chromosome (BAC) clones and VELOCIGENE® technology (see, e.g., U.S. Pat. No. 6,586,251 and Valenzuela et al. (2003), supra).

Figure 3A:
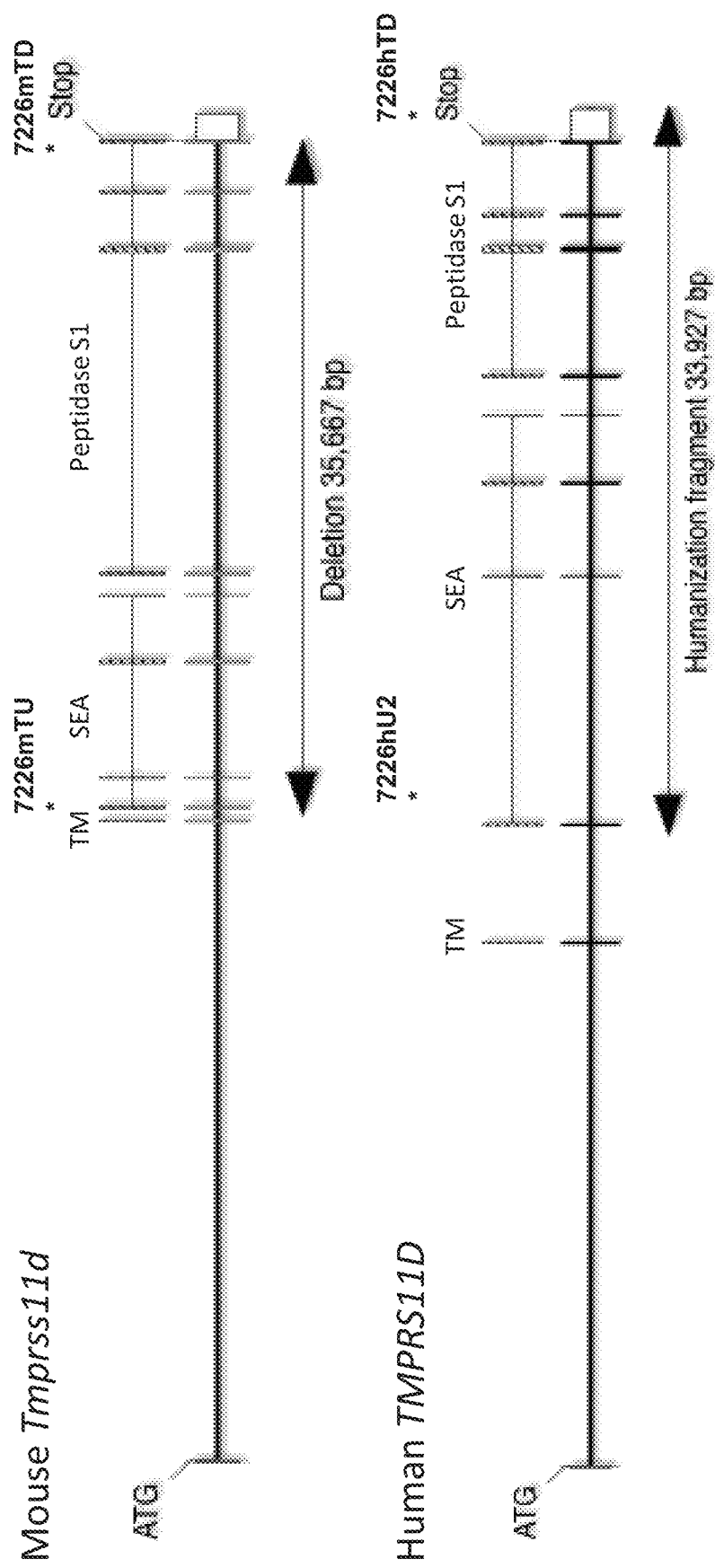
FIGS. 3A-3D. Exemplary strategy for humanization of mouse Tmprss11d.
Figure 3B:
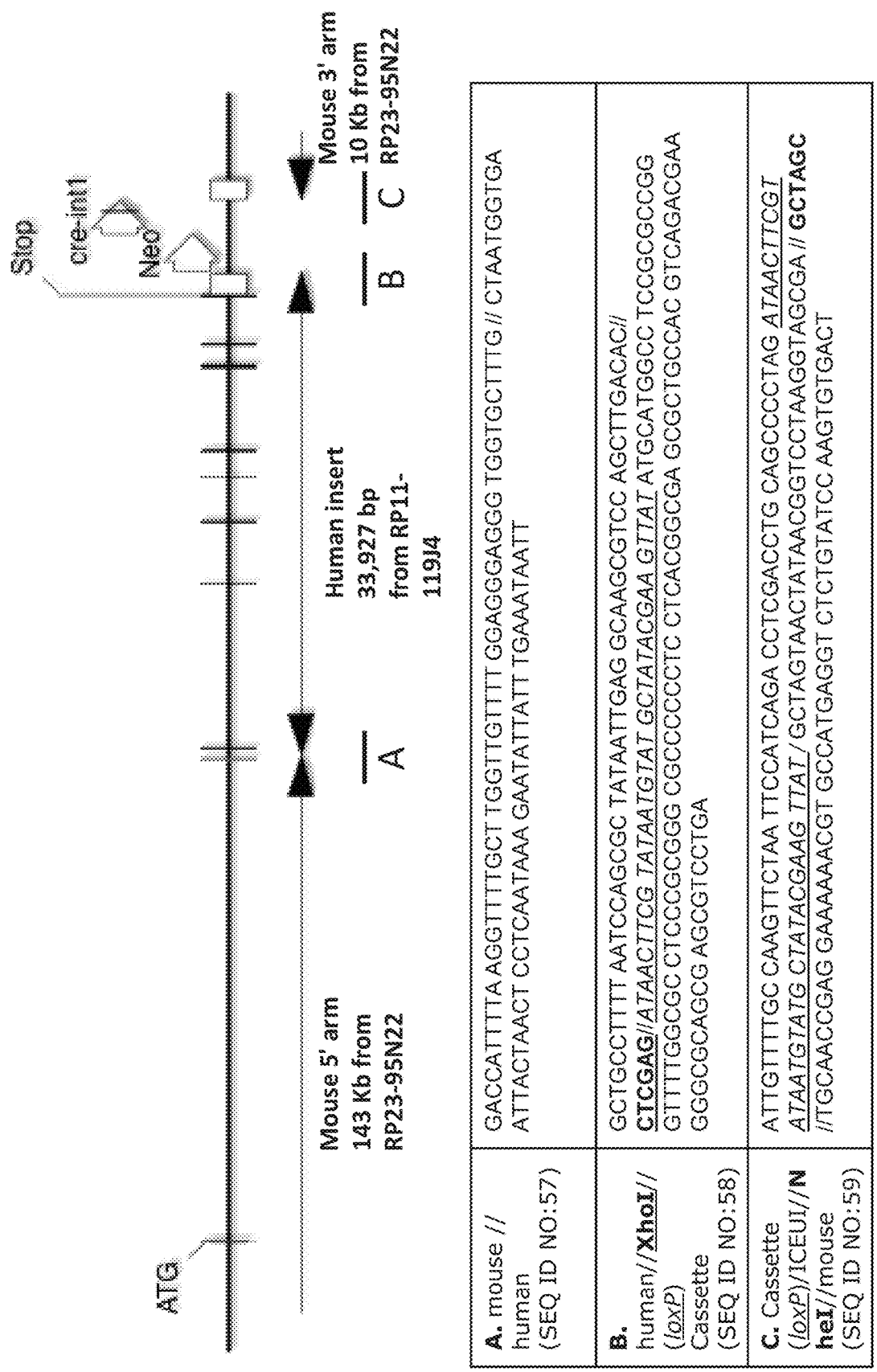

Briefly, mouse bacterial artificial chromosome (BAC) clone RP23-95N22 containing a mouse Tmprss11d gene was used and modified as follows. A DNA fragment was generated to include a 5' mouse homology nucleotide sequence, a human TMPRSS11D genomic DNA of about 33,927 bp (containing 444 bp at the 3' end of intron 2, and coding exon 3 through coding exon 10 (including the 3' UTR which is part of coding exon 10), of a human TMPRSS11D gene), a self-deleting neomycin cassette of about 4,996 bp, and a 3' mouse homology sequence. This DNA fragment was used to modify BAC clone RP23-95N22 through homologous recombination in bacterial cells. As a result, an ectodomain-encoding mouse Tmprss11d genomic fragment (of about 35,667 bp) in the BAC clone was replaced with the human TMPRSS/ID genomic fragment of about 33,927 bp, followed by a self-deleting neomycin cassette of about 4,996 bp. Specifically, the mouse Tmprss11d genomic fragment that was replaced included a 3' portion of intron 2, and coding exon 3 through the stop codon in coding exon 10 of the mouse Tmprss11d gene (FIGS. 3A-3B). The human TMPRSS11D genomic fragment that was inserted included 444 bp at the 3' end of intron 2, and coding exon 3 through coding exon 10 of a human TMPRSS11D gene (including the 3' UTR of human TMPRSS11D), and a human 3' genomic sequence of about 172 bp downstream of the 3' UTR of human TMPRSS11D (FIGS. 3A-3B). The resulting modified BAC clone included, from 5' to 3', (i) a 5' mouse homology arm containing about 143 kb of mouse genomic DNA including a mouse Tmprss11d 5' UTR, mouse Tmprss11d coding exons 1-2 and a 5' portion of intron 2; (ii) a human TMPRSS11D genomic fragment including a 3' portion of intron 2 and coding exons 3 through 10 (including the 3' UTR) of human TMPRSS11D, and a human 3' genomic sequence; (iii) a self-deleting neomycin cassette of about 4,996 bp, followed by (iv) a 3' mouse homology arm of 10 kb containing the mouse Tmprss11d 3'UTR and the remaining mouse genomic DNA in the original BAC clone. See FIGS. 3A-3B. The junction sequences are also set forth at the bottom of FIG. 3B. The part of the modified BAC clone containing the human TMPRSS11D genomic fragment and the neomycin cassette, as well as the upstream and downstream insertion junctions, is set forth in SEQ ID NO:

19. The amino acid sequence of the protein encoded by the humanized Tmprss11d gene is set forth in SEQ ID NO: 21. An alignment of this humanized Tmprss11d protein ("7226 mutant pro"), a mouse Tmprss11d protein (SEQ ID NO: 16), and a human TMPRSS11D protein (SEQ ID NO: 18), is provided in FIG. 3D.

Figure 3C:
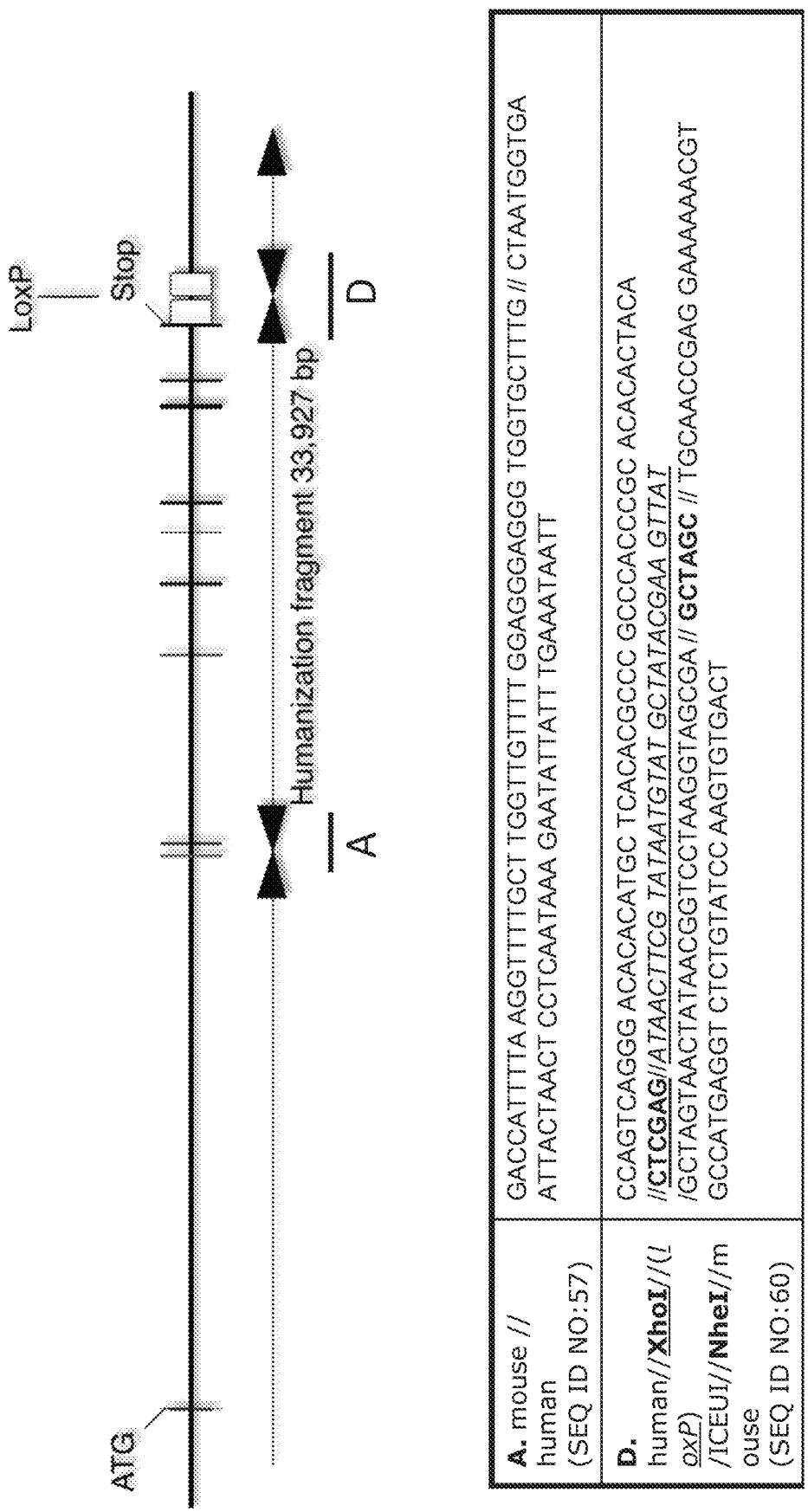
Figure 3D:
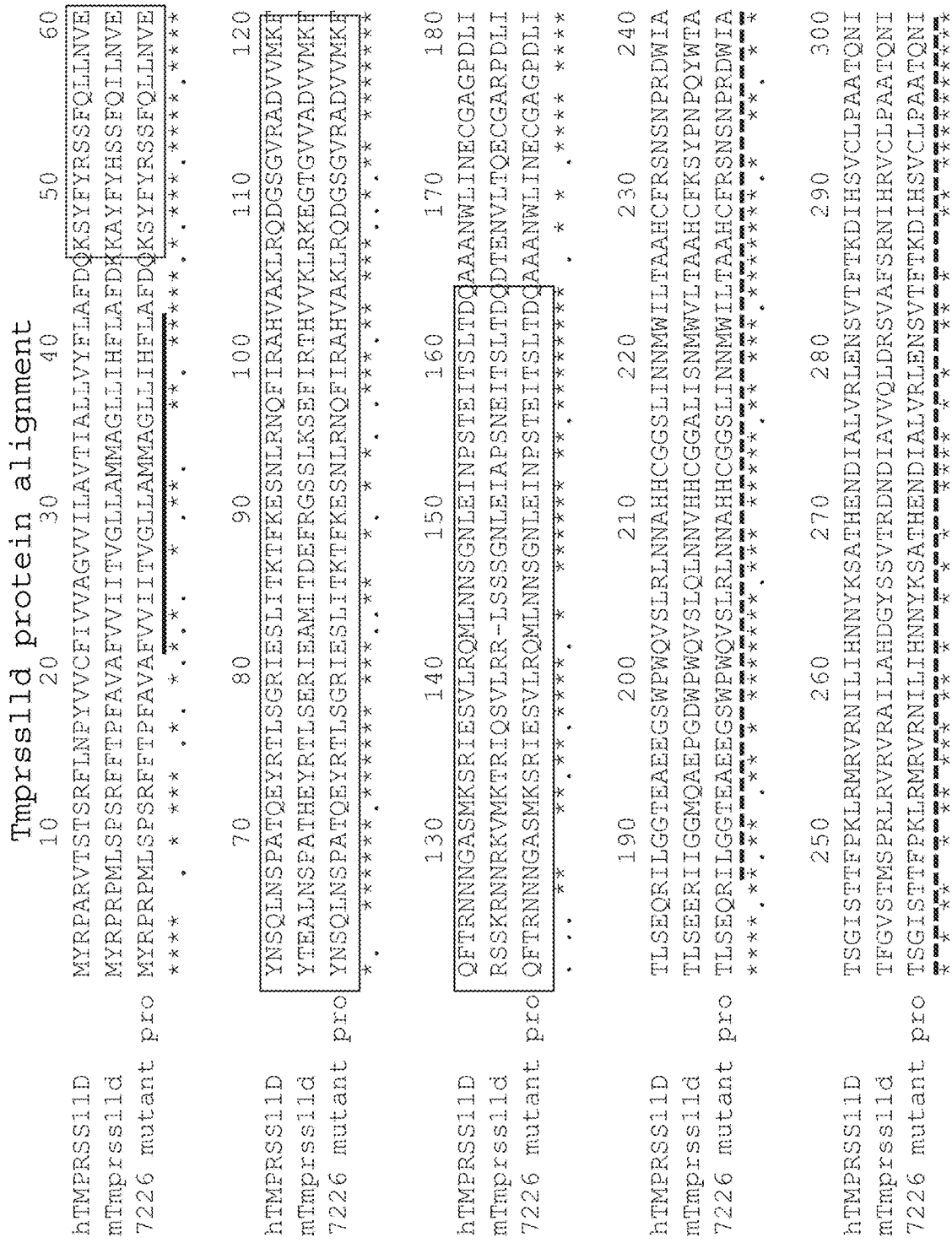
Figure 4:
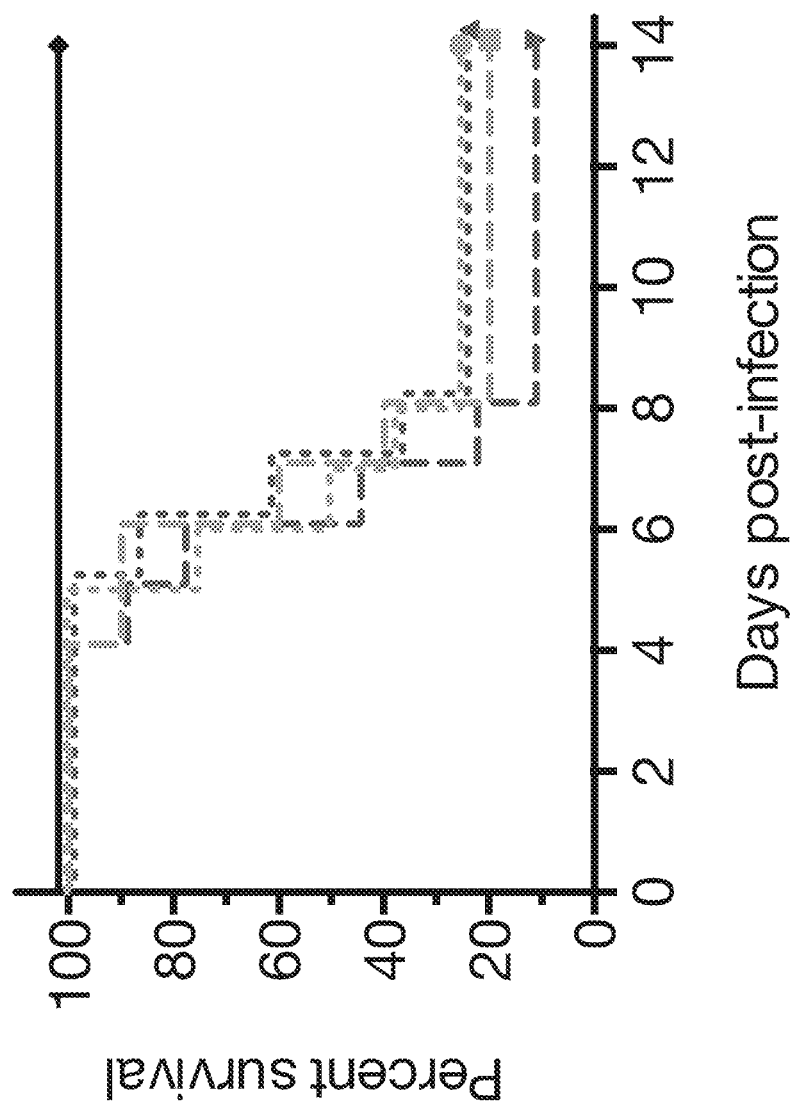
FIG. 4 depicts the results of an experiment showing that MAID7225 HumInTMPRSS4 mice do not differ in their susceptibility to challenge with high doses of severe influenza A H1N1 or severe, mouse-adapted H3N2. MAID7225 HumIn TMRPSS4 mice challenged with A/Puerto Rico/08/1934 (H1N1) (light gray circles, dotted line) showed similar survival rates compared to wild-type mice (light gray squares, dotted line). Likewise, MAID7225 HumIn TMRPSS4 mice challenged with A/Aichi/02/1968-X31 (H3N2) (dark gray triangles, dotted line) showed similar survival rates compared to wild-type mice (light gray inverse triangles, dashed line). Mice were infected IN on day 0 with either 1150 PFUs of A/Puerto Rico/08/1934 (H1N1) or 10,000 PFUs of A/Aichi/02/1968-X31 (H3N2). The control group included uninfected negative control MAID7225 HumIn TMPRSS4 and wild-type mice (black diamonds, solid line).

The modified BAC clone containing the humanized Tmprss11d gene, as described above, is used to electroporate mouse embryonic stem (ES) cells to create modified ES cells comprising a humanized Tmprss11d gene. Positively targeted ES cells containing a humanized Tmprss11d gene are identified by an assay (Valenzuela et al., supra) that detects the presence of the human TMPRSS1/D sequences (e.g., coding exons 3-10 of human TMPRSS11D) and confirms the loss and/or retention of mouse Tmprss11d sequences (e.g., loss of coding exons 3-10 of mouse Tmprss11d). Table 3 sets forth the primers and probes that were used to confirm humanization of an endogenous Tmprss11d gene as described above (FIGS. 3A-3B). Once a correctly targeted ES cell clone has been selected, the neomycin selection cassette can be excised by introducing a Cre recombinase, e.g., via electroporation. Alternatively, the neomycin selection cassette can be removed by crossing the progeny generated from the ES clone with a deletor rodent strain that expresses a Cre recombinase. The humanized Tmprss11d locus after the deletion of the cassette is depicted in FIG. 3C, with the junction sequences shown at the bottom of FIG. 3C.

Selected ES cell clones (with or without the cassette) are used to implant female mice using the VELOCIMOUSE® method (see, e.g., U.S. Pat. No. 7,294,754 and Poueymirou el al. (2007), supra) to generate a litter of pups containing a humanized Tmprss11d allele in the genome. Mice bearing a humanized Tmprss11d allele are again confirmed and identified by genotyping of DNA isolated from tail snips using a modification of allele assay (Valenzuela et al., supra) that detects the presence of the human TMPRSS11D gene sequences. Pups are genotyped and cohorts of animals heterozygous for the humanized Tmprss11d locus are selected for characterization. Animals homozygous for the humanized Tmprss11d locus are made by crossing heterozygous animals.

TABLE 3

| Name | Primer | Sequence (5'-3') | SEQ ID NO |
|---|---|---|---|
| 7226mTU | Forward | TCCTCTCCAGACAAGAAAGCT | (SEQ ID NO: 61) |
| | Probe (BHQ) | TCATAGCAGCTTTCAAATCCTAAACGTTGA | (SEQ ID NO: 62) |
| | Reverse | TCGTGTGTAGCTGGTGAGTT | (SEQ ID NO: 63) |
| 7226mTD | Forward | CATGCGATCACAGGAGGAGATC | (SEQ ID NO: 64) |
| | Probe (BHQ) | AATTGGGCCCGAAGCCAGATGC | (SEQ ID NO: 65) |
| | Reverse | CGGAAGGCTTCTGTGACTTC | (SEQ ID NO: 66) |
| 7226hTU | Forward | GTCTCCCACTTCTGACATAATGAAC | (SEQ ID NO: 67) |
| | Probe (BHQ) | CCCAGTGTTAACCCTACATCTGGTTCC | (SEQ ID NO: 68) |
| | Reverse | TGGGAAGAGACTCTTGGACA | (SEQ ID NO: 69) |
| 7226hTD | Forward | ATGAGCTCCTAGTACAGCTAAAGTT | (SEQ ID NO: 70) |
| | Probe (MGB) | ATGCATGATCATCTATGCGTCAGAGC | (SEQ ID NO: 71) |
| | Reverse | TGCCCAGATGCAGGGAGTTAG | (SEQ ID NO: 72) |

Example 4. Evaluation of Group 1 and Group 2 Influenza A Viruses in MAID7225 HumIn Vs. Wild-Type Tmprss4 Mice To validate the use of humanized Tmprss rodents as an animal model of infection, experiments were conducted to evaluate the survival of MAID7225 HumIn TMPRSS4 mice versus wild-type (WT) littermates in an influenza A group 1 and group 2 model of severe influenza infection.

MAID7225 HumIn TMPRSS4 mice are homozygous for a humanized Tmprss4 gene in its genome and were generated as described in Example 2. The viral strains used in these studies included the historical A/Puerto Rico/08/1934 (H1N1) influenza A virus group 1 isolate and an in-house mouse-adapted A/Aichi/02/1968 (HA, NA) X-31 (H3N2) influenza A virus group 2 isolate. All experiments were performed in 6-8 week-old male and female MAID7225 HumIn TMPRSS4 mice or WT littermates. Mice were challenged with 1150 plaque-forming units (PFUs) of A/Puerto Rico/08/1934 (H1N1) or 10,000 PFUs of A/Aichi/02/1968-X31 (H3N2). In these survival models, mice were challenged intranasally (IN) on day 0 post-infection (p.i.). Mice were weighed and observed daily up to day 14 p.i. and were sacrificed when they lost 20% of their starting weight. Results are reported as percent survival (Table 4).

TABLE 4

| Group ID | Number of mice per group | Percent survival (no. of surviving mice/total no. of mice in the group) |
|---|---|---|
| Uninfected control (2 HumIn, 2 WT mice) | 4 | 100 (4/4) |
| WT TMPRSS4; H1_PR34 infected | 10 | 20 (2/10) |
| HumIn TMPRSS4; H1_PR34 infected | 8 | 25 (2/8) |
| WT TMPRSS4; H3_X31 infected | 9 | 11.1 (1/9) |
| HumIn TMPRSS4; H3_X31 infected | 8 | 25 (2/8) |

The survival of MAID7225 HumIn TMPRSS4 mice was compared to WT littermates after challenge with both severe Influenza A group 1 virus [A/Puerto Rico/08/1934 (H1N1)] and a severe, mouse-adapted Influenza A group 2 virus [A/Aichi/02/1968-X31 (H3N2)](FIG. 4). Survival of MAID7225 HumIn TMPRSS4 mice was no different from wild-type mice with either the H1N1 challenge (25%; n=8 and 20%; n=10, respectively) or the H3N2 challenge (25%; n=8 and 11.1%; n=9, respectively).

The publications, websites and other reference materials referenced herein to describe the background of the invention and to provide additional detail regarding its practice are hereby incorporated by reference.

SEQUENCE LISTING

```
<160> NUMBER OF SEQ ID NOS: 72

<210> SEQ ID NO 1
<211> LENGTH: 3175
<212> TYPE: DNA
<213> ORGANISM: Mus musculus

<400> SEQUENCE: 1
gcctttcctg gccgttccct ccttctggcc gaggtgcctg cgtttagggg tgtcaccctg     60
gctcccggga cgccgcctcc ggagatttaa gcgagaactg gagtaggtcg tgtacttgga    120
gcggacgagg aagccaagag ctcggacaga ggcggagagg ggcgggaagc gcaacaggtc    180
acctggagga agccccatac tgacctcctc atgctgctga cacaggcagg atggcattga    240
actcagggtc acctccagga atcggacctt gctatgagaa ccacgggtat cagtctgagc    300
acatctgtcc tccgagacca ccagtggctc ccaatggcta caacttgtat ccagcccagt    360
actacccatc tccagtgcct cagtatgctc cgaggattac aacgcaagcc tcaacatctg    420
tcatccacac acatcccaag tcctcaggag cactgtgcac ctcaaagtct aagaaatcgc    480
tgtgtttagc cctcgccctg ggcactgtcc tcacgggagc tgctgtggct gctgtcttgc    540
tttggaggtt ctgggacagc aactgttcta cgtctgagat ggagtgtggg tcttcaggca    600
catgcatcag ctcttctctc tggtgtgacg gggtagcaca ttgtcccaac ggagaagatg    660
agaaccgttg tgttcgtctc tacggacaaa gcttcatcct ccaggtttac tcatctcaga    720
ggaaagcctg gtatcccgtg tgccaggatg attggagtga gagctacggg agagcagcat    780
gtaaagacat gggatacaag aacaattttt attctagcca agggatacca gaccagagcg    840
gggcaacgag ctttatgaag ctgaatgtga gctcaggcaa cgttgacctc tataaaaaac    900
```

```
tctaccacag tgactcatgt tcatcccgca tggtggtttc tttgcgctgt atagaatgcg    960
gggttcgctc agtgaaacgc cagagcagga ttgtgggtgg attgaatgcc tcaccaggag   1020
actggccctg gcaggtcagc ctgcacgtcc aaggcgtcca cgtctgcgga ggctccatca   1080
tcaccccga gtggattgtg acggccgccc actgtgtgga agaacccctc agcagcccga    1140
ggtactggac ggcatttgcg ggaattctga gacagtctct catgttctat ggaagtagac   1200
accaggtaga aaaagtaatt tcccatccaa attacgactc taagaccaag aataacgaca   1260
ttgctctcat gaagctgcag acacctttgg cttttaatga tctagtgaag ccagtgtgtc   1320
tgccgaaccc aggcatgatg ctagacctag accaggaatg ctggatttcg ggtgggggg    1380
ccacctatga gaagggaag acctcggacg tgttgaatgc tgccatggta cccttgatcg     1440
agccctccaa atgtaatagt aaatacatat acaacaacct aatcacacca gccatgatct   1500
gtgccggctt cctccagggg tctgtcgact cttgccaggg agacagtgga gggccgctgg   1560
ttactttgaa gaatgggatc tggtggctga ttggggacac gagctggggc tcgggctgtg   1620
ccaaggcact cagacctgga gtatacggga acgtgacggt atttacagat ggatctacc    1680
agcaaatgag ggcgaacagc taatccacgt ggctttgtcc cagacttcct ttgtcttcaa   1740
caaccttctg caagaaaacc aagggcctga attttaactt cctgtgcaca atgtaccttt   1800
tgagatgatt cgaagggcct ttcactttta ttaaacagtg acttgtttga ctgtgctccc   1860
tggtcctgtg agggcttcag tgccccaccc ctgggccact tctgcagctc ccaccagaat   1920
ggatgaccag attctgttgg gtttgggcac atagggccaa aggcagagga gggtggcact   1980
ctcatgttgg aacttctttt gggctcatgc tcaggccttt tttggatcac taaggactat   2040
gacctctgag taacctgatg acctgagaaa gagtaaggag gccaggcagg gccttgggcc   2100
caggaacagg taccttgaga gtgagagcta cccattgcct gtggcctaaa tctgctgtgc   2160
aggttgggct ggtcatactg tcatgatttc attaacagcc tgggtgaaca tggctgggag   2220
taaagggctt gctctcctgc atgttgacat gacggccctt ccaagggtg atggaggctt    2280
tcccaagcta agggcctagg cagatctctc agagcaagaa gctaatgccg gcatgtccct   2340
tgggtgagct ctacatggtg ttattcagtc tggttcttgg ctccccacta ctgtttctct   2400
cagcctctca gagcctgaaa cttacctctt agctttggct acaggcatgg cctagtacct   2460
gatggagcct gtatagctca gctaatcaaa tggaggctca ggtccatcag aatcagggac   2520
ttgtgatttc agtcacccttg cttctgggtt gtgtttcttc tcttactacc tcactgcacc   2580
tggacactag agtggatgaa tgtctggagt tcacctgcat ttggactgtg tgattgtgcc   2640
tcagacacta gacctcttcc agatggttag gttgttctgt agactggcaa tgagattaga   2700
agttcctagc ttcagataaa gatgaaagag aggagatcat tgtcttctgt cttcttctgg   2760
ccctgggttt ataccaggaa agccatgcca gaattaccaa atatgaagta tgaatgtctt   2820
acccacggtg aggctctgcc tccttctctc tgcctggttc ttcagaaggc agtgaatggg   2880
tcataactgg gactccatct ttgctgggga agtctcccca cctagggaat ggttaccact   2940
ccatgtaaag aaaactccct catgcgtcct ctgggacctt cttagatgct gtaaggtacc   3000
tacatacaga ctaaatgtgc aagcaccttg aagtgtgaga acctgtcccc tccttagctc   3060
tccttgtctt tgctgttggt tggttatttc ctgctttgtg tctgttctga gctgtgagat   3120
tccactgtga aatatatgaa taaagtatat aattctttta aaaaaaaaaa aaaaa         3175
```

<210> SEQ ID NO 2
<211> LENGTH: 490

<212> TYPE: PRT
<213> ORGANISM: Mus musculus

<400> SEQUENCE: 2

```
Met Ala Leu Asn Ser Gly Ser Pro Gly Ile Gly Pro Cys Tyr Glu
1               5                   10                  15

Asn His Gly Tyr Gln Ser Glu His Ile Cys Pro Pro Arg Pro Val
            20                  25                  30

Ala Pro Asn Gly Tyr Asn Leu Tyr Pro Ala Gln Tyr Tyr Pro Ser Pro
        35                  40                  45

Val Pro Gln Tyr Ala Pro Arg Ile Thr Thr Gln Ala Ser Thr Ser Val
    50                  55                  60

Ile His Thr His Pro Lys Ser Gly Ala Leu Cys Thr Ser Lys Ser
65                  70                  75                  80

Lys Lys Ser Leu Cys Leu Ala Leu Ala Leu Gly Thr Val Leu Thr Gly
                85                  90                  95

Ala Ala Val Ala Ala Val Leu Leu Trp Arg Phe Trp Asp Ser Asn Cys
            100                 105                 110

Ser Thr Ser Glu Met Glu Cys Gly Ser Ser Gly Thr Cys Ile Ser Ser
            115                 120                 125

Ser Leu Trp Cys Asp Gly Val Ala His Cys Pro Asn Gly Glu Asp Glu
    130                 135                 140

Asn Arg Cys Val Arg Leu Tyr Gly Gln Ser Phe Ile Leu Gln Val Tyr
145                 150                 155                 160

Ser Ser Gln Arg Lys Ala Trp Tyr Pro Val Cys Gln Asp Asp Trp Ser
                165                 170                 175

Glu Ser Tyr Gly Arg Ala Ala Cys Lys Asp Met Gly Tyr Lys Asn Asn
            180                 185                 190

Phe Tyr Ser Ser Gln Gly Ile Pro Asp Gln Ser Gly Ala Thr Ser Phe
        195                 200                 205

Met Lys Leu Asn Val Ser Ser Gly Asn Val Asp Leu Tyr Lys Lys Leu
    210                 215                 220

Tyr His Ser Asp Ser Cys Ser Ser Arg Met Val Val Ser Leu Arg Cys
225                 230                 235                 240

Ile Glu Cys Gly Val Arg Ser Val Lys Arg Gln Ser Arg Ile Val Gly
                245                 250                 255

Gly Leu Asn Ala Ser Pro Gly Asp Trp Pro Trp Gln Val Ser Leu His
            260                 265                 270

Val Gln Gly Val His Val Cys Gly Gly Ser Ile Ile Thr Pro Glu Trp
    275                 280                 285

Ile Val Thr Ala Ala His Cys Val Glu Glu Pro Leu Ser Ser Pro Arg
    290                 295                 300

Tyr Trp Thr Ala Phe Ala Gly Ile Leu Arg Gln Ser Leu Met Phe Tyr
305                 310                 315                 320

Gly Ser Arg His Gln Val Glu Lys Val Ile Ser His Pro Asn Tyr Asp
                325                 330                 335

Ser Lys Thr Lys Asn Asn Asp Ile Ala Leu Met Lys Leu Gln Thr Pro
            340                 345                 350

Leu Ala Phe Asn Asp Leu Val Lys Pro Val Cys Leu Pro Asn Pro Gly
        355                 360                 365

Met Met Leu Asp Leu Asp Gln Glu Cys Trp Ile Ser Gly Trp Gly Ala
    370                 375                 380

Thr Tyr Glu Lys Gly Lys Thr Ser Asp Val Leu Asn Ala Ala Met Val
385                 390                 395                 400
```

```
Pro Leu Ile Glu Pro Ser Lys Cys Asn Ser Lys Tyr Ile Tyr Asn Asn
            405                 410                 415
Leu Ile Thr Pro Ala Met Ile Cys Ala Gly Phe Leu Gln Gly Ser Val
            420                 425                 430
Asp Ser Cys Gln Gly Asp Ser Gly Pro Leu Val Thr Leu Lys Asn
            435                 440                 445
Gly Ile Trp Trp Leu Ile Gly Asp Thr Ser Trp Gly Ser Gly Cys Ala
            450                 455                 460
Lys Ala Leu Arg Pro Gly Val Tyr Gly Asn Val Thr Val Phe Thr Asp
465                 470                 475                 480
Trp Ile Tyr Gln Gln Met Arg Ala Asn Ser
            485                 490

<210> SEQ ID NO 3
<211> LENGTH: 3212
<212> TYPE: DNA
<213> ORGANISM: Homo sapiens

<400> SEQUENCE: 3
```

| | | | | |
|---|---|---|---|---|
| gagtaggcgc | gagctaagca | ggaggcggag | gcggaggcgg | agggcgaggg | gcggggagcg | 60 |
| ccgcctggag | cgcggcaggt | catattgaac | attccagata | cctatcatta | ctcgatgctg | 120 |
| ttgataacag | caagatggct | ttgaactcag | ggtcaccacc | agctattgga | ccttactatg | 180 |
| aaaaccatgg | ataccaaccg | gaaaacccct | atcccgcaca | gcccactgtg | gtccccactg | 240 |
| tctacgaggt | gcatccggct | cagtactacc | cgtcccccgt | gccccagtac | gccccgaggg | 300 |
| tcctgacgca | ggcttccaac | cccgtcgtct | gcacgcagcc | caaatcccca | tccgggacag | 360 |
| tgtgcacctc | aaagactaag | aaagcactgt | gcatcacctt | gacctgggg | accttcctcg | 420 |
| tgggagctgc | gctggccgct | ggcctactct | ggaagttcat | gggcagcaag | tgctccaact | 480 |
| ctgggataga | gtgcgactcc | tcaggtacct | gcatcaaccc | ctctaactgg | tgtgatggcg | 540 |
| tgtcacactg | ccccggcggg | gaggacgaga | tcggtgtgt | tcgcctctac | ggaccaaact | 600 |
| tcatccttca | ggtgtactca | tctcagagga | agtcctggca | ccctgtgtgc | caagacgact | 660 |
| ggaacgagaa | ctacgggcgg | gcggcctgca | gggacatggg | ctataagaat | aattttttact | 720 |
| ctagccaagg | aatagtggat | gacagcggat | ccaccagctt | tatgaaactg | aacacaagtg | 780 |
| ccggcaatgt | cgatatctat | aaaaaaactgt | accacagtga | tgcctgttct | tcaaaagcag | 840 |
| tggtttcttt | acgctgtata | gcctgcgggg | tcaacttgaa | ctcaagccgc | cagagcagga | 900 |
| ttgtgggcgg | cgagagcgcg | ctcccggggg | cctggccctg | gcaggtcagc | ctgcacgtcc | 960 |
| agaacgtcca | cgtgtgcgga | ggctccatca | tcacccccga | gtggatcgtg | acagccgccc | 1020 |
| actgcgtgga | aaaacctctt | aacaatccat | ggcattggac | ggcatttgcg | gggatttga | 1080 |
| gacaatcttt | catgttctat | ggagccggat | accaagtaga | aaagtgatt | tctcatccaa | 1140 |
| attatgactc | caagaccaag | aacaatgaca | ttgcgctgat | gaagctgcag | aagcctctga | 1200 |
| ctttcaacga | cctagtgaaa | ccagtgtgtc | tgcccaaccc | aggcatgatg | ctgcagccag | 1260 |
| aacagctctg | ctggatttcc | gggtgggggg | ccaccgagga | gaaagggaag | acctcagaag | 1320 |
| tgctgaacgc | tgccaaggtg | cttctcattg | agacacagag | atgcaacagc | agatatgtct | 1380 |
| atgacaaccct | gatcacacca | gccatgatct | gtgccggctt | cctgcagggg | aacgtcgatt | 1440 |
| cttgccaggg | tgacagtgga | gggcctctgg | tcacttcgaa | gaacaatatc | tggtggctga | 1500 |
| taggggatac | aagctggggt | tctggctgtg | ccaaagctta | cagaccagga | gtgtacggga | 1560 |

```
atgtgatggt attcacggac tggatttatc gacaaatgag ggcagacggc taatccacat   1620
ggtcttcgtc cttgacgtcg ttttacaaga aaacaatggg gctggttttg cttcccgtg    1680
catgatttac tcttagagat gattcagagg tcacttcatt tttattaaac agtgaacttg   1740
tctggctttg gcactctctg ccattctgtg caggctgcag tggctcccct gcccagcctg   1800
ctctccctaa ccccttgtcc gcaaggggtg atggccggct ggttgtgggc actggcggtc   1860
aagtgtggag gagaggggtg gaggctgccc cattgagatc ttcctgctga gtcctttcca   1920
ggggccaatt ttggatgagc atggagctgt cacctctcag ctgctggatg acttgagatg   1980
aaaaaggaga gacatggaaa gggagacagc caggtggcac ctgcagcggc tgccctctgg   2040
ggccacttgg tagtgtcccc agcctacctc tccacaaggg gattttgctg atgggttctt   2100
agagccttag cagccctgga tggtggccag aaataaaggg accagccctt catgggtggt   2160
gacgtggtag tcacttgtaa ggggaacaga acattttg ttcttatggg gtgagaatat    2220
agacagtgcc cttggtgcga gggaagcaat tgaaaaggaa cttgccctga gcactcctgg   2280
tgcaggtctc cacctgcaca ttgggtgggg ctcctgggag ggagactcag ccttcctcct   2340
catcctccct gacccctgctc ctagcaccct ggagagtgca catgccccctt ggtcctggca  2400
gggcgccaag tctggcacca tgttggcctc ttcaggcctg ctagtcactg gaaattgagg   2460
tccatgggg aaatcaagga tgctcagttt aaggtacact gtttccatgt tatgtttcta    2520
cacattgcta cctcagtgct cctggaaact tagcttttga tgtctccaag tagtccacct   2580
tcatttaact ctttgaaact gtatcatctt tgccaagtaa gagtggtggc ctatttcagc   2640
tgctttgaca aaatgactgg ctcctgactt aacgttctat aaatgaatgt gctgaagcaa   2700
agtgcccatg gtggcggcga agaagagaaa gatgtgtttt gttttggact ctctgtggtc   2760
ccttccaatg ctgtgggttt ccaaccaggg aagggtccc ttttgcattg ccaagtgcca    2820
taaccatgag cactactcta ccatggttct gcctcctggc caagcaggct ggtttgcaag   2880
aatgaaatga atgattctac agctaggact taaccttgaa atggaaagtc atgcaatccc   2940
atttgcagga tctgtctgtg cacatgcctc tgtagagagc agcattccca gggaccttgg   3000
aaacagttgg cactgtaagg tgcttgctcc ccaagacaca tcctaaaagg tgttgtaatg   3060
gtgaaaacgt cttccttctt tattgcccct tcttatttat gtgaacaact gtttgtcttt   3120
ttttgtatct ttttttaaact gtaaagttca attgtgaaaa tgaatatcat gcaaataaat   3180
tatgcaattt ttttttcaaa gtaaaaaaaa aa                                 3212
```

<210> SEQ ID NO 4
<211> LENGTH: 492
<212> TYPE: PRT
<213> ORGANISM: Homo sapiens

<400> SEQUENCE: 4

```
Met Ala Leu Asn Ser Gly Ser Pro Pro Ala Ile Gly Pro Tyr Tyr Glu
1               5                   10                  15

Asn His Gly Tyr Gln Pro Glu Asn Pro Tyr Pro Ala Gln Pro Thr Val
            20                  25                  30

Val Pro Thr Val Tyr Glu Val His Pro Ala Gln Tyr Tyr Pro Ser Pro
        35                  40                  45

Val Pro Gln Tyr Ala Pro Arg Val Leu Thr Gln Ala Ser Asn Pro Val
    50                  55                  60

Val Cys Thr Gln Pro Lys Ser Pro Ser Gly Thr Val Cys Thr Ser Lys
65                  70                  75                  80
```

-continued

```
Thr Lys Lys Ala Leu Cys Ile Thr Leu Thr Leu Gly Thr Phe Leu Val
                 85                  90                  95

Gly Ala Ala Leu Ala Ala Gly Leu Leu Trp Lys Phe Met Gly Ser Lys
            100                 105                 110

Cys Ser Asn Ser Gly Ile Glu Cys Asp Ser Ser Gly Thr Cys Ile Asn
            115                 120                 125

Pro Ser Asn Trp Cys Asp Gly Val Ser His Cys Pro Gly Gly Glu Asp
            130                 135                 140

Glu Asn Arg Cys Val Arg Leu Tyr Gly Pro Asn Phe Ile Leu Gln Val
145                 150                 155                 160

Tyr Ser Ser Gln Arg Lys Ser Trp His Pro Val Cys Gln Asp Asp Trp
                165                 170                 175

Asn Glu Asn Tyr Gly Arg Ala Ala Cys Arg Asp Met Gly Tyr Lys Asn
            180                 185                 190

Asn Phe Tyr Ser Ser Gln Gly Ile Val Asp Asp Ser Gly Ser Thr Ser
            195                 200                 205

Phe Met Lys Leu Asn Thr Ser Ala Gly Asn Val Asp Ile Tyr Lys Lys
            210                 215                 220

Leu Tyr His Ser Asp Ala Cys Ser Ser Lys Ala Val Val Ser Leu Arg
225                 230                 235                 240

Cys Ile Ala Cys Gly Val Asn Leu Asn Ser Ser Arg Gln Ser Arg Ile
                245                 250                 255

Val Gly Gly Glu Ser Ala Leu Pro Gly Ala Trp Pro Trp Gln Val Ser
            260                 265                 270

Leu His Val Gln Asn Val His Val Cys Gly Gly Ser Ile Ile Thr Pro
            275                 280                 285

Glu Trp Ile Val Thr Ala Ala His Cys Val Glu Lys Pro Leu Asn Asn
290                 295                 300

Pro Trp His Trp Thr Ala Phe Ala Gly Ile Leu Arg Gln Ser Phe Met
305                 310                 315                 320

Phe Tyr Gly Ala Gly Tyr Gln Val Glu Lys Val Ile Ser His Pro Asn
                325                 330                 335

Tyr Asp Ser Lys Thr Lys Asn Asn Asp Ile Ala Leu Met Lys Leu Gln
            340                 345                 350

Lys Pro Leu Thr Phe Asn Asp Leu Val Lys Pro Val Cys Leu Pro Asn
            355                 360                 365

Pro Gly Met Met Leu Gln Pro Glu Gln Leu Cys Trp Ile Ser Gly Trp
            370                 375                 380

Gly Ala Thr Glu Glu Lys Gly Lys Thr Ser Glu Val Leu Asn Ala Ala
385                 390                 395                 400

Lys Val Leu Leu Ile Glu Thr Gln Arg Cys Asn Ser Arg Tyr Val Tyr
                405                 410                 415

Asp Asn Leu Ile Thr Pro Ala Met Ile Cys Ala Gly Phe Leu Gln Gly
            420                 425                 430

Asn Val Asp Ser Cys Gln Gly Asp Ser Gly Gly Pro Leu Val Thr Ser
            435                 440                 445

Lys Asn Asn Ile Trp Trp Leu Ile Gly Asp Thr Ser Trp Gly Ser Gly
450                 455                 460

Cys Ala Lys Ala Tyr Arg Pro Gly Val Tyr Gly Asn Val Met Val Phe
465                 470                 475                 480

Thr Asp Trp Ile Tyr Arg Gln Met Arg Ala Asp Gly
                485                 490
```

<210> SEQ ID NO 5
<211> LENGTH: 27947
<212> TYPE: DNA
<213> ORGANISM: Artificial Sequence
<220> FEATURE:
<223> OTHER INFORMATION: Recombinant polynucleotide

<400> SEQUENCE: 5

| | | | | | |
|---|---|---|---|---|---|
| gcagagtcta | agaaatcgct | gtgtttagcc | ctcgccctgg | gcactgtcct | cacgggagct | 60 |
| gctgtggctg | ctgtcttgct | ttggaagttc | agtaagtgca | gggagcctcg | atcccaccat | 120 |
| gtgctcctgc | agtccccagt | gctctgagcc | agaccctgct | ctctgggcta | ttgagacctc | 180 |
| tggaggccct | ccgtgaggtt | cctctcttac | ataacgaggc | tgtctctctt | cccttctctt | 240 |
| gtttagctat | gagattgaca | catcatgggg | aaagcattta | gaatgtaccc | agtgctttgg | 300 |
| ggtgcttggt | gccacccagc | actgtgagca | caggttcttc | taccttgggg | ccacacccag | 360 |
| ttacctgtat | ctcactgcac | agcagtggct | gttggggacc | aggcccaccc | ctccatgtcc | 420 |
| cacctcctgc | aactgcagcc | tgagccttcc | catcagcctg | gggtggtgca | gacccatgtg | 480 |
| ccattgtgga | tccttcaagt | tacctgtgtg | gcagagagga | cgtgtgagtg | ccgtccaaac | 540 |
| ccaaacactg | agagggtcct | tcccattgcc | cccacgaag | taaggtgccc | cagtgctaat | 600 |
| tccacttata | cttgctggtg | gcaaggacac | ttctcctcct | tattaaagtg | ggggattggc | 660 |
| tgggtgaggt | ggctcacgcc | tgttatccca | gcactttaag | aggccaaggc | aggtggacca | 720 |
| cctgaggtca | ggagtttgag | accacaagcc | tggccaacat | gttgaaactc | catctctact | 780 |
| aaaaatacaa | aaattagtca | ggcgtggtgg | cgtgcacctg | taatcccagc | tacttaggag | 840 |
| gctggggcag | gaggatcact | tgaacccagg | agttggaggt | tgcagtgagc | caagattgtg | 900 |
| cccctgcact | ccagcctggg | tgacagaatg | agacttcatc | tcaaaaacaa | aacaaaacaa | 960 |
| aacacagtgg | ggccaggagt | tggaggctgc | agcgagctac | agtaatgcca | cggtgttcct | 1020 |
| cactccatga | ggctcattgc | gtttctcagc | ctgaagggca | cctctcttct | gttttctctg | 1080 |
| caagtgggca | gcaagtgctc | caactctggg | atagagtgcg | actcctcagg | tacctgcatc | 1140 |
| aacccctcta | actggtgtga | tggcgtgtca | cactgccccg | gcggggagga | cgagaatcgg | 1200 |
| tgtggtgagt | cagccttgac | cttgggaagg | gactcctctg | ctcaccttgg | agacagcagc | 1260 |
| cgggtccagg | ggcctttggg | tgactgggcc | tggcgtgcgt | ccagtacgct | gacacatgat | 1320 |
| gtcattgaat | ccctgctcca | ggctgagccc | tggggctcag | agaggttgtg | tttccggccc | 1380 |
| aacctcaccc | agcaggtggg | agatgacagg | gccaccgagg | actgtgtcat | tggaaccaca | 1440 |
| cgtgctctga | actgccacag | gaagtcagtt | aagatgagca | aactgtttat | aaagttggag | 1500 |
| atgcaggcta | ggaacggtgg | ctcatgcctg | taatcccagc | actttgggag | gccgaggcag | 1560 |
| atggatcacc | tgaggtcagg | agtttgagac | cagcctgacc | aatatggtga | aaccttatct | 1620 |
| ccactaaaaa | tacaaaaatt | agccaagcgc | ggtggcgggt | gcctgtaatt | ccagctattc | 1680 |
| aggaggctga | ggcaggagaa | tcacttgaac | ctggaggcg | gaggttgcag | tgagctgaga | 1740 |
| tcacgccact | gcattccagc | ctgggagaca | gagctggctc | aaaaaataaa | ttaattaatt | 1800 |
| aaaaacaaaa | ttggagatgc | actatgttat | tttcaaaaca | agctgccttt | aaagatctat | 1860 |
| ctgttgtcac | agggtgggct | catctgtttc | atttttatttt | ctgtggttta | tctatttatt | 1920 |
| cattttaatg | aactaggaag | cattgctcct | atttatggca | taccacatga | tgtttggata | 1980 |
| cgtgtatgcc | tgtggcatgg | ctaagtcaag | ctagaacatg | ggccttacct | catatacgtg | 2040 |
| tcttattaag | aacacataaa | acctactctt | gtagtgattt | tcaaatatgc | aacatatagt | 2100 |

-continued

```
ttattaactg cagtcactat gatgtacaat agattgctcg aacttattcc tcctgtctaa    2160
ctaagatttt gtgacctctg accaacatct ccccagtgtt gtcaccccc gcccccagcc     2220 tctgatagct gcctttctac tctctgcttc tgtgagtttg atgtttatac attccacatg    2280
taagtggcct catgcagtgt ttctgtctct gtgtctggct tgttcactta gcgtaatgtc    2340
ctccagcttc atctatgttg ttggaaatga caggatttcc ttctttcttg tggctgaata    2400
gtattgcctt gtgcatatac accacatttt ctttatccct tcattcactg atggactctt    2460
aggttgatgt catgtcttgg ctgttgtgaa aaatgccgca gtgagcgtgg gcgtgcaggt    2520
ccctcttcaa cacacggatt tcctttcctt tggatataaa cccagcagtg agattgctgg    2580
atcacatggc agttctgttt ctcacctttt gaggaaactc catactgttt tccataatgg    2640
ctgtagcaac ttccactccc accccacgg tgcaaagtct ccatttctct tctacaacct    2700
caccaactcc tgttatttc catctttctg atagtagcca tttgaagagg tatgagatga    2760
tacctcattg tggttttcat ttgcatttt atttgtattt ttcatgaatt tttgagggtg    2820
atttcaaggg tagttagtga ctcgaacagg gaaacgatcc tgagtatgag ggttgtgcta    2880
atcatccccc tcctgccagc tgcgtacgga atggggctct gcagatggca gggagctggc    2940
tcgtttctct ttaagagctg ccttttactt ttcttcctct tccttttaaaa cttatttcct    3000 ggccggacgc agtggctcat gcctgtaatc ccagcacttt gggaggccga ggtgggcgga    3060
tcacgaggtc aggaattcca gaccagcctg gccaacatgg tgaaacccg tctctactaa    3120 aaatacaaaa attagccaga cgtggtggtg cgggcctata gtcccagcta ctcgggaggc    3180
tgaggcagga gaatcacttg aacctgggag gaggggttg cagtgagccg agattgcgcc    3240
actgcactcc agcctgggcg acagagccag actccatctc aaaaaacaaa aaaaagttat    3300
ttcccaagca cagccatgta ttccaggctt gtggatcagc gttggtggtg gtgtgtgctc    3360
tcatatctta gttccagcta agcacactct gacatgttta cactagaacc atttgttttt    3420
tctagaaata gaaatttcag aattgtagag tcagaggact taccagaaat ctcttaggta    3480
gttctcctcc cctccctcaa gtgcagtcct aacctcctgg agttttctgt agaaaccaca    3540
agcctcagag ctggccgaga attctagcca aagattttc catgccaaag taatccccc     3600 tctcctaagg gccatccttg gtggggactg gtttcctgtt aagccctcgc tgtcagtcct    3660
ggctgtggaa tttcctggtg aggagcactg gcccgtggag ctcggccctc gtgccggcct    3720
tgagcaggcc caagtgttcc gtgttcttga tacctttcct ccagcacagt cttgcttccc    3780
agaaaaaggt ttgcacttga aaatgatgca tttgctgatt aaacatagtt cttttgcttt    3840
atttggtttc taaaataaag tgggagtttt tgagattgag taacgtgagg ttaagatagc    3900
acgtggaatg gcttttctct ttctttctat ttttttttt tttttcctgg agacagggtt    3960
tcactctgtt gcccaggctg gagtgcagag gcatgaccat ggctcactgc aacttcgatg    4020
tcctggggtt aagcgatccc ccagcctcag cccccaagt ggctgggact acaggtgctc     4080
gccaccacac ctggctaatt tttgtatttt ttgtagaaaa tgggtttcat caatgttgtc    4140
cagactggtc tcgaactcct gacctcaagc aattctcctg cctcagcctc ccagactgct    4200
gggattacag gcgtgaacta ccacgcctgg cctggaatgg cttttgatgt tctcctatgt    4260
gcacatgtgg gtgaataaac accaacaaag tccttatgtt acctgaagag ttgctctctt    4320
cttaatattt aagtcgtatt tatttaaata ctttaatagt tgtacactat taaagtatta    4380
ttaggtcaaa atcaaggaag tacaaaaggg tatgctgtga aaatctctt cttccttgct     4440 ctgcttactt acctaccccg catcccccca tacaccccag acacacacac acacacacac    4500
```

```
acacacacac acacacgcat cactcccata catgcccacc tgtttaccag ccaatcacat    4560
ttcttggggc aactcatctg agttgcttct ctttccagag agttttttgca taaagaagca    4620 caggtatttc tgcgttacca tgaccctatt tcccagtggt tcctagccag ttgactctcc    4680
tgcactggat accatcctgg acagcattcc ttagggaaat gagcccctg tttttttccca    4740 ccatggcaca gttggtcctt tgcatggacg caccattatt gcccctgtct cttcttggtg    4800
gaccttaagg ttttctccat cctttttgctg taacacacac tgctccaagt gtgtgagcat    4860
atcagtagga aacgcttcca ggagtagaac tgctaggtca gagggcgtgt ggatctgtaa    4920
cctgacagac ctagaccggc ttcagtttgg ttttatccag tttccatatt gattattcat    4980
ataaaaggaa acagacaaac ataacgctgt gcatgtattc tctcttagac cagaacaggc    5040
atagggtgca ctttaattt gtccatttcg tagagtagaa attgttttg ctgaaatgaa    5100 caccttagga tgctgaagaa tatgacccgt cccatggaaa acattcaaaa atgtgtgtag    5160
cgctttcttc ccaagggtgt gtgtgcgcat attttaacac taattcactt tctacttccg    5220
ttgctatcct ttctgtgagt cttttctcaga atctcagaaa agaaactaaa ttgttcactc    5280
tagttatcaa tgctgtactc tatacctgga atttgctaaa agggcagatt ttaagtattc    5340
tcaccacaga aaagagaaaa gaaaatggta attatgtgac gtggtggaca tgttaactag    5400
ctttattatg gtgagcattt cacagcggat atccagtcat cacgctgtac acattaaaca    5460
tgtacaattg ggttttttg agacaaggtc tccttctgtc acccagtctg gagtgcagtg    5520
gctcagtcat ggctcattgc agcctcgacc tcctgggctc aatccatcct tcccctcag    5580 cctcctgaaa agctggggcc acaggcatgt accatcatgc caggctaatg catatatatt    5640 tatattttt ggtggagatg gggttggtct cgaactctgg gctcaagtga tcctcccgcc    5700
ttgcccttcc aaagtgctga gattacaggc atgaaccaca gcaccaggcc tacatgtaaa    5760 attttattt gtcaactata ctttgacaaa gctgagaaaa aaaatcctaa tatttaaaaa    5820
aaaaaaaaaa aggactagct tgagacccttt tccagctctc tggcttatca gctgccgtct    5880
cttccgggtg cagatagctg gaagggaaag aaaatcccta aaattaccca caagccaaga    5940
atgaagtgtc tcccctttgag ccacagtggc agttttgttt ttaatcatag aagtgtattt    6000
tgagccgggt gtgctggctc acgcctgtaa tccccgcact ttgggaggcc gaggtggggg    6060
gcggaggggg tggggatcgc ctgaggtcag gagttcgaga ccagcctgac caacatggag    6120
aaaccccgtc tctactaaaa atacaaaatt agccggcgtg gtggtgcatg cctgtaatcc    6180
cagctactca tgaggctgag tcaggagaat ctcttgaacc caggaggtgg aggttgcggt    6240
gagctgagat catgccattg cactccagcc tgggaacaag aaaaaaaag aagaagaaga    6300 agaagtgtat tcatttcagt tacttttaaa aaagtgaaca gactttatat tttagagcgg    6360
ttttaggttt acagaaaatg aaacagacag ggcagcgagc tccttgtact cctccccagc    6420
acacagttgc cctgttatga acatcccaca tcagtgctgt gcgttcatta acaccgatga    6480
acctgatgca tacattatga tgaactgaag tcctggactt cacccttct cttgtacagt    6540 tctgtgggat ttgacaaatg cataatgctg tacagccaca atgatagtat cgtccagagt    6600
agttctcctg ccttaaaacc tcttttgctg cacctgtttc tctctcccca ctcacccag    6660 ctatctgatc ttcttagtgc ctccgaagtt ttggtctttt caggatgttg tagcgttgga    6720
atcatggagt atgtagcctt caccacatac accttcctcc actttgttgg cttcctttac    6780
ttagtaatat gcattcaagt ttcctccatg ccttttcatg gcttgatagc tcatttcttt    6840
```

-continued

| | | | | | |
|---|---|---|---|---|---|
| ttagcaccaa | ataatattcc | gttgtccaga | tgtagcacaa | tgtttatcca | ttcatgtaac | 6900 |
| ctgtgaccga | ctcacagata | ggatgtggaa | tcactcacca | cagaggcatt | agacaataat | 6960 |
| cagacccaag | tcatttcatg | ggggaacaag | cccacaggta | ccagactgtc | cagtgagtca | 7020 |
| gggccactcg | taggaagtaa | gaagagaggc | tagagcatag | ccaggtcctc | actttatact | 7080 |
| ttaagcccat | gtgtatttct | cccaaaccac | acagcattgt | ttccatgctt | tcagctttgc | 7140 |
| atgaataacg | tgatacttga | acgcatcatt | tatcacttgc | tctctttccc | acagcgctgt | 7200 |
| tttcaagctt | cttcctgttc | atgatgctct | gcttaaccct | taagctgcat | gggattctgt | 7260 |
| tctgtgaata | cgcccacccc | atgtattatc | ctgcccagca | aaaagtcccc | aaaactctgg | 7320 |
| atggtggtta | cctctaggga | gggagagaag | agattgggaa | tagggagcga | cttcaacggt | 7380 |
| gtttgtaatg | ttttgtttct | ttaaataaaa | gagctgagat | catttcagca | gaatgttgat | 7440 |
| ttagagtctc | ctggacaatt | tgttgctcaa | agtgctctct | taaagagcac | tttaaaaaaa | 7500 |
| aaaacctttt | atcttattat | ttatttattt | atttattgag | acggagtttt | gctctgtcac | 7560 |
| ccaggctgga | gtggagtggt | gtgatctcag | ctcactgcaa | cctttacctc | ctgggttcaa | 7620 |
| gcaattcccc | tgcctcagcc | tcccaagtag | gtgggattac | agatgcgtgc | caccacactt | 7680 |
| ggctaatttt | tgcattttag | tagagatcgg | tttctccatg | ttggccaggc | tgatctcaaa | 7740 |
| cgcctgacct | caggtgatct | gcccgccttg | gcctcccaaa | gtgctggtat | tacaggcgtg | 7800 |
| agctaccatg | cctggcttat | cttatatatt | tttaaaaaca | gcttattgag | atctaattta | 7860 |
| tgtaccataa | aattcaagta | tataattcag | tgcttttata | tataaaacat | atatatgaaa | 7920 |
| tagcttattg | agatataatt | ttttatataa | aacagcttat | tgatatgtaa | tgtatgtacc | 7980 |
| ataaaattta | aatatataat | tcactggctt | ttatatattc | acgaatatgt | gcaactatca | 8040 |
| ccacagtcaa | ttttagcata | ttttcatcag | ctcataaaga | aaccccaagc | ccttgaacta | 8100 |
| tcaccccata | tccctcctcc | cagcccgtcc | ctcctactca | taagcaacca | ctaatctact | 8160 |
| tagtgtctat | agatttccta | ctctaggcat | tccatgtgag | cgggatcatg | caatacgtgg | 8220 |
| gctcacacaa | tataagtggc | attccatgtg | agtcggctca | tgcagtatgt | ccggctcctt | 8280 |
| tcactgagca | taaggtcttc | agcactcatc | caggttgcag | cctgtgtctg | aatttcattc | 8340 |
| cctcttctgg | ctgaatcgta | ttccattgtg | tatcttggac | atatcctatt | ctgctcaccc | 8400 |
| agccgttggt | gggcgtttgg | agtgttttcg | ccttttcagct | gtttttaagag | ggttgcagtg | 8460 |
| aacatttgta | caagttttgg | acccaatgcc | tgttttcaat | tctcttgtgt | agagagcact | 8520 |
| ttttagcaga | aaaagaatag | atttgtggcc | tccctttgtg | tgcggtcagt | gccttgagaa | 8580 |
| gagtgaactg | tgctgccacc | tccggagccg | tggagagcgc | ggggcttggg | tagcagctag | 8640 |
| gacgatacaa | gttgggacaa | ggccaggtgc | aatggctcac | gcctgtaatt | ccaacacttt | 8700 |
| gggagaccga | ggcaggggga | tcacctgagg | tcaggagttc | aagaccagcc | tggccaacat | 8760 |
| ggtgaaaccc | catctctaat | aaaacagaaa | aattaactgg | acgggtggt | ggacgcctgt | 8820 |
| aatcccagct | actcgggagg | ctgaggcagg | agaatcactt | gaacctggga | ggcggaggct | 8880 |
| gcagtgagtg | gagatcagac | cactgcactt | cagcctaggt | gacagagcga | gactccgtct | 8940 |
| caaaaaaaag | aaaaaaaaag | aaagaaactc | atggataatc | ctccctctcg | tgcagttcgc | 9000 |
| ctctacggac | caaacttcat | ccttcaggtg | tactcatctc | agaggaagtc | ctggcaccct | 9060 |
| gtgtgccaag | acgactggaa | cgagaactac | gggcgggcgg | cctgcaggga | catgggctat | 9120 |
| aagtgagtat | ggggcagcac | ccgccgagtg | acagtaacag | acagcagaaa | cacgagaaga | 9180 |
| ccctctctct | gcctccctgt | gaaagcaccg | gcacatgagt | gctgggggaca | attgtcacct | 9240 |

```
tccaaaagct gagccctata accagcaggt ggaatttgtc ctgctagggc tgtgcccagc    9300
acacagacct tggctcactg ccaccttgcc ctgcctcctc cttggcctct atagactcct    9360
ggttgctcgg gagtgcccag tgctgtggtc atctggtcag aggggtaggc tgagggcgtt    9420
aggtgcctct ttttccaagg tgcctctcag ccagggtcca ttcacctccc tgggtagagg    9480
ttggaccaga acagctggcg aggagggttg ggctggggag agcagcagag acaaatcctg    9540
tgccagtttc acttcattcg ggagccatgg aagccttttg agctggggag agaatcaatc    9600
aatcagactg atacttaaaa aatgtcattc ctgctcgtag ctctgaggga aggtgggaag    9660
gcttaacagg gtgtgtgtcg cctgacagtg attcctaacg ggggtggggc ggtggttacc    9720
atttaccagc actgcctggg gagatgcggc agccctcagg catcggggga gagggtggta    9780
ggatgctact gccactttgt tttccatggg agggtcccca ggtgatttct atgcaacttt    9840
agggtattca atatgccagt tttcagaatg aattaccact cggtgagaaa gttggcatct    9900
tagctagtca ctgtgacatc cctaaacagc aggggtgaat tacacagcaa agccccccca    9960
tcacagtcca ggaacctggt ggaattgata actggggcca tgttaacatc tgtacctttt   10020
attagattaa atgtgtgtat gattatacaa tcctatgtcc ttctcatagt ttcttgatcc   10080
taacctggat aagaaacacg accaatgaag gaattttgtc tgacacttta gggttattga   10140
atcgaaaaat cgttacaata ttctagcact tggttagaac gtgtgatttt ttttcctaaa   10200
tgctaaggtt tttccctctt attctgaatg tcgtatgagc ggtattatga catagtatag   10260
gatttgtgtt tgcttatgcc ttaaccatta tcacaaataa ggttttcttt tttaggaata   10320 attttttactc tagccaagga atagtggatg acagcggatc caccagcttt atgaaactga   10380
acacaagtgc cggcaatgtc gatatctata aaaaactgta ccacaggtat gcagcaattt   10440
cttcttgaaa aattttggaa tgaaatcaac taggagacac catggggaat cgttgtcctg   10500
agtctgattt ctctgagctg caatactcgg tctggatggg ttttgcattg ggaggagatt   10560
agagtctgac caggcctggt tactctaagc agcccttggt ttattcatag gaagtggctg   10620
aggtttctct gctatttcat tttcagcctc taccgtctgc ccttgttggt agcggctcac   10680
acttgcaaca tcgacattca actctattta gttttctttc ctcttcagac atttagaggt   10740
gtacctattt tgtcagggcg tggttctagg aatccaagat aatgtctcag tgtcccagcc   10800
agggtgaccg gctcattcca gtttgccagg gacttcactg gcttgagcaa gggaagtcct   10860
gctccattcc aggcagctgg gctggctggt cccgttagcc ccaaccccgg acagcagtg    10920 ccagagggtg ctctgtgagg gatgggcagc attctggcgg cctgggaatg agttgtggtg   10980
tttccagggg gtagaagtgg gtacaagcca caggtcacat gatgagtggc tgacctggct   11040
gggagggcag aagaggggat ggacttaggc tcttcctttt gctttgcaca tatttaggat   11100
gtttgcagac ttgctatgat tgttgctgtt atgtgttttc tgatgtgaaa gatacacagt   11160
gtcctttgcc catgagctct ccttgcctcc caggtcccca gggcttatgc ctggtgtcta   11220
ggcatcacct ccctgcctgc caggtgccag gtgctgcatt tcgggggagg atgaactaat   11280
caccccgcgc cacctttcct ctgagtggga gcctggggca ggtttgcatt cctggaggcc   11340
gctggtggag gggtctgggg gcctgacttc cactgcagcc tgctgtcctg gggaatgtgg   11400
cagggcaagc ccagtgggga gggctgtgca cggccaggtg cacccatcaa aacagcaggg   11460
ctgcggtttg tccctgtgga gaagctaaac acagctgcct gggcactttg taaatgctga   11520
gtggttcttt gtctttctgg gttacacacg gaatcaggga gccaagtcca gccgggcagg   11580
```

```
gacgggggga ggggaggagg tgctgccgtc ccttggcaag agccttggga actcacaagg    11640
aggctggagg gcttggaaga aagaagagaa ggccattgtc tggtaggctc tattctatct    11700
cggtggtggt ggtgggggga ggcgcacttc ttttcctctt tctgtgcagc agttgccctt    11760
tgatgcctga gttcttggct tgttttctgt cgggcttctg tgaataacca catgtgccct    11820
ggcgctgtga ccacacaggg ctatccctac cgaccttagg attcttagga aatgtcttct    11880
cttaaagggg acatgtcttc acttggccgt gtcagtgccc cagagccaga gtccacctgg    11940
aatgcacctg tagtcactga gaacccgggg ggtgtgcctt agtaagaagg tgtcaggaag    12000
gacctattat tgtagggcct gggctcctgc aaggtggttt gggggtggtt ggaggaagca    12060
gagatttgct ctggattgga tgctgtcagg aagcaggggt aattctgtga ggctgcttta    12120 ttatttttt tctaggagga ggttggaatg aggctaggct aaagctgtga ttggtaaaga    12180
aacgtccgtc gctcaagtta gccaggacag gaggagacat cagatcgtga ttttgtggtt    12240
gtgagcacaa ggttcctgtt ctgtctgttc agacatcatt tcggaggagg ctccttgtgt    12300
cttgccccat ctcaggcatg gagggggccta gtccgatatt gacgctcagt gaataaattc    12360
aggttccgca gagcacacgg cccagctatc agggcgggcc agctctgcat gccaggggcc    12420
gcgtcttccc ttctcagcat agcctgggaa attcactgca ggacaaaatg catcagttac    12480
ttcctcttca tccataacct gggatgtttg actcccaaat gagtaactct tacgtttctt    12540
ctaatcctag ggaaactatt ggttatattg ctttcaacac tacaaattta aagcagttat    12600
aggagcccag aggtttccaa atggcttcct taaaaattag aagatgattt taaattccaa    12660
gaggaaaaac aaaactagca ttattgtata cttaccctca caaccgtcct aggagctggt    12720
acaattttaa gagaggttaa gtaacttgcc caaggtcaca ctgtggggat gtgagccgcg    12780
taccttggct cagtgtctgg tctttgccac tgtccctata tggatttact taccttattg    12840
gagttgtaac tagcagaccc ttctatgtct cagaagacag gagagggaac atcggaagaa    12900
atgactgatt tctaagcatg tgagaggcag gtgactccgc actatcgtga ccagaatttc    12960
ccctgttctt tttgcagtga tgcctgttct tcaaaagcag tggtttcttt acgctgtata    13020
ggtaagttca tctggagtcc cccttttgat acttctaact aggaaaagct ctctactttc    13080
agaacagtac tccctgtgtc tctggggcg tgggagggaa gaaggtgggg tcacgggttg    13140
gaatgtgccc agcggcgtct cgctctttcc aaggagctcc tggtttagat ttccatggcc    13200
tgtagacacc ttcagccttg ggtccaaggg acaccccctg agatcaggca cgctcaagaa    13260
gctgacaaag ccctacactt tatgccaccc atgagctgga ggcccggcag gtctctttct    13320
ccagaaagca aaggggggtg gcgttagtga gccctggcag ccacctaacg tggacttgga    13380
gcatctgcgg ggctgtggtc cagcaccacc gtgtggccac caggtgctca tcagccagtg    13440
ggacccggga ggagggacaa gaccagagaa caacagtgct cttgcctctt ctctcctgaa    13500
ttttggacgg tggcttagac ttgggtgtcc ccatctctgt gtttagagtg cttacagttt    13560
ccaaactgtt tgcaaatgtg gaagccaccg tccctctcct ctgggatggc ccagtgctgt    13620
cgtggggccg tggtcctgag ctcagctttt catttgaaga ggtggaagga gctgacaccg    13680
tcccatcccg gcagggctgg ctcaggtctt ctttaggtcc tgagtggggg tccagcacag    13740
ccccaagggt gcgtggcacc cgccctgccc tctgcccatg cactcatctc ctggtggaga    13800
agacactcac acacaggaag cagggaaggc agcagacctc actcacccct cacccctca    13860 ctcaccccct actcaccccc tcaacctctc attcaccacc caccccctcg cccccctcact    13920 cacccccctca ctccctcaac cctcactcac ctcctcactc cctcaaccct cactcacctc    13980
```

```
ctcacctcct cactctcccc ctcatccctc cctcacccca ccccgtcacc tcctcactca    14040
cctcctcacc ccctcactca cccttcaccc cctcactcac cacctcacct cctcactcac    14100
cccctactca acccctcatt caccccctcac cccctcactc accctgcac cccctcactc    14160 acccctctcat ccactcaccc acctgctcac ctcctcactc aaccccctcac cccctcacta    14220 atccctcact ccctcacccc ctcacgccct cactcacacc ttcacctcct cactcacccc    14280
ctcaccccct caacccctta cttacccct cactcatccc ttcaccccctc actcaccccc    14340 tctctcaccc attcaccccc tcactcatgc cttcaccccc tcactcacct cctcactcac    14400
accttcaccc ctcagtcacc ccctcactca cccccttcacc ccctcaatca tgccttcact    14460
ccctcactca cccctttcacc ctctgaatta ctccctcatc ccctcactca cccctcact    14520 caccccttca ccccctcacc caccacctca cccaccctc acccacccc tcacctcctt    14580 accccttcacc ccctcactc accctccacc ccctcactca ccacctcacc caccctcac    14640 ccaccccctc actcactccc tcatcccctc actcaccccc tcacccctc actcaccccc    14700 tcacccaccc ctcacccacc ccctcacccc ctcactcacc ccttcacccc ctcactcacc    14760
ccctcactca ccccttcacc ccctcactca ccacctcacc caccctcac ccaccccctc    14820 actcactccc tcaccccctc actcacccc tcacccctc actcacccc tcatctcctc    14880 actcacccc tcacctcctc actcacccgc tcacctcctc actcacccc tcgccccctc    14940 actcaccct caccccctca ccccctcact caccctcac ccctcgccc cctcactcac    15000 ccctcgccc cctcactcac ccctcaccc ctcaccccct cactcatccc ctcacctcct    15060 cactcaccc ctcacctcct cactcaccc ctcacctcct cactcaccc ctcacctcct    15120 cacccacccc ctcactcact ccctcaccccc ctcaccccct cactcacccc ctcacctcct    15180 cactcaccc ctcacctcct caccaccc ctcactcact ccctcacccc ctcaccccct    15240 cactcaccc ctcacctcct cactcacccc ctcacctcct cactcaccc ctcacctcct    15300 cactcatgcc ctcaccccct cactcaccct ttcacctcct tgctcatccc ctcacttacc    15360
ccctcacttc gtcaatcacc cccccacctc gtcaatcacc ccctcaccctt ttcactcacc    15420 ccctcactca cccccttact tcctcactta cctcctcacc ccccactcac ccctcaccc    15480 cccactcacc ccctcacccc acactcaccc cctcaccccc cactcaccccc ctcaccctc    15540 tcacctcctc actcaccccc tcacctcctc acttatcccc tcaccccctc aattaccccc    15600 tcacccctc aattactccc tcatccttc aattacccac tcaccccctc acctcctcac    15660
tcctcactca ctccctcact caccccttca ccttctcact cacctcctcg tctcctcacc    15720
ccctcactca cttccagccc tgcccctccc atcttccttt tctttgtgtg agaatctggg    15780
gtccctgagt ggtgtcagtc cctccaagac tcaaggagtc cccagggcct tgttatccag    15840
aacaccccca cctgggtccc gggagacccc atgggatcac aggagtgttc agggaagtgg    15900
tgcttcctgg gtctgggtgg gctggagggg catcctccct tccccaagag gagaccccca    15960 ggagcccct aagtccatcc ccagcagtgg tgccctgcc ctgtccttgc agcctgggag    16020
acccttggga ggggcgggcg ctgggtggct gggcggcttc tgctggtctc acccactgg    16080 cctcctgttt gtcatcctca gcctgcgggg tcaacttgaa ctcaagccgc cagagcagga    16140
ttgtgggcgg cgagagcgcg ctcccggggg cctggccctg gcaggtcagc ctgcacgtcc    16200
agaacgtcca cgtgtgcgga ggctccatca tcaccccga gtggatcgtg acagccgccc    16260
actgcgtgga aaagtatgcc aggggcggcg cgggccgggt gggggctcag ggctggccta    16320
```

```
cagccaccct gtgaccttga gcaggtctca acccttgcag ccccggcatc cttgtgttta   16380
aatggggaga gtattgcacc tgcttcctag ggctgtgaga catcaagtgc gctcatgcca   16440
ggcagtgcat ggctgtatgc actgagtgtc cctgcacgc agggcacagg gtgcaggtgg    16500
aacattctcc acgatgtcgc cgtgaccagc gttccttcca gccactgtcc tctgagctct   16560
gtcctgccct tgagcaaagc ccctgccccc tgaggtatcc tgtctccggg acgctagtcc   16620
caggagaggg cacactcaga caggcttcag gctgccctgc tggaaggtcc ctggggttaa   16680
gcgttcttgg ccacagcatt gctcatgcag agggttaggt aggggtgagg ctagccgtga   16740
cagtattagc atttatggac gctaccaccc cctccccttt tccttaaaca catagtgctt   16800
ttggtcacat gctgctttgg aggaggcctc acttggcgga tgtattttc tgccttagag    16860 agaggctgaa ctgggtttga ctgttggccc agccctctct tgctgcgtgc cttagacga    16920 ttcactcaac gtctctgatc catggcatgt acaactataa gatgggcatg cccttctcct   16980
ctcgggctgt tatgaaggtc aaggaagcaa gggctgttac ccaagggtgc tcccttctct   17040 cccctcttc acacccccag gtgctctggg ccctctagga actgggtttc tctcaagggc    17100
tgttacccaa gggtgctccc ttctctcccc ctcttcacac cactgggtgc tctgggccca   17160
ctaggagctg ggattctctt aagagggaaa ctcttggata aggaaatgg tttgattgat    17220 atcggacaag tctgttcatt agtatccatt tattaagcac ctaccatgtg ccaggaaatg   17280 cttttggcgta caaaggaaaa taagggccag tcctgctaga aatggccttg aaaccccagg   17340
gagggatgtc ggcccattgt gggtgctgca gattccttga aggtgatgca agagccagaa   17400
agaaggatga tgtgggggc tgaggcaggg agtcggggtt ggggagtgt ggggagaag     17460 gggagaccga gcacctcttc cactatctcc ctgtgtggtt tttggtgaac catcctgcct   17520
ctgggtgtct tgcctccagc ttctgacgtt ggaagttcat ccactgagag ctctgtgttt   17580
atggctctga gatactgagt ccttcttctc tcccagacct cttaacaatc catggcattg   17640
gacggcattt gcgggatt tgagacaatc tttcatgttc tatggagccg ataccaagt     17700 agaaaagtg atttctcatc caaattatga ctccaagacc aagaacaatg acattgcgct   17760
gatgaagctg cagaagcctc tgactttcaa cggtacgtgt ggctcaggct tgcaagcag   17820 gttggcagaa tcttaaagag atgttgattg gaaatgacac ttgtgctatg ccaaatggaa   17880
gggaggcatt tgcgttgagc gagggtagcg tgcagcgggt ggccaatggg agaggctcac   17940
agaggctaag agcacctgcc gcatttttggg ggaggcagca gccaccacat ctgttctgta   18000
ctgtactgag tggtggtgat tcaagccagg catggaaaag gctagaacag gcttttccca   18060
ctgcagcacc cttgacatct gggtggttct ctgttgtagg gctctcttgt gccttgtagg   18120
atgtttaaca gcgtccccag cctctaccca ctggaggcca gtagctacca agctgtgaca   18180
accagtgttg cctgctgaca ttgccaaaca tccgctttga ggcaaagtca cttccagttg   18240
agaactactg gcctaaaatg tgtaaagatc cttgattttt aaagatacat tctaaaacca   18300
agttgcttaa ttcaggacaa acatgctttc tcttagcctc ttattcggtc ccactctggt   18360
ccatccaagg gtctggaatg ttctagcccc atgtggatac agaagaagca aaacctcagc   18420
cctccctaca gcatgtctgt attcacattg ggaaatggtt cacatataga agagcgaatg   18480
cctgagcaat ggcgtggtgc ctctggggcg aaagctgact ccattgactc catcggcttt   18540
ttggctgttg cctcctgtgt gtctttcccg tcttgatcac ctggagatat gtaatttgg    18600 aagcagagct agcaaataat tcctcttata agcagagcta gcaaataatt ctacttataa   18660
gtagcataac gtcttgcctg ccagaaggag aggtctggca gggggagaaa gtgagaatgt   18720
```

```
gggacttgtt gggatgcagg gtcctctggg cagggtggcc agggtgccag gcccagcagc   18780
ctgcatgtgg gaaggccagg tggagacata ggtgatacc gcctggctca ctgtgttttc    18840
tcttcttgaa acagacctag tgaaaccagt gtgtctgccc aacccaggca tgatgctgca   18900
gccagaacag ctctgctgga tttccgggtg ggggccacc gaggagaaag gtgaggctgc    18960
tcctgggcac acaggactgc agggcccaca gatggagcat tgggttcgga agtgggaggt   19020
ccaggtttta atcccagttc tactactcaa tgactggatg actttggttg attccccag    19080 tccttgtgcc tcagtttctc catctgctaa gtgggagaaa tcctgcccag cctacctaat   19140
acactgtgtt cttatcgtga tcacacagag cagcatgtgg aatggctttt gaagtatctg   19200
ggccatacga gtttagaggt gcaggatctc ctgtgttgca ctcattgtga gtttagagct   19260
gccctggaga tcccaccaag gcctgcgtgg ctgagtgaca gggggcttgg tgaggacggg   19320
catcctggac ccatggtggc cacatctaag cctgtcctct gccctgataa ccacagagag   19380
aggctctctc cacccacttc ctttgcaatc tgcatttctc tctgacagtc tttcaaatga   19440
agggagcctg gctgcttcat ttttatggag ggttggaagt gcttagtggc aggcacaaag   19500
gttcatttta catattgttt atatccttct caaaagcgtc taggccatac agacaacaaa   19560
tcctttcaaa caaggggaaa agtacaaagg ttgggtgatt tctggggagc gtcagggaag   19620
gtagtggggg gcatcctggc tcctcatcag cagaaactta ctacagtaga gccacaggct   19680
gggcaaaaga cctcatggaa tccaagatga agggaatatc gacaaatatt tgtgcgcacc   19740
tgcacctagt acaggctggg tgctactcag gtgctgggaa tgcagaagtg aacagagtaa   19800
gacaaatgtc tctgctgtca ggagctttac ctctcttctg gatgtcggtg gtggggacgg   19860
ggcaggtgtg gtcagacaga tgggagacaa acaactgagc gaggtacttc caaacatctg   19920
agggtgggga tcacaaggtc ccggctattt tgaaggggtg gtcaggaaag gcttctcgga   19980
agaggtggca tttgagctga gactcaaatg gcaaaaatgt gtacacatca aaaaggctag   20040
tgcatgtatc ttcaggtgtg gtcaaggggc caaggaggtg ggctgggcc agattgcata    20100 ggtccttgtg gattatggtg aagacaccag cttctcatct gcttgaggtg gggagatcgt   20160
gagccgggga gtgccatgat ctggcagctg cgtggggagt ggggatgaat ggatggagac   20220
gaggatgatg gtgacaagtc cattgctgtg gttccttgag acaggaagcc agctcatagc   20280
agagtgcggg cgtggatgtg aagagatgag ggtacactag gctagagcc accagactta    20340 ctgatgggtt gcatgtctgt gggagagaga gtgagaagtc agggacgatg gctttccact   20400
ctgtggctga agcccagggg tggcgggtgg tgccattttt caagccagga aatattggtt   20460
ggtgagaatt tggggtggga gaaggtgtga cggagggttc tggttttgca cactaagccc   20520
acggtgccca gaagatgccc gaggggaggc agcaaagcga gagtgggaaa tgcagaggtg   20580
gcaagtgcag gccgtgtctt gagaagctct aatgtgcagg ggagccgaga gcaggcggc    20640 ctagggaggg tcacgtgtgc tccagaagag tgtgtgcatg ccagagggga aacaggcgcc   20700
tgtgtgtcct gggtggggtt cagtgaggag tgggaaattg gttcagcaga accaagccgt   20760
tgggtgaata agaggggat tccatggcac tgatagagcc ctatagtttc agagctggga    20820
atttctttcc ctgaagctga actccagagc tgcattcagc acaggcaccg ccagttgtaa   20880
ggagaatcca ggtttcccag gagaggggtt ggtgctggga tgagctgacc ggggcagggc   20940
tggaaaatag ggctgtgacc atctgtgtag tgcgtgtgga ggtctcaggg agggaagtgt   21000
gctctccctg cgagagctgc aggcaacact gggagctcaa caagtctccc tgtccttagg   21060
```

```
gaagacctca gaagtgctga acgctgccaa ggtgcttctc attgagacac agagatgcaa   21120
cagcagatat gtctatgaca acctgatcac accagccatg atctgtgccg gcttcctgca   21180
ggggaacgtc gattcttgcc aggtaattca acattttat tctacctttg gtccttacca    21240
gatcctactg aacccccat gagagagagg gcattcttgg ggtcagcaga gcctcctcag    21300
tgacacggag ccagctcggg gcagtcatgg gaagtgacgg ccacaaacag tgcgaacgct   21360
tctggtggca gaaggaagta cagtcaacaa atcacacaca ccctctgaaa accggtatt    21420 tggtaaaagt gccagtggaa cagaaacaag tatttagact attttaaatt atgaacggca   21480
atttatttag taacttttag cttgaacaga ttaaaattca ggatggggc tatctctttg     21540 ggggttacat ctctgttacc atcaccccett gatggtggag attcgaagcc cacacagtca  21600
ctcgtaactc acactgcgac ccccgccccc caactcctct aggcctggtc agtggtgtgc   21660
ggcagattgt gacttgattt tctgctctct gtaccttgct gtgtcccaca gggtgacagt   21720
ggagggcctc tggtcacttc gaagaacaat atctggtggc tgataggga tacaagctgg    21780 ggttctggct gtgccaaagc ttacagacca ggagtgtacg ggaatgtgat ggtattcacg   21840
gactggattt atcgacaaat gagggtaact atcctgtcct ccttctgact gtgttctccg   21900
attcctcgag ccaaagccag acatctgtta ggcgtggttc tgctgctgga agctgactgg   21960
tgaccactgg tcagcatgaa gcaaactctg cttcctccag ccacagcccc atcccccag    22020 tgtccaccca ttgcccattg cctctcactg gcttcacttg catatttccc ctggtgtttg   22080
gatgaaaagc gctggggctc agcttgtgtg aaattccttg gtgctctgcc aaccacactt   22140
cgttctggct cagctgactc agctgttcca cccaggccac ctcacatcaa acttttttt    22200 tttttttttg agatggagtc tcactgtgtc gcccaggctg gagtgcagtg gcacaatctc   22260
gactcactgc aacctttgcc tcctgggttc aagtgattct cctgcctcag cctcccaagt   22320
agctgggact acaggcatgc gccaccacgc ccagctactt tttgtatttt tagtagagat   22380 gggtttctc catgttggcc aggctggtct cgaagccctg acctcaggtg attcaccca    22440 ctcagcctcc cacagtgctg ggattacaag tgtgaaccac ggtgcccggc ctcacatgaa   22500
acttttgatt tatagagagc agagggaaga gccggctgtg cccatccttt tctggggcca   22560
tcgagtggct cctgggcagc ccccaaggtt aggaagggca ggagcagcca gggttctctg   22620
atgccccaga ctcaagcacg agggaaggtc tcaggggttc catgtgagcc tcatggatgt   22680
ctctgcttag cagagccctg gctttgggca ttgtccagat agggggtgag aaccagatct   22740
tctcatctcc aggacctcag acgtatagtt ttctcagatt tctgtgcttt ctggggctgg   22800
gctactagtg gaagaaagca gtctattctg tcttctccca aatctcccag atgcccagtc   22860
tgttgaagga ggagcagaac caggggcct ttccgctga ggcccgacct gtgtctcctt     22920
caaatgacac gcgggactca gggccttccc atgaccatgg ggcccagggg gcgtcacctg   22980
gcccagggcc cagtgctaga aacagatgac cccaggagga ggaggcaggg caggagggaa   23040
gctggcaggg ctgggatggt cagccaggct gaggggcgga ctcgcaccag gatggagcta   23100
ggaaatgatc caggtgtgtt tggcggctgc aggtgggtcc gcatggctgt gcagggaggg   23160
aagggctgcg tggcaggaga gcagccgggg gaggcccaga ctctgctgaa gagatgcctg   23220
ttgtgccggc ctccacatcc gctgcccgct ccttccggag ctcctgcccc gccatgctca   23280
gcctgactct gaccaacacg ttggagagaa gaatgatccc tttgtgctat taagcttgct   23340
tatttggttt ctaagtgctt catgcgaacc tagaggaaaa aattattttc caccttttgtt  23400 tgtcttaaga aaataacaca cttttttttt tcctatttga acaggcagac ggctaatcca   23460
```

-continued

```
catggtcttc gtccttgacg tcgttttaca agaaaacaat ggggctggtt ttgcttcccc   23520
gtgcatgatt tactcttaga gatgattcag aggtcacttc atttttatta aacagtgaac   23580
ttgtctggct ttggcactct ctgccattct gtgcaggctg cagtggctcc cctgcccagc   23640
ctgctctccc taaccccttg tccgcaaggg gtgatggccg gctggttgtg ggcactggcg   23700
gtcaagtgtg gaggagaggg gtggaggctg ccccattgag atcttcctgc tgagtccttt   23760
ccaggggcca attttggatg agcatggagc tgtcacctct cagctgctgg atgacttgag   23820
atgaaaaagg agagacatgg aaagggagac agccaggtgg cacctgcagc ggctgccctc   23880
tggggccact tggtagtgtc cccagcctac ctctccacaa ggggattttg ctgatgggtt   23940
cttagagcct tagcagccct ggatggtggc cagaaataaa gggaccagcc cttcatgggt   24000
ggtgacgtgg tagtcacttg taaggggaac agaaacattt ttgttcttat ggggtgagaa   24060
tatagacagt gcccttggtg cgagggaagc aattgaaaag gaacttgccc tgagcactcc   24120
tggtgcaggt ctccacctgc acattgggtg gggctcctgg gagggagact cagccttcct   24180
cctcatcctc cctgaccctg ctcctagcac cctggagagt gcacatgccc cttggtcctg   24240
gcagggcgcc aagtctggca ccatgttggc ctcttcaggc ctgctagtca ctggaaattg   24300
aggtccatgg gggaaatcaa ggatgctcag tttaaggtac actgtttcca tgttatgttt   24360
ctacacattg ctacctcagt gctcctggaa acttagcttt tgatgtctcc aagtagtcca   24420
ccttcattta actctttgaa actgtatcat ctttgccaag taagagtggt ggcctatttc   24480
agctgctttg acaaaatgac tggctcctga cttaacgttc tataaatgaa tgtgctgaag   24540
caaagtgccc atggtggcgg cgaagaagag aaagatgtgt tttgttttgg actctctgtg   24600
gtcccttcca atgctgtggg tttccaacca ggggaagggt ccctttttgca ttgccaagtg   24660
ccataaccat gagcactact ctaccatggt tctgcctcct ggccaagcag gctggtttgc   24720
aagaatgaaa tgaatgattc tacagctagg acttaacctt gaaatggaaa gtcatgcaat   24780
cccatttgca ggatctgtct gtgcacatgc ctctgtagag agcagcattc ccagggacct   24840
tggaaacagt tggcactgta aggtgcttgc tccccaagac acatcctaaa aggtgttgta   24900
atggtgaaaa cgtcttcctt ctttattgcc ccttcttatt tatgtgaaca actgtttgtc   24960
ttttttgta tctttttaa actgtaaagt tcaattgtga aaatgaatat catgcaaata   25020
aattatgcaa ttttttttc aaagtaacta ctgcatcttt gaagttctgc ctggtgagta   25080
ggaccagcct ccatttcctt ataagggggt gatgttgagg ctgctggtca gaggaccaaa   25140
ggtgaggcaa ggccagactt ggtgctcctg tggttctcga gataacttcg tataatgtat   25200
gctatacgaa gttatatgca tggcctccgc gccgggtttt ggcgcctccc gcgggcgccc   25260
ccctcctcac ggcgagcgct gccacgtcag acgaagggcg cagcgagcgt cctgatcctt   25320
ccgcccggac gctcaggaca gcggcccgct gctcataaga ctcggcctta gaaccccagt   25380
atcagcagaa ggacatttta ggacgggact tgggtgactc tagggcactg gttttctttc   25440
cagagagcgg aacaggcgag gaaaagtagt cccttctcgg cgattctgcg gagggatctc   25500
cgtggggcgg tgaacgccga tgattatata aggacgcgcc gggtgtggca cagctagttc   25560
cgtcgcagcc gggatttggg tcgcggttct tgtttgtgga tcgctgtgat cgtcacttgg   25620
tgagtagcgg gctgctgggc tggccggggc tttcgtggcc gccgggccgc tcggtgggac   25680
ggaagcgtgt ggagagaccg ccaagggctg tagtctgggt ccgcgagcaa ggttgccctg   25740
aactgggggt tgggggagc gcagcaaaat ggcggctgtt cccgagtctt gaatggaaga   25800
```

```
cgcttgtgag gcgggctgtg aggtcgttga acaaggtgg ggggcatggt gggcggcaag    25860
aacccaaggt cttgaggcct tcgctaatgc gggaaagctc ttattcgggt gagatgggct    25920
ggggcaccat ctggggaccc tgacgtgaag tttgtcactg actggagaac tcggtttgtc    25980
gtctgttgcg ggggcggcag ttatggcggt gccgttgggc agtgcacccg tacctttggg    26040
agcgcgcgcc ctcgtcgtgt cgtgacgtca cccgttctgt tggcttataa tgcagggtgg    26100
ggccacctgc cggtaggtgt gcggtaggct tttctccgtc gcaggacgca gggttcgggc    26160
ctagggtagg ctctcctgaa tcgacaggcg ccggacctct ggtgagggga gggataagtg    26220
aggcgtcagt ttctttggtc ggttttatgt acctatcttc ttaagtagct gaagctccgg    26280
ttttgaacta tgcgctcggg gttggcgagt gtgttttgtg aagttttta ggcacctttt    26340 gaaatgtaat catttgggtc aatatgtaat tttcagtgtt agactagtaa attgtccgct    26400
aaattctggc cgttttggc tttttgtta gacgtgttga caattaatca tcggcatagt    26460
atatcggcat agtataatac gacaaggtga ggaactaaac catgggatcg gccattgaac    26520
aagatggatt gcacgcaggt tctccggccg cttgggtgga gaggctattc ggctatgact    26580
gggcacaaca gacaatcggc tgctctgatg ccgccgtgtt ccggctgtca gcgcaggggc    26640
gcccggttct ttttgtcaag accgacctgt ccggtgccct gaatgaactg caggacgagg    26700
cagcgcggct atcgtggctg gccacgacgg gcgttccttg cgcagctgtg ctcgacgttg    26760
tcactgaagc gggaagggac tggctgctat tgggcgaagt gccggggcag gatctcctgt    26820
catctcacct tgctcctgcc gagaaagtat ccatcatggc tgatgcaatg cggcggctgc    26880
atacgcttga tccggctacc tgcccattcg accaccaagc gaaacatcgc atcgagcgag    26940
cacgtactcg gatggaagcc ggtcttgtcg atcaggatga tctggacgaa gagcatcagg    27000
ggctcgcgcc agccgaactg ttcgccaggc tcaaggcgcg catgcccgac ggcgatgatc    27060
tcgtcgtgac ccatggcgat gcctgcttgc cgaatatcat ggtggaaaat ggccgctttt    27120
ctggattcat cgactgtggc cggctgggtg tggcggaccg ctatcaggac atagcgttgg    27180
ctacccgtga tattgctgaa gagcttggcg gcgaatgggc tgaccgcttc ctcgtgcttt    27240
acggtatcgc cgctcccgat tcgcagcgca tcgccttcta tcgccttctt gacgagttct    27300
tctgagggga tccgctgtaa gtctgcagaa attgatgatc tattaaacaa taaagatgtc    27360
cactaaaatg gaagttttc ctgtcatact ttgttaagaa gggtgagaac agagtaccta    27420
cattttgaat ggaaggattg gagctacggg ggtgggggtg gggtgggatt agataaatgc    27480 ctgctctttta ctgaaggctc tttactattg ctttatgata atgtttcata gttggatatc    27540
ataatttaaa caagcaaaac caaattaagg gccagctcat tcctcccact catgatctat    27600
agatctatag atctctcgtg ggatcattgt ttttctcttg attcccactt tgtggttcta    27660
agtactgtgg tttccaaatg tgtcagtttc atagcctgaa gaacgagatc agcagcctct    27720
gttccacata cacttcattc tcagtattgt tttgccaagt tctaattcca tcagacctcg    27780
acctgcagcc cctagataac ttcgtataat gtatgctata cgaagttatg ctagtaacta    27840
taacggtcct aaggtagcga gctagctcca cgtggctttg tcccagactt cctttgtctt    27900
caacaacctt ctgcaagaaa accaagggcc tgaattttaa cttcctg               27947

<210> SEQ ID NO 6
<211> LENGTH: 25333
<212> TYPE: DNA
<213> ORGANISM: Artificial Sequence
<220> FEATURE:
<223> OTHER INFORMATION: Recombinant polynucleotide
```

<400> SEQUENCE: 6

```
gcagagtcta agaaatcgct gtgtttagcc ctcgccctgg gcactgtcct cacgggagct        60
gctgtggctg ctgtcttgct ttggaagttc agtaagtgca gggagcctcg atcccaccat       120
gtgctcctgc agtccccagt gctctgagcc agacctgct ctctgggcta ttgagacctc       180
tggaggccct ccgtgaggtt cctctcttac ataacgaggc tgtctctctt cccttctctt       240
gtttagctat gagattgaca catcatgggg aaagcattta gaatgtaccc agtgctttgg       300
ggtgcttggt gccacccagc actgtgagca caggttcttc taccttgggg ccacacccag       360
ttacctgtat ctcactgcac agcagtggct gttggggacc aggcccaccc ctccatgtcc       420
cacctcctgc aactgcagcc tgagccttcc catcagcctg gggtggtgca gacccatgtg       480
ccattgtgga tccttcaagt tacctgtgtg cagagagga cgtgtgagtg ccgtccaaac       540
ccaaacactg agagggtcct tcccattgcc cccacggaag taaggtgccc cagtgctaat       600
tccacttata cttgctggtg gcaaggacac ttctcctcct tattaaagtg ggggattggc       660
tgggtgaggt ggctcacgcc tgttatccca gcactttaag aggccaaggc aggtggacca       720
cctgaggtca ggagtttgag accacaagcc tggccaacat gttgaaactc catctctact       780
aaaaatacaa aaattagtca ggcgtggtgg cgtgcacctg taatcccagc tacttaggag       840
gctgggcag gaggatcact tgaacccagg agttggaggt tgcagtgagc caagattgtg       900
cccctgcact ccagcctggg tgacagaatg agacttcatc tcaaaaacaa aacaaaacaa       960
aacacagtgg ggccaggagt tggaggctgc agcgagctac agtaatgcca cggtgttcct      1020
cactccatga ggctcattgc gtttctcagc ctgaagggca cctctcttct gttttctctg      1080
caagtgggca gcaagtgctc caactctggg atagagtgcg actcctcagg tacctgcatc      1140
aaccctctca actggtgtga tggcgtgtca cactgccccg gcggggagga cgagaatcgg      1200
tgtggtgagt cagccttgac cttgggaagg gactcctctg ctcaccttgg agacagcagc      1260
cgggtccagg ggcctttggg tgactgggcc tggcgtgcgt ccagtacgct gacacatgat      1320
gtcattgaat ccctgctcca ggctgagccc tgggctcag agaggttgtg tttccggccc      1380
aacctcaccc agcaggtggg agatgacagg gccaccgagg actgtgtcat tggaaccaca      1440
cgtgctctga actgccacag gaagtcagtt aagatgagca aactgtttat aaagttggag      1500
atgcaggcta ggaacggtgg ctcatgcctg taatcccagc actttgggag gccgaggcag      1560
atggatcacc tgaggtcagg agtttgagac cagcctgacc aatatggtga aaccttatct      1620
ccactaaaaa tacaaaaatt agccaagcgc ggtggcgggt gcctgtaatt ccagctattc      1680
aggaggctga ggcaggagaa tcacttgaac ctgggaggcg gaggttgcag tgagctgaga      1740
tcacgccact gcattccagc ctgggagaca gagctggctc aaaaaataaa ttaattaatt      1800
aaaaacaaaa ttggagatgc actatgttat tttcaaaaca agctgccttt aaagatctat      1860
ctgttgtcac agggtgggct catctgtttc attttatttt ctgtggttta tctatttatt      1920
cattttaatg aactaggaag cattgctcct atttatggca taccacatga tgtttggata      1980
cgtgtatgcc tgtggcatgg ctaagtcaag ctagaacatg gccttacct catatacgtg      2040
tcttattaag aacacataaa acctactctt gtagtgattt tcaaatatgc aacatatagt      2100
ttattaactg cagtcactat gatgtacaat agattgctcg aacttattcc tcctgtctaa      2160
ctaagatttt gtgacctctg accaaacatct ccccagtgtt gtcacccccc gcccccagcc      2220
tctgatagct gccttctac tctctgcttc tgtgagtttg atgtttatac attccacatg      2280
```

```
taagtggcct catgcagtgt ttctgtctct gtgtctggct tgttcactta gcgtaatgtc    2340
ctccagcttc atctatgttg ttggaaatga caggatttcc ttctttcttg tggctgaata    2400
gtattgcctt gtgcatatac accacatttt ctttatccct tcattcactg atggactctt    2460
aggttgatgt catgtcttgg ctgttgtgaa aaatgccgca gtgagcgtgg gcgtgcaggt    2520
ccctcttcaa cacacggatt tcctttcctt tggatataaa cccagcagtg agattgctgg    2580
atcacatggc agtctgtttt ctcacctttt gaggaaactc catactgttt tccataatgg    2640
ctgtagcaac ttccactccc accccacgg tgcaaagtct ccatttctct tctacaacct    2700
caccaactcc tgttattttc catctttctg atagtagcca tttgaagagg tatgagatga    2760
tacctcattg tggttttcat ttgcattttt atttgtattt ttcatgaatt tttgagggtg    2820
atttcaaggg tagttagtga ctcgaacagg gaaacgatcc tgagtatgag ggttgtgcta    2880
atcatccccc tcctgccagc tgcgtacgga atggggctct gcagatggca gggagctggc    2940
tcgtttctct ttaagagctg ccttttactt ttcttcctct tcctttaaaa cttatttcct    3000
ggccggacgc agtggctcat gcctgtaatc ccagcacttt gggaggccga ggtgggcgga    3060
tcacgaggtc aggaattcca gaccagcctg gccaacatgg tgaaacccg tctctactaa    3120 aaatacaaaa attagccaga cgtggtggtg cgggcctata gtcccagcta ctcgggaggc    3180
tgaggcagga gaatcacttg aacctgggag gaggggttg cagtgagccg agattgcgcc    3240
actgcactcc agcctgggcg acagagccag actccatctc aaaaaacaaa aaaaagttat    3300
ttcccaagca cagccatgta ttccaggctt gtggatcagc gttggtggtg gtgtgtgctc    3360
tcatatctta gttccagcta agcacactct gacatgttta cactagaacc atttgttttt    3420
tctagaaata gaaatttcag aattgtagag tcagaggact taccagaaat ctcttaggta    3480
gttctcctcc cctccctcaa gtgcagtcct aacctcctgg agttttctgt agaaaccaca    3540
agcctcagag ctggccgaga attctagcca aagattttc catgccaaag taatcccccc    3600
tctcctaagg gccatccttg gtggggactg gtttcctgtt aagccctcgc tgtcagtcct    3660
ggctgtggaa tttcctggtg aggagcactg gcccgtggag ctcggccctc gtgccggcct    3720
tgagcaggcc caagtgttcc gtgttcttga taccttccct ccagcacagt cttgcttccc    3780
agaaaaaggt ttgcacttga aaatgatgca tttgctgatt aaacatagtt cttttgcttt    3840
atttggtttc taaataaag tgggagtttt tgagattgag taacgtgagg ttaagatagc    3900
acgtggaatg gcttttttctt ttctttctat ttttttttt ttttcctgg agacagggtt    3960 tcactctgtt gcccaggctg gagtgcagag gcatgaccat ggctcactgc aacttcgatg    4020
tcctggggtt aagcgatccc ccagcctcag cccccaagt ggctgggact acaggtgctc    4080
gccaccacac ctggctaatt tttgtatttt ttgtagaaaa tgggtttcat caatgttgtc    4140
cagactggtc tcgaactcct gacctcaagc aattctcctg cctcagcctc ccagactgct    4200
gggattacag gcgtgaacta ccacgcctgg cctggaatgg cttttgatgt tctcctatgt    4260
gcacatgtgg gtgaataaac accaacaaag tccttatgtt acctgaagag ttgctctctt    4320 cttaatatt aagtcgtatt tatttaaata ctttaatagt tgtacactat taaagtatta    4380
ttaggtcaaa atcaaggaag tacaaaaggg tatgctgtga aaatctctt cttccttgct    4440 ctgcttactt acctaccccg catccccca tacaccccag acacacacac acacacacac    4500
acacacacac acacacgcat cactcccata catgcccacc tgtttaccag ccaatcacat    4560
ttcttggggc aactcatctg agttgcttct ctttccagag agttttttgca taaagaagca    4620 caggtatttc tgcgttacca tgaccctatt tcccagtggt tcctagccag ttgactctcc    4680
```

| | | | | |
|---|---|---|---|---|
| tgcactggat | accatcctgg | acagcattcc | ttagggaaat | gagcccctg ttttttccca | 4740 |
| ccatggcaca | gttggtcctt | tgcatggacg | caccattatt | gccctgtct cttcttggtg | 4800 |
| gaccttaagg | ttttctccat | cctttgctg | taacacacac | tgctccaagt gtgtgagcat | 4860 |
| atcagtagga | aacgcttcca | ggagtagaac | tgctaggtca | gagggcgtgt ggatctgtaa | 4920 |
| cctgacagac | ctagaccggc | ttcagtttgg | ttttatccag | tttccatatt gattattcat | 4980 |
| ataaaaggaa | acagacaaac | ataacgctgt | gcatgtattc | tctcttagac cagaacaggc | 5040 |
| atagggtgca | cttttaattt | gtccatttcg | tagagtagaa | attgttttg ctgaaatgaa | 5100 |
| caccttagga | tgctgaagaa | tatgacccgt | cccatgaaaa | acattcaaaa atgtgtgtag | 5160 |
| cgctttcttc | ccaagggtgt | gtgtgcgcat | attttaacac | taattcactt tctacttccg | 5220 |
| ttgctatcct | ttctgtgagt | ctttctcaga | atctcagaaa | agaaactaaa ttgttcactc | 5280 |
| tagttatcaa | tgctgtactc | tatacctgga | atttgctaaa | agggcagatt ttaagtattc | 5340 |
| tcaccacaga | aaagagaaaa | gaaaatggta | attatgtgac | gtggtggaca tgttaactag | 5400 |
| ctttattatg | gtgagcattt | cacagcggat | atccagtcat | cacgctgtac acattaaaca | 5460 |
| tgtacaattg | ggttttttg | agacaaggtc | tccttctgtc | acccagtctg gagtgcagtg | 5520 |
| gctcagtcat | ggctcattgc | agcctcgacc | tcctgggctc | aatccatcct tcccctcag | 5580 |
| cctcctgaaa | agctggggcc | acaggcatgt | accatcatgc | caggctaatg catatatatt | 5640 |
| tatattttt | ggtggagatg | gggttggtct | cgaactctgg | gctcaagtga tcctcccgcc | 5700 |
| ttgccttcc | aaagtgctga | gattacaggc | atgaaccaca | gcaccaggcc tacatgtaaa | 5760 |
| attttattt | gtcaactata | ctttgacaaa | gctgagaaaa | aaaatcctaa tatttaaaaa | 5820 |
| aaaaaaaaa | aggactagct | tgagacccttt | tccagctctc | tggcttatca gctgccgtct | 5880 |
| cttccgggtg | cagatagctg | gaagggaaag | aaaatcccta | aaattaccca caagccaaga | 5940 |
| atgaagtgtc | tccctttgag | ccacagtggc | agttttgttt | taatcatag aagtgtattt | 6000 |
| tgagccgggt | gtgctggctc | acgcctgtaa | tccccgcact | ttgggaggcc gaggtggggg | 6060 |
| gcggaggggg | tggggatcgc | ctgaggtcag | gagttcgaga | ccagcctgac caacatggag | 6120 |
| aaaccccgtc | tctactaaaa | atacaaaatt | agccggcgtg | gtggtgcatg cctgtaatcc | 6180 |
| cagctactca | tgaggctgag | tcaggagaat | ctcttgaacc | caggaggtgg aggttgcggt | 6240 |
| gagctgagat | catgccattg | cactccagcc | tgggaacaag | aaaaaaaag aagaagaaga | 6300 |
| agaagtgtat | tcatttcagt | tacttttaaa | aaagtgaaca | gactttatat tttagagcgg | 6360 |
| ttttaggttt | acagaaaatg | aaacagacag | ggcagcgagc | tccttgtact cctccccagc | 6420 |
| acacagttgc | cctgttatga | acatcccaca | tcagtgctgt | gcgttcatta acaccgatga | 6480 |
| acctgatgca | tacattatga | tgaactgaag | tcctggactt | caccctttct cttgtacagt | 6540 |
| tctgtgggat | ttgacaaatg | cataatgctg | tacagccaca | atgatagtat cgtccagagt | 6600 |
| agttctcctg | ccttaaaacc | tcttttgctg | cacctgtttc | tctctcccca ctcaccccag | 6660 |
| ctatctgatc | ttcttagtgc | ctccgaagtt | ttggtctttt | caggatgttg tagcgttgga | 6720 |
| atcatggagt | atgtagcctt | caccacatac | accttccttc | actttgttgg cttcctttac | 6780 |
| ttagtaatat | gcattcaagt | ttcctccatg | ccttttcatg | gcttgatagc tcatttcttt | 6840 |
| ttagcaccaa | ataatattcc | gttgtccaga | tgtagcacaa | tgtttatcca ttcatgtaac | 6900 |
| ctgtgaccga | ctcacagata | ggatgtggaa | tcactcacca | cagaggcatt agacaataat | 6960 |
| cagacccaag | tcatttcatg | ggggaacaag | cccacaggta | ccagactgtc cagtgagtca | 7020 |

```
gggccactcg taggaagtaa aagagaggc tagagcatag ccaggtcctc actttatact      7080
ttaagcccat gtgtatttct cccaaaccac acagcattgt ttccatgctt tcagctttgc      7140
atgaataacg tgatacttga acgcatcatt tatcacttgc tctctttccc acagcgctgt      7200
tttcaagctt cttcctgttc atgatgctct gcttaaccct taagctgcat gggattctgt      7260
tctgtgaata cgcccacccc atgtattatc ctgcccagca aaagtcccc aaaactctgg       7320 atggtggtta cctctaggga gggagagaag agattgggaa tagggagcga cttcaacggt      7380
gtttgtaatg ttttgtttct ttaaataaaa gagctgagat catttcagca gaatgttgat      7440
ttagagtctc ctggacaatt tgttgctcaa agtgctctct taaagagcac tttaaaaaaa      7500
aaaacctttt atcttattat ttatttattt atttattgag acggagtttt gctctgtcac      7560
ccaggctgga gtggagtggt gtgatctcag ctcactgcaa cctttacctc ctgggttcaa      7620
gcaattcccc tgcctcagcc tcccaagtag gtgggattac agatgcgtgc caccacactt      7680
ggctaatttt tgcattttag tagagatcgg tttctccatg ttggccaggc tgatctcaaa      7740
cgcctgacct caggtgatct gcccgccttg gcctcccaaa gtgctggtat tacaggcgtg      7800
agctaccatg cctggcttat cttatatatt tttaaaaaca gcttattgag atctaattta      7860
tgtaccataa aattcaagta tataattcag tgcttttata tataaaacat atatatgaaa      7920
tagcttattg agatataatt ttttatataa aacagcttat tgatatgtaa tgtatgtacc      7980
ataaaattta aatatataat tcactggctt ttatatattc acgaatatgt gcaactatca      8040
ccacagtcaa ttttagcata ttttcatcag ctcataaaga aaccccaagc ccttgaacta      8100
tcaccccata tccctcctcc cagcccgtcc ctcctactca taagcaacca ctaatctact      8160
tagtgtctat agatttccta ctctaggcat tccatgtgag cgggatcatg caatacgtgg      8220
gctcacacaa tataagtggc attccatgtg agtcggctca tgcagtatgt ccggctcctt      8280
tcactgagca taaggtcttc agcactcatc caggttgcag cctgtgtctg aatttcattc      8340
cctcttctgg ctgaatcgta ttccattgtg tatcttggac atatcctatt ctgctcaccc      8400
agccgttggt gggcgtttgg agtgttttcg cctttcagct gtttaagag ggttgcagtg       8460 aacatttgta caagttttgg acccaatgcc tgttttcaat tctcttgtgt agagagcact      8520
ttttagcaga aaagaatag atttgtggcc tcccttgtg tgcggtcagt gccttgagaa        8580
gagtgaactg tgctgccacc tccggagccg tggagagcgc ggggcttggg tagcagctag     8640
gacgatacaa gttgggacaa ggccaggtgc aatggctcac gcctgtaatt ccaacacttt      8700
gggagaccga gcaggggga tcacctgagg tcaggagttc aagaccagcc tggccaacat       8760
ggtgaaaccc catctctaat aaaacagaaa aattaactgg acggggtggt ggacgcctgt      8820
aatcccagct actcgggagg ctgaggcagg agaatcactt gaacctggga ggcggaggct      8880
gcagtgagtg gagatcagac cactgcactt cagcctaggt gacagagcga gactccgtct      8940
caaaaaaaag aaaaaaaaag aaagaaactc atggataatc ctccctctcg tgcagttcgc      9000
ctctacggac caaacttcat ccttcaggtg tactcatctc agaggaagtc ctggcaccct      9060
gtgtgccaag acgactggaa cgagaactac gggcgggcgg cctgcaggga catgggctat     9120
aagtgagtat ggggcagcac ccgccgagtg acagtaacag acagcagaaa cacgagaaga     9180
ccctctctct gcctccctgt gaaagcaccg gcacatgagt gctgggaca attgtcacct       9240 tccaaaagct gagccctata accagcaggt ggaatttgtc ctgctagggc tgtgcccagc     9300
acacagacct tggctcactg ccaccttgcc ctgcctcctc cttggcctct atagactcct     9360
ggttgctcgg gagtgcccag tgctgtggtc atctggtcag aggggtaggc tgagggcgtt     9420
```

-continued

```
aggtgcctct ttttccaagg tgcctctcag ccagggtcca ttcacctccc tgggtagagg   9480
ttggaccaga acagctggcg aggagggttg ggctggggag agcagcagag acaaatcctg   9540
tgccagtttc acttcattcg ggagccatgg aagccttttg agctggggag agaatcaatc   9600
aatcagactg atacttaaaa aatgtcattc ctgctcgtag ctctgaggga aggtgggaag   9660
gcttaacagg gtgtgtgtcg cctgacagtg attcctaacg ggggtggggc ggtggttacc   9720
atttaccagc actgcctggg gagatgcggc agccctcagg catcggggga gagggtggta   9780
ggatgctact gccactttgt tttccatggg agggtcccca ggtgatttct atgcaacttt   9840
agggtattca atatgccagt tttcagaatg aattaccact cggtgagaaa gttggcatct   9900
tagctagtca ctgtgacatc cctaaacagc aggggtgaat tacacagcaa agccccccca   9960
tcacagtcca ggaacctggt ggaattgata actggggcca tgttaacatc tgtacctttt  10020
attagattaa atgtgtgtat gattatacaa tcctatgtcc ttctcatagt ttcttgatcc  10080
taacctggat aagaaacacg accaatgaag gaattttgtc tgacacttta gggttattga  10140
atcgaaaaat cgttacaata ttctagcact tggttagaac gtgtgatttt ttttcctaaa  10200
tgctaaggtt ttccctctt attctgaatg tcgtatgagc ggtattatga catagtatag  10260
gatttgtgtt tgcttatgcc ttaaccatta tcacaaataa ggttttcttt tttaggaata  10320
atttttactc tagccaagga atagtggatg acagcggatc caccagcttt atgaaactga  10380
acacaagtgc cggcaatgtc gatatctata aaaaactgta ccacaggtat gcagcaattt  10440
cttcttgaaa aattttggaa tgaaatcaac taggagacac catggggaat cgttgtcctg  10500
agtctgattt ctctgagctg caatactcgg tctggatggg ttttgcattg ggaggagatt  10560
agagtctgac caggcctggt tactctaagc agcccttggt ttattcatag gaagtggctg  10620
aggtttctct gctatttcat tttcagcctc taccgtctgc ccttgttggt agcggctcac  10680
acttgcaaca tcgacattca actctattta gttttctttc ctcttcagac atttagaggt  10740
gtacctattt tgtcagggcg tggttctagg aatccaagat aatgtctcag tgtcccagcc  10800
agggtgaccg gctcattcca gtttgccagg gacttcactg gcttgagcaa gggaagtcct  10860
gctccattcc aggcagctgg gctggctggt cccgttagcc caaccccgg dacagcagtg  10920
ccagagggtg ctctgtgagg gatgggcagc attctggcgg cctgggaatg agttgtggtg  10980
tttccagggg gtagaagtgg gtacaagcca caggtcacat gatgagtggc tgacctggct  11040
gggagggcag aagagggggat ggacttaggc tcttcctttt gctttgcaca tatttaggat  11100
gtttgcagac ttgctatgat tgttgctgtt atgtgttttc tgatgtgaaa gatacacagt  11160
gtcctttgcc catgagctct ccttgcctcc caggtcccca gggcttatgc ctggtgtcta  11220
ggcatcacct ccctgcctgc caggtgccag gtgctgcatt tcggggagg atgaactaat  11280
caccccgcgc cacctttcct ctgagtggga gcctggggca ggtttgcatt cctggaggcc  11340
gctggtggag gggtctgggg gcctgacttc cactgcagcc tgctgtcctg ggaatgtgg   11400
cagggcaagc ccagtgggga gggctgtgca cggccaggtg cacccatcaa aacagcaggg  11460
ctgcggtttg tccctgtgga gaagctaaac acagctgcct gggcactttg taaatgctga  11520
gtggttcttt gtctttctgg gttacacacg gaatcaggga gccaagtcca gccgggcagg  11580
gacgggggga gggaggagg tgctgccgtc ccttggcaag agccttggga actcacaagg   11640
aggctggagg gcttggaaga aagaagagaa ggccattgtc tggtaggctc tattctatct  11700
cggtggtggt ggtgggggga ggcgcacttc ttttcctctt tctgtgcagc agttgccctt  11760
```

```
tgatgcctga gttcttggct tgttttctgt cgggcttctg tgaataacca catgtgccct    11820
ggcgctgtga ccacacaggg ctatccctac cgaccttagg attcttagga aatgtcttct    11880
cttaaagggg acatgtcttc acttggccgt gtcagtgccc cagagccaga gtccacctgg    11940
aatgcacctg tagtcactga gaacccgggg ggtgtgcctt agtaagaagg tgtcaggaag    12000
gacctattat tgtagggcct gggctcctgc aaggtggttt gggggtggtt ggaggaagca    12060
gagatttgct ctggattgga tgctgtcagg aagcaggggt aattctgtga ggctgcttta    12120
ttatttttt tctaggagga ggttggaatg aggctaggct aaagctgtga ttggtaaaga    12180
aacgtccgtc gctcaagtta gccaggacag gaggagacat cagatcgtga tttttgtggtt   12240
gtgagcacaa ggttcctgtt ctgtctgttc agacatcatt tcggaggagg ctccttgtgt    12300
cttgccccat ctcaggcatg gaggggccta gtccgatatt gacgctcagt gaaataattc    12360
aggttccgca gagcacacgg cccagctatc agggcgggcc agctctgcat gccaggggcc    12420
gcgtcttccc ttctcagcat agcctgggaa attcactgca ggacaaaatg catcagttac    12480
ttcctcttca tccataacct gggatgtttg actcccaaat gagtaactct tacgtttctt    12540
ctaatcctag ggaaactatt ggttatattg cttttcaacac tacaaattta aagcagttat    12600
aggagcccag aggtttccaa atggcttcct taaaaattag aagatgattt taaattccaa    12660
gaggaaaaac aaaactagca ttattgtata cttaccctca caaccgtcct aggagctggt    12720
acaattttaa gagaggttaa gtaacttgcc caaggtcaca ctgtggggat gtgagccgcg    12780
taccttggct cagtgtctgg tctttgccac tgtccctata tggatttact taccttattg    12840
gagttgtaac tagcagaccc ttctatgtct cagaagacag gagagggaac atcggaagaa    12900
atgactgatt tctaagcatg tgagaggcag gtgactccgc actatcgtga ccagaatttc    12960
ccctgttctt tttgcagtga tgcctgttct tcaaaagcag tggtttcttt acgctgtata    13020
ggtaagttca tctggagtcc ccctttgat acttctaact aggaaaagct ctctactttc      13080
agaacagtac tccctgtgtc tctggggggcg tgggagggaa gaaggtgggg tcacgggttg    13140
gaatgtgccc agcggcgtct cgctcttttcc aaggagctcc tggtttagat ttccatggcc    13200
tgtagacacc ttcagccttg ggtccaaggg acacccctg agatcaggca cgctcaagaa     13260
gctgacaaag ccctacactt tatgccaccc atgagctgga ggcccggcag gtctctttct    13320
ccagaaagca aagggggggtg gcgttagtga gccctggcag ccacctaacg tggacttgga    13380
gcatctgcgg ggctgtggtc cagcaccacc gtgtggccac caggtgctca tcagccagtg    13440
ggacccggga ggagggacaa gaccagagaa caacagtgct cttgcctctt ctctcctgaa    13500
ttttggacgg tggcttagac ttgggtgtcc ccatctctgt gtttagagtg cttacagttt     13560
ccaaactgtt tgcaaatgtg gaagccaccg tccctctcct ctgggatggc ccagtgctgt    13620
cgtggggccg tggtcctgag ctcagctttt catttgaaga ggtggaagga gctgacaccg    13680
tcccatcccg gcagggctgg ctcaggtctt ctttaggtcc tgagtggggg tccagcacag    13740
ccccaagggt gcgtggcacc cgccctgccc tctgcccatg cactcatctc ctggtggaga    13800
agacactcac acacaggaag cagggaaggc agcagacctc actcaccct caccccctca     13860
ctcaccccct actcacccc tcaacctctc attcaccacc caccccctcg ccccctcact     13920
cacccccttca ctccctcaac cctcactcac ctcctcactc cctcaaccct cactcacctc    13980
ctcacctcct cactctcccc ctcatccctc cctcacccca cccgtcacc tcctcactca      14040
cctcctcacc ccctcactca ccccttcaccc cctcactcac cacctcacct cctcactcac    14100
cccctactca ccccctcatt cacccctcac cccctcactc accctgcac ccctcactc      14160
```

```
acccettcat ccactcaccc acctgctcac ctcctcactc aaccoctcac coootcacta    14220
atcoctcact coctcaccec ctcacgccct cactcacacc ttcacctcct cactcacccc    14280
ctcaccccct caaccoctta cttaccccct cactcatccc ttcaccoctc actcacccec    14340
tctctcaccc attcacccec tcactcatgc cttcaccccc tcactcacct cctcactcac    14400
accttcaccc ctcagtcacc ccctcactca cccottcacc ccctcaatca tgccttcact    14460
ccctcactca cccottcacc ctctgaatta ctccctcatc ccctcactca ccccctcact    14520
cacccottca ccoootcacc caccacctca cccaccoctc acccaccooc tcacctcctt    14580
accoctcacc coootcactc accoctcacc ccctcactca ccacctcacc cacccoctcac   14640
ccaccoccte actcactccc tcatccccte actcacccec tcacccocte actcacccec    14700
tcacccaccc ctcacccacc ccctcaccoc ctcactcacc ccttcacccec ctcactcacc   14760
ccctcactca ccoottcacc ccctcactca ccacctcacc cacccctcac ccaccoccte    14820
actcactccc tcaccoccte actcaccooc tcacccoctc actcaccooc tcatctcctc    14880
actcaccoce tcacctcctc actcacccge tcacctcctc actcaccooc tcgcccccte    14940
actcaccoct cacccoctca coocctcact caccoctcac ccoctcgccc cctcactcac    15000
ccoctcgccc cctcactcac ccctcaccoc ctcacccoct cactcatccc ctcacctcct    15060
cactcaccoc ctcacctcct cactcacccc tcacctcct cactcaccec ctcacctcct     15120
cacccaccoc ctcactcact ccctcaccoc ctcacccoct cactcacccc ctcacctcct    15180
cactcaccoc ctcacctcct cacccaccoc ctcactcact ccctcaccoc ctcacccoct    15240
cactcaccce ctcacctcct cactcacccc ctcacctcct cactcaccoc ctcacctcct    15300
cactcatgcc ctcacccoct cactcaccet ttcacctcct tgctcatccc ctcacttacc    15360
ccctcacttc gtcaatcacc ccoccacctc gtcaatcacc ccctcaccett ttcactcacc   15420
ccctcactca ccccettact tcctcactta cctcctcacc ccccactcac ccoctcacco    15480
cccactcacc ccctcaccoc acactcaccc cctcaccoco cactcacccc ctcacccctc    15540
tcacctcctc actcaccoco tcacctcctc acttatcccc tcaccoccte aattaccccc    15600
tcaccoccte aattactccc tcatcctttc aattacccac tcaccoccte acctcctcac    15660
tcctcactca ctccctcact cacccoccttca ccttctcact cacctcctcg tctcctcacc  15720
ccctcactca cttccagccc tgccctccc atcttcctt tctttgtgtg agaatctggg       15780
gtccctgagt ggtgtcagtc cctccaagac tcaaggagtc cccagggcct tgttatccag    15840
aacaccccca cctgggtccc gggagacccc atgggatcac aggagtgttc agggaagtgg    15900
tgcttcctgg gtctgggtgg gctggagggg catcctccct tccccaagag gagaccccca    15960
ggagcccct aagtccatcc ccagcagtgg tgccoctgcc ctgtccttgc agcctgggag     16020
acccttggga ggggcgggcg ctgggtggct gggcggcttc tgctggtctc accccactgg    16080
cctcctgttt gtcatcctca gcctgcgggg tcaacttgaa ctcaagccgc cagagcagga   16140
ttgtgggcgg cgagagcgcg ctcccggggg cctggccctg gcaggtcagc ctgcacgtcc    16200
agaacgtcca cgtgtgcgga ggctccatca tcacccccga gtggatcgtg acagccgccc   16260
actgcgtgga aaagtatgcc aggggcggcg cgggccgggt gggggctcag ggctggccta   16320
cagccaccct gtgaccttga gcaggtctca acccttgcag cccoggcatc cttgtgttta    16380
aatggggaga gtattgcacc tgcttcctag ggctgtgaga catcaagtgc gctcatgcca    16440
ggcagtgcat ggctgtatgc actgagtgtc ccctgcacgc agggcacagg gtgcaggtgg    16500
```

```
aacattctcc acgatgtcgc cgtgaccagc gttccttcca gccactgtcc tctgagctct    16560
gtcctgccct tgagcaaagc ccctgccccc tgaggtatcc tgtctccggg acgctagtcc    16620
caggagaggg cacactcaga caggcttcag gctgccctgc tggaaggtcc ctggggttaa    16680
gcgttcttgg ccacagcatt gctcatgcag agggttaggt aggggtgagg ctagccgtga    16740
cagtattagc atttatggac gctaccaccc cctccccttt tccttaaaca catagtgctt    16800
ttggtcacat gctgctttgg aggaggcctc acttggcgga tgtattttc tgccttagag     16860 agaggctgaa ctgggtttga ctgttggccc agccctctct tgctgcgtgc ccttagacga    16920
ttcactcaac gtctctgatc catggcatgt acaactataa gatgggcatg cccttctcct    16980
ctcgggctgt tatgaaggtc aaggaagcaa gggctgttac ccaagggtgc tcccttctct    17040 cccctcttc acaccccag gtgctctggg ccctctagga actgggtttc tctcaagggc      17100
tgttacccaa gggtgctccc ttctctcccc ctcttcacac cactgggtgc tctgggccca    17160
ctaggagctg ggattctctt aagagggaaa ctcttggata aggaaatgg tttgattgat     17220 atcggacaag tctgttcatt agtatccatt tattaagcac ctaccatgtg ccaggaaatg    17280
ctttggcgta caaaggaaaa taagggccag tcctgctaga aatggccttg aaaccccagg    17340
gagggatgtc ggcccattgt gggtgctgca gattccttga aggtgatgca agagccagaa    17400
agaaggatga tgtgggggc tgaggcaggg agtcggggtt gggggagtgt ggggagaag      17460 gggagaccga gcacctcttc cactatctcc ctgtgtggtt tttggtgaac catcctgcct    17520
ctgggtgtct tgcctccagc ttctgacgtt ggaagttcat ccactgagag ctctgtgttt    17580
atggctctga gatactgagt ccttcttctc tcccagacct cttaacaatc catggcattg    17640
gacggcattt gcggggattt tgagacaatc tttcatgttc tatggagccg ataccaagt     17700 agaaaagtg atttctcatc caaattatga ctccaagacc aagaacaatg acattgcgct     17760
gatgaagctg cagaagcctc tgactttcaa cggtacgtgt ggctcaggct tggcaagcag    17820
gttggcagaa tcttaaagag atgttgattg gaaatgacac ttgtgctatg ccaaatggaa    17880
gggaggcatt tgcgttgagc gagggtagcg tgcagcgggt ggccaatggg agaggctcac    17940
agaggctaag agcacctgcc gcattttggg ggaggcagca gccaccacat ctgttctgta    18000
ctgtactgag tggtggtgat tcaagccagg catggaaaag gctagaacag ggcttcccca   18060
ctgcagcacc cttgacatct gggtggttct ctgttgtagg gctctcttgt gccttgtagg    18120
atgtttaaca gcgtccccag cctctaccca ctggaggcca gtagctacca agctgtgaca    18180
accagtgttg cctgctgaca ttgccaaaca tccgctttga ggcaaagtca cttccagttg    18240
agaactactg gcctaaaatg tgtaaagatc cttgattttt aaagatacat tctaaaacca    18300
agttgcttaa ttcaggacaa acatgctttc tcttagcctc ttattcggtc ccactctggt    18360
ccatccaagg gtctggaatg ttctagcccc atgtggatac agaagaagca aaacctcagc    18420
cctccctaca gcatgtctgt attcacattg ggaaatggtt cacatataga agagcgaatg    18480
cctgagcaat ggcgtggtgc ctctggggcg aaagctgact ccattgactc catcggcttt    18540
ttggctgttg cctcctgtgt gtcttccccg tcttgatcac ctggagatat gtaattttgg    18600
aagcagagct agcaaataat tcctcttata agcagagcta gcaaataatt ctacttataa    18660
gtagcataac gtcttgcctg ccagaaggag aggtctggca gggggagaaa gtgagaatgt    18720
gggacttgtt gggatgcagg gtcctctggg cagggtggcc agggtgccag gcccagcagc    18780
ctgcatgtgg gaaggccagg tggagacata ggtgataccc gcctggctca ctgtgttttc    18840
tcttcttgaa acagacctag tgaaaccagt gtgtctgccc aacccaggca tgatgctgca    18900
```

| | |
|---|---|
| gccagaacag ctctgctgga tttccgggtg gggggccacc gaggagaaag gtgaggctgc | 18960 |
| tcctgggcac acaggactgc agggcccaca gatggagcat tgggttcgga agtgggaggt | 19020 |
| ccaggtttta atcccagttc tactactcaa tgactggatg actttggttg attccccag | 19080 |
| tccttgtgcc tcagtttctc catctgctaa gtgggagaaa tcctgcccag cctacctaat | 19140 |
| acactgtgtt cttatcgtga tcacacagag cagcatgtgg aatggctttt gaagtatctg | 19200 |
| ggccatacga gtttagaggt gcaggatctc ctgtgttgca ctcattgtga gtttagagct | 19260 |
| gccctggaga tcccaccaag gcctgcgtgg ctgagtgaca gggggcttgg tgaggacggg | 19320 |
| catcctggac ccatggtggc cacatctaag cctgtcctct gccctgataa ccacagagag | 19380 |
| aggctctctc cacccacttc ctttgcaatc tgcatttctc tctgacagtc tttcaaatga | 19440 |
| agggagcctg gctgcttcat ttttatggag ggttggaagt gcttagtggc aggcacaaag | 19500 |
| gttcattta catattgttt atatccttct caaaagcgtc taggccatac agacaacaaa | 19560 |
| tcctttcaaa caaggggaaa agtacaaagg ttgggtgatt tctggggagc gtcagggaag | 19620 |
| gtagtggggg gcatcctggc tcctcatcag cagaaactta ctacagtaga gccacaggct | 19680 |
| gggcaaaaga cctcatggaa tccaagatga agggaatatc gacaaatatt tgtgcgcacc | 19740 |
| tgcacctagt acaggctggg tgctactcag gtgctgggaa tgcagaagtg aacagagtaa | 19800 |
| gacaaatgtc tctgctgtca ggagctttac ctctcttctg gatgtcggtg gtggggacgg | 19860 |
| ggcaggtgtg gtcagacaga tgggagacaa acaactgagc gaggtacttc caaacatctg | 19920 |
| agggtgggga tcacaaggtc ccggctattt tgaaggggtg gtcaggaaag gcttctcgga | 19980 |
| agaggtggca tttgagctga gactcaaatg gcaaaaatgt gtacacatca aaaggctag | 20040 |
| tgcatgtatc ttcaggtgtg gtcaaggggc caaggaggtg ggctggggcc agattgcata | 20100 |
| ggtccttgtg gattatggtg aagacaccag cttctcatct gcttgaggtg gggagatcgt | 20160 |
| gagccgggga gtgccatgat ctggcagctg cgtggggagt ggggatgaat ggatggagac | 20220 |
| gaggatgatg gtgacaagtc cattgctgtg gttccttgag acaggaagcc agctcatagc | 20280 |
| agagtgcggg cgtggatgtg aagagatgag ggtacactag ggctagagcc accagactta | 20340 |
| ctgatgggtt gcatgtctgt gggagagaga gtgagaagtc agggacgatg gctttccact | 20400 |
| ctgtggctga agccccaggg tggcgggtgg tgccattttt caagccagga aatattggtt | 20460 |
| ggtgagaatt tggggtggga aaggtgtga cggagggttc tggttttgca cactaagccc | 20520 |
| acggtgccca gaagatgccc gaggggaggc agcaaagcga gagtgggaaa tgcagaggtg | 20580 |
| gcaagtgcag gccgtgtctt gagaagctct aatgtgcagg ggagccgaga agcaggcggc | 20640 |
| ctagggaggg tcacgtgtgc tccagaagag tgtgtgcatg ccagagggga aacaggcgcc | 20700 |
| tgtgtgtcct gggtggggtt cagtgaggag tgggaaattg gttcagcaga accaagccgt | 20760 |
| tgggtgaata agaggggat tccatggcac tgatagagcc ctatagtttc agagctggga | 20820 |
| atttctttcc ctgaagctga actccagagc tgcattcagc acaggcaccg ccagttgtaa | 20880 |
| ggagaatcca ggtttcccag gagagggggtt ggtgctggga tgagctgacc ggggcagggc | 20940 |
| tggaaaatag ggctgtgacc atctgtgtag tgcgtgtgga ggtctcaggg agggaagtgt | 21000 |
| gctctccctg cgagagctgc aggcaacact gggagctcaa caagtctccc tgtccttagg | 21060 |
| gaagacctca gaagtgctga acgctgccaa ggtgcttctc attgagacac agagatgcaa | 21120 |
| cagcagatat gtctatgaca acctgatcac accagccatg atctgtgccg gcttcctgca | 21180 |
| ggggaacgtc gattcttgcc aggtaattca acatttttat tctacctttg gtccttacca | 21240 |

```
gatcctactg aacccccat  gagagagagg gcattcttgg ggtcagcaga gcctcctcag    21300
tgacacggag ccagctcggg gcagtcatgg gaagtgacgg ccacaaacag tgcgaacgct    21360
tctggtggca gaaggaagta cagtcaacaa atcacacaca ccctctgaaa aaccggtatt   21420
tggtaaaagt gccagtggaa cagaaacaag tatttagact attttaaatt atgaacggca   21480
atttatttag taacttttag cttgaacaga ttaaaattca ggatggggggc tatctctttg   21540 ggggttacat ctctgttacc atcaccccctt gatggtggag attcgaagcc cacacagtca   21600
ctcgtaactc acactgcgac ccccgccccc caactcctct aggcctggtc agtggtgtgc   21660
ggcagattgt gacttgattt tctgctctct gtaccttgct gtgtcccaca gggtgacagt    21720
ggagggcctc tggtcacttc gaagaacaat atctggtggc tgataggga tacaagctgg     21780 ggttctggct gtgccaaagc ttacagacca ggagtgtacg ggaatgtgat ggtattcacg    21840
gactggattt atcgacaaat gagggtaact atcctgtcct ccttctgact gtgttctccg    21900
attcctcgag ccaaagccag acatctgtta ggcgtggttc tgctgctgga agctgactgg    21960
tgaccactgg tcagcatgaa gcaaactctg cttcctccag ccacagcccc atcccccag     22020 tgtccaccca ttgcccattg cctctcactg gcttcacttg catatttccc ctggtgtttg    22080
gatgaaaagc gctggggctc agcttgtgtg aaattccttg gtgctctgcc aaccacactt    22140
cgttctggct cagctgactc agctgttcca cccaggccac ctcacatcaa acttttttt    22200 ttttttttg agatggagtc tcactgtgtc gcccaggctg gagtgcagtg gcacaatctc    22260
gactcactgc aacctttgcc tcctgggttc aagtgattct cctgcctcag cctcccaagt    22320
agctgggact acaggcatgc gccaccacgc ccagctactt tttgtatttt tagtagagat   22380
ggggtttctc catgttggcc aggctggtct cgaagccctg acctcaggtg attcacccac    22440
ctcagcctcc cacagtgctg ggattacaag tgtgaaccac ggtgcccggc ctcacatgaa    22500
acttttgatt tatagagagc agagggaaga gccggctgtg cccatccttt tctggggcca    22560
tcgagtggct cctgggcagc ccccaaggtt aggaagggca ggagcagcca gggttctctg    22620
atgccccaga ctcaagcacg agggaaggtc tcaggggttc catgtgagcc tcatggatgt    22680
ctctgcttag cagagccctg gctttgggca ttgtccagat agggggtgag aaccagatct    22740
tctcatctcc aggacctcag acgtatagtt ttctcagatt tctgtgcttt ctggggctgg    22800
gctactagtg gaagaaagca gtctattctg tcttctccca aatctcccag atgcccagtc    22860
tgttgaagga ggagcagaac caggggggcct ttcccgctga ggcccgacct gtgtctcctt    22920
caaatgacac gcgggactca gggccttccc atgaccatgg ggcccagggg gcgtcacctg    22980
gcccagggcc cagtgctaga aacagatgac cccaggagga ggaggcaggg caggagggaa    23040
gctggcaggg ctgggatggt cagccaggct gaggggcgga ctcgcaccag gatgggagcta    23100 ggaaatgatc caggtgtgtt tggcggctgc aggtgggtcc gcatggctgt gcaggggggg    23160
aagggctgcg tggcaggaga gcagccgggg gaggcccaga ctctgctgaa gagatgcctg    23220
ttgtgccggc ctccacatcc gctgcccgct ccttccggag ctcctgcccc gccatgctca    23280
gcctgactct gaccaacacg ttggagagaa gaatgatccc tttgtgctat taagcttgct    23340
tatttggttt ctaagtgctt catgcgaacc tagaggaaaa aattattttc caccttttgtt   23400 tgtcttaaga aaataacaca cttttttttt tcctatttga acaggcagac ggctaatcca    23460
catggtcttc gtccttgacg tcgttttaca agaaaacaat ggggctggtt ttgcttcccc    23520
gtgcatgatt tactcttaga gatgattcag aggtcacttc attttttatta aacagtgaac    23580 ttgtctggct ttggcactct ctgccattct gtgcaggctg cagtggctcc cctgcccagc    23640
```

```
ctgctctccc taaccccttg tccgcaaggg gtgatggccg gctggttgtg ggcactggcg    23700
gtcaagtgtg gaggagaggg gtggaggctg ccccattgag atcttcctgc tgagtccttt    23760 ccagggcca attttggatg agcatggagc tgtcacctct cagctgctgg atgacttgag    23820
atgaaaaagg agagacatgg aaagggagac agccaggtgg cacctgcagc ggctgccctc    23880
tggggccact tggtagtgtc cccagcctac ctctccacaa ggggattttg ctgatgggtt    23940
cttagagcct tagcagccct ggatggtggc cagaaataaa gggaccagcc cttcatgggt    24000
ggtgacgtgg tagtcacttg taaggggaac agaaacattt tgttcttat ggggtgagaa    24060 tatagacagt gcccttggtg cgaggaagc aattgaaaag gaacttgccc tgagcactcc    24120
tggtgcaggt ctccacctgc acattgggtg gggctcctgg gagggagact cagccttcct    24180
cctcatcctc cctgaccctg ctcctagcac cctggagagt gcacatgccc cttggtcctg    24240
gcagggcgcc aagtctggca ccatgttggc ctcttcaggc ctgctagtca ctggaaattg    24300
aggtccatgg gggaaatcaa ggatgctcag tttaaggtac actgtttcca tgttatgttt    24360
ctacacattg ctacctcagt gctcctggaa acttagcttt tgatgtctcc aagtagtcca    24420
ccttcattta actctttgaa actgtatcat ctttgccaag taagagtggt ggcctatttc    24480
agctgctttg acaaaatgac tggctcctga cttaacgttc tataaatgaa tgtgctgaag    24540
caaagtgccc atggtggcgg cgaagaagag aaagatgtgt tttgttttgg actctctgtg    24600
gtcccttcca atgctgtggg tttccaacca ggggaagggt cccttttgca ttgccaagtg    24660
ccataaccat gagcactact ctaccatggt tctgcctcct ggccaagcag gctggtttgc    24720
aagaatgaaa tgaatgattc tacagctagg acttaacctt gaaatggaaa gtcatgcaat    24780
cccatttgca ggatctgtct gtgcacatgc ctctgtagag agcagcattc ccagggacct    24840
tggaaacagt tggcactgta aggtgcttgc tccccaagac acatcctaaa aggtgttgta    24900
atggtgaaaa cgtcttcctt ctttattgcc ccttcttatt tatgtgaaca actgtttgtc    24960 ttttttgta tctttttaa actgtaaagt tcaattgtga aaatgaatat catgcaaata    25020
aattatgcaa ttttttttc aaagtaacta ctgcatcttt gaagttctgc ctggtgagta    25080
ggaccagcct ccatttcctt ataagggggt gatgttgagg ctgctggtca gaggaccaaa    25140
ggtgaggcaa ggccagactt ggtgctcctg tggttctcga gataacttcg tataatgtat    25200
gctatacgaa gttatgctag taactataac ggtcctaagg tagcgagcta gctccacgtg    25260
gctttgtccc agacttcctt tgtcttcaac aaccttctgc aagaaaacca agggcctgaa    25320
ttttaacttc ctg                                                       25333
```

<210> SEQ ID NO 7
<211> LENGTH: 491
<212> TYPE: PRT
<213> ORGANISM: Artificial Sequence
<220> FEATURE:
<223> OTHER INFORMATION: Recombinant protein

<400> SEQUENCE: 7

Met Ala Leu Asn Ser Gly Ser Pro Pro Gly Ile Gly Pro Cys Tyr Glu
1               5                   10                  15

Asn His Gly Tyr Gln Ser Glu His Ile Cys Pro Pro Arg Pro Pro Val
                20                  25                  30

Ala Pro Asn Gly Tyr Asn Leu Tyr Pro Ala Gln Tyr Tyr Pro Ser Pro
            35                  40                  45

Val Pro Gln Tyr Ala Pro Arg Ile Thr Thr Gln Ala Ser Thr Ser Val

-continued

```
            50                  55                  60
Ile His Thr His Pro Lys Ser Ser Gly Ala Leu Cys Thr Ser Lys Ser
 65                      70                  75                  80

Lys Lys Ser Leu Cys Leu Ala Leu Ala Leu Gly Thr Val Leu Thr Gly
                     85                  90                  95

Ala Ala Val Ala Ala Val Leu Leu Trp Lys Phe Met Gly Ser Lys Cys
                100                 105                 110

Ser Asn Ser Gly Ile Glu Cys Asp Ser Ser Gly Thr Cys Ile Asn Pro
            115                 120                 125

Ser Asn Trp Cys Asp Gly Val Ser His Cys Pro Gly Gly Glu Asp Glu
            130                 135                 140

Asn Arg Cys Val Arg Leu Tyr Gly Pro Asn Phe Ile Leu Gln Val Tyr
145                 150                 155                 160

Ser Ser Gln Arg Lys Ser Trp His Pro Val Cys Gln Asp Asp Trp Asn
                165                 170                 175

Glu Asn Tyr Gly Arg Ala Ala Cys Arg Asp Met Gly Tyr Lys Asn Asn
                180                 185                 190

Phe Tyr Ser Ser Gln Gly Ile Val Asp Asp Ser Gly Ser Thr Ser Phe
            195                 200                 205

Met Lys Leu Asn Thr Ser Ala Gly Asn Val Asp Ile Tyr Lys Lys Leu
            210                 215                 220

Tyr His Ser Asp Ala Cys Ser Ser Lys Ala Val Val Ser Leu Arg Cys
225                 230                 235                 240

Ile Ala Cys Gly Val Asn Leu Asn Ser Ser Arg Gln Ser Arg Ile Val
                245                 250                 255

Gly Gly Glu Ser Ala Leu Pro Gly Ala Trp Pro Trp Gln Val Ser Leu
            260                 265                 270

His Val Gln Asn Val His Val Cys Gly Gly Ser Ile Ile Thr Pro Glu
            275                 280                 285

Trp Ile Val Thr Ala Ala His Cys Val Glu Lys Pro Leu Asn Asn Pro
            290                 295                 300

Trp His Trp Thr Ala Phe Ala Gly Ile Leu Arg Gln Ser Phe Met Phe
305                 310                 315                 320

Tyr Gly Ala Gly Tyr Gln Val Glu Lys Val Ile Ser His Pro Asn Tyr
                325                 330                 335

Asp Ser Lys Thr Lys Asn Asn Asp Ile Ala Leu Met Lys Leu Gln Lys
            340                 345                 350

Pro Leu Thr Phe Asn Asp Leu Val Lys Pro Val Cys Leu Pro Asn Pro
            355                 360                 365

Gly Met Met Leu Gln Pro Glu Gln Leu Cys Trp Ile Ser Gly Trp Gly
            370                 375                 380

Ala Thr Glu Glu Lys Gly Lys Thr Ser Glu Val Leu Asn Ala Ala Lys
385                 390                 395                 400

Val Leu Leu Ile Glu Thr Gln Arg Cys Asn Ser Arg Tyr Val Tyr Asp
                405                 410                 415

Asn Leu Ile Thr Pro Ala Met Ile Cys Ala Gly Phe Leu Gln Gly Asn
            420                 425                 430

Val Asp Ser Cys Gln Gly Asp Ser Gly Gly Pro Leu Val Thr Ser Lys
            435                 440                 445

Asn Asn Ile Trp Trp Leu Ile Gly Asp Thr Ser Trp Gly Ser Gly Cys
            450                 455                 460

Ala Lys Ala Tyr Arg Pro Gly Val Tyr Gly Asn Val Met Val Phe Thr
465                 470                 475                 480
```

Asp Trp Ile Tyr Arg Gln Met Arg Ala Asp Gly
               485                     490

<210> SEQ ID NO 8
<211> LENGTH: 2267
<212> TYPE: DNA
<213> ORGANISM: Mus musculus

<400> SEQUENCE: 8

| | | |
|---|---|---|
| ccggttgtgt tataggactt gaccagcccc aatagtcctc aagtcactcc tagatacagt | 60 |
| ggcaggtggt agctggcttg cggaaggaag aggaagaaga gaatgtgggc catcaaggag | 120 |
| caaggccagc cttgcacttg gccccctct gctcagtgct gaccagggct ttctgagccg | 180 |
| cttcctaatg aggctcattt gaagacccc ccccaccccc ctcctgctgt cttgggtggc | 240 |
| agagctagct ccaggctgta agaaaattag gaggattacc aaagcagtat ggagtcagac | 300 |
| agtggccaac cctcaacaa ccgtgatatt gttcccttc gcaaacccg aaggccccag | 360 |
| gagaccttca aaaggtggg gatccccatc attgcagtgc tgctgagcct gatagccctc | 420 |
| gtgattgtgg cccttctcat caaggtgatt ctggataaat actacttcat ctgcggcagt | 480 |
| ccctgacct tcattcagag gggccagttg tgtgacggcc accttgactg cgcctcaggg | 540 |
| gaggatgagg aacactgtgt caaggacttc cctgaaaagc ccggagtggc agtccggctc | 600 |
| tccaaggaca gatccaccct gcaggtgctg gatgcagcca cagggacctg gcctcagtc | 660 |
| tgtttcgaca acttcacaga agcactggcc aagacagcct gcagacagat gggctatgac | 720 |
| agccagcccg ctttcagagc agtggagatc cgtccagatc agaacctccc tgttgctcaa | 780 |
| gtcacaggaa acagccagga acttcaggtg cagaatggaa gcagatcctg cctctcaggc | 840 |
| tccctggttt ccttgcgctg ccttgactgt ggaaagagcc tgaagactcc tcgtgtggtg | 900 |
| ggtggggtgg aggcccctgt ggattcttgg ccgtggcagg tcagcatcca gtacaacaag | 960 |
| cagcatgtct gtggtgggag catcctggat ccccactgga tcctcacagc agcccactgc | 1020 |
| ttcaggaagt atcttgatgt gtcaagctgg aaggtcaggg caggctcaaa catactgggt | 1080 |
| aactctccat ccttgcctgt ggccaagatc ttcatcgctg aacccaatcc tctgtacccc | 1140 |
| aaagagaagg acattgccct tgttaagctg cagatgccac tcacattctc aggctcagtc | 1200 |
| aggcccatct gcctgccctt ctctgatgag gtgcttgtcc cagccacacc agtctgggtc | 1260 |
| attggatggg gctttacaga agaaacgga ggaaagatgt ctgacatgct actgcaggca | 1320 |
| tcagtccagg tcattgacag cacacggtgc aatgcagagg atgcctacga aggggaagtg | 1380 |
| accgctgaga tgctgtgtgc aggtaccca cagggtggca aggacacctg ccagggtgac | 1440 |
| agtggtgggc ctttgatgta ccattctgac aagtggcagg tagtaggcat cgtgagctgg | 1500 |
| ggccatggat gcggcggccc aagtactcct ggagtgtata ccaaggtcac tgcctatctc | 1560 |
| aactggatct acaatgttcg gaagtctgag atgtaacgct gccgtccccc acatccagaa | 1620 |
| gctgcttccc ttcagaccta cctacggcat gaccctcaa agtcagatat gggacaagag | 1680 |
| cctccttgaa caaactctgg tatccctgca gcaagcaagg atacattgca gaggtgcccg | 1740 |
| gagtggagtc agatgggcta gctcagccac ccctgcatct cccaaaccct gggagacatg | 1800 |
| tggcccatgg gagtaaatcc aggacattga ctcaactctc agaagtgtta ttcagtcaag | 1860 |
| gaggctctcc cttccactga aggaaggaaa gtcagctctc tcctgaaagg ccagatcact | 1920 |
| ggctgagtag atgagacaag ggtatgaaag gcctttgcca tcttctttgc ccagtcctga | 1980 |
| aagcactgac gtaagagacc agtcagttct aatgtaaggt gtatatttta gtgtcagggt | 2040 |

```
attgcaattg tcacctctgt ggtcaatatc attaaacagg tatgagaatt cgctggcata   2100
gacttcctgg tctgcttaat aagaatccaa ctaaggatgt cacatgacag tttcccagaa   2160
aatgtgaaca gtgtccatc tgacacacgg caccaatgac aaaccaaaga agttattctg    2220
cctgagtctc agttgctgaa ctaataaatt agctgcggtt tcttgca                 2267
```

```
<210> SEQ ID NO 9
<211> LENGTH: 435
<212> TYPE: PRT
<213> ORGANISM: Mus musculus

<400> SEQUENCE: 9

Met Glu Ser Asp Ser Gly Gln Pro Leu Asn Asn Arg Asp Ile Val Pro
1               5                   10                  15

Phe Arg Lys Pro Arg Arg Pro Gln Glu Thr Phe Lys Lys Val Gly Ile
            20                  25                  30

Pro Ile Ile Ala Val Leu Leu Ser Leu Ile Ala Leu Val Ile Val Ala
        35                  40                  45

Leu Leu Ile Lys Val Ile Leu Asp Lys Tyr Tyr Phe Ile Cys Gly Ser
    50                  55                  60

Pro Leu Thr Phe Ile Gln Arg Gly Gln Leu Cys Asp Gly His Leu Asp
65                  70                  75                  80

Cys Ala Ser Gly Glu Asp Glu His Cys Val Lys Asp Phe Pro Glu
                85                  90                  95

Lys Pro Gly Val Ala Val Arg Leu Ser Lys Asp Arg Ser Thr Leu Gln
            100                 105                 110

Val Leu Asp Ala Ala Thr Gly Thr Trp Ala Ser Val Cys Phe Asp Asn
        115                 120                 125

Phe Thr Glu Ala Leu Ala Lys Thr Ala Cys Arg Gln Met Gly Tyr Asp
    130                 135                 140

Ser Gln Pro Ala Phe Arg Ala Val Glu Ile Arg Pro Asp Gln Asn Leu
145                 150                 155                 160

Pro Val Ala Gln Val Thr Gly Asn Ser Gln Glu Leu Gln Val Gln Asn
                165                 170                 175

Gly Ser Arg Ser Cys Leu Ser Gly Ser Leu Val Ser Leu Arg Cys Leu
            180                 185                 190

Asp Cys Gly Lys Ser Leu Lys Thr Pro Arg Val Val Gly Gly Val Glu
        195                 200                 205

Ala Pro Val Asp Ser Trp Pro Trp Gln Val Ser Ile Gln Tyr Asn Lys
    210                 215                 220

Gln His Val Cys Gly Gly Ser Ile Leu Asp Pro His Trp Ile Leu Thr
225                 230                 235                 240

Ala Ala His Cys Phe Arg Lys Tyr Leu Asp Val Ser Ser Trp Lys Val
                245                 250                 255

Arg Ala Gly Ser Asn Ile Leu Gly Asn Ser Pro Ser Leu Pro Val Ala
            260                 265                 270

Lys Ile Phe Ile Ala Glu Pro Asn Pro Leu Tyr Pro Lys Glu Lys Asp
        275                 280                 285

Ile Ala Leu Val Lys Leu Gln Met Pro Leu Thr Phe Ser Gly Ser Val
    290                 295                 300

Arg Pro Ile Cys Leu Pro Phe Ser Asp Glu Val Leu Val Pro Ala Thr
305                 310                 315                 320

Pro Val Trp Val Ile Gly Trp Gly Phe Thr Glu Glu Asn Gly Gly Lys
                325                 330                 335
```

Met Ser Asp Met Leu Leu Gln Ala Ser Val Gln Val Ile Asp Ser Thr
            340                 345                 350

Arg Cys Asn Ala Glu Asp Ala Tyr Glu Gly Glu Val Thr Ala Glu Met
            355                 360                 365

Leu Cys Ala Gly Thr Pro Gln Gly Gly Lys Asp Thr Cys Gln Gly Asp
        370                 375                 380

Ser Gly Gly Pro Leu Met Tyr His Ser Asp Lys Trp Gln Val Val Gly
385                 390                 395                 400

Ile Val Ser Trp Gly His Gly Cys Gly Pro Ser Thr Pro Gly Val
            405                 410                 415

Tyr Thr Lys Val Thr Ala Tyr Leu Asn Trp Ile Tyr Asn Val Arg Lys
            420                 425                 430

Ser Glu Met
        435

<210> SEQ ID NO 10
<211> LENGTH: 3543
<212> TYPE: DNA
<213> ORGANISM: Homo sapiens

<400> SEQUENCE: 10

```
atcattccag tttggcaact tcacttgtag ggctgtttta atcaagctgc ccaaagtccc      60
ccaatcactc ctggaataca cagagagagg cagcagcttg tcagcggac aaggatgctg     120
ggcgtgaggg accaaggcct gccctgcact cgggcctcct ccagccagtg ctgaccaggg    180
acttctgacc tgctggccag ccaggacctg tgtggggagg ccctcctgct gccttggggt    240
gacaatctca gctccaggct acagggagac cgggaggatc acagagccag catggatcct    300
gacagtgatc aacctctgaa cagcctcgat gtcaaacccc tgcgcaaacc ccgtatcccc    360
atggagacct tcagaaaggt ggggatcccc atcatcatag cactactgag cctggcgagt    420
atcatcattg tggttgtcct catcaaggtg attctggata aatactactt cctctgcggg    480
cagcctctcc acttcatccc gaggaagcag ctgtgtgacg gagagctgga ctgtcccttg    540
ggggaggacg aggagcactg tgtcaagagc ttcccccgaag gcctgcagt ggcagtccgc    600
ctctccaagg accgatccac actgcaggtg ctggactcgg ccacagggaa ctggttctct    660
gcctgtttcg acaacttcac agaagctctc gctgagacag cctgtaggca gatgggctac    720
agcagcaaac ccactttcag agctgtggag attgggccag accaggatct ggatgttgtt    780
gaaatcacag aaaacagcca ggagcttcgc atgcggaact caagtgggcc ctgtctctca    840
ggctccctgg tctccctgca ctgtcttgcc tgtgggaaga gcctgaagac ccccgtgtg    900
gtgggtgggg aggaggcctc tgtggattct tggccttggc aggtcagcat ccagtacgac    960
aaacagcacg tctgtggagg gagcatcctg gacccccact gggtcctcac ggcagcccac   1020
tgcttcagga acataccga tgtgttcaac tggaaggtgc gggcaggctc agacaaactg    1080
ggcagcttcc catccctggc tgtggccaag atcatcatca ttgaattcaa ccccatgtac    1140
cccaaagaca atgacatcgc cctcatgaag ctgcagttcc cactcacttt ctcaggcaca    1200
gtcaggccca tctgtctgcc cttctttgat gaggagctca ctccagccac cccactctgg    1260
atcattggat ggggctttac gaagcagaat ggagggaaga tgtctgacat actgctgcag    1320
gcgtcagtcc aggtcattga cagcacacgg tgcaatgcag acgatgcgta ccaggggggaa    1380
gtcaccgaga agatgatgtg tgcaggcatc cggaaggggg tgtgacac ctgccagggt    1440
gacagtggtg ggcccctgat gtaccaatct gaccagtggc atgtggtggg catcgttagt   1500
```

```
tggggctatg gctgcggggg cccgagcacc ccaggagtat acaccaaggt ctcagcctat    1560
ctcaactgga tctacaatgt ctggaaggct gagctgtaat gctgctgccc ctttgcagtg    1620
ctgggagccg cttccttcct gccctgccca cctggggatc ccccaaagtc agacacagag    1680
caagagtccc cttgggtaca cccctctgcc cacagcctca gcatttcttg gagcagcaaa    1740
gggcctcaat tcctataaga gaccctcgca gcccagaggc gcccagagga agtcagcagc    1800
cctagctcgg ccacacttgg tgctcccagc atcccaggga gagacacagc ccactgaaca    1860
aggtctcagg ggtattgcta agccaagaag gaactttccc acactactga atggaagcag    1920
gctgtcttgt aaaagcccag atcactgtgg gctggagagg agaaggaaag ggtctgcgcc    1980
agccctgtcc gtcttcaccc atccccaagc ctactagagc aagaaaccag ttgtaatata    2040
aaatgcactg ccctactgtt ggtatgacta ccgttaccta ctgttgtcat tgttattaca    2100
gctatggcca ctattattaa agagctgtgt aacatctctg gcataggcta gctggaatgc    2160
ttgataagaa ctgagctggg atgattgaac tttcattctt tggcttgggg agaaaagaag    2220
tcctggggaa gcaattgagt ctcaaagtag aggcagggga aaaagagtt agggagacca    2280 gatctgctga gtggcagcaa gagtgagctg cagattacag aaaccagggt gagcaagttt    2340
gagtcccaca cagggccttc tccctttgcc tctttccctc cctccctgcc tgtgataatc    2400
agccaggagc cagggataac ctatgacttg ggaaagagat gagttaggca gtcaagggtg    2460
acattcaatc agggatccac aagtggctgg aaagaaatgc tggtcctgtg tcctaacttt    2520
ttccgcctgg agagccctca gtgtggcttc ttacatttaa aaaacaaaaa ggatcagctg    2580
ccaggtgtga ggcagtcccc aagctgagtt gtgaggatgt aagcatgaat aagtccctgc    2640
actcaaaatg gtcaaagaat taaaccccat ggactttttt ggcatctgta tgaaagcttg    2700
ggttttctga ggactgtctt gctatagtta agtcagatcc tagatgaaat atacttgttc    2760
atactgtact aggttcttag gaaacaacag aattcctcaa atgccaaaaa caagaaaaat    2820
agaaacccag aaacaaaac aaaataaaac aaaaccatca gaactgtgag tggaaactaa    2880
ggtgatgatc tggagcaat acactaaaat cttgggtcga gacctatatg aaggctggca    2940
gtggagctaa acctggacac actgaagaca agggagctga accagggctc ctacatgaag    3000
cagggataac tgatgcagt aaatgtggtc tcaaattgca gatggtctgg aggaaaattt    3060
cccaaattta gagcctcagg attcccaaag atcctccaaa tatgagctca caatcaaaga    3120
tcagagacgt tgaaaaataa aaacaccctt aagtgggcag cataaaaaac agctaattta    3180
gaaccccaaa ggcttcagat gtcagaatat tagagactta tgataataag caatatttgc    3240
agagtatttg tatgtgccag acactattgt aagtgcttca tcatgtactg attcatttaa    3300
tactcacaga aatctgtgag atgggtatta ttcttatcct cactctatgg attaaaaaaa    3360
ctaaggcaca aagtggttaa gctccttgcc tgagattata gactgtaagt tgaacgtgag    3420
cacttggaat acagagttca tgctgtaaac taccacacta tagggcctcc aatatgataa    3480
tttataaaat atttgaataa aaaatgaata ctagttccac atttaaaaa aaaaaaaaaa    3540 aaa                                                                 3543
```

<210> SEQ ID NO 11
<211> LENGTH: 437
<212> TYPE: PRT
<213> ORGANISM: Homo sapiens

<400> SEQUENCE: 11

```
Met Leu Gln Asp Pro Asp Ser Asp Gln Pro Leu Asn Ser Leu Asp Val
1               5                   10                  15

Lys Pro Leu Arg Lys Pro Arg Ile Pro Met Glu Thr Phe Arg Lys Val
            20                  25                  30

Gly Ile Pro Ile Ile Ile Ala Leu Leu Ser Leu Ala Ser Ile Ile Ile
            35                  40                  45

Val Val Val Leu Ile Lys Val Ile Leu Asp Lys Tyr Tyr Phe Leu Cys
        50                  55                  60

Gly Gln Pro Leu His Phe Ile Pro Arg Lys Gln Leu Cys Asp Gly Glu
65                      70                  75                  80

Leu Asp Cys Pro Leu Gly Glu Asp Glu His Cys Val Lys Ser Phe
                85                  90                  95

Pro Glu Gly Pro Ala Val Ala Val Arg Leu Ser Lys Asp Arg Ser Thr
                100                 105                 110

Leu Gln Val Leu Asp Ser Ala Thr Gly Asn Trp Phe Ser Ala Cys Phe
            115                 120                 125

Asp Asn Phe Thr Glu Ala Leu Ala Glu Thr Ala Cys Arg Gln Met Gly
    130                 135                 140

Tyr Ser Ser Lys Pro Thr Phe Arg Ala Val Glu Ile Gly Pro Asp Gln
145                 150                 155                 160

Asp Leu Asp Val Val Glu Ile Thr Glu Asn Ser Gln Glu Leu Arg Met
                165                 170                 175

Arg Asn Ser Ser Gly Pro Cys Leu Ser Gly Ser Leu Val Ser Leu His
            180                 185                 190

Cys Leu Ala Cys Gly Lys Ser Leu Lys Thr Pro Arg Val Val Gly Gly
        195                 200                 205

Glu Glu Ala Ser Val Asp Ser Trp Pro Trp Gln Val Ser Ile Gln Tyr
    210                 215                 220

Asp Lys Gln His Val Cys Gly Gly Ser Ile Leu Asp Pro His Trp Val
225                 230                 235                 240

Leu Thr Ala Ala His Cys Phe Arg Lys His Thr Asp Val Phe Asn Trp
                245                 250                 255

Lys Val Arg Ala Gly Ser Asp Lys Leu Gly Ser Phe Pro Ser Leu Ala
            260                 265                 270

Val Ala Lys Ile Ile Ile Ile Glu Phe Asn Pro Met Tyr Pro Lys Asp
        275                 280                 285

Asn Asp Ile Ala Leu Met Lys Leu Gln Phe Pro Leu Thr Phe Ser Gly
    290                 295                 300

Thr Val Arg Pro Ile Cys Leu Pro Phe Phe Asp Glu Glu Leu Thr Pro
305                 310                 315                 320

Ala Thr Pro Leu Trp Ile Ile Gly Trp Gly Phe Thr Lys Gln Asn Gly
                325                 330                 335

Gly Lys Met Ser Asp Ile Leu Leu Gln Ala Ser Val Gln Val Ile Asp
            340                 345                 350

Ser Thr Arg Cys Asn Ala Asp Asp Ala Tyr Gln Gly Glu Val Thr Glu
        355                 360                 365

Lys Met Met Cys Ala Gly Ile Pro Glu Gly Gly Val Asp Thr Cys Gln
    370                 375                 380

Gly Asp Ser Gly Gly Pro Leu Met Tyr Gln Ser Asp Gln Trp His Val
385                 390                 395                 400

Val Gly Ile Val Ser Trp Gly Tyr Gly Cys Gly Gly Pro Ser Thr Pro
                405                 410                 415

Gly Val Tyr Thr Lys Val Ser Ala Tyr Leu Asn Trp Ile Tyr Asn Val
```

Trp Lys Ala Glu Leu
            435

<210> SEQ ID NO 12
<211> LENGTH: 20078
<212> TYPE: DNA
<213> ORGANISM: Artificial Sequence
<220> FEATURE:
<223> OTHER INFORMATION: Recombinant polynucleotide

<400> SEQUENCE: 12

| | | | | | |
|---|---|---|---|---|---|
| ccacccgcac | acactacagt | cgagataact | tcgtataatg | tatgctatac | gaagttatat | 60 |
| gcatggcctc | cgcgccgggt | tttggcgcct | cccgcgggcg | cccccctcct | cacggcgagc | 120 |
| gctgccacgt | cagacgaagg | gcgcagcgag | cgtcctgatc | cttccgcccg | gacgctcagg | 180 |
| acagcggccc | gctgctcata | agactcggcc | ttagaacccc | agtatcagca | gaaggacatt | 240 |
| ttaggacggg | acttgggtga | ctctagggca | ctggtttttct | ttccagagag | cggaacaggc | 300 |
| gaggaaaagt | agtcccttct | cggcgattct | gcggagggat | ctccgtgggg | cggtgaacgc | 360 |
| cgatgattat | ataaggacgc | gccgggtgtg | gcacagctag | ttccgtcgca | gccgggattt | 420 |
| gggtcgcggt | tcttgtttgt | ggatcgctgt | gatcgtcact | tggtgagtag | cgggctgctg | 480 |
| ggctggccgg | ggctttcgtg | gccgccgggc | cgctcggtgg | gacggaagcg | tgtggagaga | 540 |
| ccgccaaggg | ctgtagtctg | ggtccgcgag | caaggttgcc | ctgaactggg | ggttgggggg | 600 |
| agcgcagcaa | aatggcggct | gttcccgagt | cttgaatgga | agacgcttgt | gaggcgggct | 660 |
| gtgaggtcgt | tgaaacaagg | tgggggggcat | ggtgggcggc | aagaacccaa | ggtcttgagg | 720 |
| ccttcgctaa | tgcgggaaag | ctcttattcg | ggtgagatgg | gctggggcac | catctgggga | 780 |
| ccctgacgtg | aagtttgtca | ctgactggag | aactcggttt | gtcgtctgtt | gcggggggcgg | 840 |
| cagttatggc | ggtgccgttg | ggcagtgcac | ccgtaccttt | gggagcgcgc | gccctcgtcg | 900 |
| tgtcgtgacg | tcacccgttc | tgttggctta | taatgcaggg | tggggccacc | tgccggtagg | 960 |
| tgtgcggtag | gcttttctcc | gtcgcaggac | gcagggttcg | ggcctagggt | aggctctcct | 1020 |
| gaatcgacag | gcgccggacc | tctggtgagg | ggagggataa | gtgaggcgtc | agtttctttg | 1080 |
| gtcggtttta | tgtacctatc | ttcttaagta | gctgaagctc | cggttttgaa | ctatgcgctc | 1140 |
| ggggttggcg | agtgtgtttt | tgtgaagtttt | ttaggcacct | tttgaaatgt | aatcatttgg | 1200 |
| gtcaatatgt | aattttcagt | gttagactag | taaattgtcc | gctaaattct | ggccgttttt | 1260 |
| ggcttttttg | ttagacgtgt | tgacaattaa | tcatcggcat | agtatatcgg | catagtataa | 1320 |
| tacgacaagg | tgaggaacta | aaccatggga | tcggccattg | aacaagatgg | attgcacgca | 1380 |
| ggttctccgg | ccgcttgggt | ggagaggcta | ttcggctatg | actgggcaca | acagacaatc | 1440 |
| ggctgctctg | atgccgccgt | gttccggctg | tcagcgcagg | ggcgcccggt | tcttttttgtc | 1500 |
| aagaccgacc | tgtccggtgc | cctgaatgaa | ctgcaggacg | aggcagcgcg | gctatcgtgg | 1560 |
| ctggccacga | cgggcgttcc | ttgcgcagct | gtgctcgacg | ttgtcactga | agcgggaagg | 1620 |
| gactggctgc | tattgggcga | agtgccgggg | caggatctcc | tgtcatctca | ccttgctcct | 1680 |
| gccgagaaag | tatccatcat | ggctgatgca | atgcggcggc | tgcatacgct | tgatccggct | 1740 |
| acctgcccat | tcgaccacca | agcgaaacat | cgcatcgagc | gagcacgtac | tcggatggaa | 1800 |
| gccggtcttg | tcgatcagga | tgatctggac | gaagagcatc | aggggctcgc | gccagccgaa | 1860 |
| ctgttcgcca | ggctcaaggc | gcgcatgccc | gacggcgatg | atctcgtcgt | gacccatggc | 1920 |

-continued

```
gatgcctgct tgccgaatat catggtggaa aatggccgct tttctggatt catcgactgt    1980
ggccggctgg gtgtgcgga ccgctatcag gacatagcgt tggctacccg tgatattgct    2040
gaagagcttg gcggcgaatg ggctgaccgc ttcctcgtgc tttacggtat cgccgctccc    2100
gattcgcagc gcatcgcctt ctatcgcctt cttgacgagt tcttctgagg ggatccgctg    2160
taagtctgca gaaattgatg atctattaaa caataaagat gtccactaaa atggaagttt    2220
ttcctgtcat actttgttaa gaagggtgag aacagagtac ctacattttg aatggaagga    2280
ttggagctac gggggtgggg gtggggtggg attagataaa tgcctgctct ttactgaagg    2340
ctctttacta ttgctttatg ataatgtttc atagttggat atcataattt aaacaagcaa    2400
aaccaaatta agggccagct cattcctccc actcatgatc tatagatcta tagatctctc    2460
gtgggatcat tgttttttctc ttgattccca ctttgtggtt ctaagtactg tggtttccaa    2520
atgtgtcagt ttcatagcct gaagaacgag atcagcagcc tctgttccac atacacttca    2580
ttctcagtat tgttttgcca agttctaatt ccatcagacc tcgacctgca gcccctagcc    2640
cgggcgccag tagcagcacc cacgtccacc ttctgtctag taatgtccaa cacctccctc    2700
agtccaaaca ctgctctgca tccatgtggc tcccatttat acctgaagca cttgatgggg    2760
cctcaatgtt ttactagagc ccacccccct gcaactctga cccctctgg atttgtctgt    2820 cagtgcctca ctgggcgtt ggataatttc ttaaaaggtc aagttccctc agcagcattc    2880
tctgagcagt ctgaagatgt gtgcttttca cagttcaaat ccatgtggct gtttcaccca    2940
cctgcctggc cttgggttat ctatcaggac ctagcctaga agcaggtgtg tggcacttaa    3000
cacctaagct gagtgactaa ctgaacactc aagtggatgc catctttgtc acttcttgac    3060
tgtgacacaa gcaactcctg atgccaaagc cctgcccacc cctctcatgc ccatatttgg    3120
acatggtaca ggtcctcact ggccatggtc tgtgaggtcc tggtcctctt tgacttcata    3180
attcctaggg gccactagta tctataagag gaagagggtg ctggctccca ggccacagcc    3240
cacaaaattc cacctgctca caggttggct ggctcgaccc agtggtgtc ccctgctctg    3300 agccagctcc cggccaagcc agcaccatgg gtaccccaa gaagaagagg aaggtgcgta    3360
ccgatttaaa ttccaattta ctgaccgtac accaaaattt gcctgcatta ccggtcgatg    3420
caacgagtga tgaggttcgc aagaacctga tggacatgtt cagggatcgc caggcgtttt    3480
ctgagcatac ctgaaaaatg cttctgtccg tttgccggtc gtgggcggca tggtgcaagt    3540
tgaataaccg gaaatggttt cccgcagaac ctgaagatgt tcgcgattat cttctatatc    3600
ttcaggcgcg cggtctggca gtaaaaacta ccagcaaca tttgggccag ctaaacatgc    3660
ttcatcgtcg gtccgggctg ccacgaccaa gtgacagcaa tgctgtttca ctggttatgc    3720
ggcggatccg aaaagaaaac gttgatgccg gtgaacgtgc aaaacaggct ctagcgttcg    3780
aacgcactga tttcgaccag gttcgttcac tcatggaaaa tagtgatcgc tgccaggata    3840
tacgtaatct ggcatttctg gggattgctt ataacaccct gttacgtata gccgaaattg    3900
ccaggatcag ggttaaagat atctcacgta ctgacggtgg gagaatgtta atccatattg    3960
gcagaacgaa aacgctggtt agcaccgcag gtgtagagaa ggcacttagc ctgggggtaa    4020
ctaaactggt cgagcgatgg atttccgtct ctggtgtagc tgatgatccg aataactacc    4080
tgttttgccg ggtcagaaaa aatggtgttg ccgcgccatc tgccaccagc cagctatcaa    4140
ctcgcgccct ggaagggatt tttgaagcaa ctcatcgatt gatttacggc gctaaggtaa    4200
atataaaatt tttaagtgta taatgtgtta aactactgat tctaattgtt tgtgtatttt    4260
aggatgactc tggtcagaga tacctggcct ggtctggaca cagtgcccgt gtcggagccg    4320
```

| | | | | | |
|---|---|---|---|---|---|
| cgcgagatat | ggcccgcgct | ggagtttcaa | taccggagat | catgcaagct | ggtggctgga | 4380 |
| ccaatgtaaa | tattgtcatg | aactatatcc | gtaacctgga | tagtgaaaca | ggggcaatgg | 4440 |
| tgcgcctgct | ggaagatggc | gattgatcta | gataagtaat | gatcataatc | agccatatca | 4500 |
| catctgtaga | ggttttactt | gctttaaaaa | acctcccaca | cctcccccctg | aacctgaaac | 4560 |
| ataaaatgaa | tgcaattgtt | gttgttaaac | ctgccctagt | tgcggccaat | tccagctgag | 4620 |
| cgtgcctccg | caccattacc | agttggtctg | gtgtcaaaaa | taataataac | cgggcagggg | 4680 |
| ggatctaagc | tctagataag | taatgatcat | aatcagccat | atcacatctg | tagaggtttt | 4740 |
| acttgcttta | aaaaacctcc | cacacctccc | cctgaacctg | aaacataaaa | tgaatgcaat | 4800 |
| tgttgttgtt | aacttgttta | ttgcagctta | taatggttac | aaataaagca | atagcatcac | 4860 |
| aaatttcaca | aataaagcat | tttttcact | gcattctagt | tgtggtttgt | ccaaactcat | 4920 |
| caatgtatct | tatcatgtct | ggataaactt | cgtataatgt | atgctatacg | aagttatgct | 4980 |
| agtaactata | acggtcctaa | ggtagcgagc | tagccaagtc | tgtgtgctac | caagtagcaa | 5040 |
| aactgagcct | ggaactcaca | catgcgtgtc | tgagagccca | gcactatcgc | caggaaaacc | 5100 |
| cagcgtctcc | ctgctcaagc | ctgaccctca | gccctctctg | cctctccctg | cacttgcctt | 5160 |
| ccagtcaagg | tgattctgga | taaatactac | ttcctctgcg | ggcagcctct | ccacttcatc | 5220 |
| ccgaggaagc | agctgtgtga | cggagagctg | gactgtccct | tgggggagga | cgaggagcac | 5280 |
| tgtgtcaaga | gcttccccga | agggcctgca | gtggcaggtg | agtgcagggt | ctgaggcaca | 5340 |
| agagaagtgg | gcccagcagg | aggtctgctc | aggcccccac | ggcccactgc | atagtatctg | 5400 |
| cccctactt | gtcactttc | atccttgttg | tataaggttc | tttgtttgtt | tgtttgttgt | 5460 |
| tgttttgagg | cagagtgctc | tgtggcccaa | gatggagtgc | agtgtcttgg | tctcggctca | 5520 |
| ctgcaacctc | tgcctcccag | tttcaagtga | ttcttctgcc | tcagcctcat | gagtagctgg | 5580 |
| gattacaggt | gccagccacc | acgcctggct | aattttttata | tttttagtag | agacggggtt | 5640 |
| ttgccacatt | ggtcaggctg | atcttgaact | cctgacctca | ggtgatctgc | ccgcctcagc | 5700 |
| ctcccaaagt | gctgggatta | caggcgtgag | ccaccgtgcc | cagctgtgta | agtttcttga | 5760 |
| gagcaggacc | ctgtcttgtc | tacctttaaa | tcctagtact | taacacacag | caaacagtaa | 5820 |
| ctatttgatg | accaaatgtg | agccagaaag | gacaggaaat | tgtaactgag | gctgccccat | 5880 |
| gcgtgctgcg | cctggtggat | ttcaggcaga | gggctagact | gggtgacctt | ggggcattcc | 5940 |
| tcctttctat | gaaatttgtt | atttcaagga | gactagaaaa | gagacttctc | agccacttcg | 6000 |
| ccagctattg | gtccttctat | tcattagtgt | ttgctgagac | atgctatgtg | acaggactga | 6060 |
| gccaggtcct | ttcaatggat | aggagatgtt | ttgagcataa | aatccacgtt | ctctcttggg | 6120 |
| ctgggctctt | ctaccttctt | cccctggtg | cttgggctct | gaagaaaaaa | agataggtag | 6180 |
| gagatgagtg | atggggcttc | tgagggcagg | gctgagtgac | tttctgtgta | tttgctcttt | 6240 |
| ctttatcaga | agtcaaatgc | ccacaggcac | ctgtcatcct | actgccagta | ggacttctca | 6300 |
| ctcaaccttc | ccctctgacc | ttacttggag | aaggacttag | gtccctctct | cagacatttc | 6360 |
| cccaggctgg | gcaagttgtg | tggaccatgg | atgggtatgt | ggtccataca | atttaaacaa | 6420 |
| gctgtatatg | gtcgctgggt | agagtgacca | cataattgat | catcaaaact | gatacctgta | 6480 |
| agagcaaaag | ggggcactat | taaccattgg | gtcagggcaa | caggtcaaaa | tggagaccta | 6540 |
| ccctgggact | tctggtcaca | ctagctactg | tcaaaatggg | gccaaatag | acaaagccaa | 6600 |
| atggaagaaa | ttcccttgac | attgaaagtg | ttggggctct | gtggcacccc | cagttctagg | 6660 |

```
ttgggggagc ttgggctggt ctcatgatga gttctgaggg ggatgggcca gttgggcccc    6720
ccgttccatc taactcaggt tccttcctc ccagtccgcc tctccaagga ccgatccaca     6780
ctgcaggtgc tggactcggc cacagggaac tggttctctg cctgtttcga caacttcaca    6840
gaagctctcg ctgagacagc ctgtaggcag atgggctaca gcaggtaacc aacctgggcc    6900
tctctccttt ttccctcctt cctccttcct cctcttcctc ctttccttcc tcccttcttc    6960
tctctttcct aaaaattacg ggcattggag ccaggcagaa tggcttttga atcccagcat    7020
ttcacttata agcaacatga agttaaattt cctaagcctc aggttcctca ggagttaatt    7080
gggggaacta atgccaacct cataggatag ttttgcaatg ccagtgagag aatgtgtgct    7140
gccctccaac acacacacac acacttctag cgtctatgca gtcctctcct ttcctttact    7200
cctcaacctt cactcctttg tgctggcttt gcaagaaact gttcctgccc agtaatacaa    7260
aagctaagtt aacttattca aagtttcgtt agttaagatt tagcttaagt gagcctagtt    7320
tcagtggggc cccatcttca gcaatcccag ctctctctgc aaatttcaaa agcagttcca    7380
aatctggagt ggatgaaaag gtgtaagatg atagtaagag taatttgcat tctatatatt    7440
tatattcact tgattttggc agaaaaccaa aaagatagtt attatatctt atatatagat    7500
atatattata tctatttcat aaataggctc aaacaaagta agtaacttgc tagggtacta    7560
gctgggaggt agagggctag aatttgagcc caagacccct aattcttgcg cattaggagt    7620
tcccacattg tttctgtttc tagactgagt aattctttat tctcatgtag gacatcatct    7680
ctaagggaag gggctaatga gatggttgat cactcagaga gtttagctgg agaggatgga    7740
aaagaaccca tacattcagt tgcagattga gatagcctat ctctggcagg cctcagattt    7800
cttcaggatt ctaacagact ggacccagag actaggccaa acaaacaaac aaacaaaaac    7860
tctactaggc agacatcacc aaccaatcac agaactctct cccatggatc cctaatacag    7920
cctcaaagtc cttttcagta aatgctccag gcagccatta caaatcaatc agaattattt    7980
gcctttctct tctctgctca acgggcttct gctgctctct actttccata gggggcaact    8040
tccattaccc tctagaaagc acaccccacc accttcattt caaggagagt gaggaactca    8100
tgcccagcac ctgctattct cccctcttcc tgcagccacg gagcccagcc tcgctgcagc    8160
cagccctgcc tccccactgt agtccagtca actgctgcat cagccgttcc tggcacagca    8220
ggctgagcct tgattatgaa acctgggtgt ctccaggggt tcttaagatg ataggctcct    8280
ggaatttctg tccttttgga gctcagtaag gcaccaaacc acctgagtct tgtgcttcac    8340
aaaatcaaag ttcatcagaa tcattcattg ggatggaatt ggtgaacaga agttaacttt    8400
cctgggaatg tccatttcca ccatattccg tccttctagg tctcagactt ctctactttc    8460
tttcctctct ctagatcgga ggcccttctt gtcctagaac cataggcatt tcaagatgtg    8520 ggagaccta gggatcatct agtccacgca tctttttttt tttttttga cagagtctca    8580 ctctgtcacc caggctggag tgcaatggca ccatctctgc ttactgcaac ctccacctcc    8640
caggttcaag tgattctttc gcctcagcct cccaagtagc tgggattaca ggcacgcacc    8700
atcatgccca gctaattttt atatttttgt agagaccgag tttcaccatg ttggccaggc    8760
tggtcttgaa ctcctgacct caggtgatcc acccacctcg gcctcccaaa gtgctgggat    8820
tacaggcgtg agccactgca cccagccccg tgcatctttt tatagagggg gaaactgagg    8880
cttggagaga cccagaaaaa gaatatgacc tgcccaaggc cacacatcaa actagtgcca    8940
gagccaggga cagaacctag atcatgagga ctcttaaaat gcactctagt cctcccaggt    9000
ctgagacttg ggtccttcca ggaagtgcca gcattcctgc ctgagaatgt gccaatccac    9060
```

```
cagtattgcc aatgactcag ccctccatgg agagcttcta ctaacattac tagcatagtt    9120
agggatggaa ggaaaagatt tagaagaggc agattcagta aaggaacaat cagagagatg    9180
gaattaatca aggaaggctt cctggaggag gaaaaacttc aacccaaggt ttgaaagtag    9240
caagcatgga ttagcaggga gaaagaggga gagtggtcca gttgagagaa acgtttgtct    9300
ggattcatat gaagacagat ctagtcctgt tctattaaat atctctaagg gggccaaaaa    9360 cataccccg ctatcaaagt cagaccagat gctttgtttg gagaacgaaa tatccacatt    9420
ccaactccct cccaggtgag aagggagcta acctgagccc ctatgcctct ttgtttccct    9480
gctgtgaacc agaagacatt gctgggatat ttgaaatagg gacagagctg gaatatgga    9540 aaggagaccc ctaacatttc tccagggctc tgggttctgg atttggattc cccacccaag    9600
aaagcaagtt acatcagcaa tgcactgagg gttgagtcct gggatgccaa gggtcggttc    9660
tttattgtat agcaaagcag gccccatctt cactgactaa gaccatctcc actccctggc    9720
cactccccac caagcattct ctgccactct ttctcctgaa agtgggggcc aactctacca    9780
tcttgttcta accccctgcc ccagctcaca actctctctc cctcttgatg tgagcagcaa    9840
acccactttc agagctgtgg agattggccc agaccaggat ctggatgttg ttgaaatcac    9900
agaaaacagc caggagcttc gcatgcggaa ctcaagtggg taagtgaggg gacaccttct    9960
ggcctacaga aggcccccac atggacgctg ctcttcaggt tgcaaccagc tcacctggaa   10020
ccccaagcag ccaggggaat gtaagcagac atcaggaaga actcctagcc agatggatca   10080
ttcaatgcca agagctatag actcacattt tggagaggtt ttctgtgttg acttgttttt   10140
aatacaatgg acagctggac aaagtgtgtt gtcctactca gagccagagg gatggataat   10200
gtgacctttc catcaatctg gatagtaaat agttttgct actgctgtag gttttctaat   10260
aaattgccca ataggcaaga ttccaaagtc actttgtcct tccctaccac ttacccagcc   10320
agagctcccc accttcttga tgctccaggg aagaggctcc atggcccttg tgggtggcct   10380
gttcctgagc ctcgccaccc tgtgttagag cagagcatcc agatgaaatc tgtcacactg   10440
tggcaaagtg gctcagagag gaggctggct tcctagcatt cagggacgtt gctgagggcc   10500
gcttattcac cgaaaataaa tcttgaaaag gacagggctg gtagcagaat gatccttttac   10560 ctaaaattct atcaaaatcc cattcttcca tttggaaagc ccacagtgtc acagactctg   10620
ttccgggctc tgtcctcttc cctcttgggt cccaggagcc caggctgggc tttgaagcag   10680
gcagggccca gcacacagta ggtactcagc agtgggggtg ttgaatccaa tcaaacggaa   10740
gtgtcaatgc aggaaatgca atggatgtca atgcagtctc caaatgttcc ccactgtgca   10800
gcttccacat tcccgaggta ttgggagggg acttgaatta acagcttcgg gaggcctgag   10860
tccctgcctc ccagctgagg aagaagctta aatcacaggg cgctgtgtct gtcttccagg   10920
ccctgtctct caggctccct ggtctccctg cactgtcttg gtgagtaccc ccaatctctg   10980
agggtttggg gcctgggcca gcaatgagca gggaggaaga ccttcatctt cactcctaaa   11040
tttctgggac tccaagtttc attctgcctt ggtctacagc cctgggctt gtcggtcaat   11100 gcccctcga gttgttggtg gccttgggca ggtcacattc ttttttctggg tctttccaag   11160 ccccagtttc ccccttctac catctgtgca tggctccatg acctaagtgg agacctggga   11220
gagagtgtta ggaagaccga aaagggcagg acggggcctc cactgcctcc catccctggt   11280
ccgggcccac atagccttct ttgtcacaat cagctcaggt atccaagatc agattaccca   11340
cattcattat ttgagcaact attcattgaa cagttagaat atgtctcact ctgtcagttg   11400
```

```
ctggctagaa gtagaaagta ccagatgagt gaaataattg gccactatcc ttggtagctg    11460
atgactaagt aagagagaga tgcaagacaa catgtggaaa atgccaaact gagtagcagt    11520
cacagttgac atgctgcaga gagagctggc cggggtcag aagacctggg caccagtcct     11580
gttcatttcc agtgtggcct cgagtcattc acctgacctc cctgaagttc attttcccaa    11640
gaagttgttt agtccaactg cccatcaagg atctttaggg acccttctag ctctaacaga    11700
ggagatcaga aaagaaaaca agcaatgtgg ctcagctcat cctacaagct tcatagagaa    11760
ctgagactgg cctggaagca tagccagaaa ttagaacgcc taagggaaga aggtcacaac    11820
gctgcctctg caatttagga gtgtatatgc tttcctgcag gatgttgaga gtttcattca    11880
ttatcgtatg cccctaccc cggcccaca atacctagtg cgtgggatct gacacgtggt      11940
ggctggtcaa tgaatgaatg aatgaatggt cacaccatct gaggttctgc actgagtagc    12000
cctgaaggct tgaagcagca taagtgacag gtcctccctt gagggcctc tgttttacca     12060 ataagccaag acctaagctc aacaacactg aaagggtggc caatacccag acagcctgt     12120 gggaattcca gagaaaggga gattcccagg gactgggggc ccaggctaaa cactgaaaaa    12180
tgcatctgta ggctcaagga ggaaaagccc atgtctgtct gtcttgccca ccactctctc    12240
ccagcaccca gcactgcccc aggacagaga gcacttgaca caagttggtt agattaatga    12300
atgatttaga gttcagtggt ccccaacctt tttggcacaa gagactggtt gcatggaaga    12360 caattttcc gcaaaccaag agggggatag agagcattag atttctctctt tttttttttt    12420 ttgagaccaa gtctggctct tgtcactcag cctggagtaa agtgttgcga tctcggctca    12480
ctgcaacctc cgcctcctgg attcaagcga ttctcctgcc tcagccccct aaatagctgg    12540
gattacaggc acccgtcacc agcccagctg ggactatagg catgtgccac catgcccggc    12600 taattttgt attttagta gagacggcgt tcaccatgt tggccaggct agtctcgaac       12660
tcctgacctc aggtgatctg cccgcctgag cctcccaaag tgctgggatt acaggcatga    12720
gctgcctcac ccagcctaaa gtctcataag gaacgtacag catagatccc tcacatgtgc    12780
agttcacaat aaggttgtgc tcctacaaga atctaacgcc acctctgatc tgacaggagg    12840
tgaagctcag gtggtcatgc tcgcttgtcc ctgccactca cttcctaatg tacagccagg    12900
ttcctaacag gccacgaacc agtgggaagg gcatcttttt ggatcaaaaa cagaattact    12960
ttttagagaa ctacaagcag atcaatttgg ctagacagag actttatatg aaacagcagg    13020
aggctgctag gaggagtgga aactctactt tgccctcaag ggagatcccg aagggctttg    13080
caggagcggg caaggtggca tgaagaaagc agtgtttgaa atcaggtggt atttgaaaag    13140 cccagcccctt ccccttagaa tggcccttct accatctgtg catggctcca caaccgtggt   13200
ggtggctgcc agaagaattg gaaaggcaga gcatgggtgg agagggggga cctgagggct    13260
ttacaggagt tccgggggtg gtgagggtgt gaaagccagg tcagtcagta ggaagacagg    13320
atgtcagatt gagagactcc cctggccggg gaaacagact tggagaaggg ggagttttgg    13380
atgagacagt ccacttccga gtcacaaaat agcttgtggg tgtctgttta ctgttactca    13440
gtgggagtgg ctgggacac gccacctggg cagggctttc gtaattctgc atcacttgtg     13500
aaggtcacag attcccagca caacggacac acccatgttc atagtctgaa ctcctaaaca    13560
catcttaaac caaaataaaa aaaaagaaa gaaagaaaga aaaggagag ggaggtttga      13620 ggaaagccta tggtctggga cactcaatac ctcccatgaa tatctcatat tgggctggtc    13680
ctctctccac tctggcccca gccataaggg ccctgcttag agcagatttt gggtgctgag    13740
tggaggcagc ctcatcccca acagcctgac ttcctgcctc ctccctgcct ctgcctgtgt    13800
```

```
ccagcctgtg ggaagagcct gaagaccccc cgtgtggtgg gtgtggagga ggcctctgtg   13860
gattcttggc cttggcaggt cagcatccag tacgacaaac agcacgtctg tggagggagc   13920
atcctggacc cccactgggt cctcacggca gcccactgct tcaggtaaga ccccagctgt   13980
aaggaggtct ctggggacca aggccagtca gggaccagag agcttggggt cctgtctcct   14040
ggcaccgtcc ttctcttcac tctcccacta gagacgtttt ccaggttgtg gtggccccaa   14100
tgagacaatg gccatgatgc cctttgttag gcttttgggt gtctgagcag agggtgctgg   14160
tcaccaagca tggcctcttc ctggtgggac accagcagat acccagagtc ctcaccccac   14220
ccccatatcg ttcaagctac aaaagctctt cccacctgcc tcaacttcca agaactcact   14280 ctcttttttgc ttgtttccag gaagttgttc cagggtctag agtcatagcc acgtcctcat   14340
tatgtctgga aactttaaaa aaattaaaga gcataggttc ctttcagtcc acagagaagc   14400
ctggccttac ctcagggaag ggctactccc agacccctt cacttttttt tttttttttt   14460
tttttttttt ttttgagaca gagtcttgct ctgttgctta ggctggagcg cagcagcatg   14520
atcttggctc actgcaacct ccgcctcctg agttcaagca attctcctgc ctcagcttcc   14580
caagtagctg ggactatagg catgggccac catgcccggc taattttgt attttggta   14640 gagacagggt ttcaccatgt tggccaggct gatctctaac tcctgacctc aagtgatctg   14700
cccacctcag cctcccaaac tgctgggatt acaggcatga gccagggcat ccggcttta   14760 tttattcatt cattcaatat ctaatgagca cctaccaggt accaaacacc agatgatgcg   14820
cccaagttca ttagacccca ccgctgtctt caaggcactc atgatctagg ccagcgtttt   14880
ttaaccactt ttttttttt tttttttgag attctggtga gagctataaa ttctttcctg   14940
gaaaaacatc tctgcacact aagctgtgcc tggcattggg aaaaagaaag cacgtaatgt   15000
aactgacagc atgagtaaca cagtgagaaa ggttggagga gagagcgcca ggacctcaga   15060
actcaggcat tagaggagcc ccttccccag ccctccttga ggtttcgttg gcaggtttc   15120 actgaggaaa aagggtcaaa tccctttttc gaatttgact tcttgtaagt gccagaagac   15180
tgccccttct ccaccatccc tgcctcacca tcatctttcc tcccaaggca gtgcatcca   15240 gcaccccgat ccctagggcc ctgggaccc agcctttggc aaagtctcct caggcttgga   15300
tcaggcctga acccagctgt ctctacccccc aggaaacata ccgatgtgtt caactggaag   15360
gtgcgggcag gctcagacaa actgggcagc ttcccatccc tggctgtggc caagatcatc   15420
atcattgaat caaccccat gtaccccaaa gacaatgaca tcgccctcat gaagctgcag   15480
ttcccactca ctttctcagg tgagaagcag ggcccaaggc cactcaagcc tcttacatca   15540
gttttcacgc ccactctgct attagctcac tgaccgccct tggcacataa tgtctcctct   15600
caagtcctca gcttgcccat ttgtctctaa tacgtcagcc taacatcact gatgccatga   15660
ggcctcctca agctgtcagc taacacctcc actccattcc ctgccagaga ttcttccaag   15720
gcctgtcttc cctatgtgga gcccctcgag tgagaactgg agtttcatcc aatcttggag   15780
ttttaggaga ccttttaaaa agattatcga gctaattccc caccactgac caacacgcaa   15840
gagcctgctc agtatccctg ccaaggagtc attgtgcccc tgtttgctct cctccagggg   15900
cagggaaccc attacctgtg aggcagccca cagagtcttt gaacagctct gttggatgcc   15960
ttgtgcttat actgaaatgt atttagatca ggattcccaa ctgtggggtc cacaagacac   16020 tggcccccttg gagaagagag gattccattg tcaaataagt ttggggaaca ttttcatact   16080
acagctccct tcttggaaca cattagttta ttaaaggtag gagaagtttt taaaataatc   16140
```

```
tgttttattg cgtttaacct acattttttta aatttatttg accacagaat cctttttttca    16200 tgctacttct attagcatcc catagaacaa gtgttctaga gaccctggtg tgaccccttt     16260
cagagagctt aactgccagg ctctcctgag ccctggtgtg tgtttcaaga tttgtgcctg     16320
ggaattgttt taatcaggta tggcaaggtg acagatacag acacagctat ctttgaaaga    16380
agagtttatt atttataatt cctgagagaa agggacatac cccacccccc aacacaggga    16440
cacccgggga agcagctggg tccaccagga ggcaggagtg aggggaaggc atggcccaga    16500
gccacctgtg gcttccatgg gcaggtctgg ccaaggtagg gtaggcaaga ttgagcatgc    16560
tcaggattgg atagtgtgga caattctcta ggctatagat gtcagcctct ggttgtctag    16620
tatctgtccc tggggtgatt tagggcaggg aaaatattgg cttggtgtct gagagtcaga    16680
taaaggaagt ggttggggat atgggctttg ggttggctgg tttgcctatt aaaggcgtgc    16740
ccaaagccaa gttgtttact atctgcagga attagctaac ccagtctctc ccagaccagc    16800
aagatcccca taatcataaa gcatcataat ttacagaaaa ttaacactta tgatgaataa    16860
aagatctcct tcttcctctg tgctcctggc aggcacagtc aggcccatct gtctgccctt    16920
ctttgatgag gagctcactc cagccacccc actctggatc attggatggg gctttacgaa    16980
gcagaatgga ggtaagtcct gggtgcagga ccacagggca ggagatgccc ttgtatgagg    17040
gagcagcttc cagaagtaat gggaaggagg accaccttcc agagaaaccc atcctggagg    17100
accaagcacc aaggcgccag gcagaaagca aagtggtttg gcaatccagg gctggggat    17160 agaaggcaag gatgggaatg tgagtgtttt taccctccca gggaagatgt ctgacatact    17220
gctgcaggcg tcagtccagg tcattgacag cacacggtgc aatgcagacg atgcgtacca    17280
gggggaagtc accgagaaga tgatgtgtgc aggcatcccg aagggggtg tggacacctg    17340 ccaggtgggg cctccaagaa tcatgggag ttctaagaat agggtttagg tcctagagag    17400
atgagaaaac ccagaggctg catgccctac aggaagcctt gcatatcatg ggcactcaat    17460
gtgtgatgat gggaggaaga gagggaggga aggaaaggat agtcagataa aagtgtacca    17520
atagatgagt gggtggatgg atggatgcag acaagcagag agatttcaaa tgtctctttc    17580
acattcgaag atgatgttac tggcctggca tggtggctca cgcttgtaat cccagcactt    17640
tgggaggctg aggcgggcag gtgatttgag gtcaggaatt caagaccagc ctggccaaca    17700
tggtgaaatc ccatctctac taaaaagaat acaaaaatta gctgggcgtg gtggcacgtg    17760
cctgtaatcc cagctacttg ggaggctgag gcaggagaat tgcttgaacc caggaggcag    17820
aggttgcagt aagctgagat tgcgccactg cactccagcc tgggtgaccc agcaagactc    17880
catctgaaaa caacaacaac aacaaagatg acattactca tccaccccac ccacccttct    17940
cactagctac agaatgatta gcccccttgag gtcaggaatc ccaggtctat tttctctgtg    18000
actctcccca agctgctgaa ctacactagg aaagaattac cgcctgcaga atgctggaag    18060
cacatctgtg tgtgccctca ccccggcctc attggccatc aggactgctt agcaatccct    18120
gtagaccttc ttcctccccc atacttccag aggatcttct gaactatttt ctttttttat    18180
tttttctttt atgttttta acagagacag ggtcactatg ttgcccagtc tggtctcaaa    18240
ctcctgggtt caaggattc tcccacctca gctttccaaa atgctgggat tacaggcatg    18300
agccatcgtg cttggcctga accatttttca ttaaaaccccc taccctactc tcacctccat    18360
ttccagtcat taaattcctt catttaagag gcatctctta gtcatcgcat gtgtgccatg    18420
aacatggtag tctttggaga cccctcaggg agctcacagt ggttgggga agggggggca    18480 ttaaacagac atttaagcta tagttttggg ttcagaggga ggaagcccca ggggctaaaa    18540
```

```
cagctgataa ggactcccag ataagtgcac ttttcactat ctggcatttt cttgttttgt    18600
tatttgcttg ttcactgtct ctcaccccat ttgatcctaa gctttctgag ggcagggatc    18660 tttgttttt  ttcatcagtt ggatcccaat tgcttagaac actacctggc acaaaatagg    18720
cactctataa gtgattacac aaattttgga acgactaggt aaacaatga  taaccaggct    18780 ttttttttt  tttttgagac tgagtctcac tctgttgccc aggctagagt gaagtggttt    18840
gatctcggct cactgcagcc tccgcctctg ggttcgaatg attctccacc tcagcctcct    18900
gagtagctgg gattacaggt gcctgccact atgcccagct aattttttgta tttgtagtag    18960 agacgggttt caccatgttg gccaggctgg tcttgaactc ctgacctcaa gtgattcacc    19020
cgcctcagcc tcccaaggtg ctgggattac aggtgtgagc caccgctcct ggccaacaac    19080
caggcttttt taagacatca ctcagagcct ttaatttgct aatgtgagtt gtgaatctct    19140
gagagaaggc taacggcatg cttgcaactt acttgtccac agacaagcct ttctgcccca    19200
gaagagaaga ccattctagg gtgctaatga gcaaagaggg tgagggtgga atatcggaga    19260
gcagcaggga gtgcagggga acagatagg  cagttcaggg agcagagaag gagaagcccc    19320
cccacctcac ctgccctccc cagcagtctc tgttctggtc tctcacaggg tgacagtggt    19380
gggcccctga tgtaccaatc tgaccagtgg catgtggtgg gcatcgttag ttggggctat    19440
ggctgcgggg gcccgagcac cccaggagta tacaccaagg tctcagccta tctcaactgg    19500
atctacaatg tctggaaggt aaggtacctt tgccctaccc actgtgcctt ccctccagtc    19560
ctctacctgg ggggtgccaa tccatcctca ggtttgattt aaatggttct gacaactctt    19620
tacatcccaa ataactttcc ctccaagcaa gggacagcct gagattgcac tattaaggct    19680
gaaattcctt aggtcagaga tttctgataa atgcaaatac cttagggaat agaacacacc    19740
aagcctttct ttctcttttc tgacagaatg agactatcag atcctttcta gagagaagat    19800
tctgataagg aagagagtgg aaaggctcat gagacctcct ggccctctgc agggtaggga    19860
gagaagcaaa gtgtttcaga aaaggaagac tcacgttaca catgtcacca ctttgtccag    19920
tttcagataa tctgactttc tcttcatcgg tctctcttat tctaggctga gctgtaacgc    19980
tgccgtcccc cacatccaga agctgcttcc cttcagacct acctacggca tgacccctca    20040
aagtcagata tgggacaaga gcctccttga acaaactc                           20078
```

<210> SEQ ID NO 13
<211> LENGTH: 15159
<212> TYPE: DNA
<213> ORGANISM: Artificial Sequence
<220> FEATURE:
<223> OTHER INFORMATION: Recombinant polynucleotide

<400> SEQUENCE: 13

```
ccacccgcac acactacagt cgagataact tcgtataatg tatgctatac gaagttatgc        60
tagtaactat aacggtccta aggtagcgag ctagccaagt ctgtgtgcta ccaagtagca       120
aaactgagcc tggaactcac acatgcgtgt ctgagagccc agcactatcg ccaggaaaac       180
ccagcgtctc cctgctcaag cctgaccctc agccctctct gcctctccct gcacttgcct       240
tccagtcaag gtgattctgg ataaatacta cttcctctgc gggcagcctc tccacttcat       300
cccgaggaag cagctgtgtg acggagagct ggactgtccc ttgggggagg acgaggagca       360
ctgtgtcaag agcttccccg aagggcctgc agtggcaggt gagtgcaggg tctgaggcac       420
aagagaagtg ggcccagcag gaggtctgct caggccccca cggcccactg catagtatct       480
```

-continued

| | | |
|---|---|---|
| gccccctact tgtcactttt catccttgtt gtataaggtt ctttgtttgt ttgtttgttg | 540 | |
| ttgttttgag gcagagtgct ctgtggccca agatggagtg cagtgtcttg gtctcggctc | 600 | |
| actgcaacct ctgcctccca gtttcaagtg attcttctgc ctcagcctca tgagtagctg | 660 | |
| ggattacagg tgccagccac cacgcctggc taatttttat attttagta gagacggggt | 720 | |
| tttgccacat tggtcaggct gatcttgaac tcctgacctc aggtgatctg cccgcctcag | 780 | |
| cctcccaaag tgctgggatt acaggcgtga gccaccgtgc ccagctgtgt aagtttcttg | 840 | |
| agagcaggac cctgtcttgt ctacctttaa atcctagtac ttaacacaca gcaaacagta | 900 | |
| actatttgat gaccaaatgt gagccagaaa ggacaggaaa ttgtaactga gctgccccca | 960 | |
| tgcgtgctgc gcctggtgga tttcaggcag agggctagac tgggtgacct tggggcattc | 1020 | |
| ctcctttcta tgaaatttgt tatttcaagg agactagaaa agagacttct cagccacttc | 1080 | |
| gccagctatt ggtccttcta ttcattagtg tttgctgaga catgctatgt gacaggactg | 1140 | |
| agccaggtcc tttcaatgga taggagatgt tttgagcata aaatccacgt tctctcttgg | 1200 | |
| gctgggctct tctaccttct tcccctggt gcttgggctc tgaagaaaaa aagataggta | 1260 | |
| ggagatgagt gatggggctt ctgagggcag ggctgagtga cttctgtgt atttgctctt | 1320 | |
| tctttatcag aagtcaaatg cccacaggca cctgtcatcc tactgccagt aggacttctc | 1380 | |
| actcaacctt cccctctgac cttacttgga gaaggactta ggtccctctc tcagacattt | 1440 | |
| ccccaggctg gcaagttgt gtggaccatg gatgggtatg tggtccatac aatttaaaca | 1500 | |
| agctgtatat ggtcgctggg tagagtgacc acataattga tcatcaaaac tgatacctgt | 1560 | |
| aagagcaaaa gggggcacta ttaaccattg ggtcagggca acaggtcaaa atggagacct | 1620 | |
| accctgggac ttctggtcac actagctact gtcaaaatgg ggcccaaata gacaaagcca | 1680 | |
| aatgaagaa attcccttga cattgaaagt gttgggctc tgtggcaccc ccagttctag | 1740 | |
| gttggggag cttgggctgg tctcatgatg agttctgagg gggatgggcc agttgggccc | 1800 | |
| cccgttccat ctaactcagg ttccttttcct cccagtccgc ctctccaagg accgatccac | 1860 | |
| actgcaggtg ctggactcgg ccacagggaa ctggttctct gcctgtttcg acaacttcac | 1920 | |
| agaagctctc gctgagacag cctgtaggca gatgggctac agcaggtaac caacctgggc | 1980 | |
| ctctctcctt tttccctcct tcctccttcc tcctcttcct cctttccttc ctcccttctt | 2040 | |
| ctctcttttcc taaaaattac gggcattgga gccaggcaga atggcttttg aatcccagca | 2100 | |
| tttcacttat aagcaacatg aagttaaatt tcctaagcct caggttcctc aggagttaat | 2160 | |
| tgggggaact aatgccaacc tcataggata gttttgcaat gccagtgaga gaatgtgtgc | 2220 | |
| tgccctccaa cacacacaca cacacttcta gcgtctatgc agtcctctcc tttcctttac | 2280 | |
| tcctcaacct tcactccttt gtgctggctt tgcaagaaac tgttcctgcc cagtaataca | 2340 | |
| aaagctaagt taacttattc aaagtttcgt tagttaagat ttagcttaag tgagcctagt | 2400 | |
| ttcagtgggg ccccatcttc agcaatccca gctctctctg caaatttcaa aagcagttcc | 2460 | |
| aaatctggag tggatgaaaa ggtgtaagat gatagtaaga gtaatttgca ttctatatat | 2520 | |
| ttatattcac ttgattttgg cagaaaacca aaaagatagt tattatatct tatatataga | 2580 | |
| tatatattat atctatttca taaataggct caaacaaagt aagtaacttg ctagggtact | 2640 | |
| agctgggagg tagagggcta gaatttgagc ccaagacccc taattcttgc gcattaggag | 2700 | |
| ttcccacatt gtttctgttt ctagactgag taattcttta ttctcatgta ggacatcatc | 2760 | |
| tctaagggaa ggggctaatg agatggttga tcactcagag agtttagctg gagaggatgg | 2820 | |
| aaaagaaccc atacattcag ttgcagattg agatagccta tctctggcag gcctcagatt | 2880 | |

```
tcttcaggat tctaacagac tggacccaga gactaggcca aacaaacaaa caaacaaaaa    2940
ctctactagg cagacatcac caaccaatca cagaactctc tcccatggat ccctaataca    3000
gcctcaaagt cctttccagt aaatgctcca ggcagccatt acaaatcaat cagaattatt    3060
tgcctttctc ttctctgctc aacgggcttc tgctgctctc tactttccat aggggcaac     3120
ttccattacc ctctagaaag cacaccccac caccttcatt tcaaggagag tgaggaactc    3180
atgcccagca cctgctattc tcccctcttc ctgcagccac ggagcccagc ctcgctgcag    3240
ccagccctgc ctccccactg tagtccagtc aactgctgca tcagccgttc ctggcacagc    3300
aggctgagcc ttgattatga aacctgggtg tctccagggg ttcttaagat gataggctcc    3360
tggaatttct gtccttttgg agctcagtaa ggcaccaaac cacctgagtc ttgtgcttca    3420
caaaatcaaa gttcatcaga atcattcatt gggatgaat tggtgaacag aagttaactt     3480
tcctgggaat gtccatttcc accatattcc gtccttctag gtctcagact tctctactt     3540
ctttcctctc tctagatcgg aggcccttct tgtcctagaa ccataggcat ttcaagatgt    3600
gggagaccct agggatcatc tagtccacgc atctttttt ttttttttg acagagtctc      3660
actctgtcac ccaggctgga gtgcaatggc accatctctg cttactgcaa cctccacctc    3720
ccaggttcaa gtgattcttt cgcctcagcc tcccaagtag ctgggattac aggcacgcac    3780
catcatgccc agctaatttt tatattttg tagagaccga gtttcaccat gttggccagg     3840
ctggtcttga actcctgacc tcaggtgatc cacccacctc ggcctcccaa agtgctggga    3900
ttacaggcgt gagccactgc acccagcccc gtgcatcttt ttatagaggg ggaaactgag    3960
gcttggagag acccagaaaa agaatatgac ctgcccaagg ccacacatca aactagtgcc    4020
agagccaggg acagaaccta gatcatgagg actcttaaaa tgcactctag tcctcccagg    4080
tctgagactt gggtccttcc aggaagtgcc agcattcctg cctgagaatg tgccaatcca    4140
ccagtattgc caatgactca gccctccatg gagagcttct actaacatta ctagcatagt    4200
tagggatgga aggaaaagat ttagaagagg cagattcagt aaaggaacaa tcagagagat    4260
ggaattaatc aaggaaggct tcctggagga ggaaaaactt caacccaagg tttgaaagta    4320
gcaagcatgg attagcaggg agaaagaggg agagtggtcc agttgagaga aacgtttgtc    4380
tggattcata tgaagacaga tctagtcctg ttctattaaa tatctctaag ggggccaaaa    4440
acataccccc gctatcaaag tcagaccaga tgctttgttt ggagaacgaa atatccacat    4500
tccaactccc tcccaggtga gaagggagct aacctgagcc cctatgcctc tttgtttccc    4560
tgctgtgaac cagaagacat tgctgggata tttgaaatag ggacagagct gggaatatgg    4620
aaaggagacc cctaacattt ctccagggct ctgggttctg gatttggatt ccccacccaa    4680
gaaagcaagt tacatcagca atgcactgag ggttgagtcc tgggatgcca agggtcggtt    4740
ctttattgta tagcaaagca ggccccatct tcactgacta agaccatctc cactccctgg    4800
ccactcccca ccaagcattc tctgccactc tttctcctga agtgggggc caactctacc     4860
atcttgttct aacccctgc cccagctcac aactctctct ccctcttgat gtgagcagca     4920
aacccacttt cagagctgtg gagattggcc cagaccagga tctggatgtt gttgaaatca    4980
cagaaaacag ccaggagctt cgcatgcgga actcaagtgg gtaagtgagg ggacaccttc    5040
tggcctacag aaggccccca catggacgct gctcttcagg ttgcaaccag ctcacctgga    5100
acccccaagca gccaggggaa tgtaagcaga catcaggaag aactcctagc cagatggatc   5160
attcaatgcc aagagctata gactcacatt ttggagaggt tttctgtgtt gacttgtttt    5220
```

```
taatacaatg gacagctgga caaagtgtgt tgtcctactc agagccagag ggatggataa    5280
tgtgaccttt ccatcaatct ggatagtaaa tagtttttgc tactgctgta ggttttctaa    5340
taaattgccc aataggcaag attccaaagt cactttgtcc ttccctacca cttacccagc    5400
cagagctccc caccttcttg atgctccagg gaagaggctc catggccctt gtgggtggcc    5460
tgttcctgag cctcgccacc ctgtgttaga gcagagcatc cagatgaaat ctgtcacact    5520
gtggcaaagt ggctcagaga ggaggctggc ttcctagcat tcaggacgt tgctgagggc     5580 cgcttattca ccgaaaataa atcttgaaaa ggacagggct ggtagcagaa tgatccttta    5640
cctaaaattc tatcaaaatc ccattcttcc atttggaaag cccacagtgt cacagactct    5700
gttccgggct ctgtcctctt ccctcttggg tcccaggagc ccaggctggg ctttgaagca    5760
ggcagggccc agcacacagt aggtactcag cagtgggggt gttgaatcca atcaaacgga    5820
agtgtcaatg caggaaatgc aatggatgtc aatgcagtct ccaaatgttc cccactgtgc    5880
agcttccaca ttcccgaggt attgggaggg acttgaatt aacagcttcg ggaggcctga    5940
gtccctgcct cccagctgag gaagaagctt aaatcacagg gcgctgtgtc tgtcttccag    6000
gccctgtctc tcaggctccc tggtctccct gcactgtctt ggtgagtacc cccaatctct    6060
gagggtttgg ggcctgggcc agcaatgagc agggaggaag accttcatct tcactcctaa    6120
atttctggga ctccaagttt cattctgcct tggtctacag cccttgggct tgtcggtcaa    6180 tgcccctcg agttgttggt ggccttgggc aggtcacatt ctttttctgg gtctttccaa    6240
gccccagttt ccccttcta ccatctgtgc atggctccat gacctaagtg gagacctggg    6300
agagagtgtt aggaagaccg aaaagggcag gacgggcct ccactgcctc ccatccctgg    6360
tccgggccca catagccttc tttgtcacaa tcagctcagg tatccaagat cagattaccc    6420
acattcatta tttgagcaac tattcattga acagttagaa tatgtctcac tctgtcagtt    6480
gctggctaga agtagaaagt accagatgag tgaaataatt ggccactatc cttggtagct    6540
gatgactaag taagagagag atgcaagaca acatgtggaa aatgccaaac tgagtagcag    6600
tcacagttga catgctgcag agagagctgg ccggggtca aagacctgg gcaccagtcc     6660 tgttcatttc cagtgtggcc tcgagtcatt cacctgacct ccctgaagtt catttttccca   6720 agaagttgtt tagtccaact gcccatcaag gatctttagg gaccccttcta gctctaacag   6780 aggagatcag aaaagaaaac aagcaatgtg gctcagctca tcctacaagc ttcatagaga    6840
actgagactg gcctggaagc atagccagaa attagaacgc taagggaag aaggtcacaa     6900 cgctgcctct gcaatttagg agtgtatatg ctttcctgca ggatgttgag agtttcattc    6960
attatcgtat gcccccctacc ccggcccac aatacctagt gcgtgggatc tgacacgtgg    7020
tggctggtca atgaatgaat gaatgaatgg tcacaccatc tgaggttctg cactgagtag    7080
ccctgaaggc ttgaagcagc ataagtgaca ggtcctccct tgaggggcct ctgttttacc    7140
aataagccaa gacctaagct caacaacact gaaagggtgg ccaatacccca ggacagcctg   7200 tgggaattcc agagaaaggg agattcccag ggactgggg cccaggctaa acactgaaaa     7260
atgcatctgt aggctcaagg aggaaaagcc catgtctgtc tgtcttgccc accactctct    7320
cccagcaccc agcactgccc caggacagag agcacttgac acaagttggt tagattaatg    7380
aatgatttag agttcagtgg tccccaacct ttttggcaca agagactggt tgcatggaag    7440 acaattttc cgcaaaccaa gagggggata gagagcatta gattctctct ttttttttt      7500 tttgagacca agtctggctc ttgtcactca gcctggagta aagtgttgcg atctcggctc    7560
actgcaacct ccgcctcctg gattcaagcg attctcctgc ctcagcccccc taaatagctg   7620
```

```
ggattacagg cacccgtcac cagcccagct gggactatag gcatgtgcca ccatgcccgg    7680 ctaattttg tatttttagt agagacggcg tttcaccatg ttggccaggc tagtctcgaa      7740
ctcctgacct caggtgatct gcccgcctga gcctcccaaa gtgctgggat tacaggcatg     7800
agctgcctca cccagcctaa agtctcataa ggaacgtaca gcatagatcc ctcacatgtg    7860
cagttcacaa taaggttgtg ctcctacaag aatctaacgc cacctctgat ctgacaggag    7920
gtgaagctca ggtggtcatg ctcgcttgtc cctgccactc acttcctaat gtacagccag    7980
gttcctaaca ggccacgaac cagtgggaag ggcatctttt tggatcaaaa acagaattac    8040
tttttagaga actacaagca gatcaatttg gctagacaga gactttatat gaaacagcag    8100
gaggctgcta ggaggagtgg aaactctact ttgccctcaa gggagatccc gaagggcttt    8160
gcaggagcgg gcaaggtggc atgaagaaag cagtgtttga aatcaggtgg tatttgaaaa    8220
gcccagccct tccccttaga atggcccttc taccatctgt gcatggctcc acaaccgtgg    8280
tggtggctgc cagaagaatt ggaaaggcag agcatgggtg gagagggggg acctgagggc    8340
tttacaggag ttccgggggt ggtgagggtg tgaaagccag gtcagtcagt aggaagacag    8400
gatgtcagat tgagagactc ccctggccgg ggaaacagac ttggagaagg gggagttttg    8460
gatgagacag tccacttccg agtcacaaaa tagcttgtgg gtgtctgttt actgttactc    8520
agtgggagtg gctggggaca cgccacctgg gcagggcttt cgtaattctg catcacttgt    8580
gaaggtcaca gattcccagc acaacggaca cacccatgtt catagtctga actcctaaac    8640
acatcttaaa ccaaaataaa aaaaaagaa agaaagaaag aaaaaggaga gggaggtttg    8700
aggaaagcct atggtctggg acactcaata cctcccatga atatctcata ttgggctggt    8760
cctctctcca ctctggcccc agccataagg gccctgctta gagcagattt tgggtgctga    8820
gtggaggcag cctcatcccc aacagcctga cttcctgcct cctccctgcc tctgcctgtg    8880
tccagcctgt gggaagagcc tgaagacccc ccgtgtggtg ggtgtggagg aggcctctgt    8940
ggattcttgg ccttggcagg tcagcatcca gtacgacaaa cagcacgtct gtggagggag    9000
catcctggac ccccactggg tcctcacggc agcccactgc ttcaggtaag accccagctg    9060
taaggaggtc tctggggacc aaggccagtc agggaccaga gagcttgggg tcctgtctcc    9120
tggcaccgtc cttctcttca ctctcccact agagacgttt tccaggttgt ggtggcccca    9180
atgagacaat ggccatgatg ccctttgtta ggcttttggg tgtctgagca gagggtgctg    9240
gtcaccaagc atggcctctt cctggtggga caccagcaga tacccagagt cctcacccca    9300 ccccatatc gttcaagcta caaaagctct tcccacctgc ctcaacttcc aagaactcac    9360 tctcttttg cttgtttcca ggaagttgtt ccagggtcta gagtcatagc cacgtcctca    9420
ttatgtctgg aaactttaaa aaattaaag agcataggtt cctttcagtc cacagagaag    9480
cctggcctta cctcagggaa gggctactcc cagacccct tcacttttt tttttttt        9540 ttttttttt tttttgagac agagtcttgc tctgttgctt aggctggagc gcagcagcat    9600
gatcttggct cactgcaacc tccgcctcct gagttcaagc aattctcctg cctcagcttc    9660
ccaagtagct gggactatag gcatgggcca ccatgcccgg ctaattttg tattttggt     9720 agagacaggg tttcaccatg ttggccaggc tgatctctaa ctcctgacct caagtgatct    9780
gcccacctca gcctcccaaa ctgctgggat tacaggcatg agccagggca tccggctttt    9840
atttattcat tcattcaata tctaatgagc acctaccagg taccaaacac cagatgatgc    9900
gcccaagttc attagacccc accgctgtct tcaaggcact catgatctag gccagcgttt    9960
```

| | |
|---|---|
| tttaaccact tttttttttt ttttttttga gattctggtg agagctataa attctttcct | 10020 |
| ggaaaaacat ctctgcacac taagctgtgc ctggcattgg gaaaaagaaa gcacgtaatg | 10080 |
| taactgacag catgagtaac acagtgagaa aggttggagg agagagcgcc aggacctcag | 10140 |
| aactcaggca ttagaggagc cccttcccca gccctccttg aggtttcgtt gggcaggttt | 10200 |
| cactgaggaa aaagggtcaa atcccttttt cgaatttgac ttcttgtaag tgccagaaga | 10260 |
| ctgccccttc tccaccatcc ctgcctcacc atcatctttc ctcccaaggc agtgacatcc | 10320 |
| agcacccga tccctagggc cctggggacc cagcctttgg caaagtctcc tcaggcttgg | 10380 |
| atcaggcctg aacccagctg tctctacccc caggaaacat accgatgtgt caactggaa | 10440 |
| ggtgcgggca ggctcagaca aactgggcag cttcccatcc ctggctgtgg ccaagatcat | 10500 |
| catcattgaa ttcaaccca tgtaccccaa agacaatgac atcgccctca tgaagctgca | 10560 |
| gttcccactc actttctcag gtgagaagca gggcccaagg ccactcaagc ctcttacatc | 10620 |
| agttttcacg cccactctgc tattagctca ctgaccgccc ttggcacata atgtctcctc | 10680 |
| tcaagtcctc agcttgccca tttgtctcta atacgtcagc ctaacatcac tgatgccatg | 10740 |
| aggcctcctc aagctgtcag ctaacacctc cactccattc cctgccagag attcttccaa | 10800 |
| ggcctgtctt ccctatgtgg agcccctcga gtgagaactg gagtttcatc caatcttgga | 10860 |
| gttttaggag acctttaaa aagattatcg agctaattcc ccaccactga ccaacacgca | 10920 |
| agagcctgct cagtatccct gccaaggagt cattgtgccc ctgtttgctc tcctccaggg | 10980 |
| gcagggaacc cattacctgt gaggcagccc acagagtctt tgaacagctc tgttggatgc | 11040 |
| cttgtgctta tactgaaatg tatttagatc aggattccca actgtggggt ccacaagaca | 11100 |
| ctggccct ggagaagaga ggattccatt gtcaaataag tttggggaac attttcatac | 11160 |
| tacagctccc ttcttggaac acattagttt attaaaggta ggagaagttt ttaaaataat | 11220 |
| ctgttttatt gcgtttaacc tacatttttt aaatttattt gaccacagaa tccttttttc | 11280 |
| atgctacttc tattagcatc ccatagaaca agtgttctag agaccctggt gtgacccctt | 11340 |
| tcagagagct taactgccag gctctcctga gccctggtgt gtgtttcaag atttgtgcct | 11400 |
| gggaattgtt ttaatcaggt atggcaaggt gacagataca gacacagcta tctttgaaag | 11460 |
| aagagtttat tatttataat tcctgagaga aagggacata ccccacccc caacacaggg | 11520 |
| acacccgggg aagcagctgg gtccaccagg aggcaggagt gaggggaagg catggccag | 11580 |
| agccacctgt ggcttccatg ggcaggtctg gccaaggtag ggtaggcaag attgagcatg | 11640 |
| ctcaggattg gatagtgtgg acaattctct aggctataga tgtcagcctc tggttgtcta | 11700 |
| gtatctgtcc ctggggtgat ttagggcagg gaaaatattg gcttggtgtc tgagagtcag | 11760 |
| ataaaggaag tggttgggga tatgggcttt gggttggctg gtttgcctat taaaggcgtg | 11820 |
| cccaaagcca agttgtttac tatctgcagg aattagctaa cccagtctct cccagaccag | 11880 |
| caagatcccc ataatcataa agcatcataa tttacagaaa attaacactt atgatgaata | 11940 |
| aaagatctcc ttcttcctct gtgctcctgg caggcacagt caggcccatc tgtctgccct | 12000 |
| tctttgatga ggagctcact ccagccaccc cactctggat cattggatgg ggctttacga | 12060 |
| agcagaatgg aggtaagtcc tgggtgcagg accacagggc aggagatgcc cttgtatgag | 12120 |
| ggagcagctt ccagaagtaa tgggaaggag gaccacccct cagagaaacc catcctggag | 12180 |
| gaccaagcac caaggcgcca ggcagaaagc aaagtggttt ggcaatccag ggctggggga | 12240 |
| tagaaggcaa ggatgggaat gtgagtgttt ttaccctccc agggaagatg tctgacatac | 12300 |
| tgctgcaggc gtcagtccag gtcattgaca gcacacggtg caatgcagac gatgcgtacc | 12360 |

```
aggggggaagt caccgagaaag atgatgtgtg caggcatccc ggaagggggt gtggacacct    12420
gccaggtggg gcctccaaga atcatgggga gttctaagaa tagggtttag gtcctagaga    12480
gatgagaaaa cccagaggct gcatgccta caggaagcct tgcatatcat gggcactcaa    12540
tgtgtgatga tgggaggaag agagggaggg aaggaaagga tagtcagata aaagtgtacc    12600
aatagatgag tgggtggatg gatggatgca gacaagcaga gagatttcaa atgtctcttt    12660
cacattcgaa gatgatgtta ctggcctggc atggtggctc acgcttgtaa tcccagcact    12720
ttgggaggct gaggcgggca ggtgatttga ggtcaggaat tcaagaccag cctggccaac    12780
atggtgaaat cccatctcta ctaaaaagaa tacaaaaatt agctgggcgt ggtggcacgt    12840
gcctgtaatc ccagctactt gggaggctga ggcaggagaa ttgcttgaac ccaggaggca    12900
gaggttgcag taagctgaga ttgcgccact gcactccagc ctgggtgacc cagcaagact    12960
ccatctgaaa acaacaacaa caacaaagat gacattactc atccaccca cccaccctc    13020
tcactagcta cagaatgatt agcccttga ggtcaggaat cccaggtcta ttttctctgt    13080
gactctcccc aagctgctga actacactag gaaagaatta ccgcctgcag aatgctggaa    13140
gcacatctgt gtgtgccctc accccggcct cattggccat caggactgct tagcaatccc    13200
tgtagaccctt cttcctcccc catacttcca gaggatcttc tgaactattt tcttttttta    13260
tttttctttt tatgtttttt aacagagaca gggtcactat gttgcccagt ctggtctcaa    13320
actcctgggt tcaagggatt ctcccacctc agctttccaa aatgctggga ttacaggcat    13380
gagccatcgt gcttggcctg aaccatttc attaaaaccc ctaccctact ctcacctcca    13440
tttccagtca ttaaattcct tcatttaaga ggcatctctt agtcatcgca tgtgtgccat    13500
gaacatggta gtctttggag acccctcagg gagctcacag tggttggggg aaagggggggc    13560
attaaacaga catttaagct atagttttgg gttcagaggg aggaagcccc aggggctaaa    13620
acagctgata aggactccca gataagtgca cttttcacta tctggcatt tcttgttttg    13680
ttatttgctt gttcactgtc tctcaccccca tttgatccta agctttctga gggcagggat    13740
cttttgttttt tttcatcagt tggatcccaa ttgcttagaa cactacctgg cacaaaatag    13800
gcactctata agtgattaca caaattttgg aacgactagg ttaaacaatg ataaccaggc    13860
tttttttttt tttttgaga ctgagtctca ctctgttgcc caggctagag tgaagtggtt    13920
tgatctcggc tcactgcagc ctccgcctct gggttcgaat gattctccac ctcagcctcc    13980
tgagtagctg ggattacagg tgcctgccac tatgcccagc taatttttgt atttgtagta    14040
gagacggggtt tcaccatgtt ggccaggctg gtcttgaact cctgacctca agtgattcac    14100
ccgcctcagc ctcccaaggt gctgggatta caggtgtgag ccaccgctcc tggccaacaa    14160
ccaggctttt ttaagacatc actcagagcc tttaatttgc taatgtgagt tgtgaatctc    14220
tgagagaagg ctaacggcat gcttgcaact tacttgtcca cagacaagcc tttctgcccc    14280
agaagagaag accattctag ggtgctaatg agcaaagagg gtgagggtgg aatatcggag    14340
agcagcaggg agtgcagggg aacagatagg ccagttcagg gagcagagaa ggagaagccc    14400
ccccacctca cctgccctcc ccagcagtct ctgttctggt ctctcacagg gtgacagtgg    14460
tgggcccctg atgtaccaat ctgaccagtg gcatgtggtg ggcatcgtta gttggggcta    14520
tggctgcggg ggcccgagca ccccaggagt atacaccaag gtctcagcct atctcaactg    14580
gatctacaat gtctggaagg taaggtacct ttgcccctacc cactgtgcct tcctccagt    14640
cctctacctg gggggtgcca atccatcctc aggtttgatt taaatggttc tgacaactct    14700
```

-continued

```
ttacatccca aataactttc cctccaagca agggacagcc tgagattgca ctattaaggc    14760
tgaaattcct taggtcagag atttctgata aatgcaaata ccttagggaa tagaacacac    14820
caagcctttc tttctctttt ctgacagaat gagactatca gatcctttct agagagaaga    14880
ttctgataag gaagagagtg gaaaggctca tgagacctcc tggccctctg cagggtaggg    14940
agagaagcaa agtgtttcag aaaaggaaga ctcacgttac acatgtcacc actttgtcca    15000
gtttcagata atctgacttt ctcttcatcg gtctctctta ttctaggctg agctgtaacg    15060
ctgccgtccc ccacatccag aagctgcttc ccttcagacc tacctacggc atgacccctc    15120
aaagtcagat atgggacaag agcctccttg aacaaactc                           15159
```

<210> SEQ ID NO 14
<211> LENGTH: 435
<212> TYPE: PRT
<213> ORGANISM: Artificial Sequence
<220> FEATURE:
<223> OTHER INFORMATION: Recombinant protein

<400> SEQUENCE: 14

```
Met Glu Ser Asp Ser Gly Gln Pro Leu Asn Asn Arg Asp Ile Val Pro
1               5                   10                  15

Phe Arg Lys Pro Arg Arg Pro Gln Glu Thr Phe Lys Lys Val Gly Ile
            20                  25                  30

Pro Ile Ile Ala Val Leu Leu Ser Leu Ile Ala Leu Val Ile Val Ala
        35                  40                  45

Leu Leu Ile Lys Val Ile Leu Asp Lys Tyr Tyr Phe Leu Cys Gly Gln
    50                  55                  60

Pro Leu His Phe Ile Pro Arg Lys Gln Leu Cys Asp Gly Glu Leu Asp
65                  70                  75                  80

Cys Pro Leu Gly Glu Asp Glu His Cys Val Lys Ser Phe Pro Glu
                85                  90                  95

Gly Pro Ala Val Ala Val Arg Leu Ser Lys Asp Arg Ser Thr Leu Gln
            100                 105                 110

Val Leu Asp Ser Ala Thr Gly Asn Trp Phe Ser Ala Cys Phe Asp Asn
        115                 120                 125

Phe Thr Glu Ala Leu Ala Glu Thr Ala Cys Arg Gln Met Gly Tyr Ser
    130                 135                 140

Ser Lys Pro Thr Phe Arg Ala Val Glu Ile Gly Pro Asp Gln Asp Leu
145                 150                 155                 160

Asp Val Val Glu Ile Thr Glu Asn Ser Gln Glu Leu Arg Met Arg Asn
                165                 170                 175

Ser Ser Gly Pro Cys Leu Ser Gly Ser Leu Val Ser Leu His Cys Leu
            180                 185                 190

Ala Cys Gly Lys Ser Leu Lys Thr Pro Arg Val Val Gly Val Glu Glu
        195                 200                 205

Ala Ser Val Asp Ser Trp Pro Trp Gln Val Ser Ile Gln Tyr Asp Lys
    210                 215                 220

Gln His Val Cys Gly Gly Ser Ile Leu Asp Pro His Trp Val Leu Thr
225                 230                 235                 240

Ala Ala His Cys Phe Arg Lys His Thr Asp Val Phe Asn Trp Lys Val
                245                 250                 255

Arg Ala Gly Ser Asp Lys Leu Gly Ser Phe Pro Ser Leu Ala Val Ala
            260                 265                 270

Lys Ile Ile Ile Ile Glu Phe Asn Pro Met Tyr Pro Lys Asp Asn Asp
        275                 280                 285
```

```
Ile Ala Leu Met Lys Leu Gln Phe Pro Leu Thr Phe Ser Gly Thr Val
    290                 295                 300
Arg Pro Ile Cys Leu Pro Phe Phe Asp Glu Glu Leu Thr Pro Ala Thr
305                 310                 315                 320
Pro Leu Trp Ile Ile Gly Trp Gly Phe Thr Lys Gln Asn Gly Gly Lys
                325                 330                 335
Met Ser Asp Ile Leu Leu Gln Ala Ser Val Gln Val Ile Asp Ser Thr
                340                 345                 350
Arg Cys Asn Ala Asp Asp Ala Tyr Gln Gly Glu Val Thr Glu Lys Met
            355                 360                 365
Met Cys Ala Gly Ile Pro Glu Gly Gly Val Asp Thr Cys Gln Gly Asp
            370                 375                 380
Ser Gly Gly Pro Leu Met Tyr Gln Ser Asp Gln Trp His Val Val Gly
385                 390                 395                 400
Ile Val Ser Trp Gly Tyr Gly Cys Gly Gly Pro Ser Thr Pro Gly Val
                405                 410                 415
Tyr Thr Lys Val Ser Ala Tyr Leu Asn Trp Ile Tyr Asn Val Trp Lys
                420                 425                 430
Ala Glu Leu
        435

<210> SEQ ID NO 15
<211> LENGTH: 2046
<212> TYPE: DNA
<213> ORGANISM: Mus musculus

<400> SEQUENCE: 15
cagaaacaag gacctcttca ttattcaaga gtaaaatgta taggccaaga ccaatgctat      60
caccgtcaag attcttcact cccttttgcag tagctttcgt tgtcataata acggtagggc    120
tcctggccat gatggcaggt ctacttattc acttttttagc ttttgacaag aaagcttact    180
tttatcatag cagctttcaa atcctaaacg ttgaatacac tgaggcttta aactcaccag    240
ctacacacga atacagaacc ttgagtgaaa gaattgaggc tatgattact gatgaatttc    300
gaggatcaag tctaaaaagt gagtttatca ggacacatgt tgtcaaacta agaaaagaag    360
ggactggtgt ggttgcggat gttgtcatga aatttcgatc tagtaaacgt aacaacagaa    420
aggtaatgaa aaccagaatt caatctgtgc tacgaagact cagcagctct ggaaacttgg    480
aaatagcccc ttcgaatgag ataacatcac tcactgacca ggatacagaa atgttttga    540 ctcaagaatg tggagcacgt ccagacctta acactgtc agaagagaga atcattggag    600
gcatgcaagc tgagcccggt gactggccct ggcaagtcag tctacagctc aataatgtcc    660
accactgtgg aggtgccctg atcagtaaca tgtgggtcct gacagcagct cattgcttca    720
aaagctatcc taatcctcaa tattggacag ccacctttgg ggtttctaca atgagcccta    780
ggctgagagt gagagtaagg gctatttttag cccacgacgg gtacagctcc gtaactcgtg    840
acaatgacat cgcagttgta caacttgaca gatctgtcgc cttttccaga aatatccata    900
gggtatgtct cccagcagca acccaaaata tcatccctgg ttctgtcgca tatgttacag    960 gatgggggatc tctcacatat ggaggcaacg cagtcacaaa tctacggcaa ggagaggtca   1020
gaataataag ttcagaggaa tgcaatacgc cagctggtta cagtggaagt gtcttgccag   1080
gaatgctgtg tgctggaatg cgttcagggg ccgtggatgc atgccagggt gattcaggtg   1140
gcccgctagt acaagaagac tcaaggcggc tttggtttgt tgtgggcatt gtgagctggg   1200
```

```
gatatcagtg tggcctccca ataagccag gcgtgtatac tcgagtgaca gcctaccgca    1260
actggatcag acagcagacg ggaatctagt gcaaccgagg aaaaaacgtg ccatgaggtc    1320
tctgtatcca agtgtgactg actcggatgc catggcttca catttcaact gcaaaggaga    1380
ctggaaatgc cccttctgaa cgtcccatta cataaatatg gtttaactgt ttagtatttc    1440
tttgtcggta cagatttta ctttcttgag gaaaaaaaaa acatgaacat ggctaagtaa    1500
gaattatgtt aggctagtaa caggaagaca tttattacat gggtggtcag gtgtagtagt    1560
gagaagtcag gtaagttaag tcaataattt acagaaaata atgtcaggta gtcctaacgt    1620
taaatatgtg aggccacaga acaaatagtg ttagaactga agccatccca agtatttaac    1680
atttgttttc aagtgaaact aagaaacaga cttacatata gttttaatgg tgaattttca    1740
ttttaaatat tttatctaca tagaaaagac atatctcctt catgaagaag ctgaggtgat    1800
gaatcaacac agcctcttca gctatgtttg caaccacaag atttgtggga agaaatccc    1860 tactaccaac ttcctactgt tggcattatt ttttagagta acacgacgca caatagcaaa    1920
atttaagtaa caaattaaaa gttaatgatg aagaagaagt aaagagtttg tttgcaaaga    1980
caaaaattaa acagattaat atcaataaat ctggagacag aagggtctca gattcatatt    2040
ctctct                                                              2046

<210> SEQ ID NO 16
<211> LENGTH: 417
<212> TYPE: PRT
<213> ORGANISM: Mus musculus

<400> SEQUENCE: 16

Met Tyr Arg Pro Arg Pro Met Leu Ser Pro Ser Arg Phe Phe Thr Pro
1               5                   10                  15

Phe Ala Val Ala Phe Val Val Ile Ile Thr Val Gly Leu Leu Ala Met
            20                  25                  30

Met Ala Gly Leu Leu Ile His Phe Leu Ala Phe Asp Lys Lys Ala Tyr
        35                  40                  45

Phe Tyr His Ser Ser Phe Gln Ile Leu Asn Val Glu Tyr Thr Glu Ala
    50                  55                  60

Leu Asn Ser Pro Ala Thr His Glu Tyr Arg Thr Leu Ser Glu Arg Ile
65                  70                  75                  80

Glu Ala Met Ile Thr Asp Glu Phe Arg Gly Ser Ser Leu Lys Ser Glu
                85                  90                  95

Phe Ile Arg Thr His Val Val Lys Leu Arg Lys Glu Gly Thr Gly Val
            100                 105                 110

Val Ala Asp Val Val Met Lys Phe Arg Ser Ser Lys Arg Asn Asn Arg
        115                 120                 125

Lys Val Met Lys Thr Arg Ile Gln Ser Val Leu Arg Arg Leu Ser Ser
    130                 135                 140

Ser Gly Asn Leu Glu Ile Ala Pro Ser Asn Glu Ile Thr Ser Leu Thr
145                 150                 155                 160

Asp Gln Asp Thr Glu Asn Val Leu Thr Gln Glu Cys Gly Ala Arg Pro
                165                 170                 175

Asp Leu Ile Thr Leu Ser Glu Glu Arg Ile Ile Gly Gly Met Gln Ala
            180                 185                 190

Glu Pro Gly Asp Trp Pro Trp Gln Val Ser Leu Gln Leu Asn Asn Val
        195                 200                 205

His His Cys Gly Gly Ala Leu Ile Ser Asn Met Trp Val Leu Thr Ala
    210                 215                 220
```

```
Ala His Cys Phe Lys Ser Tyr Pro Asn Pro Gln Tyr Trp Thr Ala Thr
225                 230                 235                 240

Phe Gly Val Ser Thr Met Ser Pro Arg Leu Arg Val Arg Val Arg Ala
            245                 250                 255

Ile Leu Ala His Asp Gly Tyr Ser Ser Val Thr Arg Asp Asn Asp Ile
        260                 265                 270

Ala Val Val Gln Leu Asp Arg Ser Val Ala Phe Ser Arg Asn Ile His
    275                 280                 285

Arg Val Cys Leu Pro Ala Ala Thr Gln Asn Ile Ile Pro Gly Ser Val
290                 295                 300

Ala Tyr Val Thr Gly Trp Gly Ser Leu Thr Tyr Gly Gly Asn Ala Val
305                 310                 315                 320

Thr Asn Leu Arg Gln Gly Glu Val Arg Ile Ile Ser Ser Glu Glu Cys
                325                 330                 335

Asn Thr Pro Ala Gly Tyr Ser Gly Ser Val Leu Pro Gly Met Leu Cys
            340                 345                 350

Ala Gly Met Arg Ser Gly Ala Val Asp Ala Cys Gln Gly Asp Ser Gly
        355                 360                 365

Gly Pro Leu Val Gln Glu Asp Ser Arg Arg Leu Trp Phe Val Val Gly
    370                 375                 380

Ile Val Ser Trp Gly Tyr Gln Cys Gly Leu Pro Asn Lys Pro Gly Val
385                 390                 395                 400

Tyr Thr Arg Val Thr Ala Tyr Arg Asn Trp Ile Arg Gln Gln Thr Gly
                405                 410                 415

Ile
```

<210> SEQ ID NO 17
<211> LENGTH: 2800
<212> TYPE: DNA
<213> ORGANISM: Homo sapiens

<400> SEQUENCE: 17

```
atttgagtgg gaatctcaaa gcagttgagt aggcagaaaa aagaacctct tcattaagga      60
ttaaaatgta taggccagca cgtgtaactt cgacttcaag atttctgaat ccatatgtag     120
tatgttttcat tgtcgtcgca ggggtagtga tcctggcagt caccatagct ctacttgttt    180
acttttagc ttttgatcaa aaatcttact tttataggag cagttttcaa ctcctaaatg      240
ttgaatataa tagtcagtta aattcaccag ctacacagga atacaggact ttgagtggaa    300
gaattgaatc tctgattact aaaacattca agaatcaaa tttaagaaat cagttcatca     360
gagctcatgt tgccaaactg aggcaagatg gtagtggtgt gagagcggat gttgtcatga    420
aatttcaatt cactagaaat aacaatggag catcaatgaa aagcagaatt gagtctgttt    480
tacgacaaat gctgaataac tctggaaacc tggaaataaa cccttcaact gagataacat    540
cacttactga ccaggctgca gcaaattggc ttattaatga atgtggggcc ggtccagacc    600
taataacatt gtctgagcag agaatccttg gaggcactga ggctgaggag ggaagctggc    660
cgtggcaagt cagtctgcgg ctcaataatg cccaccactg tggaggcagc ctgatcaata    720
acatgtggat cctgacagca gctcactgct tcagaagcaa ctctaatcct cgtgactgga    780
ttgccacgtc tggtatttcc acaacatttc ctaaactaag aatgagagta agaaatatt     840
taattcataa caattataaa tctgcaactc atgaaaatga cattgcactt gtgagacttg    900
agaacagtgt caccttttacc aaagatatcc atagtgtgtg tctcccagct gctacccaga    960
```

```
atattccacc tggctctact gcttatgtaa caggatgggg cgctcaagaa tatgctggcc    1020
acacagttcc agagctaagg caaggacagg tcagaataat aagtaatgat gtatgtaatg    1080
caccacatag ttataatgga gccatcttgt ctggaatgct gtgtgctgga gtacctcaag    1140
gtggagtgga cgcatgtcag ggtgactctg gtggcccact agtacaagaa gactcacggc    1200
ggctttggtt tattgtgggg atagtaagct ggggagatca gtgtggcctg ccggataagc    1260
caggagtgta tactcgagtg acagcctacc ttgactggat taggcaacaa actgggatct    1320
agtgcaacaa gtgcatccct gttgcaaagt ctgtatgcag gtgtgcctgt cttaaattcc    1380
aaagctttac atttcaactg aaaaagaaac tagaaatgtc ctaatttaac atcttgttac    1440
ataaatatgg tttaacaaac actgtttaac cttttctttat tattaaaggt tttctatttt    1500
ctccagagaa ctatatgaat gttgcatagt actgtggctg tgtaacagaa gaaacacact    1560
aaactaatta caaagttaac aatttcatta cagttgtgct aaatgcccgt agtgagaaga    1620
acaggaacct tgagcatgta tagtagagga acctgcacag gtctgatggg tcagaggggt    1680
cttctctggg tttcactgag gatgagaagt aagcaaactg tggaaacatg caaggaaaa     1740 agtgatagaa taatattcaa gacaaaaaga acagtatgag gcaagagaaa taatatgtat    1800
ttaaaatttt tggttactca atatcttata cttagtatga gtcctaaaat taaaaatgtg    1860
aaactgttgt actatacgta taacctaacc ttaattattc tgtaagaaca tgcttccata    1920
ggaaatagtg gataattttc agctatttaa ggcaaaagct aaaatagttc actcctcaac    1980
tgagacccaa agaattatag atatttttca tgatgaccca tgaaaaatat cactcatcta    2040
cataaaggag agactatatc tattttatag agaagctaag aaatataccct acacaaactt    2100 gtcaggtgct ttacaactac atagtacttt taacaacaa ataataatt ttaagaatga     2160 aaaatttaat catcgggaag aacgtcccac tacagacttc ctatcactgg cagttatatt    2220
tttgagcgta aaagggtcgt caaacgctaa atctaagtaa cgaattgaaa gtttaaagag    2280
ggggaagagt tggtttgcaa aggaaaagtt taaatagctt aatatcaata gaatgatcct    2340
gaagacagaa aaaactttgt cactcttcct ctctcatttt ctttctctct ctctcccctt    2400
ctcatacaca tgcctccccc accaaagaat ataatgtaaa ttaaatccac taaaatgtaa    2460
tggcatgaaa atctctgtag tctgaatcac taatattcct gagttttat gagctcctag     2520 tacagctaaa gtttgcctat gcatgatcat ctatgcgtca gagcttcctc cttctacaag    2580
ctaactccct gcatctgggc atcaggactg ctccatacat ttgctgaaaa cttcttgtat    2640
ttcctgatgt aaaattgtgc aaacacctac aataaagcca tctactttta gggaaaggga    2700
gttgaaaatg caaccaactc ttggcgaact gtacaaacaa atctttgcta tactttattt    2760
caaataaatt cttttaaaa taaaaaaaaa aaaaaaaaa                            2800
```

<210> SEQ ID NO 18
<211> LENGTH: 418
<212> TYPE: PRT
<213> ORGANISM: Homo sapiens

<400> SEQUENCE: 18

```
Met Tyr Arg Pro Ala Arg Val Thr Ser Thr Ser Arg Phe Leu Asn Pro
1               5                   10                  15

Tyr Val Val Cys Phe Ile Val Val Ala Gly Val Val Ile Leu Ala Val
            20                  25                  30

Thr Ile Ala Leu Leu Val Tyr Phe Leu Ala Phe Asp Gln Lys Ser Tyr
        35                  40                  45
```

Phe Tyr Arg Ser Ser Phe Gln Leu Leu Asn Val Glu Tyr Asn Ser Gln
 50                  55                  60

Leu Asn Ser Pro Ala Thr Gln Glu Tyr Arg Thr Leu Ser Gly Arg Ile
 65                  70                  75                  80

Glu Ser Leu Ile Thr Lys Thr Phe Lys Glu Ser Asn Leu Arg Asn Gln
                 85                  90                  95

Phe Ile Arg Ala His Val Ala Lys Leu Arg Gln Asp Gly Ser Gly Val
            100                 105                 110

Arg Ala Asp Val Val Met Lys Phe Gln Phe Thr Arg Asn Asn Asn Gly
        115                 120                 125

Ala Ser Met Lys Ser Arg Ile Glu Ser Val Leu Arg Gln Met Leu Asn
    130                 135                 140

Asn Ser Gly Asn Leu Glu Ile Asn Pro Ser Thr Glu Ile Thr Ser Leu
145                 150                 155                 160

Thr Asp Gln Ala Ala Ala Asn Trp Leu Ile Asn Glu Cys Gly Ala Gly
                165                 170                 175

Pro Asp Leu Ile Thr Leu Ser Gly Gln Arg Ile Leu Gly Gly Thr Glu
            180                 185                 190

Ala Glu Glu Gly Ser Trp Pro Trp Gln Val Ser Leu Arg Leu Asn Asn
        195                 200                 205

Ala His His Cys Gly Gly Ser Leu Ile Asn Asn Met Trp Ile Leu Thr
    210                 215                 220

Ala Ala His Cys Phe Arg Ser Asn Ser Asn Pro Arg Asp Trp Ile Ala
225                 230                 235                 240

Thr Ser Gly Ile Ser Thr Thr Phe Pro Lys Leu Arg Met Arg Val Arg
                245                 250                 255

Asn Ile Leu Ile His Asn Asn Tyr Lys Ser Ala Thr His Glu Asn Asp
            260                 265                 270

Ile Ala Leu Val Arg Leu Glu Asn Ser Val Thr Phe Thr Lys Asp Ile
        275                 280                 285

His Ser Val Cys Leu Pro Ala Ala Thr Gln Asn Ile Pro Pro Gly Ser
    290                 295                 300

Thr Ala Tyr Val Thr Gly Trp Gly Ala Gln Glu Tyr Ala Gly His Thr
305                 310                 315                 320

Val Pro Glu Leu Arg Gln Gly Gln Val Arg Ile Ile Ser Asn Asp Val
                325                 330                 335

Cys Asn Ala Pro His Ser Tyr Asn Gly Ala Ile Leu Ser Gly Met Leu
            340                 345                 350

Cys Ala Gly Val Pro Gln Gly Gly Val Asp Ala Cys Gln Gly Asp Ser
        355                 360                 365

Gly Gly Pro Leu Val Gln Glu Asp Ser Arg Arg Leu Trp Phe Ile Val
    370                 375                 380

Gly Ile Val Ser Trp Gly Asp Gln Cys Gly Leu Pro Asp Lys Pro Gly
385                 390                 395                 400

Val Tyr Thr Arg Val Thr Ala Tyr Leu Asp Trp Ile Arg Gln Gln Thr
                405                 410                 415

Gly Ile

<210> SEQ ID NO 19
<211> LENGTH: 38992
<212> TYPE: DNA
<213> ORGANISM: Artificial Sequence
<220> FEATURE:
<223> OTHER INFORMATION: Recombinant polynucleotide

```
<400> SEQUENCE: 19
gagggagggt ggtgctttgc taatggtgaa ttactaactc ctcaataaag aatattattt      60
gaaataattt ttgaaatttc ataattactt tgggttcttt cttaatgata aataaataat     120
agtatattac aaacatacat taatatttcc tgaatgaata caccacaaat ctcccttaaa     180
atatagcaag aataaaaatt atactatttc tgacaatttt taatttctca aataataata     240
ccactctgat ttttaaacat ctacaccact ctggctttgc caatcttttt aaaaattgaa     300
aagataataa ttttatcata attacactga agcatagaac ttttttcttc aaggaaagca     360
aattttttgaa attctataat ataacctccc ataatcctga ataaattaaa ggttcaacaa     420
cttagtaaag taagactgac cttcccttt atttcttttt cagatcaaaa atcttacttt     480
tataggagca gttttcaact cctaaatgtt gaatataata gtcagttaaa ttcaccagct     540
acacaggaat acaggacttt gagtggaaga attgaatctc tggtaagtta atatttgtct     600
ttgctctttta ttccattata aaatgaatat gataataaac ctaatgtttt gtaatatatt     660
ttcagttgct aagtgctcta catatttccc ttccttgaat ggtgaaacat gtgtttctct     720
ctgcttttat ccagttagtt tactcatata ctggttctta ttcacatctt tgtcatgagt     780
aaaaagtgtt agaaaggcca cgagtaaata tgcatttat ttgtttatga attcaaaatac    840
taaaagttttt ttatttgttt aattaagcat tgacattgtc ttttttaaatt cttttcatt    900
taccttcttc cctcttcctt atccaactaa agacgcaaag caggaggtgt taaaaaacag     960
gtttaccata tcagcagtaa catagtttgg acaacattac actttggttc aatgatagac    1020
atagaagttt gaacagaaat atgcaaagca agtttgagct ctaacttgaa gagagcctct    1080
gggtgcctgc caggaaacct cacgagtgga cccttaacat tcatgtgtca ccacaaacta    1140
ggggctgccc tttagttttg accagtctca gtgtcactca cttacccta cctttttcaaa    1200
aaaaagtcct aagaatataa agtaattcaa tggttctaca attttagcat gtaactgagt    1260
cacctggcag ggttgctttg gtgagctcaa gataaaattt tatcagcatt tctacatttt    1320
ctggaatatt ccttaatcca ggcttttaat cccttggtgc ttttctgaac cactgcaatg    1380
agcttctaac tgttctcact gtgtgcaggc tctttccctt ctaatctaat ttacacactt    1440
ctgaacacaa atctctcaca gcctgtttcc ttcatgttac ctccagctca agacttttg     1500
cctacaaaat aaaattcaaa cttgttagct aagcaccttc tcatgtctat gctttggctc    1560
atatttcagc catcgtgtgc cccacttatt cttatagcca acctgaaaag ccatctttta    1620
taagaaacta cctctgctct ccatgattgg atataattaa tcctccttcc acatcacctc    1680
gccacaaaat tgtatctgtg ttgatctcat gccacatacc tgtatgtatt ttatattata    1740
aatatttgca gacttgttta atttgccatg ttagactaag ttccatgaag acagctccat    1800
atccattcca tttttatata tccacaacat ttggtcgggt tgatgcttaa taaatgttta    1860
ttgaaggaac aggagtctcc cacttctgac ataatgaact tatttccccc agtgttaacc    1920
ctacatctgg ttcctgtcca agagtctctt cccaaatcat tctgattcaa ctgttcattc    1980
tgatctcatt aaacatttaa atgatatatc taacttcgct tgctttattc tatgctcatc    2040
ctgcagtctc ctcataactt ggtttcaatg atgcttgctt ctagagaaaa aaatgtatta    2100
aataagctta tgattcagtc ctccagctgt gatggttctc actgaacatt agctcagtgg    2160
ttttcgaagt atggtctcta gcataaccta gaaacttgtt agaaatgcaa attcttgggc    2220
tcaccaagac atactaaatc aaaaattctg acattggggc ctagaaatct gtgttttaac    2280
aagcctgcca gtgcagcctg gtcccttttc ttctcggagc cccactcaaa gctttcagtg    2340
```

```
ctcatctccc accaatgaca gggtcctcta tggaaaccgg caggacggtt ccaactcta    2400 actacgtttt agagtttgct tcctagggct atccaggcac caagtatcac aggttagttt    2460
cccagggaag cagactctga gacttgcatg cagggagtgt ctctggggtg ctctcaacca    2520
acaccttcag gaagagaagg aagcagcatt gggcagaggc atagtcaaac tacagtgctg    2580
ttggcacaga agactgaagg gagtcagagc caggggtag aggtgggccc ttagcatcca    2640
tccttcacca ttaggtgtga gttgccccac ctccttgatg tgtaacctc agtcccaagg    2700 tgggtgggag tgcagcagag cagcccctac aagggccaaa ccagagatac accaggcgcc    2760
agaagtgctg ccaggaata gagaggaaag gatgggctta aggtaggatc cacagaactt    2820
ggcaatggat tagaagacag gatgagaagt gacaggttaa cactaacaca gaaatgtcta    2880
acttcggtag ataatggtgc cattggctag aagaggaaac cgaaatgaaa gcaggttgtt    2940
cagggagaca aaagttcact gtggacatct cagcagagtg attcagtggg gaaaggaatg    3000
gatgcccaga ccacctcaga ggaagatcta agctggagcc agcaataaag atacaagatg    3060
aacaatccct aacgaactgc tcctcagcca tgctccccag acacgctgct tcagatttat    3120
agtccgggtg aggctaggag gtgcgcctcc ctcagtggag gacagcaaag caccagtggc    3180
tccagggagt taaaatcttt tgataatttt tgttctagca tctgtctgca gagctgtctc    3240
tcagccattg cctgccttta cacaggagtg cagtccgaaa ttgggagatg agtgaaattt    3300
attatgccta gagatctgga tccccagttg tttgggagta tattttctga accacttgtt    3360
ggtttaagta atgcagattt attgatgcca cttctcttga atctgtgact ctggacccac    3420
catctaagtg aatgtgcaga gggaacggaa tggctgcaat agatctccat taaaaccagt    3480
gcatcctccc agacacatac agtagtaggg aggtgagtca atgtcaggac agcaccagct    3540
cccgcttcgg tacatttcca aagttctcag tctgtgtaca aaggtttgct ctggggcagc    3600
agaaatagcc ctgggcaggt agtcaaaggc ctggtttgat ttcctccact tccaggcaag    3660
tcactcgaag gctcacaggc ttttttcctca cctgccacat gggtccagtg agatctactg    3720
agctgtaaat aatgaaatga gtgtgtgtgc agtcatctat aagttgtaaa gtactagaaa    3780
atggtgaaac tttgggattt gggctattta aggctgaatg ctaaaaatgt caggcattgt    3840
ggagaaagga atttaaatat aagattgatt gactgggatt taaagacaaa tgaaggcaca    3900
cacgcaagtg cacacccaca ctgacactgc acagctcccg ttggaggcat atcctgacca    3960
tgcagacctg gggctctgcc tgtccaagtg cactccttta ctacataaac cctccttctc    4020 ttttgggct gtcaccccac cagagctggc accgagccct tgctgctgcg cttccctggg    4080
gtgtcagctt ttgacagggt gtttcctccc tctgcaggag ccttaacatc ccttggactt    4140 ccttccccc acccaccccc agcagtttta tctcttccta actcgggacc ctttttttcc    4200
cacacaaagt ttattgtcag ttgctggttt catctgtttg agcggctgca acaaaatacc    4260
atagactggg tggcatatgc acgacaaaaa tttatttctc acaggagaag tcaaagatta    4320
atgcaccagc agatctggtg tctgaggggc caccttctgg tttgtagatg atgctttcta    4380
gttaaaacac ctatttaaca cactattaaa cactaagtgt gttaaatagt gcagttgatg    4440
tatttgtcat gtcacccttta tcatacacta aatccttctt tgtctttttt tctgtactct    4500
aatctctttc tgtaagtaat ctttgcttgc agcagtagga tatttagagt actgtggctt    4560
gacaatatat ttagtatttc aagatttcca tgaaattctt ctgatgtatg agttccctag    4620
ttaatcttac atatgtatcc ctttgtaaaa acactttgaa catttaaaat gatacatgaa    4680
```

```
tagtactcta atacaatgcc ataaaaatta taaatcattt gtatagactg gtaagtaaag    4740
attgtgagat taagaaacgc atcaaaggcc attgagctgg aaagtggtat aatgagaatt    4800
caaaccaggg tctcttgact caaaatctaa ggatcatacc atttctcatg ataatatgag    4860
tattattgtt atctctatcc catagacaaa gtgttaacac tgaatgagca gtgaaatagt    4920
ctcagaattt tttattttat ttagcaattc acttgtcatt tctggtcctc agtttattca    4980
cgagtaaaat aaaatagttg gactagataa tttctatagt acattcttac acaaaaaatc    5040
tatgattttg ttattttaa tgtgatatac tcatggcact cattcacctc attttcccag     5100
cctgcctcac tggtcattac ttctctgtgt tctttacagg ctcccccctcc tctacactgc   5160 cattaaatat tgaaacacct caaagcttta cttatgtcca cctctcctct gacactatca    5220
ttctgtctag atgatcccat acatacatgc ccattacttc aacctgtatt tatacgccaa    5280
tgattcacta tatttccagc ctagacattc ttttgtactc tagttaccag cttgatatcc    5340
ttacatggct gtttcaaaac aactcaaata tattatctct caaaatcaaa ctcatgatgt    5400
ccccacacca tcctagcttt ccaccaacaa tacctatccc tattaatagc aataccattt    5460
attcagttat ccaaatcaaa aacctagaat tcatccttaa aattctacta tcattccaaa    5520
tatcctatcc atcagcagcc actgtattct taatcccctg tatttccttc aaatccattc    5580
acctctctcc atatccattg ctgcatgact atccaagcca tcgcctctac cctagggtac    5640
caaaatagca acaaacctaa tctgttcatt tgcattattt tttctccaaa actgattatc    5700
tatatgtagc aagacagatt gttctcaaat tgcaaatccc actatattat cctcttgctt    5760
caaacacttc catggtttcc cattgtttat gataaaacca aatgcttcaa gttcgaagac    5820
cggcatgatt gggaatttcc tgtcacccta gcctacttgc tctccatggt acagttgcac    5880
tggctttctt tcattcctta agtacaacct gtttcctccc acctcaggac tgtgcatgtg    5940
ccattcattc tgctgaggag cctttttcct tccacttcaa tcagctaagt ctgattcttc    6000
ctgacaatct cagctcaata agcatttcct ctaagaaatg tctctaatat cattaattgg    6060
ctcaggtccc tctactgtat tgctgcactt ttcacagtta taatttttact taattatgaa   6120 tgattatttg attaggtcta tttccatcca ttagacataa gcttcatgat ggccagatta    6180 ctgtttttcta tccatcgttg tattccaata cctgacagaa ggagggcggg aggtggtggc   6240
acacaagaga tgctcaaaaa caattgttga ataagtaaat gaatgaggcc atttagaaat    6300
aacgaaagta cctgtttaca aagtacatgt atcaaaacta tgaatgcatt ctacttacat    6360
ggttttctcc aaataaaaca aaagacttca atcaggatta atacctggga taaactgagt    6420
cattaaatct ctcctttgcc atcaggagtg acattgaaac aaatgtctgc aaacaacaaa    6480 tactttttc ccaaaatata ttgaatggca tttccataaa caaactagaa catgggagga    6540
gaaagaaagc aatattaatt taaaattaat cttatcacat aacttatacc atcagggatt    6600
tcgggtaaaa ttccttttcag gcacatccat ttaacaagaa ttgattgtta ctgaaagcct   6660
agaagagaat ttggcacata cttggtgttc aaatatttgt tgactgagtg aataaatgat    6720
gcaagtgtct aagaaacaca aaataaggac atgattacag tcacggtgga gttcacagtc    6780
atctccaaaa tgaggatatg catcccaggg aggaccaaca attcattgga gtgctgaaat    6840
aaaatactca aaggtcattt tacatgtatt ttttctctaa attactttc ttaagacaca     6900 gaaaacaaaa aaagaaactt agctttgtta ctttctaaca aatagttaaa tcattaaaca    6960
ggattgacac tagcatcctt gtttggtctt atgccttagg ggaacatgaa atgtgtgaag    7020
acattctgag atctgaggga agggtagaca gtaatacagt gggactgacc aggcttcagc    7080
```

```
acacctttac ctcctctcag cagatttcag tgatgagcag tttacaacta gattgaaaga    7140
ttatattatc tagttctaaa agaaaactaa gcctcccaaa agcaacaagg gaactgagag    7200
gaatcctgca aaacaaaaac aaattttaaa acttgcactt tgtaataacc ctaatatgta    7260
atcacagtaa tgaacagtaa gataatgaca gaactgacat atttccttat ctattaaagc    7320
catattaaca ggtaaagcaa tgccagtcag tggtacactt cttagaagat atttaataca    7380
tactagacac atacacacac acaacatttt ccttcaaggt gtatgtatca gaaaatcact    7440
ttttaaggcc ggatgcagtg gctcaggcct gtaatcccag cactttggga ggccgacgtg    7500
ggcggatcat ctgaggtcag gagttcaaga ccagcctgcc caacatggcg aaaccccatc    7560
tctacaaaaa tacaaaaatt agccagggat gatggtggat gcttgtagtc ccagctactc    7620
aagaggcaga gcaggagaa tcacttgaac ctgggaggca gaggttgcag tgagccaaga    7680
tcacccattg cactccagcc tgggcaacag agtgagactc tgtctcaaaa aaaaaaaaat    7740 cacttttag ataaaattca tgctatagag agaagactat gaaaatatgt ttagcaatgt     7800
gtccatcatt aggtgattga gtttcctttt gttttgtttt actgaaaatc atataaagta    7860
tgttatctgt aaaagttctc tgacatgcac acataaaaat ttgggagaaa agattaacta    7920
taatgtttaa tagattttgt acacatttct ttaaaatat ataaaacaca cacctttca     7980 attggtttgc aagaataacc aattgacatc atggaaaatg gaaattcact tgctgaattt    8040
taacaaaaat ttgcatgatg agtgagactg acaacttagt gtcatgattt aatgaattat    8100
gccaatggta aacttcatgc acatggggcc aggtaattat gtggaaactt tttcaatgct    8160
taaagccaag tattgaaatt aaacttagaa tcagaccttt gaaccatttt atgacaatgt    8220
tcaaaaatta taaattctat ccacttatat tataatatta aaaatatcat tacaaaaaaa    8280
acctgtgttt attttataac tcagccttt taatttctaa tttcataaat atattataat    8340
ggatattgtt agtaatgtag tattattaca tgtatataat ttataagtaa atatacatgt    8400
tttggctact catgcataaa atgtttcacc cataggagca cataatcaga aatgtctgga    8460
gaccattata gtaatagata gatcatattg ccacatattt tatctcctcc ttgacaactg    8520
agctttccag atcttctggt gaaacgaaag agaaagttgt aacagaagag tgattaaaat    8580
gacaaaagca ttacttctat tacttctatt ctaataatat gagcaaagct ataactatca    8640
agtaataatg cactaaagaa ggtgattaat ctgatatatt cacaggcaac taataagacc    8700
tttctattgc agccatgaaa aatatgtgac aattatagat atcctgtgtg cagtgtttca    8760
acctttatgt gacctgttct actaacagat ttagtgatgt tcactttgtt agaattttct    8820
tacacatgcc ataacttgct tcagtctttt gattatgaat attatggata ttaaggattc    8880
tagactattc tagatttaaa aaataatatt gtcacctcaa tcagaaggga aatattaaat    8940
agttctcatt ttttcaatgt ttactcagtt tttgtccaat gtaatgaaag tgtcagcagt    9000
acaggttaca aaataaaatg tgtattaaag taaactcatt tgaacaggtt aataattgta    9060
gagggaggga aaaggctaaa agattgaatg taaaacttat gaaaagtaga tacatcgtct    9120
ctatgatttg cagtagtcaa ctgcatacag atgaatcatt ttaatacacg ttaactactt    9180
tccttttaca gatggagaaa ctgagaggaa gaaagtttat atggttcatt aaactttgtg    9240
atgcaagcta aactaacctg tctctgtatt ttccatctac tgcccttatc actatctcat    9300
tagaatactc ttcaagcatc tccttactga ttttcttacc aagcatttgt taagttctaa    9360
tgagagttgg tagtaacatt ttcacccact ctgtgaaata tgaaatctta ttcataggcc    9420
```

```
tcttctttta  ttcttgtatt  tgcatatcaa  ccaattaatc  aacttgcttt  ctttatgttg   9480
cttattatct  tagtccttac  taaattgcct  cttaatgttg  tccacataac  agaaatgtta   9540
aggtggatac  ttaacatttt  agtccagtct  agccggtgcc  agtgcaatgc  caaatcatga   9600
attaaaatat  aattacaaga  accacttatc  aaattttaac  aattccttca  gctttgtgac   9660
agttttttct  acttcgatta  aagtcaagta  aaattaaagt  taaatatttt  tattaaaata   9720
tctcctttaa  cattccatat  taataaacat  attaaagctc  atgcttctaa  gtagattact   9780
agaagttact  ttatcgaatt  acagcaatgg  ttaattctag  atcatagaat  ttagaatgac   9840
tttttgcctt  cttcttttt  ttcctttttt  taaacagag  tcttgctctg  ttgtccaggc   9900
tggagtgtac  tggcgcgatc  ttgactcact  gcgacctctg  ccctgcaggt  tcaagtgatt   9960
ctcctgcccc  agcctcttaa  gtagttggga  ttacaggtgc  ctgccaccac  acctggctaa  10020
tttttttttt  gtatttttag  gagagacagg  gtttcaccat  gttggccaga  ctggtctcga  10080
actcctgacc  tcaagtgatc  cacttgcctc  agcctcccaa  agtgctggga  ttacaggtgt  10140
gagccactgt  gcctggcctg  acttttgct  ttcttcttaa  tacttactag  tatttcttga  10200
attttaaaa  aagaaacata  aagtactttg  ataaaaccaa  cagtctcatt  gttcttaaaa  10260
ttgttcaaag  gttctctgga  aaaaaaaag  aaaattatca  tttggttaag  aatcatgttg  10320
gtctgacatc  aatcatccta  taggagtgaa  tattgaaaaa  gtaagatata  ttgtggtata  10380
atcgagattg  cataaatttt  accattttg  agaagaatct  gctccaaatc  ctggcttaat  10440
gtaatatcca  gcatgctact  taattttctt  gtcttcacct  tttcatatcc  acatccacct  10500
aggtgccacc  tcacagtata  agccagcata  atccattctt  ctcaatgaaa  ccacaataca  10560
tctgaccctg  catctcagga  gaactgtatc  agccacagca  cttccagttg  actatgaatc  10620
tgaatgttat  gcctcaggag  aaacatcctt  gctgggactg  agtagtgatt  caaggagata  10680
gttatgattc  agtcaagaaa  ttaataatta  gtgttatttt  tattattgag  acagagtctc  10740
gttctgtagc  ccaggctgga  gtacagtggc  atgatctcgg  ctcactgcaa  cctctacctc  10800
cccggttcaa  gtgattctcc  tgcctcagcc  tcccaaataa  ctgggacagc  aggcacttgc  10860
caccacgcct  agctaatttt  ttgtattttt  agtagagacg  gagtttcacc  gtgttagcca  10920
ggatggtctc  gatctcctga  cctcaaggtc  cacctgcctc  agcctcccaa  agtgctggga  10980
ttacaggcgt  gagccactgc  gcccggccat  aaattattaa  ctgagccagg  cacagtggta  11040
cacacttata  gtcccagata  ctcaggagac  tgaggttgga  gtatccttt  ttatgttatt  11100
ttatttttaa  ttattatggg  tacataatag  gtgtacatac  ccatggagta  caagtcatgt  11160
tctgatacag  acacataatg  tttaataatc  acatcagggt  aattgggata  tccatcacct  11220
caagcattta  tctttctttg  tgttaggaac  attccacctc  cactcttgga  ataggcaccc  11280
tgttgtgcta  ttaaatacga  ggtcttattc  atttcatcta  actatatttt  tctacccatt  11340
aaccatcacc  tcttttcccc  tcttccccac  tacctttcct  gtgaggctgc  aggattctta  11400
agcacaacag  ttagaggcca  gcctggacaa  catagtgaga  ctcaatttct  aaaaaataaa  11460
aaagaaatta  ccaactaatg  ctaaaaaaat  agtctctgat  gcttaggtat  gaattagaaa  11520
tgaccaaaaa  aaaaaaaaa  aaaaagactg  ccctttgctt  ccttctcccc  ttctcttcaa  11580
gttttccatt  gctactcatt  ttagtctggt  ttaatcaggt  ttcatccatt  aaaagcaatt  11640
gttgggatca  cacattttga  gttgtgtcag  tggacttccc  tcatgctggc  atgattcctg  11700
ccccaagccc  ttagtaaaag  ccaccaagcc  atataacata  atctctcatt  gagtaaaaca  11760
tctgatgtgt  ttagaatgac  ttctagcaaa  aaaccagcct  gtccagcatc  atctctgtat  11820
```

```
aacagataaa ggaataggta ctgcatcaaa aggttataga acctgcccaa atcaatccca    11880
tgtgttttgc aatggaatta ggttgaacta aagtgaaaat tcagttttct actcctcatt    11940
aacatgtctc atgttgcaag gttgagagga aggagaagaa gaactgtatt tacagagaga   12000 ttcccctct ctttctttct acagattact aaaacattca aagaatcaaa tttaagaaat    12060
cagttcatca gagctcatgt tgccaaactg aggtgagtgg aactgtagaa aaaatattta   12120
agtatagata caatgtggca tacttgactt tttgtcacag aatgaatagt aaatgacatg   12180
ttcagataag ttgttgtaat attatgaaaa tagtatttta gtcagcttaa aaaccaatgc   12240
caaaaaagcc aaacatatga tctatttagc tactaatgta aataaccata ttatatctat   12300
tcttattggg aagaggaaga aggggtggag agagagttgg ggtgaaggta cagtaacaag   12360
gccatcctat tgtaaaactc cagtggatat cattcacagt gcagcctatg taaacagtcc   12420
ctcctggagt tgtacaatgc tgtggtttgg gtgtatccat ccaagatcaa gacactatga   12480
ccaacatcaa aagtggcttt ttggttttat ctgcctgatg tgctataata aaagggtatt   12540
atggccaaat ccaaggcatg tctatcatga attaataata ggaggagtag cagcatgcat   12600
gctagttatt tgccattcct gccttagtta aatatgatgt gataaaacca gccttttccaa   12660 ctgaaatagt cacctttact gactctcccg caaatgtctc aaatgaccac attgctctag   12720
tctttaaata atatgcaata gttctttggt agaagaggaa ttatactaat tctttctcaa   12780
atactagcat cacaagaaaa ttaattcttg ttctctggag agtcacctag taagtatctg   12840
gagcacagat gtctggtcag gtaagttttg atgaggagtt aaagggataa gaagagtcca   12900
tgagaagggt attttccaaa acacctttcg gtcaattcag tgcacattca cttagtactt   12960
tcttgtcagt atctgtatca gccactaatg ttcaaaagtg agtaagccct gaaaacctgt   13020
aggactacat gagccttctg cctttctct ccttttgttc acttcccact tatcactcaa    13080
tcctctgcaa cctggcttca ataccaccat aaaatatcaa ctgctcttgc cgattcaaca    13140
atgacatcca gataacaaaa tccaaagaaa ccacatcagt cctattcttg gacctttcaa    13200
cagtatttgg tcctgttggc ctgtcactcc ttgaaatagg actatccctt ggtttgcatg    13260
gccttgtata ccctgatttt ccccttacct ccctagctat tccttcttag tttccttac     13320 taggtcttac ttctttgtat attccttaaa tgttgctgaa catcaggctg tgctctaggc    13380
ctctcatctt ctcaggtcac actctctcct ttccttggcc ttcactgcca cccatatgct    13440
gagtgctctc aaagttgtat ctctaggcca gtcctctttt gcctccaaac atgaatatat   13500
gcagccatct acttggtacc atcacatgga taattctcat gatctcttcc agtatgactg   13560
cttctttatt tttttctggg ctcttttta gcattgcttt acatggaact ttatcatgtc    13620
tctcaacctc tattttatct tttatctatg tatgtagagt ctgtgtaatt tcttcatctc   13680
ttttagataa ctaatatctc ttcagctttg acttgtattc tgtgtaaccc atttattgcg   13740
ttttcaattt caatgagtat gttttcctat ctgcaagttc tatttgtttc ttttgagaat   13800
cttcctggtc tttaaacac atttcttatt ttaattttg ggggtaccta gtagttgtat      13860
gtattttggg agtacatgag atgttttgat acaagcaaac aatgcataat aatcacattg    13920
tgtaaaatgg ggtatccatc ccctcaagca tttatccttt tgttacaaa caatccaatt    13980 atattctttt agttatttt aaatgtacaa ttaaattatt attgaccata gtgactctgt     14040
tgtgctatca gatactaggt gatctttaa aaataatgtt ttctacttaa tctcattttt    14100
atgattccct cttttacgtc atttgtcatt tcaaatacag tcacttgtct gttgattcta   14160
```

-continued

```
ttatgtgaag tttttgagga taatcttttt gttactttga ttccaccttg gtatggtttg    14220
gctgtgcccc cactaaaatc tcatcttgaa ctctggttcc cataataccc acatgttgtg    14280
ggagggacct tgtgggaggt gattagatta tagggacgtt tccccccttt gctctgttct    14340 tttcctgcc accatgtaag aaagatgtgt ttgcttcccc ttctgccatg attgtaaatt     14400
tcctgaggcc tccgcagcca tgcaggacct cttttctttg taaattaccc agtctccggc    14460
ggttctttat agctccgtga gaaaaaacta atacacacct catgatgtat tgtttaccac    14520
tgaaattgta tgcttaaatt taatctcact tgggaccctg tacaacctag acttaacata    14580
tctacctcca gagcagttac atctgtcaga cattctagag gaatcagcag cacatggact    14640 tgttgttgt taatttgttg tcggggggagg ggggagggat agcattagga gatacaccta    14700
atgctaaatg acgagttaat gggtgcagca caccaacatg gcacatgtat acatatgtaa    14760
caaacctgca cgttgtgcac atataccta aaacttaaag tataataata ataaaattaa     14820
aaaaaaaaag gttctgggag tattcaggta gtattaatga agattcagac atcgtgcagc    14880
caggcccatg cttatgaatt ttcaggtgat acttcttttt cttttttctt aatttaaagc    14940
tggatctcgg aaacagataa atttatttt ttatgacatg acgagcattt ttttcattct     15000
agttcatgct gttattgggt gtttagttct ttgagactcc tggcctttt ctaaaacctc     15060 aagttcaact tcctatttg cactggccca aggtcccatc tccagtctct atgtaaatgc     15120
taaacataag cctgtggaat attctagtct caccacatac tattcacatt cttctttgtt    15180
tttggtcttc caggattttc cttactttc tatgaaccca gtcttgcatt tgaaatggaa     15240
tttattatat attatctatc ctttctattt gttttatgca gaaagtgttt tctaaaatta    15300
tttaggcttc catattgcta gacatggaag ttgtaattat ttgttcagtg cctgtttcta    15360
catctaaact gcaagaccca tatggcaact gtgaatctta gtcccagcta atttctgaag    15420
cttagaatag tgcctagcac aagaagttgt ttatctaaca ttttttaaaaa taatattaa    15480 attcatatct ggaatgaata ttaagttaga gctggtcatt gaggtgagag gaggaagcca    15540
agagagaata tgagagcctc aaagccaaat atctttaatg tactttttca gaaaagaaga    15600
cagccaatgt caggtggagg aactggttta tgaggtaact ttcctggaag aaaatagaaa    15660
ttactgaggt tttagataat ccaaatattt aatcaagtca ccaaggttta ttgtggggaa    15720
tctttattat taattaaaat gagtgatgaa atcttaatat acgacaaaag ttaaatttg     15780 cttttgcagg cagatgaatg gtctaggtat caaaaaatta agttgagtct ctaactcaca    15840
caaatttaca accctatcac tttatgaatt tgtttaggag attattttta ataacactgg    15900
tgaagtctaa gaatagctaa aatttatagt acacttattg tgtgctattg actcttcttt    15960
gaagttttgc atatagtgat tcatctaatc ttcataaccc attttacatg tgaagaaact    16020
tagatataga aagattaaga aacttacata acttatccaa agttacacag taaaactctg    16080
gcattataac ttcaaaatca gctatcctac agtgagtaca gtgttctgtg cattgaaatc    16140
aaataagtga gatagcatcg tgatatagta ttacgtatgc aaaacactgtt acagagatct   16200 gtctaaagtt aaattccaca aatgaattct ttaaagggt ttaatcaaga agaatatata    16260
aacaggatgg tgaaaattg tcatattatt tgttttttaa aatatcttta tgatttacag    16320
gcaagatggt agtggtgtga gagcggatgt tgtcatgaaa tttcaattca ctagaaataa    16380
caatggagca tcaatgaaaa gcagaattga gtctgttta cgacaaatgc tgaataactc    16440
tggaaacctg gaaataaacc cttcaactga gataacatgt aagtataatt tttcataaac    16500
aattttattt caatatatcc ctcaagttta ccaattcaaa ttcatatttt aattgagagg    16560
```

```
ctgactttc tttctttgaa actaaactgt gaaaacaatc cattaaaaag ctaaatatac   16620
catatagctc cctaacgtaa atcattctaa gacttaaaga atcatttggc atttatatag   16680
taaattttat ttgctaaaaa ttctcattaa ttatccctgc aacattcctt atgagtgatg   16740
ttactgtcag atgtcattag tggataggcc ataggagggg tacatagatg ctcaaggtca   16800
gagaactatt taattaatga tccacctcag aggcttcttc attttcttt gtaacattta    16860 tcacaattga aattacaaag ttatctgtgt aaattttgta ttgtttggct tcatcctaca   16920
ctgtaatcat cctaaaagaa agaaccagtc aaccttcttc atcctactac cctcctacca   16980
cccagtctcc atcatataac acatattcaa taaataattc ttgcatgact gaagaaaag    17040 aaataatata tgcatagaat ttaaggacat tcctccaagt tggttacatt ctgctagttt   17100
aataagccat tatttcttct cgatgagctc aagattaaaa ggattttgat gattcccata   17160
ctagactggt aggtaccagt tacagatgta ctaactgtta aatattgaaa tgctttccta   17220
tttgttggta aacaattact gcatcaggcc cacaaagttg tcttccgaga tgtttcaaat   17280
ccactgcccc tgctgctaaa gagttatgct tagcaaagca aagcactcta agacactgct   17340
ccaactccat ggcctgattg catctttat gactggccaa tgctcacgca ctgcagttg     17400 ttaggtagtt gaatattacc tctgcttcca cacattaagg aatgctcccg aacgcacttc   17460
ccaagtgttt atttatttat cattatacta gacaatatgg tgatacgatg gtcacagaat   17520
agcggtttcc acctccagag cccataatct agttgaaggg aaagatattc caacacaaga   17580
gtgttgacaa tcaagataga atatgatcaa gggcccagtg tgaggcccag gcaatgatca   17640
ctgcaggaat ctggggaaga aagagaccag cgtgcttggg atatctagca aaagtttcat   17700
gaaggagaat ggactttgac tttgaaatat gggtaggatt tacatatttt gagatgagaa   17760
aaagaaagtt cccagagaag gaaagcatga aaaggcaaac agtctgtact gaacgcgatg   17820
ctttgacaga ataatgaaga aagggacctg ctggaatgat tgatcagtgt tcatcattca   17880
caccatcatc atcaaaacac ttatttaatg agaacttact gttttttagg catggcttta   17940
atgccctata tgaattttt tcttgattaa tccttacaac aaacatatcc catagatagt   18000
tttattgtcc cccttagaaa agataaattg cctaggctga cacagtcagt atatgaggca   18060
gtcaggattc aaactaagtc tgtttgttca aaaaattaag aatggccagc ttttaaaat    18120 tttctgtctc cagaagtatg atttggctcc actgaagttt gcaaaacaaa tgtgataccc   18180
aaaccttgtg aaacttttag tgggaaataa cttgcataa gtcggtttga gagagcgtgg    18240
aaacctgtct tgaaaagttt taatttaact tgcaggaaat aaaaatgatg ggtttctcaa   18300
ttaaaatttt caatcaagga aggatatgag ctaacataac attttttaa aaagatcagt    18360 ctggtaaggt agaggtgcat aaactgaaaa ggagcaaaag tggtggaatt cagttagaaa   18420
attattgtaa ctgtactgat gtcaaatgat gaaaccatga actaaagtag taccaaaagg   18480
agtgaggagg atggaataat tcaaaagata gaggacagat gtgcagaacc tggagattat   18540
aagatgtgaa aggaggagtt tgagaaaatt tcagattttg gaagtggtgt cattttacta   18600
aaaggatata ataagtagca aattttggat aaagttgggt cccactgagt ttgagatggc   18660
tgttggacat gcagagaaaa ctgtcttgta tgctgttctt aaattgaaat agacagacct   18720
ttaccctctg atactgacat attttccttt ccaggctcac cctccatttc cctaaacaca   18780
acacatgcac tagctctcct tactttattg ctccacaaac atcttacacc tccaagcatt   18840
tgtgcccact gtaccttcta tctggaatct cttttgtcct cttgtgtgcc tgaaaaattc   18900
```

```
ctttcagatc ttcaaaatac agtgcagatg ctatttcttc tagctcaaat attatctcct    18960
ccatataatt taattactct cttttttctt ttctctactt tgcacttaca tttatttgaa    19020
tgattgcttg attaatttct acctgtaaat tatgtgaggg caggtcctct atattttgct    19080
cgcagttaaa tctgcagcac ttattataga gtggtatcat tagagtaata tacatatatt    19140
tgaggacatg ataaattaac ttcccctata gtatttatca cattgcatct caatgacttg    19200
cttatgtttc tgttttccca tataaattga gtaacttgaa aaagagata tctattaagt    19260 atttaatgag aaattaaagt acaaacttta gtatgcataa caacaaattg ggaaaaggtt    19320
gtaaacaaag agatttgtag ggcccatgag ttagagatcg tttcagcagg tctgaaagga    19380
agcctaggaa tctgcatttt agaggaccac ctcccaaccc caacaagtaa ttctgcttct    19440
tgttgtctgg gtactgtact ttaagaaatt atggtgaaat gatatcagcc tttattgtat    19500
ttatcttatt ctcatttttt aatactagca cttactgacc aggctgcagc aaattggctt    19560
attaatggta agttttaata ttattttgta actgtaattt gccaaatcat aaagagtaaa    19620
agtgcaagtc ttttgtgtac ttttggccaa ggcagtatct atcaagttga tgtctttgtt    19680
cttagttcgc tcaggtggtg ttgaaacaag acagtgctga tcccaagtgt cccatggagt    19740
ggactttagg tttccccttt ccttttagaa aaggaagaa gttgtagtgg aggactaccc    19800
actctgcact caaaattgcc ctcatgaaaa tttctttggc agctttgaga acctttact    19860 gccctggttc taaggtggca tttctgtaga cttacaaatt atgtttgatg acccgttta    19920 tgtagcttct cctaaccacc agagtagctt gctttgttgt gaattcaggt taatcacaaa    19980
gtataataaa aaagaattgt cagaagtctt cccagctttg ggtctataac ctgaaggaaa    20040
agtcactact cttcaacatc atcctatgta ctctcaggct aggatagcag aaatgcaatc    20100
cctagaaaac agcaacttac ttctctgacc aaaaaaatgc agttaaaaat tagttcaatg    20160
tacctggtag ctggcctatc ttaggtactt cagtgatttt acaaagtgat ggtagtccta    20220
tgggtgtttt tcagcttcac tacgtattta attcatgctt attgttaatg aaactgtgat    20280
aagcaattta ctagggtatt tgtttgggag atgccacaaa ggaacacatg tatctcttaa    20340
tggaagcctg gtcctccttt atccaggaaa tttgctagga aaaaaaagcc tttaggtggt    20400
tgtgctatta aaccagggca ctacttaaaa gccagcccag caatagttgt gtgatttacc    20460
attaatttct tagtaataga ccacacaaaa gaagaaaatt atgggaatgc gagttgagag    20520
gaattgggtg atcagcctac cccagcccgt ttcagctctg gccagtagac tattcacgag    20580
ctctttgaaa acatttaaat aaaccttatt tagatactag aaaccctctg tcaccctcaa    20640
gaatattctg tggtatagcg actcctttat gagggcatgt ttggtaatac agcatcagtc    20700
ttggaggtgg actggattct acaaggtgaa ctgcagtcac taaggagtct tttggatgag    20760
accagttttc ctccaacttc aatgtgtgca tgaacctcac atcaaaatgt agctttagat    20820
ttgtcccatg atgtggttcc aagaatcagc acttctaata agtttccagg ggatgcccat    20880
gctgcaggcc cacaaaccac actgagcata gcaagactat tgagaaaaag gaaatttccc    20940
aggagtctgt ggcctgagct ggcacatcca ataatgacct atcttaacct caactcatga    21000
ggaattccag ggaactctga agctgctcaa aatttgaagc ctatatgcca actaaattca    21060
gaaatgttct ccaaaatgct atctataagc aacagtagtc acaaatgcat tgtagaaata    21120
tatcgatcat gcttttggaa aaatccagca tgtcctgagg aagaatgtat aagacataaa    21180
agtcataaat tatggaaaga ctcttcagct tcttccaaat gtaaggaat catgatcttc    21240 ccagcacatt aatgcccttt ctcattagaa tgtggggccg gtccagacct aataacattg    21300
```

```
tctgagcaga gaatccttgg aggcactgag gctgaggagg gaagctggcc gtggcaagtc    21360
agtctgcggc tcaataatgc ccaccactgt ggaggcagcc tgatcaataa catgtggatc    21420
ctgacagcag ctcactgctt cagaaggtga ggccaccact acctacccat ctgggaacaa    21480
ttagaataga caggtcatga agactgcacc ctctaccctc ggattgaatt gagccagaaa    21540
taattcaatg caaaaaaatc agtaagaatt ttcttcctat tcatgaaagg aaaaggattt    21600 ttcccctttta gcatgctaat ttagtgctat ttctctgttt caggtaataa tatattagca    21660
cagtaaagaa caaagattta tatgtcagaa tgttttttaa atcctagcta taaaagctta    21720
agaaatttac taaatctcca taagctttat ttttttttcca aattaaggga caacactgtt    21780
atctgtgact tagtgttact ggtagcattg agtacactaa tgtaaacata cgttaaatgt    21840
tagcgaaacg aattgctgtg gaagatttgc acattatatc atgggagctg atggctaacc    21900
tagagactgc cccatgccat taatttattc attcataaag attattgagt atctagtatg    21960
agcacagtgt tatatattgt agaagctact agtataaaca aagtattgcc tctgccttca    22020
aagagcttac actcgaatgt tggaatcaga atgcacaaaa ataatgatca attacaatga    22080
gtagcataaa taaaattaat gtaggcaact tacaagaatt cttaattgag gtgactaaac    22140
tattgccaac actagggtga tatgctacca gtggcgagta ggttgcataa acttacctta    22200
ttggtaaaaa gaaaagttca cattgctcat aaaagaagga ttttagattt cagcataact    22260
aaaatctgtt tcaaacctgc cttgttactg gggcatcgca gaccacaaca gttgttggga    22320
acttaactca aaaagttcac ccagaaaaat aatggagatt tgaactcgtg tgcccctgac    22380
catatcaatt ttcttctcag actcttactc taaactggac ctccttatca cacacacaaa    22440
gccttccata ggcagatcaa tccagtctta tttctcaaag catgtacctt gagcttcaga    22500
taaacagcat tgttctcttc ccctggactc ttcctacatt tccctaccta tgagtatctg    22560
atcaatctgc ttatccttga aatgttaata tatttaccac atctctattt gaattttatg    22620 aaattttga taatttctaa gtagtttttt cagatttata ggcactactt catggtacag    22680
tgactgttac aaacgtattt gttaaattta gaaggaataa agatttaaaa gactagggta    22740
gttactgaac taaagtttta ggaaatccca aattatttca aattttttctt atggtaattt    22800 tatgacttaa tatttttata tgcagtgaac aaatttgaaa ctttaaaaga tactcccaga    22860
attatcagtt ttctgatgta gattggcaaa tttattacta tatcccaaat aacccaagag    22920
acaaaattca caaaaacatt tcaattttca ttgccacttg aaaggccaaa aagcagaaat    22980
ggcacgcatt gatttcaatc gtactcttga gtgtgggaac caggaattaa aatacctgga    23040
cttatcaggc acttagcata accaagaacg gaatagaaac ctccctggat tctaagccct    23100
attcagtccc aatcaccaaa aaccaagtaa acgatatcac tataatgaaa gccacagtta    23160
taaatatcga caacgattac caaaggaatc catggaactt tgaattttgc cacccacat    23220 ccttctattc attaccatga ttgatccact aaagctaaca gactctgtga accttgtatt    23280
ggacccctcc ctaaagacct gattgtcact gagaaccatc agtgaggatt tgtttgggc    23340 atgaccagcc ttcatcaaa gtacatagaa gtgatgaggt cttatcaaag aggattattg    23400
aattatcacc tcttctatgt agctttccct gatactctct ttcctctcca ttgagttcca    23460
cagaaatttt tttatctgcc tttaacagtt gtcctcatga tttgtgatat ttgacttacc    23520
tcttgtcagt ttccttcact agtgtagagt tcctcaaaga aagagaccat aattactat    23580 attttttattc ctggagactc atactattcc ttatacaaag tagacactta acaatggctt    23640
```

```
gttgaactat aattaatgaa aataatagct accttcatga aagttcactt tgtgccaaac    23700
actatagttg acataataca tttgtctcat taatacttaa caattgtgtg agaaggtatc    23760
accaatcaca ttttatatgt aaataaaccc cagagctatt aattaacttg tcataaataa    23820
cacttttcat atgtggcata gccaagattt aaatataaat gttactggtt ccaaaatgat    23880
gctctaattc acttgctgga aagaaggaaa ggaagaaaat aaacgagtgg aaggaagaga    23940
gggagggaag agagaaaagg aaggaaagaa aaaagagtct cttcagaacc ttcactgtaa    24000
agactccgag caaagaagt tgaatataaa aacaacatag gtttgtttgt tttctaatat    24060
tttttcttca aaattttaa ctcaggttca ctcttacaca aactactgtg tcttataaaa    24120
gtatttccgg tcatagaatt tttattttct gtattaactc cactatctaa tctccataaa    24180
actcctaaat tggtattatc ggtaacattt tgttttact caaccttag gaacaatgtt    24240 aagttaatca gccctccaca tcacagatcc ttattttcat cagtctgtac aaggcatttc    24300 tctcattta attttttttc ctcctgtcat ccctggattt cactttcact gccctccttc    24360
cacccatatg cctcatacta atatattcga aatatacatg tcttaaaggt acatgcacgc    24420
acctacaaaa cctatagtgt tttttgtat gtatatgtct ttaatttaaa taagtagcat    24480
tgtgtaaaag tctaatattg tttcttactg ttttcactca attcttggaa ttttcatctg    24540
atgcactgct gcatagcacc ccatggtatg cagccaccat atttccttca tccaattagg    24600
ttgcatgacc taccttccca ttgccacaaa gagtacacac aaaatatttg tacttatctt    24660
tctgtaaacc ttcaggaatt tcagaagcac acatgcaggc tgctaaatat accagaatac    24720
tttccagcca cttaaatctt taccagtatt gcaaaagagg ccccatttcc ctccacatca    24780
acatttagta ttattctttt gtttaagttt tatcaatctt ttaaatgtac acaagatgct    24840 cattttata attttaattt ctcagattac tagtttgagt atcttttcat atatctaaga    24900
gctgttttga tctcccctac catgaactgc cactaatatt ctttgcctat tttacaatgg    24960
tttttctgct tatttattac tggtttacag acttttaaaa tatattctac aaaaattta    25020 gacattaaac attaccaata ttttcccatg gttcctcatc catctggtaa acttgtctat    25080
ggtatatcta attttgattt aatagaattc attctatttt tacctttag tttgtgtttt    25140 tgttgtttag ccaaaaagtc cccattccta ggtcataaag gtaatgtcct ttttttttt    25200 ttaacgctac tgttctctct ctgtctcccc ctatgtatat aggtgcacat atacttgtac    25260
acacatacat atacctatat atgaggggag ttcgataagt ttatggaaaa taaaattaaa    25320
agataaaata aaaaattata aactttattt ctcaacataa gctccttcaa gttcaagaca    25380
cttttgtaag caataatacc agccatatcg tccatcccta aagaactgag ggtcctgaga    25440
atttaactat gtcaatgcag tcttttttac attacttttt tacagtactt attgatgaaa    25500
aatgggtgcc ttttaaagat tgttttaaga ttagggaaca aaaataagtc agaggaagtc    25560
aaatcaggac tgaaaggtgg atgcctagtg atttattgct gaaactttca taaaactaac    25620
cttatttgat gagaggaatg agcatgagca tggttgtgat ggagaagaac tctggtggag    25680
ctttcctgga cacttttct actaaagctt tggctaactt tcttactctc ataagaagaa    25740
gatgttattt ttcactgacc ctttagaagg tcaacaagca aaatgccttc agcatcccaa    25800
atgtctgttg tcatgacttt tgttcttgac tagtctggtt ttgctttgac tggaccactt    25860
ctacctcttt atagccattg ctttgatggt gctttgtctt caagattgta ttagtaaagc    25920
catatttcat cttctgttac aattcttcaa agaaatactt cagaatcttg atctgacatg    25980
tttaaaattt ctattggaag ctctgacctt gggtgcagct gatctgggcg aaacagtttt    26040
```

```
ggcatccatc aagtagaaag tttgctcaac tttagttttt cagtcagaat tgtataagct   26100
gaaccagttg agatgtctat ggtgttgtct attgtttctc acagttaatt gttggtcctc   26160
tttgagacat gaacaagatg aaattttcc  tagcaaactg atgtggatga tctgttgctg   26220
cgggcttcac cctcaacaac atctctttct ttcttgaaac aaattatcca ttagtaaact   26280
gatgattggg ggagatgctg tccccataaa cttttgtaa  ggcataaata atttcaccat   26340
tcttccagtt tcaccataaa tttgactttt ttttgcttca attttagcag cattcatgtt   26400
gctttgataa gagctctttt caaattcatg tcttattcct cttagtgcct caaactagat   26460
cttgttcagt atgacaagtt agtatgagtt tatctgcatg caaaaatctt tgaaatccat   26520
gcatagtttg tttataatat acattttcaa tgaacttttg aagacccat  acatacatat   26580 gtatatat   gcacacacac acacacacac acaccaaaat cttcaaccat tatcagactt   26640
agtgcagaaa aattattcat ccattaacaa gataagaatg cccccttatca tcactactat   26700 ttaaatggag ctcctggcta aaggaaaaga cagggattga aaaaaattag ttaaatctaa   26760
aatgtttatt atttcaggtt tcttagttgc ttaaatggga agggaggtat ggacaaaaga   26820
gaaatcaaag atatttgtgt tatgctactt atcattaaag tatcagaata acttcattgg   26880
aatagaaaaa caccaagatc accccacgat atgttttcta aaatcttctc catttcttta   26940
gacaagtgac catgtattcg gccagtgaag aattaaactc acttgccagc ttataatgca   27000
ggaaaatata gcaaagagat gtggatccaa tagtttctag atagtggtac aggatggcta   27060
agatgaattt atatatctga aatgttcaca aattccctac tcatatagca tgttttcata   27120
atgttttagc aactctaatc ctcgtgactg gattgccacg tctggtattt ccacaacatt   27180
tcctaaacta agaatgagag taagaaatat tttaattcat aacaattata aatctgcaac   27240
tcatgaaaat gacattgcac ttgtgagact tgagaacagt gtcaccttta ccaaagatat   27300
ccatagtgtg tgtctcccag ctgctaccca gaatattcca cctggctcta ctgcttatgt   27360
aacaggatgg ggcgctcaag aatatgctgg taagtgtctc ggaaaaaaaa attaacaata   27420
gaaatgtctt atatttgcta ttaggtaatt ttttaaatta ggaaacatct ggaataggtg   27480
tttctattct tctacagaca gaaccattct atattctgct cagcccaagc tctggctacc   27540
cctgagtctc cttagcaaag caaagcaatg ctccagaaac tatgggaatt ctcaaatata   27600
gtaataggaa aatgtaaaag aaagttatga agacacgagt tctttaataa tccagagatt   27660
ctataagatt caaatagctt ccctataaac aataaaaaag attttgtttg tttgtttgtt   27720
tgcttgtttt ttagagacaa agactttctc agactggagt gcagtggtgc aatcatggct   27780
tactgcagcc tcaaactctg gtcttaagaa atcctcttgc ttcagcctcc caagtagcta   27840
gaattataaa taagtgtgta ccaccatacc cagctttttt tttttttttc tacagacagg   27900
ttcttgctct gttgcccagg ctggtctgga attcctgccc tcaagccatc ctcctgcctt   27960
gttggcctcc caaagcaatg ggaggattta gattagacat tgtatgaggg cttaataatc   28020
cttaaggtat taactgccct ttaaagtatt ctgggatatg gcaaaactc  gatgtgtata   28080 taaacattgg tcatatttgt ttattgaatg aataaaatgg aaactaaaat gaggacaatg   28140
cacaagagct actagaacca gtaagagtat cagcgaagga gtggaagggt agcattgaca   28200
atttccctgg gcttttaccc atgttgtaga ttgtctctcc aaggaataat acaaagcctt   28260
aatagtccta gaacacattc tattgtgttc ttatggccca agtaaattg  gtgtagtaga   28320 taacatttgc accagtcatg aaaaactatt ggtgtcattc tgagagtaca tcaatataaa   28380
```

```
atagactagt tctttagcct tgaaactaga ctggtttctc ttttgctgct aggttaaagg   28440
ttattcaata tgtaatcttc caatccaaaa tctgtcagtg gataatttaa aagcttttag   28500
tcaattttaa gatatttgtt ttcttaaaat tttaagggc actgtgtcac aaagctaaag    28560
aaaaaaaaga aaaaaaaact gatctgtgaa aggggttatc ctcatctact tgggaatttc   28620
tggctgcgaa gaaactccaa agtaaatctt tagaagcctt cattgttaaa tatgaaataa   28680
tgtttggagt acatttattt cttctcaaat ttattatagg gtcaataatg tacacatctt   28740
gaagtccatt tttttcctgc ttttataaca aacaggccac acagttccag agctaaggca   28800
aggacaggtc agaataataa gtaatgatgt atgtaatgca ccacatagtt ataatggagc   28860
catcttgtct ggaatgctgt gtgctggagt acctcaaggt ggagtggacg catgtcaggt   28920
aagctcaaga caatctcatc catgtcatca tccaagaagt gtataagcac ttcctagtat   28980
gtgataatgt gatagacata agtgtaacag ttacaataca cagccctgtt cctctaaaat   29040
ttataatcta gattttagaa ataaattttt ttatgaatga agtttatcta tcatgaaagc   29100
attaactctg agaggccaaa ttacagagta gttaaccatc caaagctcaa gaatcagaaa   29160
gacctcgatt tgaattcctt aacctctatt accaagtctc taactaaaag ctggggataa   29220
tcataatagc acctaacttt tgggtacta agaaaagtta aatgaagact aaatatatca    29280
ggcacatggt aaacaacaaa gaatctcat ctatttcact attattaatg tagaccatgg    29340
tcactcgtgt taataacttt aacctcaacc ttttaactgc tgtgaaggat taaataaaaa   29400
attaatcact atattataaa aattaattga tatataataa atgaattta agagatacgt    29460 aataattcat ggactccttg aagatagaaa atttatacaa aatcctagta atttgagtca   29520
caaaagctcc tacaataatg aaacagtatg aatgaaaaag aaaagaaata actattatat   29580
ttggatctag cccataattt ttaaccaaat gcacaaaaac aaacaacaaa tatgaaattc   29640
tcactgtaaa gtgattaaaa tcaaatttga attctaaaat tttaaattaa attatctaaa   29700
cataattgat gcagttatat gttttaatag gttttgttca catatctgaa atccaactcc   29760
acacagtagc aggaacagct ggtgtcagaa attaaatatt cttttagtct ggagttttaa   29820
aaaatcaatc tgtttacttg agtaatttgt tgctgttttc atgggtgaat tgtatacaga   29880
aggataagaa ttattcttcg catcaaaagg tcactgactt tcatatttag tgctcatggt   29940
ctttaaaaag tggataaaaa gtagttctca catttcatgg aaagccccca atccatgagc   30000
acatttccca aaatgaaaca ttttatcaa ctgcaagttg tgtgtaggtg gagatttgtt    30060
tttcaattgt caagatactg ttaattaccc agtccttat ctccttttgg tggagatgtc    30120
tctgtgctag gaaacccttc ttgctctcct tcctgtttct cttttactac tggccctgaa   30180
acaacaaatt ctcaagtttc atgacagctt tccaaagaat ccatcaatca aataagcaac   30240
acaactcgac actgacaatt ccagacctac taagagcatt aattaagact taaaaataaa   30300
catgagtttt aaaagggtgt tattcattat tttcccattt ataacgtccc ttaccttctg   30360
tccttcagtg catacaaatt attatcttcc ttgaagccca gttcaagccg tacctcacca   30420
tgataccttc catgtatatt ccactctagg cctcactgat ttttaactga aatactataa   30480
tgcatagttc acacttaaaa aaaaaaaaaa aacacagcac tttacataag agcttacagg   30540
atcctatttg ttttatccat tcttttgttc attttttacaa tcattaattc aaaggaatta   30600
tattaattac tttctatgca cccgacgttg tgttaacaca acaatactat ccctgcattc   30660
agcaagtcta tggtctacaa gagaggacac aaattcaaat gtctgtagtc aagcagtgaa   30720
gctggctaga tatggaaaaa ttacaagtcc ctcttgcttt aacatttgct tgcccacatt   30780
```

```
tggtcagaca tcatgcaaaa taatttctca ctatagaaaa aaaaacacta caaaaacaat    30840
aatataaaga actgagaact ggttaactga agcatgcata tgtcatctaa aagaagcagg    30900
tgacgaccag cttcatgaag tacttgccat gcatattggc acttcacaca ctgacccttc    30960
tccccaccta gaccagtaat taaacaggta tggatgagct agctactaag agcagccaac    31020
tgaatagctg actaacttag aagcacactt ggtaataata gctgactttt attagtactg    31080
actatactat atgctaagct gtactcaaag tgctttgagt tttaaactga tacaaacatt    31140
atatgaggaa acagaggtac agagagctat tcaccagctt accaaaggtc acatagctgg    31200
taagtggagg acttaaaccc agactatcta gtttcagaac ccacagactt aatccatcgt    31260
gcagaacata agacatactc catctgtctc cccaactagg ttattatgtg cacaaatatt    31320
tattggttgg ttggttcatt attatgactg ggtggtaagt atgtcattag gagtgttttg    31380
cttatgacta tataaatttc ttcaccaaaa gaagactttc tgatgatata ctatgcatca    31440
gacaccacgc agggtgctaa ggttaggaag ataagtgaga cttctagaaa ctcattcatt    31500
caacaaatat ctcctaaggg ctagaagctt aggtttcagc agtgaacaga ataggtatgt    31560
tctctttcgt gttggacctt atagtatatc tgggaaaaca gacattgaat aaatatcaca    31620
aatgcaagtg agtgtttcag agacatgcag ctgctacatc aaaacaaaac agaacaaaac    31680
aaacaaacaa aaactgacca gtgggattaa gtgtaaatag gcacacaaat gcacaaatat    31740
gcttttataa aatagtgaag cagtgacaga gacacacaca agatataaag acacaatgaa    31800
gaacaattga gcccaaagct ggaaagggtg agagtgtgaa ggaaaaaggt tgatcagaga    31860
agttttcccg aaggagagaa agcctggatg attaggaggc aaccactcgg tgactgaggg    31920
aaatctgaaa aatgtatttg tcatcttctc agacttgctg aaggaatgac ttgggtactt    31980
tgaggatttc agtaattttt ccatgacttg gtataatatt tcaaaaggaa ataggctgac    32040
tttatttgta taatgaatgt gactccttcc tcgactgcca tagaaataaa ctccttaata    32100
ttttgggttt gtctttgcac ttaagtaatc agtcattctg ttttttttaca gggtgactct    32160 ggtggcccac tagtacaaga agactcacgg cggctttggt ttattgtggg gatagtaagc    32220
tggggagatc agtgtggcct gccggataag ccaggagtgt atactcgagt gacagcctac    32280
cttgactgga ttaggcaaca aactgggatc tagtgcaaca agtgcatccc tgttgcaaag    32340
tctgtatgca ggtgtgcctg tcttaaattc caaagcttta catttcaact gaaaagaaa    32400 ctagaaatgt cctaatttaa catcttgtta cataaatatg gtttaacaaa cactgtttaa    32460 cctttctttta ttattaaagg ttttctattt tctccagaga actatatgaa tgttgcatag    32520
tactgtggct gtgtaacaga agaaacacac taaactaatt acaaagttaa caatttcatt    32580
acagttgtgc taaatgcccg tagtgagaag aacaggaacc ttgagcatgt atagtagagg    32640
aacctgcaca ggtctgatgg gtcagagggg tcttctctgg gtttcactga ggatgagaag    32700
taagcaaact gtggaaacat gcaaaggaaa aagtgataga ataatattca agacaaaaag    32760
aacagtatga ggcaagagaa ataatatgta tttaaaattt ttggttactc aatatcttat    32820
acttagtatg agtcctaaaa ttaaaaatgt gaaactgttg tactatacgt ataacctaac    32880
cttaattatt ctgtaagaac atgcttccat aggaaatagt ggataatttt cagctattta    32940
aggcaaaagc taaaatagtt cactcctcaa ctgagaccca agaattata gatattttc    33000 atgatgaccc atgaaaaata tcactcatct acataaagga gagactatat ctattttata    33060
gagaagctaa gaaatatacc tacacaaact tgtcaggtgc tttacaacta catagtactt    33120
```

-continued

```
tttaacaaca aaataataat tttaagaatg aaaaatttaa tcatcgggaa gaacgtccca    33180
ctacagactt cctatcactg gcagttatat ttttgagcgt aaaagggtcg tcaaacgcta    33240
aatctaagta acgaattgaa agtttaaaga gggggaagag ttggtttgca aaggaaaagt    33300
ttaaatagct taatatcaat agaatgatcc tgaagacaga aaaaactttg tcactcttcc    33360
tctctcattt tctttctctc tctctcccct tctcatacac atgcctcccc caccaaagaa    33420
tataatgtaa attaaatcca ctaaaatgta atggcatgaa atctctgta gtctgaatca     33480
ctaatattcc tgagttttta tgagctccta gtacagctaa agtttgccta tgcatgatca    33540
tctatgcgtc agagcttcct ccttctacaa gctaactccc tgcatctggg catcaggact    33600
gctccataca tttgctgaaa acttcttgta tttcctgatg taaaattgtg caaacaccta    33660
caataaagcc atctactttt agggaaaggg agttgaaaat gcaaccaact cttggcgaac    33720
tgtacaaaca aatctttgct atactttatt tcaaataaat tcttttttaaa ataatttccc   33780
tgcctaatta tttatggaag ttatgacttt tgaaggacaa ttcaaaacca tttatttaat    33840
tggttctgca atgaaagaac tgccccatat actctactaa aggcttggca ctttctgctg    33900
ccttttaatc cagcgctata attgaggcaa gcgtccagct tgacacctcg agataacttc    33960
gtataatgta tgctatacga agttatatgc atggcctccg cgccgggttt tggcgcctcc    34020
cgcgggcgcc cccctcctca cggcgagcgc tgccacgtca gacgaagggc gcagcgagcg    34080
tcctgatcct tccgcccgga cgctcaggac agcggcccgc tgctcataag actcggcctt    34140
agaaccccag tatcagcaga aggacatttt aggacgggac ttgggtgact ctagggcact    34200
ggttttcttt ccagagagcg gaacaggcga ggaaaagtag tcccttctcg gcgattctgc    34260
ggagggatct ccgtggggcg gtgaacgccg atgattatat aaggacgcgc cgggtgtggc    34320
acagctagtt ccgtcgcagc cgggatttgg gtcgcggttc ttgtttgtgg atcgctgtga    34380
tcgtcacttg gtgagtagcg ggctgctggg ctggccgggg ctttcgtggc cgccgggccg    34440
ctcggtggga cggaagcgtg tggagagacc gccaagggct gtagtctggg tccgcgagca    34500
aggttgccct gaactggggg ttgggggagg cgcagcaaaa tggcggctgt tcccgagtct    34560
tgaatggaag acgcttgtga ggcgggctgt gaggtcgttg aaacaaggtg gggggcatgg    34620
tgggcggcaa gaacccaagg tcttgaggcc ttcgctaatg cgggaaagct cttattcggg    34680
tgagatgggc tggggcacca tctgggggacc ctgacgtgaa gtttgtcact gactggagaa    34740
ctcggttttgt cgtctgttgc gggggcggca gttatggcgg tgccgttggg cagtgcaccc    34800
gtacctttgg gagcgcgcgc cctcgtcgtg tcgtgacgtc acccgttctg ttggcttata    34860
atgcagggtg gggccacctg ccggtaggtg tgcggtaggc ttttctccgt cgcaggacgc    34920
agggttcggg cctagggtag gctctcctga atcgacaggc gccggacctc tggtgagggg    34980
agggataagt gaggcgtcag tttctttggt cggttttatg tacctatctt cttaagtagc    35040
tgaagctccg gttttgaact atgcgctcgg ggttggcgag tgtgttttgt gaagttttt    35100
aggcaccttt tgaaatgtaa tcatttgggt caatatgtaa ttttcagtgt tagactagta    35160
aattgtccgc taaattctgg ccgttttttgg cttttttgtt agacgtgttg acaattaatc    35220
atcggcatag tatatcggca tagtataata cgacaaggtg aggaactaaa ccatgggatc    35280
ggccattgaa caagatggat tgcacgcagg ttctccggcc gcttgggtgg agaggctatt    35340
cggctatgac tgggcacaac agacaatcgg ctgctctgat gccgccgtgt tccggctgtc    35400
agcgcagggg cgcccggttc ttttttgtcaa gaccgacctg tccggtgccc tgaatgaact    35460
gcaggacgag gcagcgcggc tatcgtggct ggccacgacg ggcgttcctt gcgcagctgt    35520
```

```
gctcgacgtt gtcactgaag cgggaaggga ctggctgcta ttgggcgaag tgccggggca  35580
ggatctcctg tcatctcacc ttgctcctgc cgagaaagta tccatcatgg ctgatgcaat  35640
gcggcggctg catacgcttg atccggctac ctgcccattc gaccaccaag cgaaacatcg  35700
catcgagcga gcacgtactc ggatggaagc cggtcttgtc gatcaggatg atctggacga  35760
agagcatcag gggctcgcgc cagccgaact gttcgccagg ctcaaggcgc gcatgcccga  35820
cggcgatgat ctcgtcgtga cccatggcga tgcctgcttg ccgaatatca tggtggaaaa  35880
tggccgcttt tctggattca tcgactgtgg ccggctgggt gtggcggacc gctatcagga  35940
catagcgttg gctacccgtg atattgctga agagcttggc ggcgaatggg ctgaccgctt  36000
cctcgtgctt tacggtatcg ccgctcccga ttcgcagcgc atcgccttct atcgccttct  36060
tgacgagttc ttctgagggg atccgctgta agtctgcaga aattgatgat ctattaaaca  36120
ataaagatgt ccactaaaat ggaagttttt cctgtcatac tttgttaaga agggtgagaa  36180
cagagtacct acattttgaa tggaaggatt ggagctacgg gggtgggggt ggggtgggat  36240
tagataaatg cctgctcttt actgaaggct ctttactatt gctttatgat aatgtttcat  36300
agttggatat cataatttaa acaagcaaaa ccaaattaag ggccagctca ttcctcccac  36360
tcatgatcta tagatctata gatctctcgt gggatcattg ttttttctctt gattcccact  36420 ttgtggttct aagtactgtg gtttccaaat gtgtcagttt catagcctga gaacgagat  36480 cagcagcctc tgttccacat acacttcatt ctcagtattg ttttgccaag ttctaattcc  36540
atcagacctc gacctgcagc ccctagcccg ggcgccagta gcagcaccca cgtccacctt  36600
ctgtctagta atgtccaaca cctccctcag tccaaacact gctctgcatc catgtggctc  36660
ccatttatac ctgaagcact tgatggggcc tcaatgtttt actagagccc acccccctgc  36720
aactctgaga ccctctggat ttgtctgtca gtgcctcact ggggcgttgg ataatttctt  36780
aaaaggtcaa gttccctcag cagcattctc tgagcagtct gaagatgtgt gcttttcaca  36840
gttcaaatcc atgtggctgt ttcacccacc tgcctggcct tgggttatct atcaggacct  36900
agcctagaag caggtgtgtg gcacttaaca cctaagctga gtgactaact gaacactcaa  36960
gtggatgcca tctttgtcac ttcttgactg tgacacaagc aactcctgat gccaaagccc  37020
tgcccacccc tctcatgccc atatttggac atggtacagg tcctcactgg ccatggtctg  37080
tgaggtcctg gtcctctttg acttcataat tcctaggggc cactagtatc tataagagga  37140
agagggtgct ggctcccagg ccacagccca caaaattcca cctgctcaca ggttggctgg  37200
ctcgacccag gtggtgtccc ctgctctgag ccagctcccg gccaagccag caccatgggt  37260 accccaaga agaagaggaa ggtgcgtacc gatttaaatt ccaatttact gaccgtacac  37320
caaaatttgc ctgcattacc ggtcgatgca acgagtgatg aggttcgcaa gaacctgatg  37380
gacatgttca gggatcgcca ggcgttttct gagcatacct ggaaaatgct tctgtccgtt  37440
tgccggtcgt gggcggcatg gtgcaagttg aataaccgga aatggtttcc cgcagaacct  37500
gaagatgttc gcgattatct tctatatctt caggcgcgcg gtctggcagt aaaaactatc  37560
cagcaacatt tgggccagct aaacatgctt catcgtcggt ccgggctgcc acgaccaagt  37620
gacagcaatg ctgtttcact ggttatgcgg cggatccgaa agaaaacgt tgatgccggt  37680 gaacgtgcaa aacaggctct agcgttcgaa cgcactgatt tcgaccaggt tcgttcactc  37740
atggaaaata gtgatcgctg ccaggatata cgtaatctgg catttctggg gattgcttat  37800
aacaccctgt tacgtatagc cgaaattgcc aggatcaggg ttaaagatat ctcacgtact  37860
```

| | |
|---|---:|
| gacggtggga gaatgttaat ccatattggc agaacgaaaa cgctggttag caccgcaggt | 37920 |
| gtagagaagg cacttagcct gggggtaact aaactggtcg agcgatggat ttccgtctct | 37980 |
| ggtgtagctg atgatccgaa taactacctg ttttgccggg tcagaaaaaa tggtgttgcc | 38040 |
| gcgccatctg ccaccagcca gctatcaact cgcgccctgg aagggatttt tgaagcaact | 38100 |
| catcgattga tttacggcgc taaggtaaat ataaaatttt taagtgtata atgtgttaaa | 38160 |
| ctactgattc taattgtttg tgtattttag gatgactctg gtcagagata cctggcctgg | 38220 |
| tctggacaca gtgcccgtgt cggagccgcg cgagatatgg cccgcgctgg agtttcaata | 38280 |
| ccggagatca tgcaagctgg tggctggacc aatgtaaata ttgtcatgaa ctatatccgt | 38340 |
| aacctggata gtgaaacagg ggcaatggtg cgcctgctgg aagatggcga ttgatctaga | 38400 |
| taagtaatga tcataatcag ccatatcaca tctgtagagg ttttacttgc tttaaaaaac | 38460 |
| ctcccacacc tccccctgaa cctgaaacat aaaatgaatg caattgttgt tgttaaacct | 38520 |
| gccctagttg cggccaattc cagctgagcg tgcctccgca ccattaccag ttggtctggt | 38580 |
| gtcaaaaata ataataaccg ggcagggggg atctaagctc tagataagta atgatcataa | 38640 |
| tcagccatat cacatctgta gaggttttac ttgctttaaa aaacctccca cacctccccc | 38700 |
| tgaacctgaa acataaaatg aatgcaattg ttgttgttaa cttgtttatt gcagcttata | 38760 |
| atggttacaa ataaagcaat agcatcacaa atttcacaaa taaagcattt ttttcactgc | 38820 |
| attctagttg tggtttgtcc aaactcatca atgtatctta tcatgtctgg aataacttcg | 38880 |
| tataatgtat gctatacgaa gttatgctag taactataac ggtcctaagg tagcgagcta | 38940 |
| gctgcaaccg aggaaaaaac gtgccatgag gtctctgtat ccaagtgtga ct | 38992 |

<210> SEQ ID NO 20
<211> LENGTH: 34073
<212> TYPE: DNA
<213> ORGANISM: Artificial Sequence
<220> FEATURE:
<223> OTHER INFORMATION: Recombinant polynucleotide

<400> SEQUENCE: 20

| | |
|---|---:|
| gagggagggt ggtgctttgc taatggtgaa ttactaactc ctcaataaag aatattattt | 60 |
| gaaataattt ttgaaatttc ataattactt tgggttcttt cttaatgata aataaataat | 120 |
| agtatattac aaacatacat taatatttcc tgaatgaata caccacaaat ctcccttaaa | 180 |
| atatagcaag aataaaaatt atactatttc tgacaatttt taatttctca ataataata | 240 |
| ccactctgat ttttaaacat ctacaccact ctggctttgc caatcttttt aaaaattgaa | 300 |
| aagataataa ttttatcata attacactga agcatagaac ttttctttc aaggaaagca | 360 |
| aattttgaa attctataat ataacctccc ataatcctga ataaattaaa ggttcaacaa | 420 |
| cttagtaaag taagactgac cttcccttttt atttcttttt cagatcaaaa atcttacttt | 480 |
| tataggagca gttttcaact cctaaatgtt gaatataata gtcagttaaa ttcaccagct | 540 |
| acacaggaat acaggacttt gagtggaaga attgaatctc tggtaagtta atatttgtct | 600 |
| ttgctcttta ttccattata aaatgaatat gataataaac ctaatgtttt gtaatatatt | 660 |
| ttcagttgct aagtgctcta catattttcc ttccttgaat ggtgaaacat gtgtttctct | 720 |
| ctgcttttat ccagttagtt tactcatata ctggttctta ttcacatctt tgtcatgagt | 780 |
| aaaaagtgtt agaaaggcca cgagtaaata tgcattttat ttgttatga attcaaatac | 840 |
| taaaagtttt ttatttgttt aattaagcat tgacattgtc ttttttaaatt cttttcatttt | 900 |
| taccttcttc cctcttcctt atccaactaa agacgcaaag caggaggtgt taaaaaacag | 960 |

```
gtttaccata tcagcagtaa catagtttgg acaacattac actttggttc aatgatagac   1020
atagaagttt gaacagaaat atgcaaagca agtttgagct ctaacttgaa gagagcctct   1080
gggtgcctgc caggaaacct cacgagtgga cccttaacat tcatgtgtca ccacaaacta   1140
ggggctgccc tttagttttg accagtctca gtgtcactca cttacccta  ccttttcaaa   1200 aaaaagtcct aagaatataa agtaattcaa tggttctaca attttagcat gtaactgagt   1260
cacctggcag ggttgctttg gtgagctcaa gataaaattt tatcagcatt tctacatttt   1320
ctggaatatt ccttaatcca ggcttttaat cccttggtgc ttttctgaac cactgcaatg   1380
agcttctaac tgttctcact gtgtgcaggc tcttttcctt ctaatctaat ttacacactt   1440
ctgaacacaa atctctcaca gcctgtttcc ttcatgttac ctccagctca agactttttg   1500
cctacaaaat aaaattcaaa cttgttagct aagcaccttc tcatgtctat gctttggctc   1560
atatttcagc catcgtgtgc cccacttatt cttatagcca acctgaaaag ccatctttta   1620
taagaaacta cctctgctct ccatgattgg atataattaa tcctccttcc acatcacctc   1680
gccacaaaat tgtatctgtg ttgatctcat gccacatacc tgtatgtatt ttatattata   1740
aatatttgca gacttgttta atttgccatg ttagactaag ttccatgaag acagctccat   1800
atccattcca ttttatata  tccacaacat ttggtcgggt tgatgcttaa taaatgttta   1860
ttgaaggaac aggagtctcc cacttctgac ataatgaact tatttccccc agtgttaacc   1920
ctacatctgg ttcctgtcca agagtctctt cccaaatcat tctgattcaa ctgttcattc   1980
tgatctcatt aaacatttaa atgatatatc taacttcgct tgctttattc tatgctcatc   2040
ctgcagtctc ctcataactt ggtttcaatg atgcttgctt ctagagaaaa aaatgtatta   2100
aataagctta tgattcagtc ctccagctgt gatggttctc actgaacatt agctcagtgg   2160
ttttcgaagt atggtctcta gcataaccta gaaacttgtt agaaatgcaa attcttgggc   2220
tcaccaagac atactaaatc aaaaattctg acattggggc ctagaaatct gtgttttaac   2280
aagcctgcca gtgcagcctg gtccctttc  ttctcggagc cccactcaaa gctttcagtg   2340
ctcatctccc accaatgaca gggtcctcta tggaaaccgg caggacggtt tccaactcta   2400
actacgtttt agagtttgct tcctagggct atccaggcac caagtatcac aggttagttt   2460
cccagggaag cagactctga acttgcatg  cagggagtgt ctctggggtg ctctcaacca   2520
acaccttcag gaagagaagg aagcagcatt gggcagaggc atagtcaaac tacagtgctg   2580
ttggcacaga agactgaagg gagtcagagc caggggtag  aggtgggccc ttagcatcca   2640
tccttcacca ttaggtgtga gttgccccac ctccttgatg gtgtaacctc agtcccaagg   2700
tgggtgggag tgcagcagag cagcccctac aagggccaaa ccagagatac accaggcgcc   2760
agaagtgctg ccaggaata  gagaggaaag gatgggctta aggtaggatc cacagaactt   2820
ggcaatggat tagaagacag gatgagaagt gacaggttaa cactaacaca gaaatgtcta   2880
acttcggtag ataatggtgc cattggctag aagaggaaac cgaaatgaaa gcaggttgtt   2940
cagggagaca aaagttcact gtggacatct cagcagagtg attcagtggg gaaaggaatg   3000
gatgcccaga ccacctcaga ggaagatcta agctggagcc agcaataaag atacaagatg   3060
aacaatccct aacgaactgc tcctcagcca tgctccccag acacgctgct tcagatttat   3120
agtccgggtg aggctaggag gtgcgcctcc ctcagtggag gacagcaaag caccagtggc   3180
tccagggagt taaatctttt tgataatttt tgttctagca tctgtctgca gagctgtctc   3240
tcagccattg cctgccttta cacaggagtg cagtccgaaa ttgggagatg agtgaaattt   3300
```

```
attatgccta gagatctgga tccccagttg tttgggagta tattttctga accacttgtt    3360
ggtttaagta atgcagattt attgatgcca cttctcttga atctgtgact ctggacccac    3420
catctaagtg aatgtgcaga gggaacggaa tggctgcaat agatctccat taaaaccagt    3480
gcatcctccc agacacatac agtagtaggg aggtgagtca atgtcaggac agcaccagct    3540
cccgcttcgg tacatttcca aagttctcag tctgtgtaca aaggtttgct ctggggcagc    3600
agaaatagcc ctgggcaggt agtcaaaggc ctggtttgat ttcctccact tccaggcaag    3660
tcactcgaag gctcacaggc ttttttcctca cctgccacat gggtccagtg agatctactg    3720
agctgtaaat aatgaaatga gtgtgtgtgc agtcatctat aagttgtaaa gtactagaaa    3780
atggtgaaac tttgggattt gggctattta aggctgaatg ctaaaaatgt caggcattgt    3840
ggagaaagga atttaaatat aagattgatt gactgggatt taaagacaaa tgaaggcaca    3900
cacgcaagtg cacacccaca ctgacactgc acagctcccg ttggaggcat atcctgacca    3960
tgcagacctg gggctctgcc tgtccaagtg cactccttta ctacataaac cctccttctc    4020
ttttggggct gtcaccccac cagagctggc accgagccct tgctgctgcg cttccctggg    4080
gtgtcagctt ttgacagggt gtttcctccc tctgcaggag ccttaacatc ccttggactt    4140
ccttccccccc acccaccccc agcagttttta tctcttccta actcgggacc ctttttttcc    4200
cacacaaagt ttattgtcag ttgctggttt catctgtttg agcggctgca acaaaatacc    4260
atagactggg tggcatatgc acgacaaaaa tttattctc acaggagaag tcaaagatta    4320
atgcaccagc agatctggtg tctgaggggc caccttctgg tttgtagatg atgctttcta    4380
gttaaaacac ctatttaaca cactattaaa cactaagtgt gttaaatagt gcagttgatg    4440
tatttgtcat gtcacccttta tcatacacta aatccttctt tgtcttttt tctgtactct    4500
aatctctttc tgtaagtaat ctttgcttgc agcagtagga tatttagagt actgtggctt    4560
gacaatatat ttagtatttc aagatttcca tgaaattctt ctgatgtatg agttccctag    4620
ttaatcttac atatgtatcc ctttgtaaaa acactttgaa catttaaaat gatacatgaa    4680
tagtactcta atacaatgcc ataaaaatta taaatcattt gtatagactg gtaagtaaag    4740
attgtgagat taagaaacgc atcaaaggcc attgagctgg aaagtggtat aatgagaatt    4800
caaaccaggg tctcttgact caaaatctaa ggatcatacc atttctcatg ataatatgag    4860
tattattgtt atctctatcc catagacaaa gtgttaacac tgaatgagca gtgaaatagt    4920
ctcagaattt tttatttat ttagcaattc acttgtcatt tctggtcctc agtttattca    4980
cgagtaaaat aaaatagttg gactagataa tttctatagt acattcttac acaaaaaatc    5040
tatgattttg ttattttaa tgtgatatac tcatggcact cattcacctc attttcccag    5100
cctgcctcac tggtcattac ttctctgtgt tctttacagg ctcccccctcc tctacactgc    5160
cattaaatat tgaaacacct caaagcttta cttatgtcca cctctcctct gacactatca    5220
ttctgtctag atgatcccat acatacatgc ccattacttc aacctgtatt tatacgccaa    5280
tgattcacta tatttccagc ctagacattc ttttgtactc tagttaccag cttgatatcc    5340
ttacatggct gtttcaaaac aactcaaata tattatctct caaaatcaaa ctcatgatgt    5400
ccccacacca tcctagcttt ccaccaacaa tacctatccc tattaatagc aataccattt    5460
attcagttat ccaaatcaaa aacctagaat tcatccttaa aattctacta tcattccaaa    5520
tatcctatcc atcagcagcc actgtattct taatcccctg tatttccttc aaatccattc    5580
acctctctcc atatccattg ctgcatgact atccaagcca tcgcctctac cctagggtac    5640
caaaatagca acaaacctaa tctgttcatt tgcattattt tttctccaaa actgattatc    5700
```

```
tatatgtagc aagacagatt gttctcaaat tgcaaatccc actatattat cctcttgctt    5760
caaacacttc catggtttcc cattgtttat gataaaacca aatgcttcaa gttcgaagac    5820
cggcatgatt gggaatttcc tgtcacccta gcctacttgc tctccatggt acagttgcac    5880
tggctttctt tcattcctta agtacaacct gtttcctccc acctcaggac tgtgcatgtg    5940
ccattcattc tgctgaggag ccttttcct tccacttcaa tcagctaagt ctgattcttc     6000
ctgacaatct cagctcaata agcatttcct ctaagaaatg tctctaatat cattaattgg    6060
ctcaggtccc tctactgtat tgctgcactt tcacagtta taatttact taattatgaa      6120 tgattatttg attaggtcta tttccatcca ttagacataa gcttcatgat ggccagatta    6180
ctgttttcta tccatcgttg tattccaata cctgacagaa ggagggcggg aggtggtggc    6240
acacaagaga tgctcaaaaa caattgttga ataagtaaat gaatgaggcc atttagaaat    6300
aacgaaagta cctgtttaca aagtacatgt atcaaaacta tgaatgcatt ctacttacat    6360
ggttttctcc aaataaaaca aaagacttca atcaggatta atacctggga taaactgagt    6420
cattaaatct ctcctttgcc atcaggagtg acattgaaac aaatgtctgc aaacaacaaa    6480
tacttttttc ccaaaatata ttgaatggca tttccataaa caaactagaa catgggagga    6540
gaaagaaagc aatattaatt taaaattaat cttatcacat aacttatacc atcagggatt    6600
tcgggtaaaa ttcctttcag gcacatccat ttaacaagaa ttgattgtta ctgaaagcct    6660
agaagagaat ttggcacata cttggtgttc aaatatttgt tgactgagtg aataaatgat    6720
gcaagtgtct aagaaacaca aaataaggac atgattacag tcacggtgga gttcacagtc    6780
atctccaaaa tgaggatatg catcccaggg aggaccaaca attcattgga gtgctgaaat    6840
aaaatactca aaggtcattt tacatgtatt ttttctctaa attacttttc ttaagacaca    6900
gaaaacaaaa aagaaactt agctttgtta cttttctaaca aatagttaaa tcattaaaca    6960
ggattgacac tagcatccct gtttggtctt atgccttagg ggaacatgaa atgtgtgaag    7020
acattctgag atctgaggga agggtagaca gtaatacagt gggactgacc aggcttcagc    7080
acacctttac ctcctctcag cagatttcag tgatgagcag tttacaacta gattgaaaga    7140
ttatattatc tagttctaaa agaaaactaa gcctcccaaa agcaacaagg gaactgagag    7200
gaatcctgca aaacaaaaac aaattttaaa acttgcactt tgtaataacc ctaatatgta    7260
atcacagtaa tgaacagtaa gataatgaca gaactgacat atttccttat ctattaaagc    7320
catattaaca ggtaaagcaa tgccagtcag tggtacactt cttagaagat atttaataca    7380
tactagacac atacacacac acaacatttt ccttcaaggt gtatgtatca gaaaatcact    7440
ttttaaggcc ggatgcagtg gctcaggcct gtaatcccag cactttggga ggccgacgtg    7500
ggcggatcat ctgaggtcag gagttcaaga ccagcctgcc caacatggcg aaaccccatc    7560
tctacaaaaa tacaaaaatt agccagggat gatggtggat gcttgtagtc ccagctactc    7620
aagaggcaga ggcaggagaa tcacttgaac ctggaggca gaggttgcag tgagccaaga    7680
tcacccattg cactccagcc tgggcaacag agtgagactc tgtctcaaaa aaaaaaaaat    7740 cacttttag ataaaattca tgctatagag agaagactat gaaatatgt ttagcaatgt      7800 gtccatcatt aggtgattga gtttcctttt gtttgtttt actgaaaatc atataaagta     7860
tgttatctgt aaaagttctc tgacatgcac acataaaaat ttgggagaaa agattaacta    7920
taatgtttaa tagattttgt acacatttct ttaaaaatat ataaaacaca cacctttca     7980 attggtttgc aagaataacc aattgacatc atggaaaatg gaaattcact tgctgaattt    8040
```

```
taacaaaaat ttgcatgatg agtgagactg acaacttagt gtcatgattt aatgaattat     8100
gccaatggta aacttcatgc acatggggcc aggtaattat gtggaaactt tttcaatgct     8160
taaagccaag tattgaaatt aaacttagaa tcagacctt  gaaccatttt atgacaatgt     8220
tcaaaaatta taaattctat ccacttatat tataatatta aaaatatcat tacaaaaaaa     8280
acctgtgttt atttttataac tcagcctttt taatttctaa tttcataaat atattataat     8340
ggatattgtt agtaatgtag tattattaca tgtatataat ttataagtaa atatacatgt     8400
tttggctact catgcataaa atgtttcacc cataggagca cataatcaga aatgtctgga     8460
gaccattata gtaatagata gatcatattg ccacatattt tatctcctcc ttgacaactg     8520
agctttccag atcttctggt gaaacgaaag agaaagttgt aacagaagag tgattaaaat     8580
gacaaaagca ttacttctat tacttctatt ctaataatat gagcaaagct ataactatca     8640
agtaataatg cactaaagaa ggtgattaat ctgatatatt cacaggcaac taataagacc     8700
tttctattgc agccatgaaa aatatgtgac aattatagat atcctgtgtg cagtgtttca     8760
acctttatgt gacctgttct actaacagat ttagtgatgt tcactttgtt agaattttct     8820
tacacatgcc ataacttgct tcagtctttt gattatgaat attatggata ttaaggattc     8880
tagactattc tagatttaaa aaataatatt gtcacctcaa tcagaaggga aatattaaat     8940
agttctcatt ttttcaatgt ttactcagtt tttgtccaat gtaatgaaag tgtcagcagt     9000
acaggttaca aaataaaatg tgtattaaag taaactcatt tgaacaggtt aataattgta     9060
gagggaggga aaaggctaaa agattgaatg taaaacttat gaaaagtaga tacatcgtct     9120
ctatgatttg cagtagtcaa ctgcatacag atgaatcatt ttaatacacg ttaactactt     9180
tccttttaca gatggagaaa ctgagaggaa gaaagtttat atggttcatt aaactttgtg     9240
atgcaagcta aactaacctg tctctgtatt ttccatctac tgcccttatc actatctcat     9300
tagaatactc ttcaagcatc tccttactga ttttcttacc aagcatttgt taagttctaa     9360
tgagagttgg tagtaacatt ttcacccact ctgtgaaata tgaaatctta ttcataggcc     9420
tcttctttta ttcttgtatt tgcatatcaa ccaattaatc aacttgcttt ctttatgttg     9480
cttattatct tagtccttac taaattgcct cttaatgttg tccacataac agaaatgtta     9540
aggtggatac ttaacatttt agtccagtct agccggtgcc agtgcaatgc caaatcatga     9600
attaaaatat aattacaaga accacttatc aaattttaac aattccttca gctttgtgac     9660
agttttttct acttcgatta aagtcaagta aaattaaagt taaatatttt tattaaaata     9720
tctcctttaa cattccatat taataaacat attaaagctc atgcttctaa gtagattact     9780
agaagttact ttatcgaatt acagcaatgg ttaattctag atcatagaat ttagaatgac     9840
tttttgcctt cttctttttt ttcctttttt taaacagag  tcttgctctg ttgtccaggc     9900
tggagtgtac tggcgcgatc ttgactcact gcgacctctg ccctgcaggt tcaagtgatt     9960
ctcctgcccc agcctcttaa gtagttggga ttacaggtgc ctgccaccac acctggctaa    10020
tttttttttt gtatttttag gagagacagg gtttcaccat gttggccaga ctggtctcga    10080
actcctgacc tcaagtgatc cacttgcctc agcctcccaa agtgctggga ttacaggtgt    10140
gagccactgt gcctggcctg acttttttgct ttcttcttaa tacttactag tatttcttga    10200 attttttaaaa aagaaacata aagtactttg ataaaaccaa cagtctcatt gttcttaaaa    10260
ttgttcaaag gttctctgga aaaaaaaaag aaaattatca tttggttaag aatcatgttg    10320
gtctgacatc aatcatccta taggagtgaa tattgaaaaa gtaagatata ttgtggtata    10380
atcgagattg cataaatttt accatttttg agaagaatct gctccaaatc ctggcttaat    10440
```

```
gtaatatcca gcatgctact taattttctt gtcttcacct tttcatatcc acatccacct    10500
aggtgccacc tcacagtata agccagcata atccattctt ctcaatgaaa ccacaataca    10560
tctgaccctg catctcagga gaactgtatc agccacagca cttccagttg actatgaatc    10620
tgaatgttat gcctcaggag aaacatcctt gctgggactg agtagtgatt caaggagata    10680
gttatgattc agtcaagaaa ttaataatta gtgttatttt tattattgag acagagtctc    10740
gttctgtagc ccaggctgga gtacagtggc atgatctcgg ctcactgcaa cctctacctc    10800
cccggttcaa gtgattctcc tgcctcagcc tcccaaataa ctgggacagc aggcacttgc    10860
caccacgcct agctaatttt ttgtattttt agtagagacg gagtttcacc gtgttagcca    10920
ggatggtctc gatctcctga cctcaaggtc cacctgcctc agcctcccaa agtgctggga    10980
ttacaggcgt gagccactgc gcccggccat aaattattaa ctgagccagg cacagtggta    11040
cacacttata gtcccagata ctcaggagac tgaggttgga gtatcctttt ttatgttatt    11100
ttatttttaa ttattatggg tacataatag gtgtacatac ccatggagta caagtcatgt    11160
tctgatacag acacataatg tttaataatc acatcagggt aattgggata tccatcacct    11220
caagcattta tctttctttg tgttaggaac attccacctc cactcttgga ataggcaccc    11280
tgttgtgcta ttaaatacga ggtcttattc atttcatcta actatatttt tctacccatt    11340
aaccatcacc tcttttcccc tcttccccac tacctttcct gtgaggctgc aggattctta    11400
agcacaacag ttagaggcca gcctggacaa catagtgaga ctcaatttct aaaaaataaa    11460
aaagaaatta ccaactaatg ctaaaaaaat agtctctgat gcttaggtat gaattagaaa    11520
tgaccaaaaa aaaaaaaaaa aaaagactg ccctttgctt ccttctcccc ttctcttcaa    11580
gttttccatt gctactcatt ttagtctggt ttaatcaggt ttcatccatt aaaagcaatt    11640
gttgggatca cacattttga gttgtgtcag tggacttccc tcatgctggc atgattcctg    11700
ccccaagccc ttagtaaaag ccaccaagcc atataacata atctctcatt gagtaaaaca    11760
tctgatgtgt ttagaatgac ttctagcaaa aaaccagcct gtccagcatc atctctgtat    11820
aacagataaa ggaataggta ctgcatcaaa aggttataga acctgcccaa atcaatccca    11880
tgtgttttgc aatggaatta ggttgaacta aagtgaaaat tcagttttct actcctcatt    11940
aacatgtctc atgttgcaag gttgagagga aggagaagaa gaactgtatt tacagagaga    12000 ttcccctct ctttctttct acagattact aaaacattca aagaatcaaa tttaagaaat    12060
cagttcatca gagctcatgt tgccaaactg aggtgagtgg aactgtagaa aaaatattta    12120
agtatagata caatgtggca tacttgactt tttgtcacag aatgaatagt aaatgacatg    12180
ttcagataag ttgttgtaat attatgaaaa tagtatttta gtcagcttaa aaaccaatgc    12240
caaaaaagcc aaacatatga tctatttagc tactaatgta ataaccata ttatatctat    12300 tcttattggg aagaggaaga aggggtggag agagagttgg ggtgaaggta cagtaacaag    12360
gccatcctat tgtaaaactc cagtggatat cattcacagt gcagcctatg taaacagtcc    12420
ctcctggagt tgtacaatgc tgtggtttgg gtgtatccat ccaagatcaa gacactatga    12480
ccaacatcaa aagtggcttt ttggttttat ctgcctgatg tgctataata aaagggtatt    12540
atggccaaat ccaaggcatg tctatcatga attaataata ggaggagtag cagcatgcat    12600
gctagttatt tgccattcct gccttagtta aatatgatgt gataaaacca gcctttccaa    12660
ctgaaatagt cacctttact gactctcccg caaatgtctc aaatgaccac attgctctag    12720
tctttaaata atatgcaata gttctttggt agaagaggaa ttatactaat tctttctcaa    12780
```

```
atactagcat cacaagaaaa ttaattcttg ttctctggag agtcacctag taagtatctg    12840
gagcacagat gtctggtcag gtaagttttg atgaggagtt aaagggataa gaagagtcca    12900
tgagaagggt attttccaaa acaccttcg gtcaattcag tgcacattca cttagtactt    12960
tcttgtcagt atctgtatca gccactaatg ttcaaaagtg agtaagccct gaaaacctgt    13020
aggactacat gagccttctg cctttctct cctttgttc acttcccact tatcactcaa      13080
tcctctgcaa cctggcttca ataccaccat aaaatatcaa ctgctcttgc cgattcaaca    13140
atgacatcca gataacaaaa tccaaagaaa ccacatcagt cctattcttg gacctttcaa    13200
cagtatttgg tcctgttggc ctgtcactcc ttgaaatagg actatccctt ggtttgcatg    13260
gccttgtata ccctgatttt ccccttacct ccctagctat tccttcttag tttcctttac    13320
taggtcttac ttctttgtat attccttaaa tgttgctgaa catcaggctg tgctctaggc    13380
ctctcatctt ctcaggtcac actctctcct ttccttggcc ttcactgcca cccatatgct    13440
gagtgctctc aaagttgtat ctctaggcca gtcctctttt gcctccaaac atgaatatat    13500
gcagccatct acttggtacc atcacatgga taattctcat gatctcttcc agtatgactg    13560
cttctttatt tttttctggg ctcttttta gcattgcttt acatggaact ttatcatgtc     13620
tctcaacctc tattttatct tttatctatg tatgtagagt ctgtgtaatt tcttcatctc    13680
ttttagataa ctaatatctc ttcagctttg acttgtattc tgtgtaaccc atttattgcg    13740
ttttcaattt caatgagtat gttttcctat ctgcaagttc tatttgtttc ttttgagaat    13800
cttcctggtc ttttaaacac atttcttatt ttaattttg gggtaccta gtagttgtat      13860 gtatttttgg agtacatgag atgttttgat acaagcaaac aatgcataat aatcacattg    13920
tgtaaaatgg ggtatccatc ccctcaagca tttatccttt gtgttacaaa caatccaatt    13980
atattctttt agttattttt aaatgtacaa ttaaattatt attgaccata gtgactctgt    14040
tgtgctatca gatactaggt gatcttttaa aaataatgtt ttctacttaa tctcattttt    14100
atgattccct ctttacgtc atttgtcatt tcaaatacag tcacttgtct gttgattcta    14160
ttatgtgaag ttttttgagga taatcttttt gttactttga ttccaccttg gtatggtttg    14220
gctgtgcccc cactaaaatc tcatcttgaa ctctggttcc cataataccc acatgttgtg    14280
ggagggacct tgtgggaggt gattagatta tagggacgtt tcccccctttt gctctgttct   14340 ttttcctgcc accatgtaag aaagatgtgt ttgcttcccc ttctgccatg attgtaaatt    14400
tcctgaggcc tccgcagcca tgcaggacct cttttctttg taaattaccc agtctccggc    14460
ggttctttat agctccgtga gaaaaaacta atacacacct catgatgtat tgtttaccac    14520
tgaaattgta tgcttaaatt taatctcact tgggaccctg tacaacctag acttaacata    14580
tctacctcca gagcagttac atctgtcaga cattctagag gaatcagcag cacatggact    14640
ttgttgttgt taatttgttg tcggggagg ggggagggat agcattagga gatacaccta     14700
atgctaaatg acgagttaat gggtgcagca caccaacatg gcacatgtat acatatgtaa    14760
caaacctgca cgttgtgcac atataccctaa aacttaaag tataataata ataaaattaa    14820
aaaaaaaaag gttctgggag tattcaggta gtattaatga agattcagac atcgtgcagc    14880
caggcccatg cttatgaatt ttcaggtgat acttcttttt ctttttcttt aatttaaagc    14940
tggatctcgg aaacagataa atttatttt ttatgacatg acgagcattt ttttcattct     15000
agttcatgct gttattgggt gtttagttct ttgagactcc tggcctttt ctaaaacctc     15060 aagttcaact tccatttgg cactggccca aggtcccatc tccagtctct atgtaaatgc     15120
taaacataag cctgtggaat attctagtct caccacatac tattcacatt cttctttgtt    15180
```

-continued

```
tttggtcttc caggattttc cttacttttc tatgaaccca gtcttgcatt tgaaatggaa  15240
tttattatat attatctatc ctttctattt gttttatgca gaaagtgttt tctaaaatta  15300
tttaggcttc catattgcta gacatggaag ttgtaattat ttgttcagtg cctgtttcta  15360
catctaaact gcaagaccca tatggcaact gtgaatctta gtcccagcta atttctgaag  15420
cttagaatag tgcctagcac aagaagttgt ttatctaaca ttttttaaaaa taaatattaa  15480
attcatatct ggaatgaata ttaagttaga gctggtcatt gaggtgagag gaggaagcca  15540
agagagaata tgagagcctc aaagccaaat atctttaatg tacttttca gaaaagaaga  15600
cagccaatgt caggtggagg aactggttta tgaggtaact ttcctggaag aaaatagaaa  15660
ttactgaggt tttagataat ccaaatattt aatcaagtca ccaaggttta ttgtggggaa  15720
tctttattat taattaaaat gagtgatgaa atcttaatat acgacaaaag ttaaaatttg  15780
cttttgcagg cagatgaatg gtctaggtat caaaaaatta agttgagtct ctaactcaca  15840
caaatttaca accctatcac tttatgaatt tgtttaggag attattttta ataacactgg  15900
tgaagtctaa gaatagctaa aatttatagt acacttattg tgtgctattg actcttcttt  15960
gaagttttgc atatagtgat tcatctaatc ttcataaccc attttacatg tgaagaaact  16020
tagatataga aagattaaga aacttacata acttatccaa agttacacag taaaactctg  16080
gcattataac ttcaaaatca gctatcctac agtgagtaca gtgttctgtg cattgaaatc  16140
aaataagtga gatagcatcg tgatatagta ttacgtatgc aaacactgtt acagagatct  16200
gtctaaagtt aaattccaca aatgaattct ttaaaagggt ttaatcaaga agaatatata  16260
aacaggatgg tgaaaaattg tcatattatt tgttttttaa aatatcttta tgatttacag  16320
gcaagatggt agtggtgtga gagcggatgt tgtcatgaaa tttcaattca ctagaaataa  16380
caatggagca tcaatgaaaa gcagaattga gtctgttta cgacaaatgc tgaataactc  16440
tggaaacctg gaaataaacc cttcaactga gataacatgt aagtataatt tttcataaac  16500
aatttattt caatatatcc ctcaagttta ccaattcaaa ttcatatttt aattgagagg  16560
ctgactttc tttctttgaa actaaactgt gaaaacaatc cattaaaaag ctaaatatac  16620
catatagctc cctaacgtaa atcattctaa gacttaaaga atcatttggc atttatatag  16680
taaattttat ttgctaaaaa ttctcattaa ttatccctgc aacattcctt atgagtgatg  16740
ttactgtcag atgtcattag tggataggcc ataggagggg tacatagatg ctcaaggtca  16800
gagaactatt taattaatga tccacctcag aggcttcttc attttctttt gtaacattta  16860
tcacaattga aattacaaag ttatctgtgt aaattttgta ttgtttggct tcatcctaca  16920
ctgtaatcat cctaaaagaa agaaccagtc aaccttcttc atcctactac cctcctacca  16980
cccagtctcc atcatataac acatattcaa taaataattc ttgcatgact gaagaaaaag  17040
aaataatata tgcatagaat ttaaggacat tcctccaagt tggttacatt ctgctagttt  17100
aataagccat tatttcttct cgatgagctc aagattaaaa ggattttgat gattcccata  17160
ctagactggt aggtaccagt tacagatgta ctaactgtta aatattgaaa tgctttccta  17220
tttgttggta aacaattact gcatcaggcc cacaaagttg tcttccgaga tgtttcaaat  17280
ccactgcccc tgctgctaaa gagttatgct tagcaaagca aagcactcta agacactgct  17340
ccaactccat ggcctgattg catctttat gactggccaa tgctcacgca ctgcagtttg  17400
ttaggtagtt gaatattacc tctgcttcca cacattaagg aatgctcccg aacgcacttc  17460
ccaagtgttt atttatttat cattatacta gacaatatgg tgatacgatg gtcacagaat  17520
```

```
agcggtttcc acctccagag cccataatct agttgaaggg aaagatattc caacacaaga    17580
gtgttgacaa tcaagataga atatgatcaa gggcccagtg tgaggcccag gcaatgatca    17640
ctgcaggaat ctggggaaga aagagaccag cgtgcttggg atatctagca aaagtttcat    17700
gaaggagaat ggactttgac tttgaaatat gggtaggatt tacatatttt gagatgagaa    17760
aaagaaagtt cccagagaag gaaagcatga aaaggcaaac agtctgtact gaacgcgatg    17820
ctttgacaga ataatgaaga aagggacctg ctggaatgat tgatcagtgt tcatcattca    17880
caccatcatc atcaaaacac ttatttaatg agaacttact gttttttagg catggcttta    17940
atgccctata tgaattttt tcttgattaa tccttacaac aaacatatcc catagatagt      18000
tttattgtcc cccttagaaa agataaattg cctaggctga cacagtcagt atatgaggca    18060
gtcaggattc aaactaagtc tgtttgttca aaaaattaag aatggccagc tttttaaaat    18120
tttctgtctc cagaagtatg atttggctcc actgaagttt gcaaacaaa tgtgataccc     18180 aaaccttgtg aaacttttag tgggaaataa ctttgcataa gtcggtttga gagagcgtgg    18240
aaacctgtct tgaaaagttt taatttaact tgcaggaaat aaaaatgatg ggtttctcaa    18300
ttaaaaattt caatcaagga aggatatgag ctaacataac atttttttaa aaagatcagt    18360
ctggtaaggt agaggtgcat aaactgaaaa ggagcaaaag tggtggaatt cagttagaaa    18420
attattgtaa ctgtactgat gtcaaatgat gaaaccatga actaaagtag taccaaaagg    18480
agtgaggagg atggaataat tcaaaagata gaggacagat gtgcagaacc tggagattat    18540
aagatgtgaa aggaggagtt tgagaaaatt tcagattttg gaagtggtgt cattttacta    18600
aaaggatata ataagtagca aattttggat aaagttgggt cccactgagt ttgagatggc    18660
tgttggacat gcagagaaaa ctgtcttgta tgctgttctt aaattgaaat agacagacct    18720
ttaccctctg atactgacat attttccttt ccaggctcac cctccatttc cctaaacaca    18780
acacatgcac tagctctcct tactttattg ctccacaaac atcttacacc tccaagcatt    18840
tgtgcccact gtaccttcta tctggaatct ctttttgtcct cttgtgtgcc tgaaaaattc     18900
ctttcagatc ttcaaaatac agtgcagatg ctatttcttc tagctcaaat attatctcct    18960
ccatataatt taattactct cttttttctt ttctctactt tgcacttaca tttatttgaa    19020
tgattgcttg attaatttct acctgtaaat tatgtgaggg caggtcctct atattttgct    19080
cgcagttaaa tctgcagcac ttattataga gtggtatcat tagagtaata tacatatatt    19140
tgaggacatg ataaattaac ttcccctata gtatttatca cattgcatct caatgacttg    19200
cttatgtttc tgttttccca tataaattga gtaacttgaa aaaagagata tctattaagt    19260
atttaatgag aaattaaagt acaaacttta gtatgcataa caacaaattg ggaaaaggtt    19320
gtaaacaaag agatttgtag ggcccatgag ttagagatcg tttcagcagg tctgaaagga    19380
agcctaggaa tctgcatttt agaggaccac ctcccaaccc caacaagtaa ttctgcttct    19440
tgttgtctgg gtactgtact ttaagaaatt atggtgaaat gatatcagcc tttattgtat    19500
ttatcttatt ctcattttt aatactagca cttactgacc aggctgcagc aaattggctt     19560
attaatggta agttttaata ttattttgta actgtaattt gccaaatcat aaagagtaaa    19620
agtgcaagtc ttttgtgtac ttttggccaa ggcagtatct atcaagttga tgtctttgtt    19680
cttagttcgc tcaggtggtg ttgaaacaag acagtgctga tcccaagtgt cccatggagt    19740
ggactttagg tttccccttt ccttttagaa aaaggaagaa gttgtagtgg aggactaccc    19800
actctgcact caaaattgcc ctcatgaaaa tttcttggc agcttgaga accttttact       19860 gccctggttc taaggtggca tttctgtaga cttacaaatt atgtttgatg acaccgttta    19920
```

```
tgtagcttct cctaaccacc agagtagctt gctttgttgt gaattcaggt taatcacaaa   19980
gtataataaa aaagaattgt cagaagtctt cccagctttg ggtctataac ctgaaggaaa   20040
agtcactact cttcaacatc atcctatgta ctctcaggct aggatagcag aaatgcaatc   20100
cctagaaaac agcaacttac ttctctgacc aaaaaaatgc agttaaaaat tagttcaatg   20160
tacctggtag ctggcctatc ttaggtactt cagtgatttt acaaagtgat ggtagtccta   20220
tgggtgtttt tcagcttcac tacgtattta attcatgctt attgttaatg aaactgtgat   20280
aagcaattta ctagggtatt tgtttgggag atgccacaaa ggaacacatg tatctcttaa   20340
tggaagcctg gtcctccttt atccaggaaa tttgctagga aaaaaagcc tttaggtggt    20400 tgtgctatta aaccagggca ctacttaaaa gccagcccag caatagttgt gtgatttacc   20460
attaatttct tagtaataga ccacacaaaa gaagaaaatt atgggaatgc gagttgagag   20520
gaattgggtg atcagcctac cccagcccgt ttcagctctg gccagtagac tattcacgag   20580
ctctttgaaa acatttaaat aaaccttatt tagatactag aaaccctctg tcaccctcaa   20640
gaatattctg tggtatagcg actcctttat gagggcatgt ttggtaatac agcatcagtc   20700
ttggaggtgg actggattct acaaggtgaa ctgcagtcac taaggagtct tttggatgag   20760
accagttttc ctccaacttc aatgtgtgca tgaacctcac atcaaaatgt agctttagat   20820
ttgtcccatg atgtggttcc aagaatcagc acttctaata agtttccagg ggatgcccat   20880
gctgcaggcc cacaaaccac actgagcata gcaagactat tgagaaaaag gaaatttccc   20940
aggagtctgt ggcctgagct ggcacatcca ataatgacct atcttaacct caactcatga   21000
ggaattccag ggaactctga agctgctcaa aatttgaagc ctatatgcca actaaattca   21060
gaaatgttct ccaaaatgct atctataagc aacagtagtc acaaatgcat tgtagaaata   21120
tatcgatcat gcttttgga aaatccagca tgtcctgagg aagaatgtat aagacataaa    21180
agtcataaat tatggaaaga ctcttcagct tcttccaaat gtaaggaat catgatcttc    21240 ccagcacatt aatgcccttt ctcattagaa tgtggggccg gtccagacct aataacattg   21300
tctgagcaga gaatccttgg aggcactgag gctgaggagg gaagctggcc gtggcaagtc   21360
agtctgcggc tcaataatgc ccaccactgt ggaggcagcc tgatcaataa catgtggatc   21420
ctgacagcag ctcactgctt cagaaggtga ggccaccact acctacccat ctgggaacaa   21480
ttagaataga caggtcatga agactgcacc ctctacccta ggattgaatt gagccagaaa   21540
taattcaatg caaaaaaatc agtaagaatt ttcttcctat tcatgaaagg aaaaggattt   21600 ttcccctta gcatgctaat ttagtgctat ttctctgttt caggtaataa tatattagca    21660
cagtaaagaa caaagattta tatgtcagaa tgttttttaa atcctagcta taaaagctta   21720
agaaatttac taaatctcca taagctttat ttttttttcca aattaaggga caacactgtt   21780
atctgtgact tagtgttact ggtagcattg agtacactaa tgtaaacata cgttaaatgt   21840
tagcgaaacg aattgctgtg gaagatttgc acattatatc atgggagctg atggctaacc   21900
tagagactgc cccatgccat taatttattc attcataaag attattgagt atctagtatg   21960
agcacagtgt tatatattgt agaagctact agtataaaca agtattgcc tctgccttca    22020 aagagcttac actcgaatgt tggaatcaga atgcacaaaa ataatgatca attacaatga   22080
gtagcataaa taaaattaat gtaggcaact tacaagaatt cttaattgag gtgactaaac   22140
tattgccaac actagggtga tatgctacca gtggcgagta ggttgcataa acttaccttga  22200 ttggtaaaaa gaaaagttca cattgctcat aaaagaagga ttttagattt cagcataact   22260
```

```
aaaatctgtt tcaaacctgc cttgttactg gggcatcgca gaccacaaca gttgttggga   22320
acttaactca aaaagttcac ccagaaaaat aatggagatt tgaactcgtg tgccccctgac  22380 catatcaatt ttcttctcag actcttactc taaactggac ctccttatca cacacacaaa   22440
gccttccata ggcagatcaa tccagtctta tttctcaaag catgtacctt gagcttcaga   22500
taaacagcat tgttctcttc ccctggactc ttcctacatt tccctaccta tgagtatctg   22560
atcaatctgc ttatccttga aatgttaata tatttaccac atctctattt gaattttatg   22620 aaattttga taatttctaa gtagttttt cagatttata ggcactactt catggtacag    22680
tgactgttac aaacgtattt gttaaattta gaaggaataa agatttaaaa gactagggta   22740
gttactgaac taaagtttta ggaaatccca aattatttca aattttttctt atggtaattt  22800 tatgacttaa tattttata tgcagtgaac aaatttgaaa ctttaaaaga tactcccaga    22860
attatcagtt ttctgatgta gattggcaaa tttattacta tatcccaaat aacccaagag   22920
acaaaattca caaaaacatt tcaattttca ttgccacttg aaaggccaaa aagcagaaat   22980
ggcacgcatt gatttcaatc gtactcttga gtgtgggaac caggaattaa aatacctgga   23040
cttatcaggc acttagcata accaagaacg gaatagaaac ctccctggat tctaagccct   23100
attcagtccc aatcaccaaa aaccaagtaa acgatatcac tataatgaaa gccacagtta   23160
taaatatcga caacgattac caaaggaatc catggaactt tgaattttgc caccccacat   23220
ccttctattc attaccatga ttgatccact aaagctaaca gactctgtga accttgtatt   23280 ggaccctcc ctaaagacct gattgtcact gagaaccatc agtgaggatt tgtttggggc    23340
atgaccagcc ttcatcaaa gtacatagaa gtgatgaggt cttatcaaag aggattattg    23400
aattatcacc tcttctatgt agctttccct gatactctct ttcctctcca ttgagttcca   23460
cagaaatttt tttatctgcc tttaacagtt gtcctcatga tttgtgatat ttgacttacc   23520
tcttgtcagt ttccttcact agtgtagagt tcctcaaaga aagagaccat aattacttat   23580 attttttattc ctggagactc atactattcc ttatacaaag tagacactta acaatggctt   23640
gttgaactat aattaatgaa ataatagct accttcatga aagttcactt tgtgccaaac    23700
actatagttg acataataca tttgtctcat taatacttaa caattgtgtg agaaggtatc   23760
accaatcaca ttttatatgt aaataaaccc cagagctatt aattaacttg tcataaataa   23820
cacttttcat atgtggcata gccaagattt aaatataaat gttactggtt ccaaaatgat   23880
gctctaattc acttgctgga aagaaggaaa ggaagaaaat aaacgagtgg aaggaagaga   23940
gggagggaag agagaaaagg aaggaaagaa aaaagagtct cttcagaacc ttcactgtaa   24000
agactccgag caaaagaagt tgaatataaa aacaacatag gtttgtttgt tttctaatat   24060
tttttcttca aaattttaa ctcaggttca ctcttacaca aactactgtg tcttataaaa     24120
gtatttccgg tcatagaatt tttattttct gtattaactc cactatctaa tctccataaa   24180
actcctaaat tggtattatc ggtaacattt tgtttttact caaccctag gaacaatgtt    24240 aagttaatca gccctccaca tcacagatcc ttatttcat cagtctgtac aaggcatttc    24300 tctcattttta atttttttc ctcctgtcat ccctggattt cactttcact gccctccttc   24360
cacccatatg cctcatacta atatattcga aatatacatg tcttaaaggt acatgcacgc   24420
acctacaaaa cctatagtgt ttttttgtat gtatatgtct ttaatttaaa taagtagcat   24480
tgtgtaaaag tctaatattg tttcttactg ttttcactca attcttggaa ttttcatctg   24540
atgcactgct gcatagcacc ccatggtatg cagccaccat atttccttca tccaattagg   24600
ttgcatgacc taccttccca ttgccacaaa gagtacacac aaaatatttg tacttatctt   24660
```

```
tctgtaaacc ttcaggaatt tcagaagcac acatgcaggc tgctaaatat accagaatac   24720
tttccagcca cttaaatctt taccagtatt gcaaaagagg ccccatttcc ctccacatca   24780
acatttagta ttattctttt gtttaagttt tatcaatctt ttaaatgtac acaagatgct   24840 cattttata attttaattt ctcagattac tagtttgagt atcttttcat atatctaaga    24900
gctgttttga tctcccctac catgaactgc cactaatatt ctttgcctat tttacaatgg   24960
tttttctgct tatttattac tggtttacag acttttaaaa tatattctac aaaaatttta   25020
gacattaaac attaccaata ttttcccatg gttcctcatc catctggtaa acttgtctat   25080
ggtatatcta atttttgattt aatagaattc attctatttt tacctttag tttgtgtttt    25140 tgttgtttag ccaaaaagtc cccattccta ggtcataaag gtaatgtcct ttttttttt    25200 ttaacgctac tgttctctct ctgtctcccc ctatgtatat aggtgcacat atacttgtac   25260
acacatacat atacctatat atgaggggag ttcgataagt ttatggaaaa taaaattaaa   25320
agataaaata aaaaattata aactttattt ctcaacataa gctccttcaa gttcaagaca   25380
cttttgtaag caataatacc agccatatcg tccatcccta aagaactgag ggtcctgaga   25440
atttaactat gtcaatgcag tctttttac attactttt tacagtactt attgatgaaa     25500
aatgggtgcc ttttaaagat tgttttaaga ttagggaaca aaataagtc agaggaagtc    25560 aaatcaggac tgaaaggtgg atgcctagtg atttattgct gaaactttca taaaactaac   25620
cttatttgat gagaggaatg agcatgagca tggttgtgat ggagaagaac tctggtggag   25680 cttttcctgga cacttttct actaaagctt tggctaactt tcttactctc ataagaagaa   25740
gatgttattt ttcactgacc ctttagaagg tcaacaagca aaatgccttc agcatcccaa   25800
atgtctgttg tcatgacttt tgttcttgac tagtctggtt ttgctttgac tggaccactt   25860
ctacctcttt atagccattg ctttgatggt gctttgtctt caagattgta ttagtaaagc   25920
catatttcat cttctgttac aattcttcaa agaaatactt cagaatcttg atctgacatg   25980
tttaaaattt ctattggaag ctctgacctt gggtgcagct gatctgggcg aaacagtttt   26040
ggcatccatc aagtagaaag tttgctcaac tttagttttt cagtcagaat tgtataagct   26100
gaaccagttg agatgtctat ggtgttgtct attgtttctc acagttaatt gttggtcctc   26160
tttgagacat gaacaagatg aaattttcc tagcaaactg atgtggatga tctgttgctg    26220
cgggcttcac cctcaacaac atctctttct ttccttgaaac aaattatcca ttagtaaact  26280
gatgattggg ggagatgctg tccccataaa cttttgtaa ggcataaata atttcaccat   26340
tcttccagtt tcaccataaa tttgacgttt ttttgcttca atttagcag cattcatgtt   26400 gctttgataa gagctctttt caaattcatg tcttattcct cttagtgcct caaactagat  26460
cttgttcagt atgacaagtt agtatgagtt tatctgcatg caaaaatctt tgaaatccat  26520
gcatagtttg tttataatat acattttcaa tgaacttttg aagacccat acatacatat    26580 gtatatat gcacacacac acacacacac acaccaaaat cttcaaccat tatcagactt    26640
agtgcagaaa aattattcat ccattaacaa gataagaatg ccccttatca tcactactat   26700
ttaaatggag ctcctggcta aaggaaaaga cagggattga aaaaaattag ttaaatctaa   26760
aatgtttatt atttcaggtt tcttagttgc ttaaatggga agggaggtat ggacaaaaga   26820
gaaatcaaag atatttgtgt tatgctactt atcattaaag tatcagaata acttcattgg   26880
aatagaaaaa caccaagatc accccacgat atgttttcta aaatcttctc catttctta    26940 gacaagtgac catgtattcg gccagtgaag aattaaactc acttgccagc ttataatgca   27000
```

```
ggaaaatata gcaaagagat gtggatccaa tagtttctag atagtggtac aggatggcta   27060
agatgaattt atatatctga aatgttcaca aattccctac tcatatagca tgttttcata   27120
atgttttagc aactctaatc ctcgtgactg gattgccacg tctggtattt ccacaacatt   27180
tcctaaacta agaatgagag taagaaatat tttaattcat aacaattata aatctgcaac   27240
tcatgaaaat gacattgcac ttgtgagact tgagaacagt gtcaccttta ccaaagatat   27300
ccatagtgtg tgtctcccag ctgctaccca gaatattcca cctggctcta ctgcttatgt   27360
aacaggatgg ggcgctcaag aatatgctgg taagtgtctc ggaaaaaaaa attaacaata   27420
gaaatgtctt atatttgcta ttaggtaatt ttttaaatta ggaaacatct ggaataggtg   27480
tttctattct tctacagaca gaaccattct atattctgct cagcccaagc tctggctacc   27540
cctgagtctc cttagcaaag caaagcaatg ctccagaaac tatgggaatt ctcaaatata   27600
gtaataggaa aatgtaaaag aaagttatga agacacgagt tctttaataa tccagagatt   27660
ctataagatt caaatagctt ccctataaac aataaaaaag attttgtttg tttgtttgtt   27720
tgcttgtttt ttagagacaa agactttctc agactggagt gcagtggtgc aatcatggct   27780
tactgcagcc tcaaactctg gtcttaagaa atcctcttgc ttcagcctcc caagtagcta   27840
gaattataaa taagtgtgta ccaccatacc cagcttttttt ttttttttttc tacagacagg   27900 ttcttgctct gttgcccagg ctggtctgga attcctgccc tcaagccatc ctcctgcctt   27960
gttggcctcc caaagcaatg ggaggattta gattagacat tgtatgaggg cttaataatc   28020
cttaaggtat taactgccct ttaaagtatt ctgggatatg gcaaaaactc gatgtgtata   28080
taaacattgg tcatatttgt ttattgaatg aataaaatgg aaactaaaat gaggacaatg   28140
cacaagagct actagaacca gtaagagtat cagcgaagga gtggaagggt agcattgaca   28200
atttccctgg gcttttaccc atgttgtaga ttgtctctcc aaggaataat acaaagcctt   28260
aatagtccta gaacacattc tattgtgttc ttatggccca aagtaaattg gtgtagtaga   28320
taacatttgc accagtcatg aaaaactatt ggtgtcattc tgagagtaca tcaatataaa   28380
atagactagt tctttagcct tgaaactaga ctggtttctc ttttgctgct aggttaaagg   28440
ttattcaata tgtaatcttc caatccaaaa tctgtcagtg gataatttaa aagcttttag   28500
tcaattttaa gatatttgtt ttcttaaaat tttaaggggc actgtgtcac aaagctaaag   28560
aaaaaaaaga aaaaaaaact gatctgtgaa aggggttatc ctcatctact tggggaattt   28620
tggctgcgaa gaaactccaa agtaaatctt tagaagcctt cattgttaaa tatgaaataa   28680
tgtttggagt acatttattt cttctcaaat ttattatagg gtcaataatg tacacatctt   28740
gaagtccatt tttttcctgc ttttataaca aacaggccac acagttccag agctaaggca   28800
aggacaggtc agaataataa gtaatgatgt atgtaatgca ccacatagtt ataatggagc   28860
catcttgtct ggaatgctgt gtgctggagt acctcaaggt ggagtggacg catgtcaggt   28920
aagctcaaga caatctcatc catgtcatca tccaagaagt gtataagcac ttcctagtat   28980
gtgataatgt gatagacata agtgtaacag ttacaataca cagccctgtt cctctaaaat   29040
ttataatcta gattttagaa ataaattttt ttatgaatga agtttatcta tcatgaaagc   29100
attaactctg agaggccaaa ttacagagta gttaaccatc caaagctcaa gaatcagaaa   29160
gacctcgatt tgaattcctt aacctctatt accaagtctc taactaaaag ctggggataa   29220
tcataatagc acctaacttt tgggtactaa agaaagttaa aatgaagact aaatatatca   29280
ggcacatggt aaacaacaaa gaaatctcat ctatttcact attattaatg tagaccatgg   29340
tcactcgtgt taataacttt aacctcaacc ttttaactgc tgtgaaggat taaataaaaa   29400
```

```
attaatcact atattataaa aattaattga tatataataa atgaattta  agagatacgt  29460 aataattcat ggactccttg aagatagaaa atttatacaa aatcctagta atttgagtca  29520
caaaagctcc tacaataatg aaacagtatg aatgaaaaag aaaagaaata actattatat  29580
ttggatctag cccataattt ttaaccaaat gcacaaaaac aaacaacaaa tatgaaattc  29640
tcactgtaaa gtgattaaaa tcaaatttga attctaaaat tttaaattaa attatctaaa  29700
cataattgat gcagttatat gttttaatag gttttgttca catatctgaa atccaactcc  29760
acacagtagc aggaacagct ggtgtcagaa attaaatatt cttttagtct ggagttttaa  29820
aaaatcaatc tgtttacttg agtaatttgt tgctgttttc atgggtgaat tgtatacaga  29880
aggataagaa ttattcttcg catcaaaagg tcactgactt tcatatttag tgctcatggt  29940
ctttaaaaag tggataaaaa gtagttctca catttcatgg aaagccccca atccatgagc  30000
acatttccca aaatgaaaca ttttatcaa  ctgcaagttg tgtgtaggtg gagatttgtt  30060
tttcaattgt caagatactg ttaattaccc agtcctttat ctccttttgg tggagatgtc  30120
tctgtgctag gaaacccttc ttgctctcct tcctgtttct cttttactac tggccctgaa  30180
acaacaaatt ctcaagtttc atgacagctt tccaaagaat ccatcaatca aataagcaac  30240
acaactcgac actgacaatt ccagacctac taagagcatt aattaagact taaaaataaa  30300
catgagtttt aaaagggtgt tattcattat tttcccattt ataacgtccc ttaccttctg  30360
tccttcagtg catacaaatt attatcttcc ttgaagccca gttcaagccg tacctcacca  30420
tgataccttc catgtatatt ccactctagg cctcactgat ttttaactga atactataa   30480 tgcatagttc acacttaaaa aaaaaaaaaa aacacagcac tttacataag agcttacagg  30540
atcctatttg ttttatccat tcttttgttc atttttacaa tcattaattc aaaggaatta  30600
tattaattac tttctatgca cccgacgttg tgttaacaca caatactat  ccctgcattc  30660 agcaagtcta tggtctacaa gagaggacac aaattcaaat gtctgtagtc aagcagtgaa  30720
gctggctaga tatggaaaaa ttacaagtcc ctcttgcttt aacatttgct tgcccacatt  30780
tggtcagaca tcatgcaaaa taatttctca ctatagaaaa aaaaacacta caaaacaat   30840 aatataaaga actgagaact ggttaactga agcatgcata tgtcatctaa aagaagcagg  30900
tgacgaccag cttcatgaag tacttgccat gcatattggc acttcacaca ctgacccttc  30960
tccccaccta gaccagtaat taaacaggta tggatgagct agctactaag agcagccaac  31020
tgaatagctg actaacttag aagcacactt ggtaataata gctgactttt attagtactg  31080
actatactat atgctaagct gtactcaaag tgctttgagt tttaaactga tacaaacatt  31140
atatgaggaa acagaggtac agagagctat tcaccagctt accaaaggtc acatagctgg  31200
taagtggagg acttaaaccc agactatcta gtttcagaac ccacagactt aatccatcgt  31260
gcagaacata agacatactc catctgtctc cccaactagg ttattatgtg cacaaatatt  31320
tattggttgg ttggttcatt attatgactg ggtggtaagt atgtcattag gagtgttttg  31380
cttatgacta tataaatttc ttcaccaaaa gaagactttc tgatgatata ctatgcatca  31440
gacaccacgc agggtgctaa ggttaggaag ataagtgaga cttctagaaa ctcattcatt  31500
caacaaatat ctcctaaggg ctagaagctt aggtttcagc agtgaacaga ataggtatgt  31560
tctctttcgt gttggacctt atagtatatc tgggaaaaca gacattgaat aaatatcaca  31620
aatgcaagtg agtgtttcag agacatgcag ctgctcatc  aaaacaaaac agaacaaaac  31680
aaacaaacaa aaactgacca gtgggattaa gtgtaaatag gcacacaaat gcacaaatat  31740
```

-continued

```
gcttttataa aatagtgaag cagtgacaga gacacacaca agatataaag acacaatgaa     31800
gaacaattga gcccaaagct ggaaagggtg agagtgtgaa ggaaaaaggt tgatcagaga     31860
agttttcccg aaggagagaa agcctggatg attaggaggc aaccactcgg tgactgaggg     31920
aaatctgaaa aatgtatttg tcatcttctc agacttgctg aaggaatgac ttgggtactt     31980
tgaggatttc agtaattttt ccatgacttg gtataatatt tcaaaaggaa ataggctgac     32040
tttatttgta taatgaatgt gactccttcc tcgactgcca tagaaataaa ctccttaata     32100
ttttgggttt gtctttgcac ttaagtaatc agtcattctg ttttttttaca gggtgactct     32160 ggtggcccac tagtacaaga agactcacgg cggctttggt ttattgtggg gatagtaagc     32220
tggggagatc agtgtggcct gccggataag ccaggagtgt atactcgagt gacagcctac     32280
cttgactgga ttaggcaaca aactgggatc tagtgcaaca agtgcatccc tgttgcaaag     32340
tctgtatgca ggtgtgcctg tcttaaattc caaagcttta catttcaact gaaaagaaa      32400 ctagaaatgt cctaatttaa catcttgtta cataaatatg gtttaacaaa cactgtttaa     32460 ccttttcttta ttattaaagg ttttctattt tctccagaga actatatgaa tgttgcatag    32520
tactgtggct gtgtaacaga agaaacacac taaactaatt acaaagttaa caatttcatt    32580
acagttgtgc taaatgcccg tagtgagaag aacaggaacc ttgagcatgt atagtagagg    32640
aacctgcaca ggtctgatgg gtcagagggg tcttctctgg gtttcactga ggatgagaag    32700
taagcaaact gtggaaacat gcaaggaaa aagtgataga ataatattca agacaaaag     32760 aacagtatga ggcaagagaa ataatatgta tttaaaattt ttggttactc aatatcttat    32820
acttagtatg agtcctaaaa ttaaaaatgt gaaactgttg tactatacgt ataacctaac    32880
cttaattatt ctgtaagaac atgcttccat aggaaatagt ggataatttt cagctattta    32940
aggcaaaagc taaatagtt cactcctcaa ctgagaccca aagaattata gatatttttc     33000
atgatgaccc atgaaaaata tcactcatct acataaagga gagactatat ctattttata   33060
gagaagctaa gaaatatacc tacacaaact tgtcaggtgc tttacaacta catagtactt    33120
tttaacaaca aataataat tttaagaatg aaaaatttaa tcatcgggaa gaacgtccca     33180
ctacagactt cctatcactg gcagttatat ttttgagcgt aaaagggtcg tcaaacgcta    33240
aatctaagta acgaattgaa agtttaaaga gggggaagag ttggttttgca aaggaaaagt   33300 ttaaatagct taatatcaat agaatgatcc tgaagacaga aaaaactttg tcactcttcc    33360
tctctcattt tctttctctc tctctccct tctcatacac atgcctcccc caccaaagaa     33420
tataatgtaa attaaatcca ctaaaatgta atggcatgaa atctctgta gtctgaatca     33480 ctaatattcc tgagttttta tgagctccta gtacagctaa agtttgccta tgcatgatca    33540
tctatgcgtc agagcttcct ccttctacaa gctaactccc tgcatctggg catcaggact    33600
gctccataca tttgctgaaa acttcttgta tttcctgatg taaaattgtg caaacaccta    33660
caataaagcc atctactttt agggaaaggg agttgaaaat gcaaccaact cttggcgaac    33720
tgtacaaaca aatctttgct atactttatt tcaaataaat tctttttaaa ataatttccc    33780
tgcctaatta tttatggaag ttatgacttt tgaaggacaa ttcaaaacca tttatttaat    33840
tggttctgca atgaaagaac tgccccatat actctactaa aggcttggca ctttctgctg    33900
ccttttaatc cagcgctata attgaggcaa gcgtccagct tgacacctcg agataacttc    33960
gtataatgta tgctatacga agttatgcta gtaactataa cggtcctaag gtagcgagct    34020
agctgcaacc gaggaaaaaa cgtgccatga ggtctctgta tccaagtgtg act           34073
```

```
<210> SEQ ID NO 21
<211> LENGTH: 418
<212> TYPE: PRT
<213> ORGANISM: Artificial Sequence
<220> FEATURE:
<223> OTHER INFORMATION: Recombinant protein

<400> SEQUENCE: 21

Met Tyr Arg Pro Arg Pro Met Leu Ser Pro Ser Arg Phe Phe Thr Pro
1               5                   10                  15

Phe Ala Val Ala Phe Val Val Ile Ile Thr Val Gly Leu Leu Ala Met
                20                  25                  30

Met Ala Gly Leu Leu Ile His Phe Leu Ala Phe Asp Gln Lys Ser Tyr
            35                  40                  45

Phe Tyr Arg Ser Ser Phe Gln Leu Leu Asn Val Glu Tyr Asn Ser Gln
    50                  55                  60

Leu Asn Ser Pro Ala Thr Gln Glu Tyr Arg Thr Leu Ser Gly Arg Ile
65                  70                  75                  80

Glu Ser Leu Ile Thr Lys Thr Phe Lys Glu Ser Asn Leu Arg Asn Gln
                85                  90                  95

Phe Ile Arg Ala His Val Ala Lys Leu Arg Gln Asp Gly Ser Gly Val
                100                 105                 110

Arg Ala Asp Val Val Met Lys Phe Gln Phe Thr Arg Asn Asn Asn Gly
            115                 120                 125

Ala Ser Met Lys Ser Arg Ile Glu Ser Val Leu Arg Gln Met Leu Asn
        130                 135                 140

Asn Ser Gly Asn Leu Glu Ile Asn Pro Ser Thr Glu Ile Thr Ser Leu
145                 150                 155                 160

Thr Asp Gln Ala Ala Ala Asn Trp Leu Ile Asn Glu Cys Gly Ala Gly
                165                 170                 175

Pro Asp Leu Ile Thr Leu Ser Glu Gln Arg Ile Leu Gly Gly Thr Glu
                180                 185                 190

Ala Glu Glu Gly Ser Trp Pro Trp Gln Val Ser Leu Arg Leu Asn Asn
            195                 200                 205

Ala His His Cys Gly Gly Ser Leu Ile Asn Asn Met Trp Ile Leu Thr
        210                 215                 220

Ala Ala His Cys Phe Arg Ser Asn Ser Asn Pro Arg Asp Trp Ile Ala
225                 230                 235                 240

Thr Ser Gly Ile Ser Thr Thr Phe Pro Lys Leu Arg Met Arg Val Arg
                245                 250                 255

Asn Ile Leu Ile His Asn Asn Tyr Lys Ser Ala Thr His Glu Asn Asp
            260                 265                 270

Ile Ala Leu Val Arg Leu Glu Asn Ser Val Thr Phe Thr Lys Asp Ile
        275                 280                 285

His Ser Val Cys Leu Pro Ala Ala Thr Gln Asn Ile Pro Pro Gly Ser
        290                 295                 300

Thr Ala Tyr Val Thr Gly Trp Gly Ala Gln Glu Tyr Ala Gly His Thr
305                 310                 315                 320

Val Pro Glu Leu Arg Gln Gly Gln Val Arg Ile Ile Ser Asn Asp Val
                325                 330                 335

Cys Asn Ala Pro His Ser Tyr Asn Gly Ala Ile Leu Ser Gly Met Leu
            340                 345                 350

Cys Ala Gly Val Pro Gln Gly Gly Val Asp Ala Cys Gln Gly Asp Ser
        355                 360                 365

Gly Gly Pro Leu Val Gln Glu Asp Ser Arg Arg Leu Trp Phe Ile Val
```

```
                370              375              380
Gly Ile Val Ser Trp Gly Asp Gln Cys Gly Leu Pro Asp Lys Pro Gly
385              390              395              400

Val Tyr Thr Arg Val Thr Ala Tyr Leu Asp Trp Ile Arg Gln Gln Thr
                405              410              415

Gly Ile

<210> SEQ ID NO 22
<211> LENGTH: 257
<212> TYPE: DNA
<213> ORGANISM: Artificial Sequence
<220> FEATURE:
<223> OTHER INFORMATION: synthetic oligonucleotide

<400> SEQUENCE: 22
agcacccctc tcttccgcag agtctaagaa atcgctgtgt ttagccctcg ccctgggcac      60
tgtcctcacg ggagctgctg tggctgctgt cttgctttgg aagttcagta agtgcaggga    120
gcctcgatcc caccatgtgc tcctgcagtc cccagtgctc tgagccagac cctgctctct    180
gggctattga gacctctgga ggccctccgt gaggttcctc tcttacataa cgaggctgtc    240
tctcttccct tctcttg                                                   257

<210> SEQ ID NO 23
<211> LENGTH: 190
<212> TYPE: DNA
<213> ORGANISM: Artificial Sequence
<220> FEATURE:
<223> OTHER INFORMATION: synthetic oligonucleotide

<400> SEQUENCE: 23
ggtcagagga ccaaaggtga ggcaaggcca gacttggtgc tcctgtggtt ctcgagataa     60
cttcgtataa tgtatgctat acgaagttat atgcatggcc tccgcgccgg gttttggcgc    120
ctcccgcggg cgccccctc ctcacggcga gcgctgccac gtcagacgaa gggcgcagcg    180
agcgtcctga                                                          190

<210> SEQ ID NO 24
<211> LENGTH: 171
<212> TYPE: DNA
<213> ORGANISM: Artificial Sequence
<220> FEATURE:
<223> OTHER INFORMATION: synthetic oligonucleotide

<400> SEQUENCE: 24
attgttttgc caagttctaa ttccatcaga cctcgacctg cagcccctag ataacttcgt     60
ataatgtatg ctatacgaag ttatgctagt aactataacg gtcctaaggt agcgagctag    120
ctccacgtgg ctttgtccca gacttccttt gtcttcaaca accttctgca a             171

<210> SEQ ID NO 25
<211> LENGTH: 177
<212> TYPE: DNA
<213> ORGANISM: Artificial Sequence
<220> FEATURE:
<223> OTHER INFORMATION: synthetic oligonucleotide

<400> SEQUENCE: 25
ggtcagagga ccaaaggtga ggcaaggcca gacttggtgc tcctgtggtt ctcgagataa     60
cttcgtataa tgtatgctat acgaagttat gctagtaact ataacggtcc taaggtagcg    120
agctagctcc acgtggcttt gtcccagact tcctttgtct tcaacaacct tctgcaa       177
```

<210> SEQ ID NO 26
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 26
gccgtgactg tgaccttctc                                            20

<210> SEQ ID NO 27
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 27
tggaggagcc acctgatgcc tc                                         22

<210> SEQ ID NO 28
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 28
gccttgccct caatggaaac                                            20

<210> SEQ ID NO 29
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 29
ggttgcacag caaggaagaa g                                          21

<210> SEQ ID NO 30
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 30
ccaggagttc ctgtgagcct accc                                       24

<210> SEQ ID NO 31
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 31
tggaatggaa ggagctggag                                            20

<210> SEQ ID NO 32
<211> LENGTH: 19
<212> TYPE: DNA
<213> ORGANISM: Artificial Sequence
<220> FEATURE:

<223> OTHER INFORMATION: synthetic oligonucleotide

<400> SEQUENCE: 32
gtcccacctc ctgcaactg                                                    19

<210> SEQ ID NO 33
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 33
tgagccttcc catcagcctg gg                                                22

<210> SEQ ID NO 34
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 34
ccacaatggc acatgggtct g                                                 21

<210> SEQ ID NO 35
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 35
ggtgcttgct ccccaaga                                                     18

<210> SEQ ID NO 36
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 36
cctaaaaggt gttgtaatgg                                                   20

<210> SEQ ID NO 37
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 37
ggcaataaag aaggaagacg tttt                                              24

<210> SEQ ID NO 38
<211> LENGTH: 120
<212> TYPE: DNA
<213> ORGANISM: Artificial Sequence
<220> FEATURE:
<223> OTHER INFORMATION: synthetic oligonucleotide

<400> SEQUENCE: 38
ccagtcaggg acacacatgc tcacacgccc gcccacccgc acacactaca gtcgagataa       60
cttcgtataa tgtatgctat acgaagttat atgcatggcc tccgcgccgg gttttggcgc      120

<210> SEQ ID NO 39
<211> LENGTH: 198
<212> TYPE: DNA
<213> ORGANISM: Artificial Sequence
<220> FEATURE:
<223> OTHER INFORMATION: synthetic oligonucleotide

<400> SEQUENCE: 39

```
attctagttg tggtttgtcc aaactcatca atgtatctta tcatgtctgg ataacttcg      60 tataatgtat gctatacgaa gttatgctag taactataac ggtcctaagg tagcgagcta    120
gccaagtctg tgtgctacca agtagcaaaa ctgagcctgg aactcacaca tgcgtgtctg    180
agagcccagc actatcgc                                                  198
```

<210> SEQ ID NO 40
<211> LENGTH: 100
<212> TYPE: DNA
<213> ORGANISM: Artificial Sequence
<220> FEATURE:
<223> OTHER INFORMATION: synthetic oligonucleotide

<400> SEQUENCE: 40

```
taatctgact ttctcttcat cggtctctct tattctaggc tgagctgtaa cgctgccgtc     60
ccccacatcc agaagctgct tcccttcaga cctacctacg                          100
```

<210> SEQ ID NO 41
<211> LENGTH: 177
<212> TYPE: DNA
<213> ORGANISM: Artificial Sequence
<220> FEATURE:
<223> OTHER INFORMATION: synthetic oligonucleotide

<400> SEQUENCE: 41

```
ccagtcaggg acacacatgc tcacacgccc gcccacccgc acacactaca gtcgagataa     60
cttcgtataa tgtatgctat acgaagttat gctagtaact ataacggtcc taaggtagcg    120
agctagccaa gtctgtgtgc taccaagtag caaaactgag cctggaactc acacatg       177
```

<210> SEQ ID NO 42
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 42

```
gagcagggcc atgacacat                                                  19
```

<210> SEQ ID NO 43
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 43

```
accattagat cccagcactg gaca                                            24
```

<210> SEQ ID NO 44
<211> LENGTH: 20
<212> TYPE: DNA
<213> ORGANISM: Artificial Sequence
<220> FEATURE:

<223> OTHER INFORMATION: synthetic oligonucleotide

<400> SEQUENCE: 44
aaacccttcc cgagagagaa                                                    20

<210> SEQ ID NO 45
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 45
gaggaacact gtgtcaagga ctt                                                23

<210> SEQ ID NO 46
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 46
cctgaaaagc ccggagtggc ag                                                 22

<210> SEQ ID NO 47
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 47
gggcagagac cacatctga                                                     19

<210> SEQ ID NO 48
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 48
ggaagccctc tctcgatact tg                                                 22

<210> SEQ ID NO 49
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 49
ttctaccctg agggcatgca gc                                                 22

<210> SEQ ID NO 50
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 50
tgggatgtag aaggttgtca ga                                                 22

```
<210> SEQ ID NO 51
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 51
ctgagcctgg aactcacaca tg                                              22

<210> SEQ ID NO 52
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 52
tctgagagcc cagcactatc gcc                                             23

<210> SEQ ID NO 53
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 53
gctgagggtc aggcttgag                                                  19

<210> SEQ ID NO 54
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 54
tctgcagggt agggagagaa g                                               21

<210> SEQ ID NO 55
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 55
tgtttcagaa aaggaagact cacgttaca                                       29

<210> SEQ ID NO 56
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 56
gagaccgatg aagagaaagt caga                                            24

<210> SEQ ID NO 57
<211> LENGTH: 100
<212> TYPE: DNA
<213> ORGANISM: Artificial Sequence
<220> FEATURE:
<223> OTHER INFORMATION: synthetic oligonucleotide
```

<400> SEQUENCE: 57
gaccatttta aggttttgct tggttgtttt ggagggaggg tggtgctttg ctaatggtga      60
attactaact cctcaataaa gaatattatt tgaaataatt                            100

<210> SEQ ID NO 58
<211> LENGTH: 190
<212> TYPE: DNA
<213> ORGANISM: Artificial Sequence
<220> FEATURE:
<223> OTHER INFORMATION: synthetic oligonucleotide

<400> SEQUENCE: 58 gctgccttttt aatccagcgc tataattgag gcaagcgtcc agcttgacac ctcgagataa     60
cttcgtataa tgtatgctat acgaagttat atgcatggcc tccgcgccgg gttttggcgc     120
ctcccgcggg cgccccctc ctcacggcga gcgctgccac gtcagacgaa gggcgcagcg      180
agcgtcctga                                                             190

<210> SEQ ID NO 59
<211> LENGTH: 171
<212> TYPE: DNA
<213> ORGANISM: Artificial Sequence
<220> FEATURE:
<223> OTHER INFORMATION: synthetic oligonucleotide

<400> SEQUENCE: 59
attgttttgc caagttctaa ttccatcaga cctcgacctg cagcccctag ataacttcgt     60
ataatgtatg ctatacgaag ttatgctagt aactataacg gtcctaaggt agcgagctag    120
ctgcaaccga ggaaaaaacg tgccatgagg tctctgtatc caagtgtgac t              171

<210> SEQ ID NO 60
<211> LENGTH: 177
<212> TYPE: DNA
<213> ORGANISM: Artificial Sequence
<220> FEATURE:
<223> OTHER INFORMATION: synthetic oligonucleotide

<400> SEQUENCE: 60
ccagtcaggg acacacatgc tcacacgccc gcccacccgc acacactaca ctcgagataa    60
cttcgtataa tgtatgctat acgaagttat gctagtaact ataacggtcc taaggtagcg    120
agctagctgc aaccgaggaa aaacgtgcc atgaggtctc tgtatccaag tgtgact        177

<210> SEQ ID NO 61
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 61
tcctctccag acaagaaagc t                                                21

<210> SEQ ID NO 62
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 62
tcatagcagc tttcaaatcc taaacgttga                                       30

<210> SEQ ID NO 63
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 63
tcgtgtgtag ctggtgagtt                                                  20

<210> SEQ ID NO 64
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 64
catgcgatca caggaggaga tc                                               22

<210> SEQ ID NO 65
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 65
aattgggccc gaagccagat gc                                               22

<210> SEQ ID NO 66
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 66
cggaaggctt ctgtgacttc                                                  20

<210> SEQ ID NO 67
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 67
gtctcccact tctgacataa tgaac                                            25

<210> SEQ ID NO 68
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 68
cccagtgtta accctacatc tggttcc                                          27

<210> SEQ ID NO 69
<211> LENGTH: 20
<212> TYPE: DNA
<213> ORGANISM: Artificial Sequence
<220> FEATURE:

```
<223> OTHER INFORMATION: synthetic oligonucleotide

<400> SEQUENCE: 69
tgggaagaga ctcttggaca                                                    20

<210> SEQ ID NO 70
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 70
atgagctcct agtacagcta aagtt                                              25

<210> SEQ ID NO 71
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 71
atgcatgatc atctatgcgt cagagc                                             26

<210> SEQ ID NO 72
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 72
tgcccagatg cagggagtta g                                                  21
```

What is claimed is:

1. A rodent ES cell, comprising a replacement of a nucleotide sequence of an endogenous rodent Tmprss4 gene at an endogenous rodent Tmprss4 locus with a nucleotide sequence of a human TMPRSS4 gene to form a humanized Tmprss4 gene,
   wherein the humanized Tmprss4 gene is under control of the promoter of the endogenous rodent Tmprss4 gene at the endogenous rodent Tmprss4 locus, and
   wherein the humanized Tmprss4 gene encodes a humanized Tmprss4 protein that comprises (i) an ectodomain of the human TMPRSS4 protein encoded by the human TMPRSS4 gene, and (ii) a cytoplasmic and transmembrane portion encoded by the endogenous rodent Tmprss4 gene.

2. The rodent ES cell of claim 1, wherein the ectodomain comprises amino acid residues K54-L437 of SEQ ID NO: 11.

3. The rodent ES cell of claim 1, wherein the nucleotide sequence of the human TMPRSS4 gene comprises coding exon 4 through the stop codon in coding exon 13 of the human TMPRSS4 gene.

4. The rodent ES cell of claim 3, wherein the stop codon of the human TMPRSS4 gene is followed by the 3' UTR of the endogenous rodent Tmprss4 gene.

5. The rodent ES cell of claim 3, wherein the humanized Tmprss4 gene comprises coding exon 1 through coding exon 3 of the endogenous rodent Tmprss4 gene, and coding exon 4 through the stop codon in coding exon 13 of the human TMPRSS4 gene.

6. The rodent ES cell of claim 1, wherein the rodent ES cell is a mouse ES cell.

7. The rodent ES cell of claim 1, wherein the rodent ES cell is a rat ES cell.

8. The rodent ES cell of claim 2, wherein the rodent ES cell is a mouse ES cell.

9. The rodent ES cell of claim 2, wherein the rodent ES cell is a rat ES cell.

10. The rodent ES cell of claim 3, wherein the rodent ES cell is a mouse ES cell.

11. The rodent ES cell of claim 3, wherein the rodent ES cell is a rat ES cell.

12. The rodent ES cell of claim 4, wherein the rodent ES cell is a mouse ES cell.

13. The rodent ES cell of claim 4, wherein the rodent ES cell is a rat ES cell.

14. The rodent ES cell of claim 5, wherein the rodent ES cell is a mouse ES cell.

15. The rodent ES cell of claim 5, wherein the rodent ES cell is a rat ES cell.

16. A rodent ES cell, comprising a replacement of a nucleotide sequence of an endogenous rodent Tmprss11d gene at an endogenous rodent Tmprss11d locus with a nucleotide sequence of a human TMPRSS11D gene to form a humanized Tmprss11d gene,
   wherein the humanized Tmprss11d gene is under control of the promoter of the endogenous rodent Tmprss11d gene at the endogenous rodent Tmprss11d locus, and
   wherein the humanized Tmprss11d gene encodes a humanized Tmprss11d protein that comprises (i) an ectodomain of the human TMPRSS11D protein encoded by the human TMPRSS11D gene, and (ii) a cytoplasmic and transmembrane portion encoded by the endogenous rodent Tmprss11d gene.

17. The rodent ES cell of claim 16, wherein the ectodomain comprises amino acid residues A42 to 1418 of SEQ ID NO: 18.

18. The rodent ES cell of claim 16, wherein the nucleotide sequence of the human TMPRSS11D gene comprises coding exon 3 through the stop codon in coding exon 10 of the human TMPRSS11D gene.

19. The rodent ES cell of claim 16, further comprising the 3' UTR of the human TMPRSS11D gene.

20. The rodent ES cell of claim 16, wherein the humanized Tmprss11d gene comprises coding exons 1-2 of the endogenous rodent Tmprss11d gene, and coding exons 3 through coding exon 10 of the human TMPRSS11D gene.

21. The rodent ES cell of claim 16, wherein the rodent ES cell is a mouse ES cell or a rat ES cell.

* * * * *